(12) United States Patent
Crosetto

(10) Patent No.: US 7,180,074 B1
(45) Date of Patent: Feb. 20, 2007

(54) METHOD AND APPARATUS FOR WHOLE-BODY, THREE-DIMENSIONAL, DYNAMIC PET/CT EXAMINATION

(76) Inventor: Dario B. Crosetto, 900 Hideaway Pl., DeSoto, TX (US) 75115

( * ) Notice: Subject to any disclaimer, the term of this patent is extended or adjusted under 35 U.S.C. 154(b) by 0 days.

(21) Appl. No.: 11/180,009

(22) Filed: Jul. 12, 2005

Related U.S. Application Data

(63) Continuation of application No. 10/185,904, filed on Jun. 27, 2002.

(60) Provisional application No. 60/301,545, filed on Jun. 27, 2001, provisional application No. 60/309,018, filed on Jul. 31, 2001.

(51) Int. Cl.
*G01T 1/00* (2006.01)

(52) U.S. Cl. ............................................. 250/370.09

(58) Field of Classification Search .......... 250/370.09, 250/363.03, 363.04
See application file for complete search history.

(56) References Cited

U.S. PATENT DOCUMENTS

| | | | | |
|---|---|---|---|---|
| 4,837,439 A * | 6/1989 | Genna et al. | ................ | 250/368 |
| 5,329,124 A * | 7/1994 | Yamamoto et al. | ......... | 250/367 |
| 5,453,623 A * | 9/1995 | Wong et al. | ........... | 250/363.03 |
| 6,087,663 A * | 7/2000 | Moisan et al. | ............... | 250/367 |
| 6,552,348 B2 * | 4/2003 | Cherry et al. | .......... | 250/363.03 |
| 6,841,783 B2 * | 1/2005 | Malmin | ....................... | 250/368 |
| 6,909,097 B2 * | 6/2005 | Schreiner et al. | ........... | 250/366 |
| 6,956,214 B2 * | 10/2005 | Wong et al. | ................ | 250/368 |

* cited by examiner

*Primary Examiner*—Otilia Gabor
(74) *Attorney, Agent, or Firm*—Jones Day; Brett Lovejoy

(57) ABSTRACT

A body scanning system includes a CT transmitter and a PET configured to radiate along a significant portion of the body and a plurality of sensors configured to detect photons along the same portion of the body. In order to facilitate the efficient collection of photons and to process the data on a real time basis, the body scanning system includes a new data processing pipeline that includes a sequentially implemented parallel processor that is operable to create images in real time notwithstanding the significant amounts of data generated by the CT and PET radiating devices.

17 Claims, 44 Drawing Sheets

Figure 1:
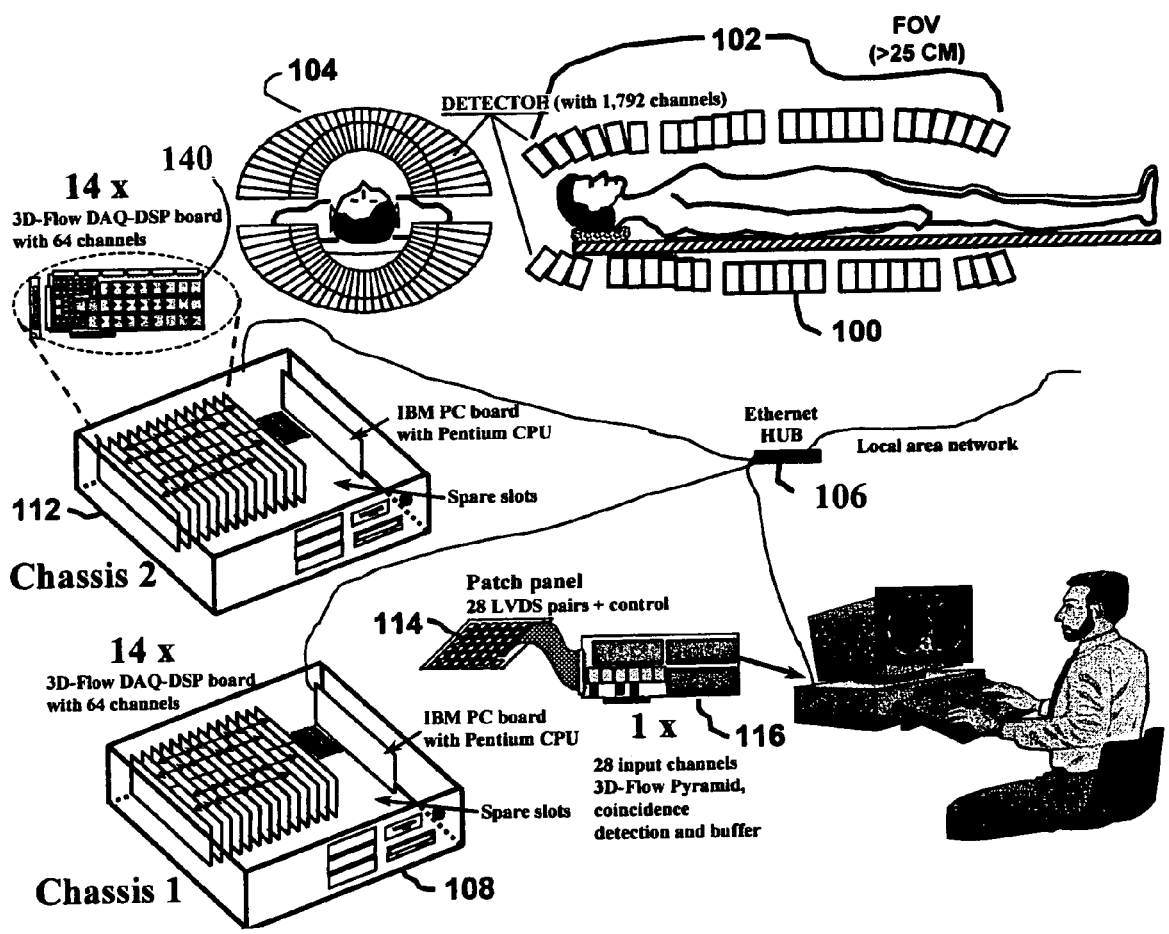

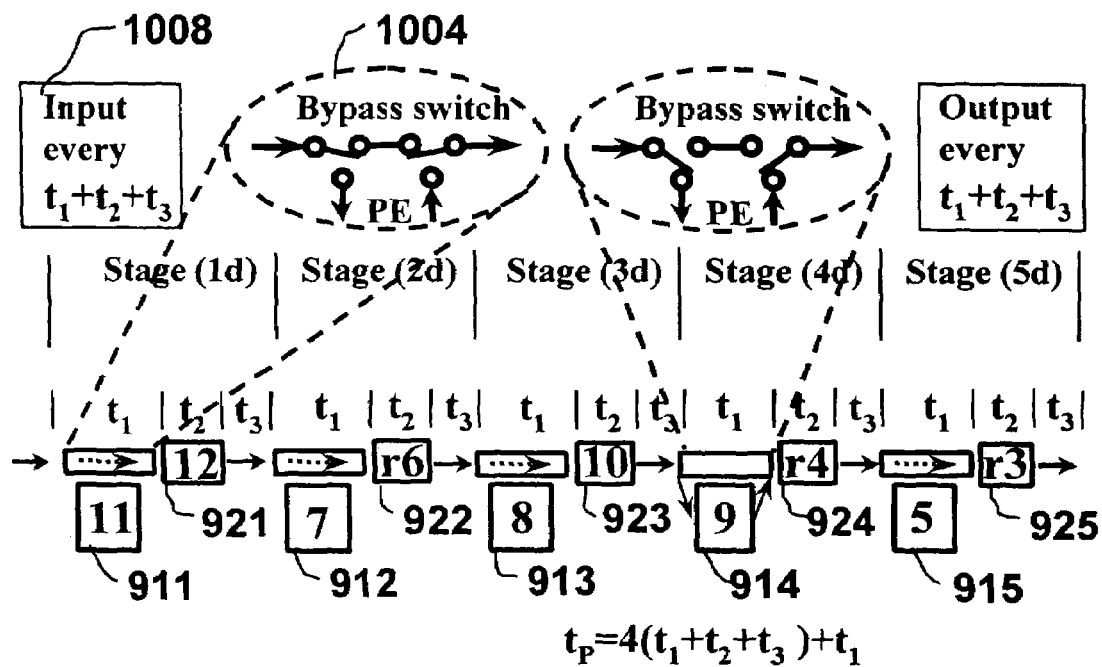
Fig. 10
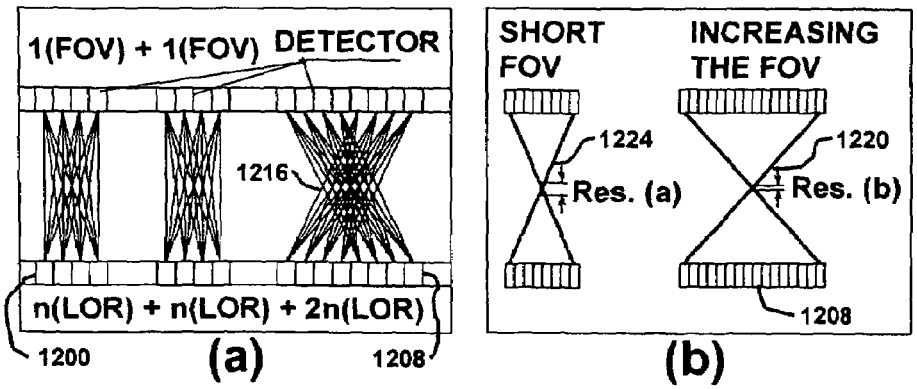
Fig. 11
Fig. 12

Changing the role of PET to screening for cancer

| Current PET systems | | | | PET capabilities of the 3D-CBS | | |
|---|---|---|---|---|---|---|
| Radiation dose | ($^{15}$O-water 277 mrem) MBq | 7/12 of 66 mCi = 38.5 mCi = 1,424 MBq | | 7/12 of 2.2 mCi = 1.2 mCi = 47.4 MBq | ($^{15}$O-water 9.2 mrem) MBq | |
| | | MBq = million Becquerel = million disintegration (or million coincidences) per second | | | | |
| Photons not scattered and/or absorbed in the body | 214 | ~15% | (1) 7% to 25% pair of photons in time coincidence leave the body | | ~15% | 7.1 |
| Field-of-view (FOV) | 18 | ~8.5% | (2) FOV 15-25 cm — Photons lost / Photons lost / FOV / Brick wall (B) | FOV 157.4 cm — Photons lost / Broken wall (B) | ~95% | 6.7 |
| Solid angle | 3.2 | ~18% | (3) Photons lost / Photons lost | Photons lost | ~92% | 6.2 |
| Stopping power (SP) | 2.5 | ~80% | (4) Stopping power + photofraction + crystal scatter  SP year 1990 (30 mm = 95%)  years 1998-2000 (10 mm = 57%) [Photons] | Crystal  SP for 25 mm thick = 91%  [Photon not stopped] | ~80% | 5 |
| Electronics (Photon identification) (Coincidence detection) | 0.2 | ~8.1% | (5) Bottle neck (C)  Module dead-time for 1-2 μs, when hit found  0.5 - 1 MHz  Boundary 2x2 block  Limited analog proc.  Poor timing resolution  Poor Signal-to-Noise  Brick wall (A)  - Poor photon identification  - Dead time  (6) Bottle neck (C) Bottle neck (D)  0.5 - 1 MHz  4 MHz  1,344 ch. 56 ch.  DETECTOR  Brick wall (B)  Too many LOR  LOR (700) | Bottle neck (C)  3D-Flow DSP  20 MHz  NO Boundary limit  DSP on Ch. + neighbors  DSP on timing resol.  DSP S/N improvement  Broken wall (A)  Bottle neck (D)  40 MHz  6 vs. > 700 (exorbitant number for FOV = 157 cm) comparisons  Coincidence B-D  Broken wall (B) | ~95% | 4.7 |
| | 0.014% Efficiency | | 0.2 million coincidences/sec found | 4.7 million coincidences/sec found | 10% Efficiency | |

Fig. 14

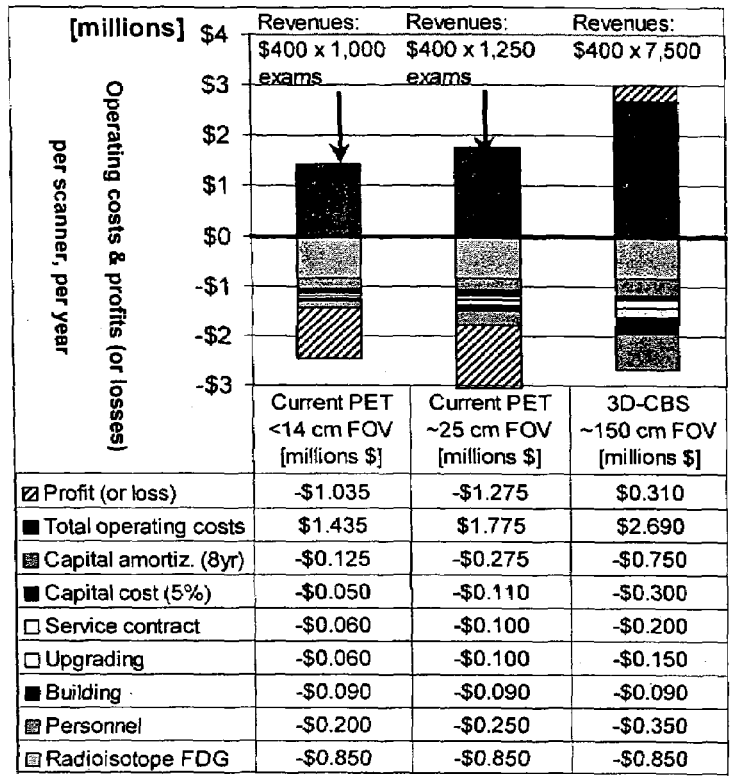
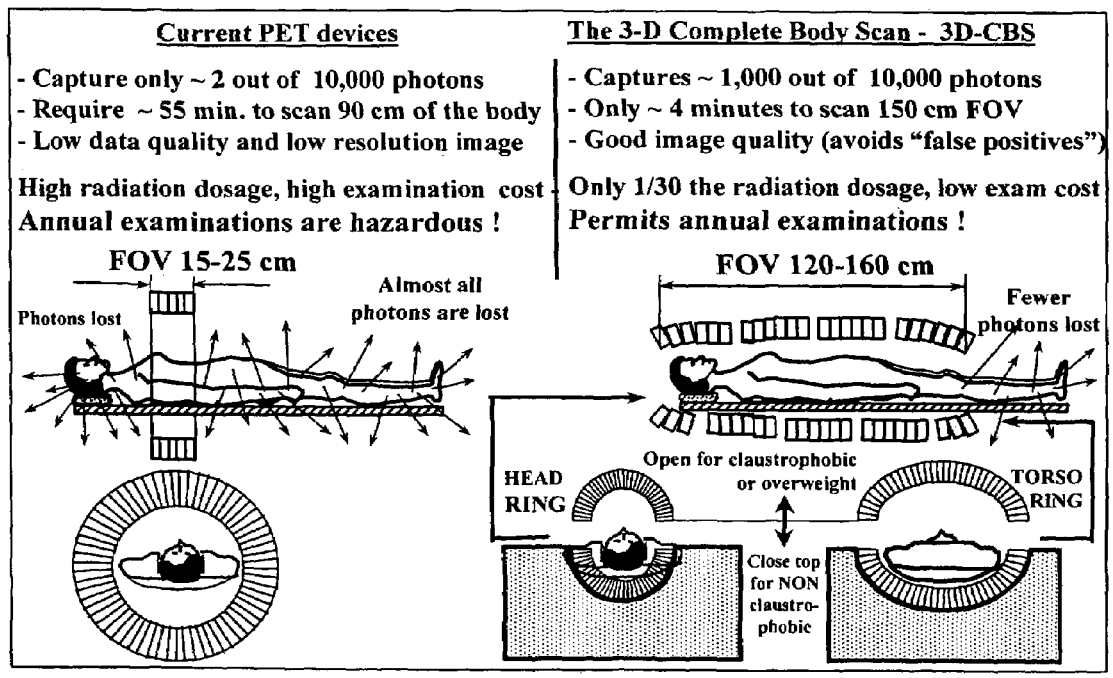
Fig. 15

Solution No. 1

Solution No. 2

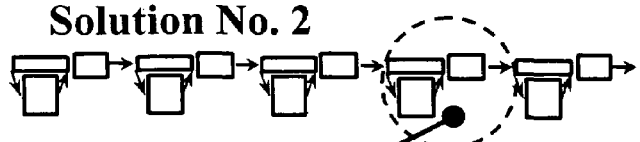

Longest unpartitionable operation

General Switch
- short-long PCB traces, crosstalk, signal skew
- high fanout, high power dissipation
- ground bounce, noise, timing problems
- no modularity, higher PCB/component costs Solution No. 3

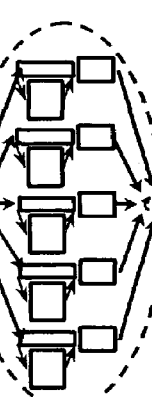

Bypass Switch
- short PCB traces, no crosstalk, no signal skew
- one unit load, very low power dissipation
- no ground bounce, low noise, matched imped.
- modularity, low PCB/component costs Solution No. 4

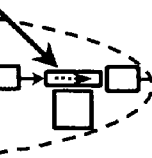

Fig. 22

Random Event

Multiple Event

Compton scattered Event

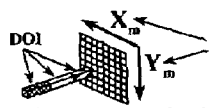 # CENTROID CALCULATION

3D-Flow System

- NO Boundary limitation,
- NO duplication of events (local maxima)
- Suitable for "continuous" or "block" detectors.
- Flexible clustering/centroid 2x2, 3x3, 4x4, or 5x5,
- The energy of each PMT is checked if head of a cluster against its neighbors (3, 8, 15, or 24)
- Digital signal processing, high S/N ratio

Current PET systems

- Boundary limitation at the block and module segmentation.
- Missing the detection of photons at the block boundaries, poor S/N ratio and lack of Signal Processing
- Fixed, hard-wired architecture for 2x2 centroid
- Analog signal processing

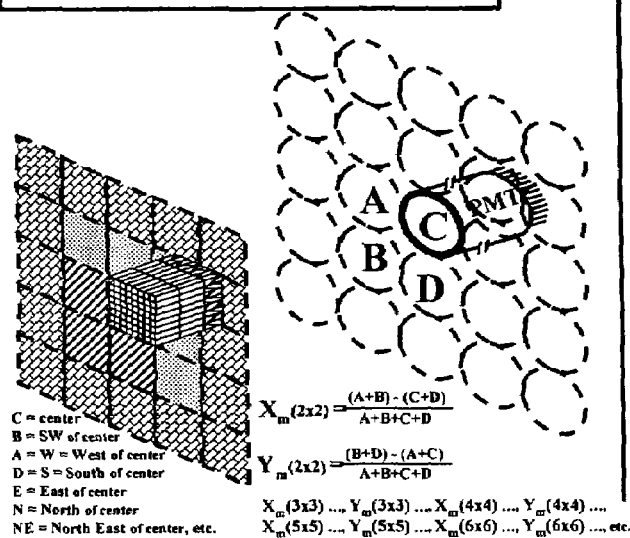

C = center
B = SW of center
A = W = West of center
D = S = South of center
E = East of center
N = North of center
NE = North East of center, etc.

$$X_m(2x2) = \frac{(A+B)-(C+D)}{A+B+C+D}$$

$$Y_m(2x2) = \frac{(B+D)-(A+C)}{A+B+C+D}$$

$X_m(3x3)$ ..., $Y_m(3x3)$ ..., $X_m(4x4)$ ..., $Y_m(4x4)$ ...
$X_m(5x5)$ ..., $Y_m(5x5)$ ..., $X_m(6x6)$ ..., $Y_m(6x6)$ ..., etc.

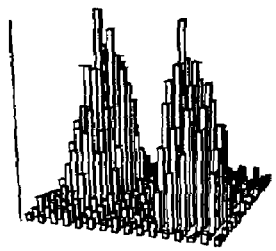

(a)

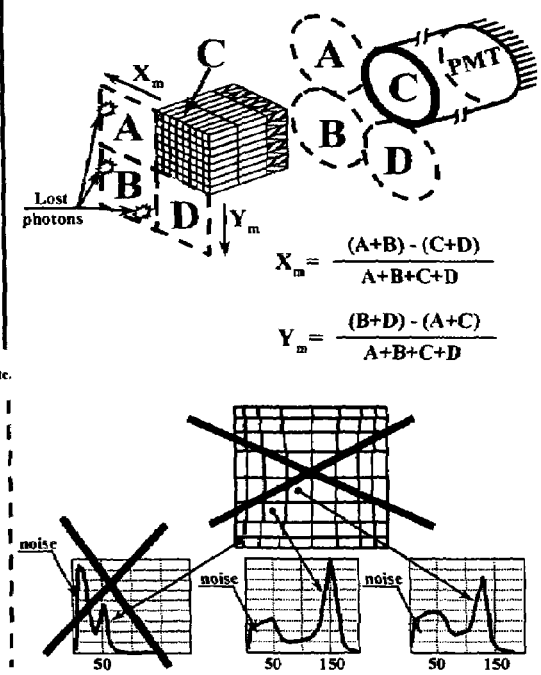

$$X_m = \frac{(A+B)-(C+D)}{A+B+C+D}$$

$$Y_m = \frac{(B+D)-(A+C)}{A+B+C+D}$$

(b1) (b2) (b3)

Fig. 33

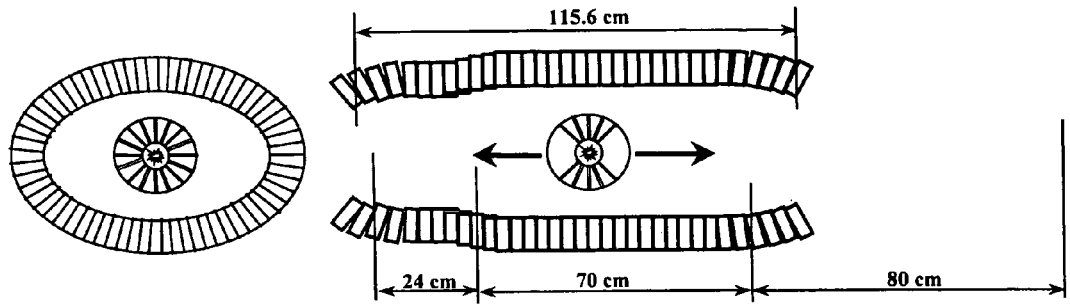

Fig. 37

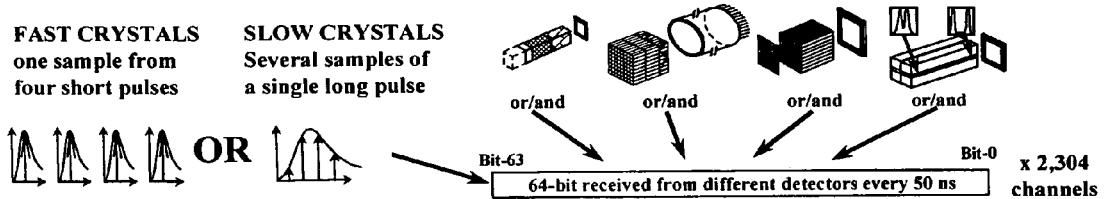

| Step 1-6 | | |
|---|---|---|
| - Get data from detectors, convert ADC counts into energy value through Lookup Table.<br>- Fetch four signals from fast crystals, TOF/decay time information, calculate DOI, or<br>- integrate signals from slow crystals, calculate DOI (signal decay time) and check for pileup.<br>- Calculate attenuation. Calculate Time Stamp. | READ:<br>TOF (+ crystal location reduction factor obtained from calibration)<br>CACULATE: Attenuation | READ (or calculate):<br>Signal decay time<br>CACULATE: DOI |

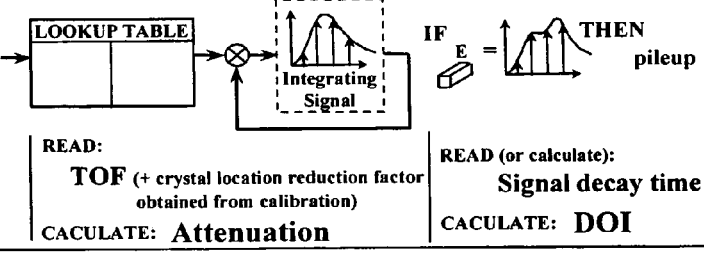

| Step 7 | Send data to North, East, West and South neighbors and save energy photon in R46. Increment Time stamp.<br>Instruction: DM4 to E, E to North, E to East, E to West, E to South, E to CR, CR to R46, R11 to A, LD A1 A, ASL A2 8, A1lo to C, C to DR, DR to 59. | 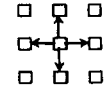 |
|---|---|---|

| Step 8 | Save first 3x3 data into Sum1, route 3x3 corner values.<br>Instruction: A2 to B, R22 to E, CMPU BE, R5 to A, R58 to D, AND A1 AD, R46 to C, LD A2 C, North to East, West to North, South to West, East to South. | 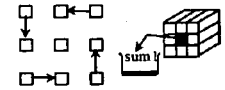 |
|---|---|---|

| Step 9 | Get energies from four NEWS neighbors, add them, and save into registers R0, R16, R32, R48 for local maxima calculation.<br>Instruction: ADDACCS A2 CD, ADDS A1 BE, North to E, E to AR, AR to R0, East to B, B to BR, BR to R16, West to C, C to CR, CR to R32, South to D, D to DR, DR to R48. | 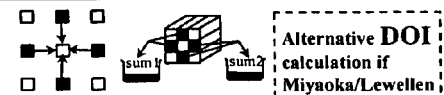 | Alternative DOI calculation if Miyaoka/Lewellen light sharing or Moses/Derenzo signal ratio from two sensors is used |
|---|---|---|---|

| Step 10 | Get energies from four corner neighbors, add them, and save into registers R1,R17,R33,R49 for local maxima calculation.<br>Instruction: ADDACCS A2 CD, ADDACCS A1 AB, North to A, A to AR, AR to R1, East to B, B to BR, BR to R17, West to C, C to CR, CR to R33, South to D, D to DR, DR to R49. |  |
|---|---|---|

| Step 11-14 | | |
|---|---|---|
| Compare 9 energy values for "Local Maxima" in one CPU clock cycle. Add partial sums, Sum1 and Sum2. Check for "photopeak" and "scattered." Calculate 3x3 "centroid." Format output word, or reject event. | 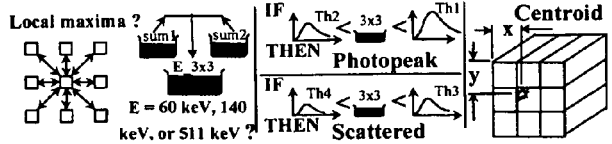 | |

Fig. 38

| Step 7 | Send energy photon of detector module to North, East, West and South neighbors and save into R46. Increment Time stamp.<br>Instruction: DM4 to E, E to North, E to East, E to West, E to South, E to CR, CR to R46, R11 to A, LD A1 A, ASL A2 8, A1lo to C, C to DR, DR to 59. | 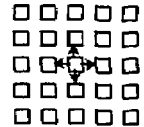 |
|---|---|---|
| Step 8 | Save first 3x3 data into Sum1, route 3x3 values.<br>Instruction: A2 to B, R22 to E, CMPU BE, R5 to A, R58 to D, AND A1 AD, R46 to C, LD A2lo C, North to East, West to North, South to West, East to South. | 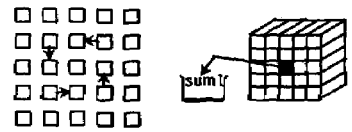 |
| Step 9 | Get energies from four NEWS neighbors, add them, and save into registers R0, R16, R32, R48 for local maxima calculation, route 3x3 values.<br>Instruction: ADDACCS A2 CD, ADDS A1 BE, North to E, E to AR, AR to R0, East to B, B to BR, BR to R16, West to C, C to CR, CR to R32, South to D, D to DR, DR to R48, North to West, West to South, South to East, East to North. | 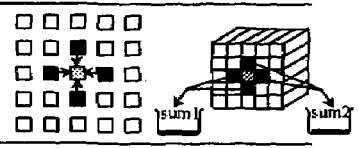 |
| Step 10 | Get energies from four inner corner neighbors, add them, and save into registers R1,R17,R33,R49 for local maxima calculation, route 3x3 values.<br>instruction: ADDACCS A2 CD, ADDACCS A1 AB, North to A, A to AR, AR to R1, East to B, B to BR, BR to R17, West to C, C to CR, CR to R33, South to D, D to DR, DR to R49, North to East, East to South, South to West, West to North. | 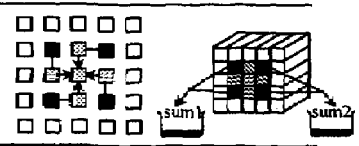 |
| Step 11 | Get energies from four outer neighbors, add them, and save into registers R2,R18,R34,R50 for local maxima calculation, route 3x3 values.<br>Instruction: ADDACCS A2 CD, ADDACCS A1 AB, North to A, A to AR, AR to R2, East to B, B to BR, BR to R18, West to C, C to CR, CR to R34, South to D, D to DR, DR to R50, North to East, East to South, South to West, West to North. | 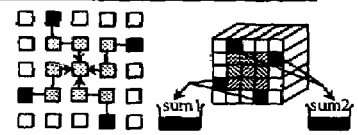 |
| Step 12 | Get energies from four more outer neighbors, add them, and save into registers R3,R19,R35,R51 for local maxima calculation, route 3x3 values.<br>Instruction: ADDACCS A2 CD, ADDACCS A1 AB, North to A, A to AR, AR to R3, East to B, B to BR, BR to R19, West to C, C to CR, CR to R35, South to D, D to DR, DR to R51, North to South, East to West, West to East, South to North. | 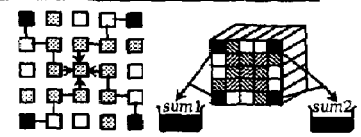 |
| Step 13 | Get energies from four more outer neighbors, add them, and save into registers R4,R20,R36,R52 for local maxima calculation.<br>Instruction: ADDACCS A2 CD, ADDACCS A1 AB, North to A, A to AR, AR to R4, East to B, B to BR, BR to R20, West to C, C to CR, CR to R36, South to D, D to DR, DR to R52. |  |
| Step 14 | Get energies from four more outer neighbors, add them, and save into registers R5,R21,R37,R53 for local maxima calculation.<br>Instruction: ADDACCS A2 CD, ADDACCS A1 AB, North to A, A to AR, AR to R5, East to B, B to BR, BR to R21, West to C, C to CR, CR to R37, South to D, D to DR, DR to R53. | 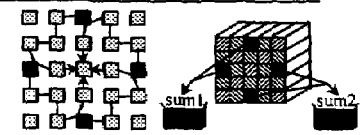 |
| Step 15 | Compare 25 values for "Local Maxima" in one CPU clock cycle. Add partial sums Sum1 and Sum2.<br>Instruction: ACCS A2 A, A1lo to A, R46 to C, CMPU 24 C | |

Fig. 39

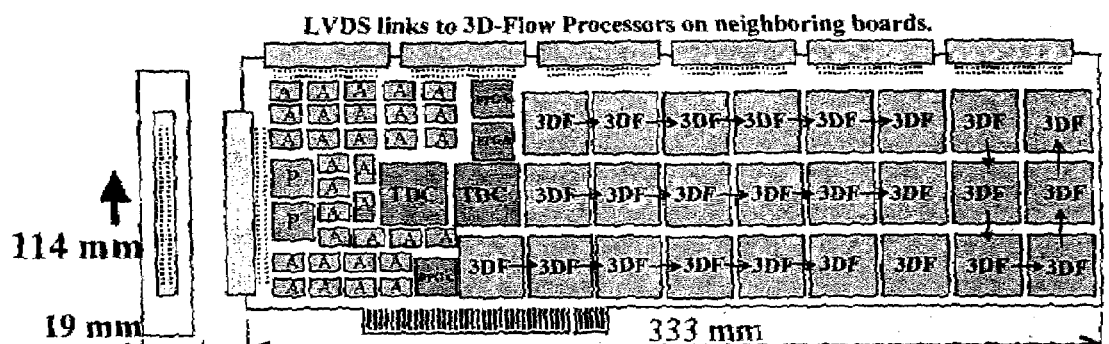
64 channels IBM PC compatible board (front view). One analog channel to one 3D-Flow processor
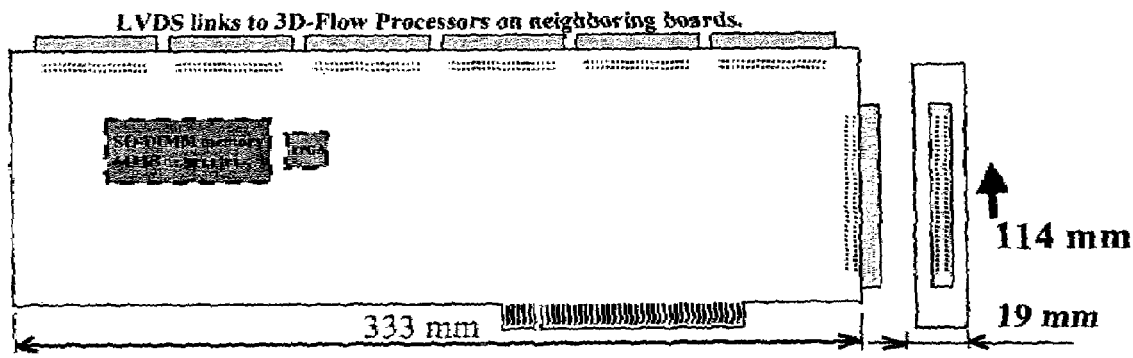
64 channels IBM PC compatible board (rear view). One analog channel to one 3D-Flow processor
Fig. 50

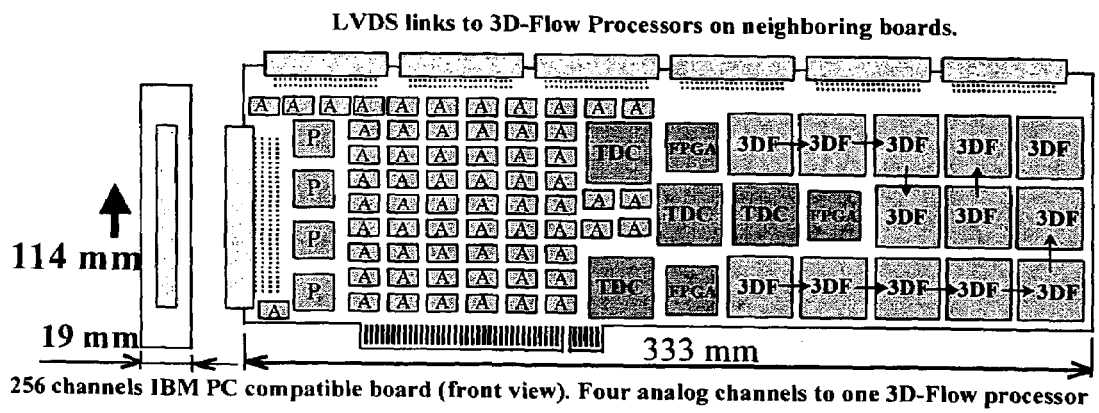
256 channels IBM PC compatible board (front view). Four analog channels to one 3D-Flow processor
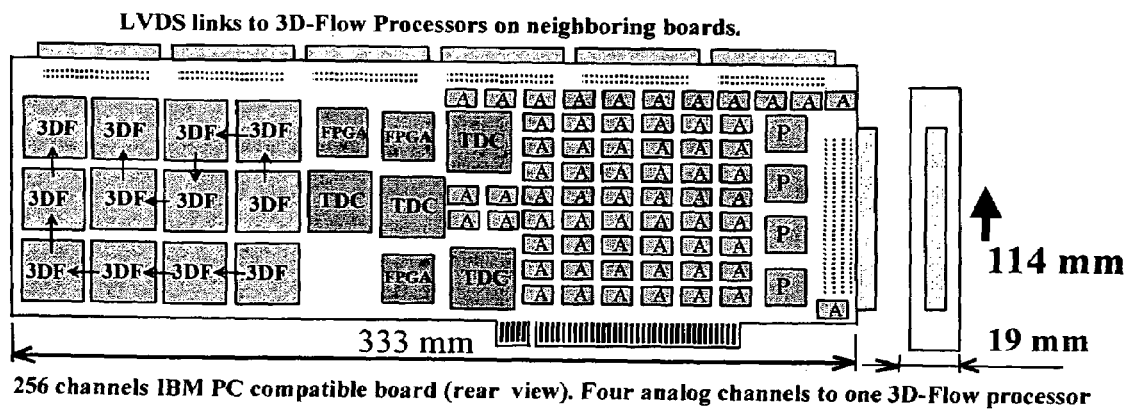
256 channels IBM PC compatible board (rear view). Four analog channels to one 3D-Flow processor
Fig. 51

64 analog channels VME board (front view).
One analog channel to one 3D-Flow processor.

64 analog channels VME board (rear view).

256 analog channels VME board (front view)
Four analog channels to one 3D-Flow processor.

256 analog channels VME board (rear view).

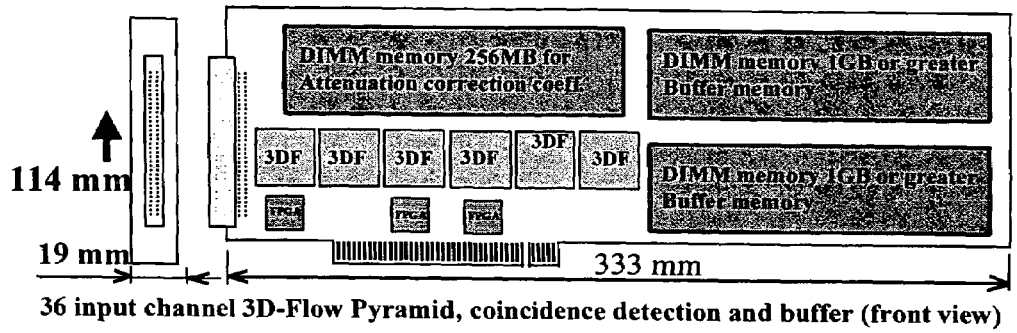
36 input channel 3D-Flow Pyramid, coincidence detection and buffer (front view)
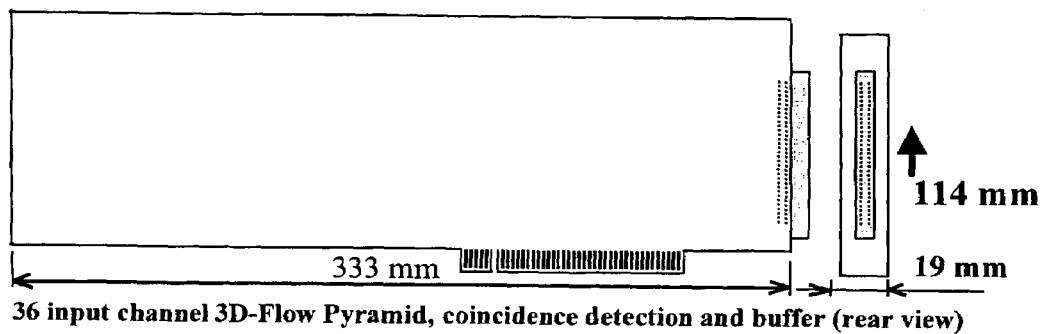
36 input channel 3D-Flow Pyramid, coincidence detection and buffer (rear view)
Fig. 54
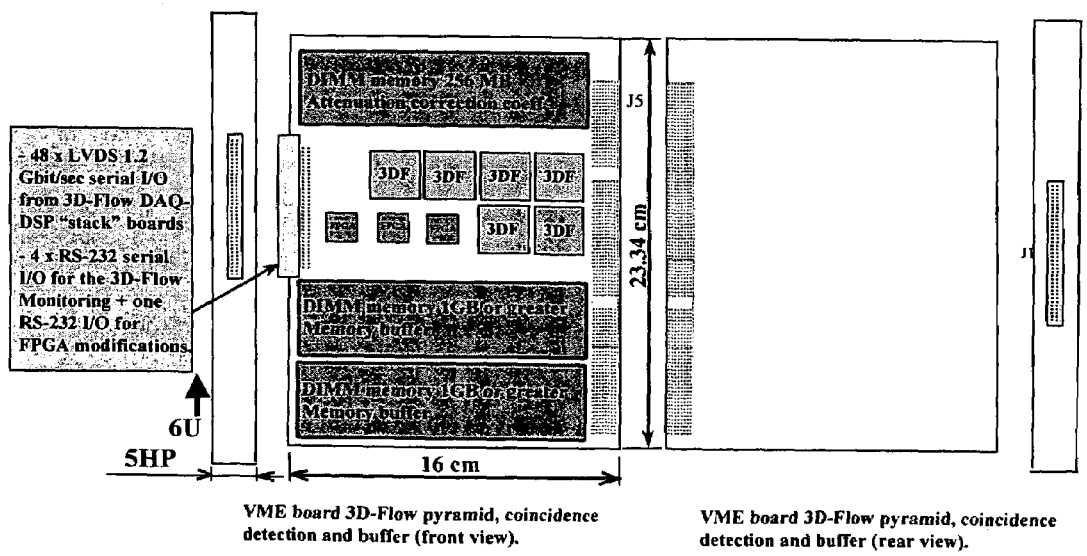
VME board 3D-Flow pyramid, coincidence detection and buffer (front view).
VME board 3D-Flow pyramid, coincidence detection and buffer (rear view).
Fig. 55

METHOD AND APPARATUS FOR WHOLE-BODY, THREE-DIMENSIONAL, DYNAMIC PET/CT EXAMINATION

1 RELATED APPLICATIONS

This application is a continuation of and claims priority to co-pending U.S. non-provisional patent application Ser. No. 10/185,904, filed June 27, 2002 and entitled "Method and Apparatus for Whole-Body, Three-Dimensional, Dynamic PET/CT Examination", which claims benefit of provisional application Ser. No. 60/301,545, filed Jun. 27, 2001 and entitled "Method and Apparatus for Whole-Body Annual PET/CT Examination" and provisional application Ser. No. 60/309,018, filed Jul. 31, 2001 and entitled "Method and Apparatus for Whole-Body, Three-Dimensional, Dynamic PET/CT Examination", the disclosure of each of which is incorporated herein in its entirety.

2 FIELD OF THE INVENTION

The present invention relates to: computer architecture, system architecture, parallel-processing, pipelining, multiplexing, pattern recognition algorithms, detector assembly and nuclear medicine imaging system and in particular to the electronics and detectors of apparatus detecting photons in emission and transmission mode.

3 BACKGROUND OF THE INVENTION

3.1 How do Imaging Scanners and the 3-D Complete Body Scan Work

Figure 5:
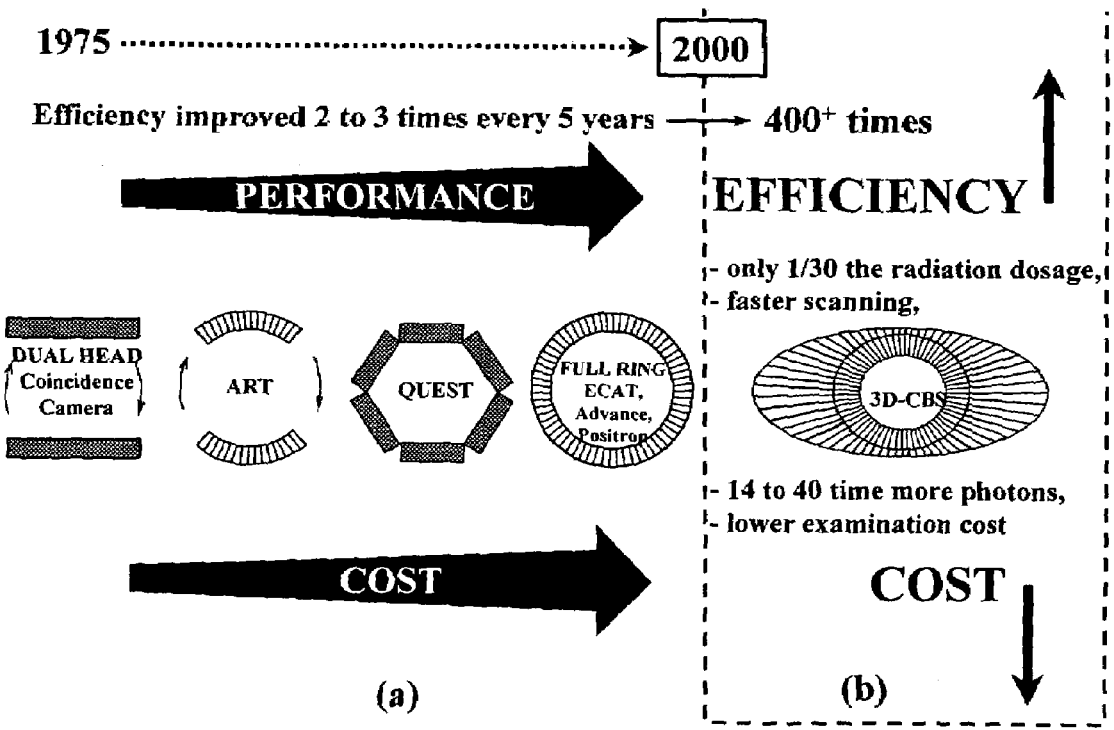

FIG. 5 shows (a) the evolution of PET instruments in the past several years and (b) includes a comparison to the approach described in this document.

Figure 16:
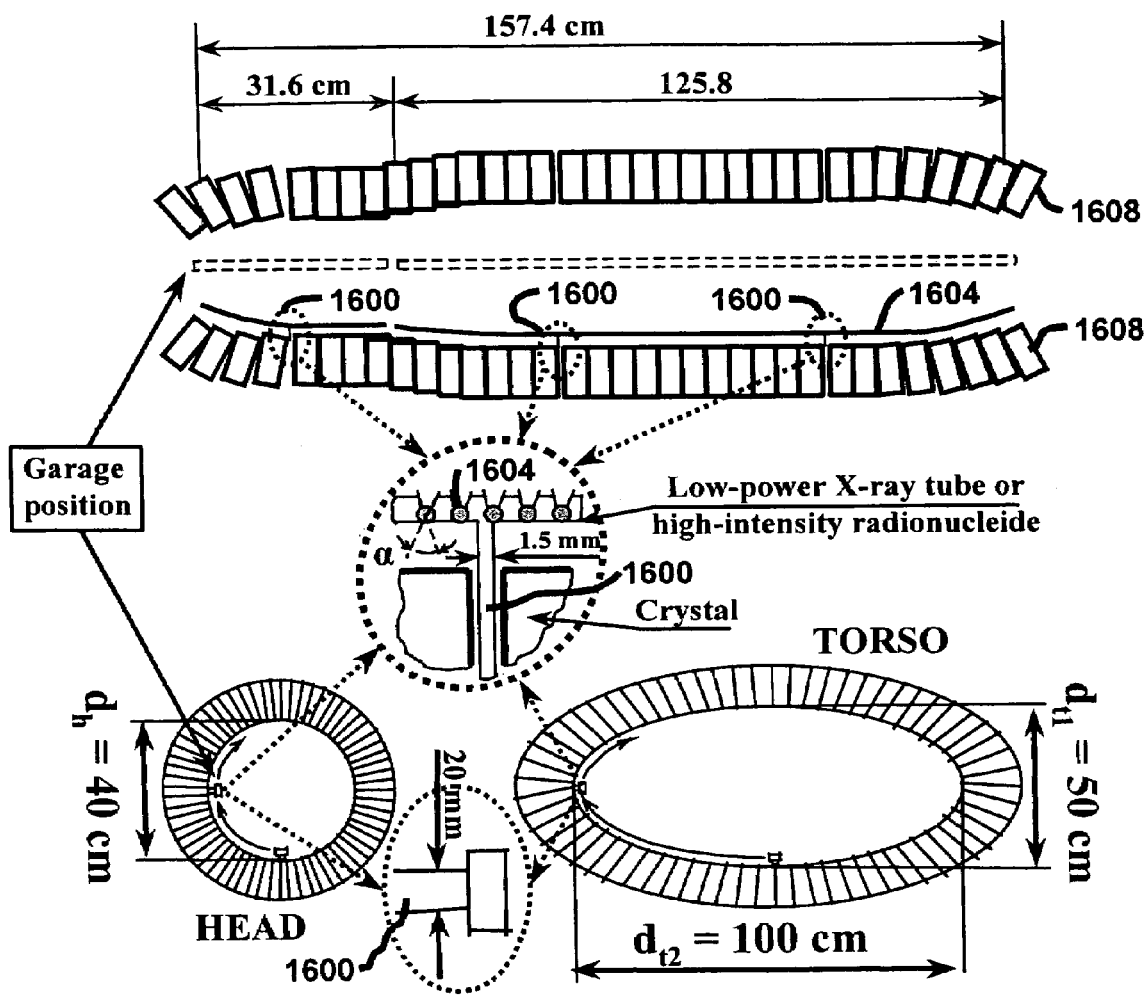
Figure 17:
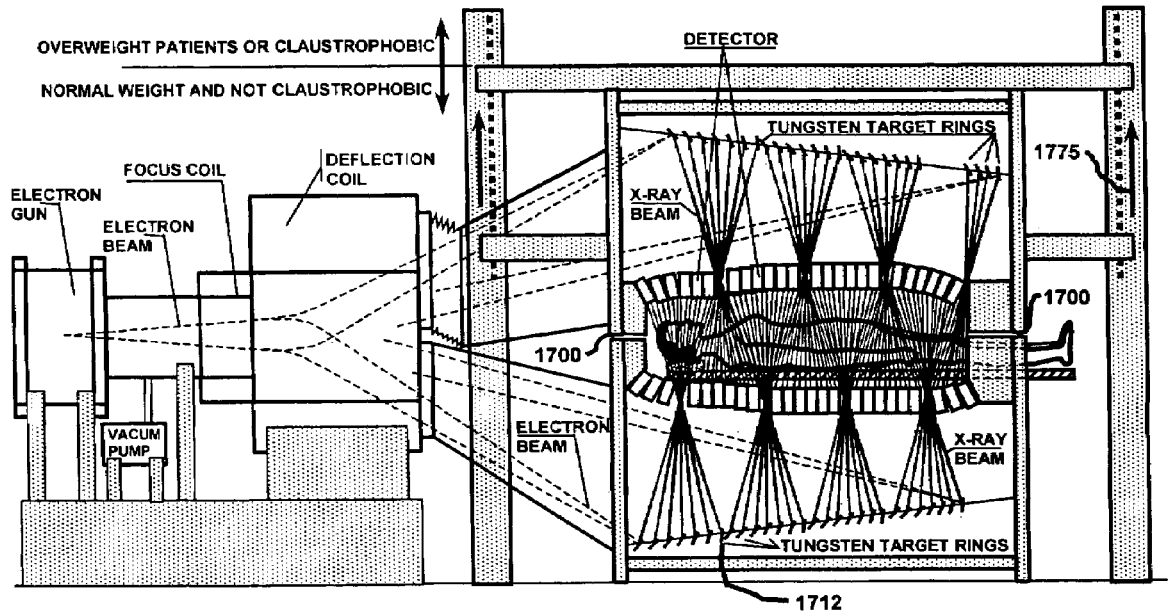
Figure 56:
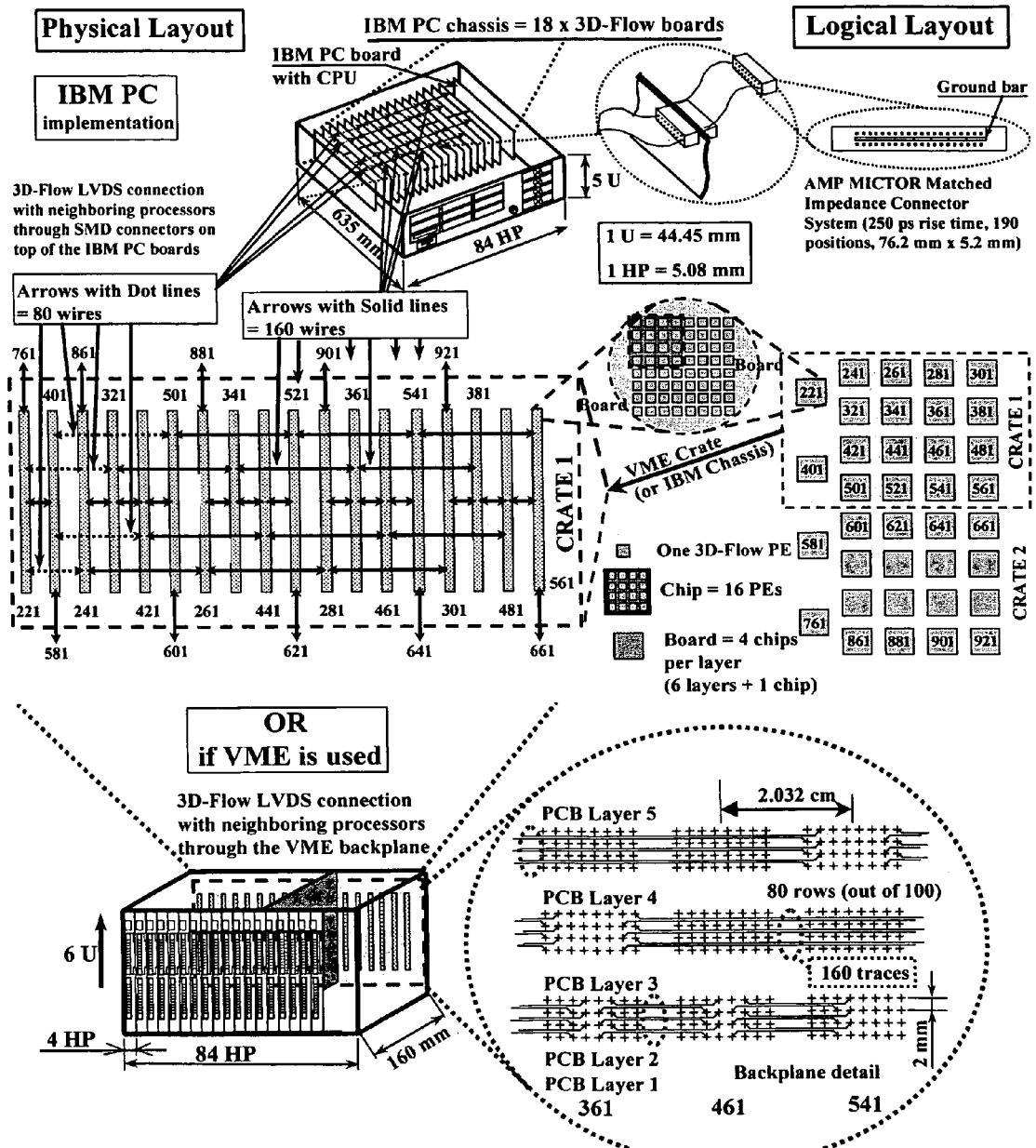

The reduction in radiation dose required to be delivered to the patient, the lower examination cost, the faster scanning time, the better quality image obtained by accumulating more photons in coincidences shown in FIG. 5b (3D-CBS), are provided by the new gantry design and the new approach of the electronics as described in Section 6.2, Section 6.3, and shown in FIG. 16 and FIG. 17. The elimination of the bottleneck on input is described in Section 6.6.7.1.3; the elimination of the bottleneck on output is described in Section 6.6.8.1.4. The elimination of the detector boundaries is described in Section 6.6.7.1.2, and its implementation is shown in FIG. 56; and the elimination of the limitation on the coincidence detection is described in Section 6.6.8, and in Section 6.5.14.

3.2 Solution Needed to Overcome the Efficiency Limitation Imposed by the Architectural Approach of Current Imaging Devices.

3.2.1 Why PET has Not Been Widely Used in the Past 25 Years in Spite of the Excellent, Fast Detectors Available for 10 Years The advent of PET in the last 25 years has not had a striking impact in hospital practice and has not been widely used because the electronics with the capability of fully exploiting the superiority of the PET technique has never been designed. Currently the best PET detect about 2 photons out of 10,000 (see references [1], and [2]). If used in 2-D mode, they can detect about 2 out of 100,000, while the Single Photon Emission Computed Tomography (SPECT) devices can detect only about 1 out of 200,000 photons (for one head SPECT; and about 1 out of 100,000 for two heads SPECT) emitted by the source.

The aim of this 3D-CBS design is to detect about 1,000 out of 10,000 photons emitted by the source.

Low efficiency in detecting photons without the capability of fully extracting the photon's properties gives poor images that cannot show small tumors, making the device unsuitable for early detection. In addition, it requires high radiation to the patient, which prevents annual examination; and it requires more imaging time, which limits its use to fewer patients per hour, driving the examination cost very high.

The great potential of PET is exploited only if it does not require the use of a lead collimator between the patient and the detector, and if it has an efficient electronics that does not saturate and that fully extracts particle properties using a thorough real-time algorithm.

Conversely, the advances in detector technology have been superb, providing for more than 10 years fast crystals (e.g., LSO with a decay time of the order of 40 ns) and the construction of detectors with small crystals that help to limit to a small area of the detector the dead time of a crystal that received a photon.

3.2.2 Measurements Showing that the Electronics is the Factor Limiting Efficiency in Current PET and Those Under Design That the electronics is the limiting factor of the efficiency of current PET (besides the plots of PET working in 3-D as described later) is shown by the fact that some PETs currently used in hospitals operate in what is called 2-D mode. 2-D refers to the use of a lead collimator placed in front of the detector. This is used to limit the number of photons hitting the detector (in particular for body scan where Compton scattering is more numerous than in a smaller volume head-scan) because the electronics cannot handle the unregulated rate of photons hitting the detector. The real-time algorithm of current PET cannot thoroughly process all the information necessary to separate a good event from bad events. It is unfortunate that a superior technology such as positron emission is employed in several PETs now in use in hospitals as if it were a SPECT, where the direction of the photons is determined by the holes of a lead collimator. This obviously will prevent many photons not sufficiently aligned with the holes of the collimator from ever reaching the detector.

The saturation of the electronics of current PET, even during levels of low radiation activity; is confirmed in the measurements of the sensitivity reported in the articles of the past 25 years and is graphically represented in a form similar to FIG. 6a.

Figure 2:
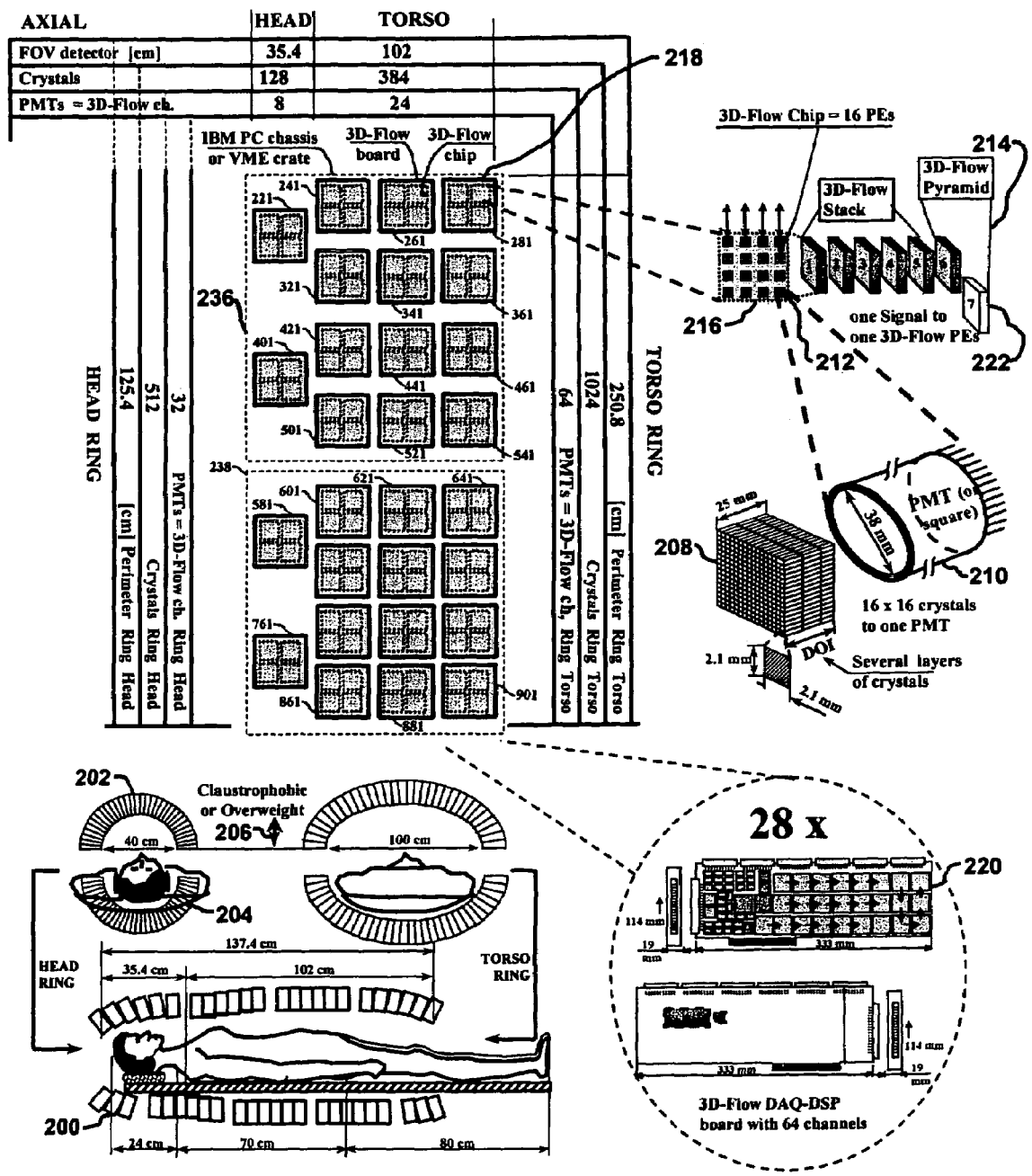
Figure 3:
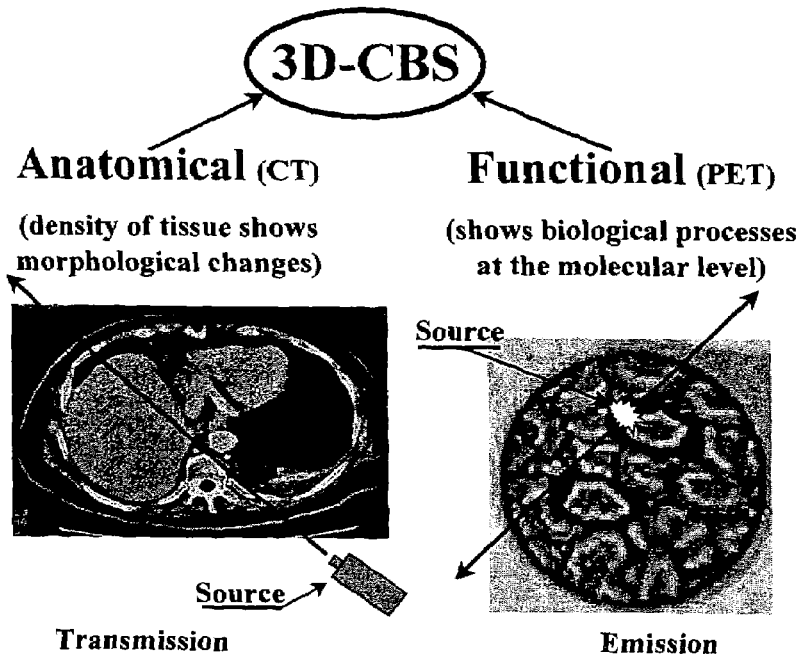

The limitation caused by the saturation of the CTI/Siemens electronics [3] (at 10 Mcps), is shown in FIG. 3 of [4]. This is a simulation made by Moses and Huber (see reference [4]) of a PET camera that completely encloses a small animal in a volume formed by 6 planar banks of detector modules. The caption of FIG. 3 of reference [4] says: "The random fraction is small due to the absence of "out of field" activity implicit with complete solid angle coverage, as well as a short coincidence windows. The total scatter event rate is 11% of the total true event rate. A maximum system count rate of 10 Mcps is assumed." The plots shown in FIG. 3 of [4] are compared with the measurements of the sensitivity of the existing MicroPET with short FOV and thin (10 mm) crystals of the CTI/Siemens [5]. The latter also reveal saturation of the electronics in FIG. 2a of [5].

3.2.3 Efficiency Limitation Imposed by the Architectural Approach of Current Imaging Devices.

After having studied the behavior of the physics experiment in a PET detector we can plot the performance of PETs with different FOV in detecting coincidences vs. the activity of the γ-rays created inside the body, the ones that leaves the body and the ones that hit the detector aperture for different detector FOV.

Figure 7:
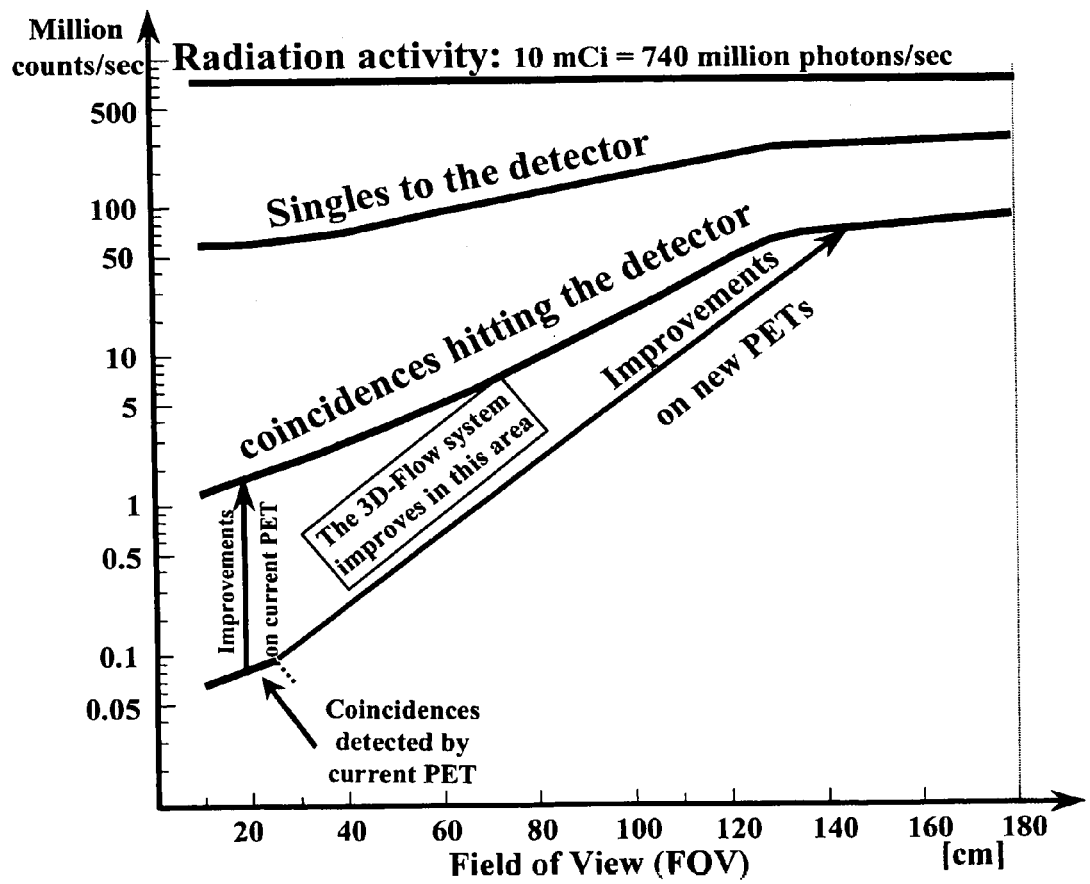

FIG. 7 shows the plot of the previous graph with the performance of the current PET systems added to it for graphical comparison. The curve at bottom has been calculated from the measurement of the performance of a few of the latest models of whole-body PET systems and/or simulations as reported in recent articles (see the following paragraphs in this section).

In particular one can find on page 115 of reference [6] the description of a PET examination using the model by Siemens ECAT EXACT HR providing an efficiency of only being 0.0193%.

A second reference [2] (on page 1405, FIG. 8) describes a PET examination using GE Advance with the injection of 8.5 mCi $^{18}$FDG in a human, yielding a total efficiency of 0.022%.

The efficiency of the most advanced current PET devices is even lower when performance measurements are made using radiotracers such as $^{15}$O-water, which generates a higher radiation activity for a shorter time.

For example, the results of the PET brain examination performed with the GE Advance Positron Emission Tomograph on humans using 66 mCi of intravenous injection of the radiotracer 15O-water, yield a total efficiency of 0.0014%. (See reference [2])

CTI/Siemens and General Electric have not proposed increasing the field of view to 120 cm, which would capture most of the radiation delivered to the patient instead of capturing only about 0.022% of the coincidence photons generated, because the current approach that they are using of checking for coincidences on each Line-Of-Response (LOR) would require the number of LOR to increase as the formula $((n \times (n-1)/4)$. Using the current CTI/Siemens and GE approach, the complexity of the electronics would increase enormously, or, alternatively, one would have to drop many photons from being checked. In that case, however, no significant advantage is provided to the patient, because the radiation and the cost have not been lowered.

During these past 25 years, the problem of the electronics has always been considered greater than the benefit which would accrue from the availability of a more efficient PET device. However, a device capable of shortening the examination time would in effect lower the cost per examination, since more patients could be examined each hour. Even more important, lowering the radiation dose to the patient, would enable patients to take the examination more often.

FIG. 7 shows an area where improvements of the current PET devices are necessary, including increasing the Field-Of-View and improving the electronics.

3.3 Deficiencies of Current Medical Imaging Instrumentation.

Although the CT images are of good quality at the expenses of a relatively high x-ray beam (which should be lowered in order to lower the risk to the patient), the PET images are of poor quality because only a few emitted photons from the patient's body are captured by the PET detector. Other deficiencies of the current PET machines are: low coverage of the entire body, false positives, high radiation dose, slow scanning, high examination costs. The increased efficiency of the 3D-CBS in capturing photons, will provide improvements in both: lowering the radiation dosage for CT scan and improve the PET image quality (in addition to also lower PET radiation dosage).

Briefly, following is a list of the main areas of inefficiencies in the current PET which prevent maximum exploitation of positron emission technology.

1. The image quality of current PET is poor because it has:
   a. a short FOV, limit by a non efficient electronics that do not offset the cost of the detector if the FOV were increased (see also next section about the false positive and false negatives);
   b. no accurate time-stamp assigned to each photon (a) limiting the detection of neighboring photons emitted within a short time interval, (b) causing long dead-time of the electronics and (c) increasing randoms, or photons in time coincidence belonging to two different events, (most PETs do not have any photon time-stamp assignment);
   c. analog signal processing on the front-end electronics limiting photon identification because of poor extraction of the characteristics of the incident photon and absence of the capability to improve signal-to-noise (S/N) ratio;
   d. detector boundary limitation to 2×2 PMT blocks, no correlation between signals from neighboring detector blocks, no full energy reconstruction of the photons that hit the detector, (most of current PET do not attempt to make any energy reconstruction of the event, but take decisions in accepting or rejecting first a photon and later an event based on the threshold of a single signal).
   e. dead-time of the electronics. Dead-time of the electronics is due to any bottleneck (e.g., multiplexing of data from many lines to a single line, saturation on input, processing, saturation on output) present at any stage of the electronics;
   f. saturation of the electronics at the input stage due to its inability to detect and process two nearby photons that hit the detector within a short time interval;
   g. costly and inefficient coincidence detection circuit (most current PET [20], [18] have a coincidence detection circuit that tests for coincidence all possible combinations of the Lines of Response (LOR) passing through the patient's body). Although current PET have made a compromise in coincidence detection efficiency versus circuit complexity, by using a coarse segmentation of the detector in order to reduce the number of LOR to be tested for coincidence, that approach is however an impediment to increasing the FOV (See more details in Section 14.7.2 of [7] and Section 6.3 of [12]). This approach adds unnecessary complexity to the electronics of the current PET and makes it unreasonably costly to build a circuit with an acceptable efficiency when more detector elements are added to the detector (which is required in extending the FOV);
   h. saturation of the electronics at the output stage due to the limiting architecture of the coincidence detection circuit (See Section 5.6.8.1.4);
   i. High number of "Randoms" due to the non accurate measurement of the photon arrival time and to the long (about 12 ns) time window used when determining if two photons belong to the same event;
   j. Poor measurement of the attenuation of different tissues at different locations in a patient's body. These measurements are necessary for calculating the attenuation correction coefficients for PET scan;

2. The false positives and false negatives shown in images from current PET, are a consequence of all of the above not having: (a) a DSP (see Section 7.2) on each electronic channel, with neighboring signal correlation capabilities, which extracts with zero dead time, the full characteristics of the incident photon and improves the S/N ratio of the each signal before adding it to other signals, (b) good attenuation correction coefficients, (c) a good, efficient, and simple coincidence detection circuit, and (d) a sufficiently long FOV (which prevent capturing most photons as shown on the left side of FIG. 12) that are the impediments in obtaining good quality images;

3. The high radiation dose delivered to the patient is required by the current PET because each examination needs more than 20 million photons in coincidence (or a number that provides a sufficient statistic to build an image). The short FOV and the inefficient electronics allow to accumulate fewer than 2 photons in coincidence every 10,000 emitted. This inefficiency requires to administer necessarily high radiation dosage to the patient in order to keep the examination time within an hour.

4. The slow scanning time is because of the short FOV of the current PET and of the low efficiency of the electronics. The limited efficiency mentioned above of 2 out of 10,000 requires long acquisition time. Examinations longer than one hour are unacceptable because (a) the biological process desired to observe and the radioisotope decay activity would be over, (b) the patient would be uncomfortable, and (c) the cost would be even higher that what it already is;

5. The current high cost of the examination is due to:
   the high cost of the huge dose of radioisotope required;
   the slow scanning time that allows only six to seven patients per day to be examined; and
   the cost of highly paid personnel who must operate the slow machine.

4 SUMMARY OF THE INVENTION

The 3-D Complete Body Scan (3D-CBS) medical imaging device combines the features of anatomical imaging capability of the Computed Tomography (CT) with the functional imaging capability of the Positron Emission Tomography (PET). FIG. 1 shows the layout of the components of the 3D-CBS, and FIG. 2 show the logical and physical layout of the 3D-CBS. More specifically, a detector 100 is coupled to produce electrical signal representing detected photons to an image processing and data acquisition board 140. Data acquisition board 140 is one of 14 boards per chassis 108, 112 in the described embodiment of the invention. In the described system, 64 channels per data acquisition board 140 are used to transmit the electrical signals. Each data acquisition board 140 has 64 inputs and one output channel. Moreover, one chassis 112 includes 14 data acquisition boards 140. Chassis 112 produces 14 output signals, one per data acquisition board, that are transmitted, e.g., over a local area network and hub 104, to a patch panel 114 that in turn transmits the signals to a pyramid board 116 that generates an image for display for the operator. FIG. 1 also displays some functional components of the layout and design. Detector 100 has distinct features in terms of not only extending the length of the crystal detectors or "field of view" 102 to cover a significant length of the body (more than 25 cm of detectors). Field of view 102 is geometrically shaped to fit the contours of the body, with a narrowing near the head, to allow for a complete scan at once and to cost effectively increase the length of the detectors and to minimize the distance between the detectors and the emitting source (in FIG. 1, the human body). The design will allow field of view 102 to not only extend beyond 25 cm, but to be over one meter in length. The body fitting contour of detector 100 also enables the simplest possible PET electronics necessary to operate PET calculations in real time. Elliptical crystal design 104 also cost effectively increases the length of the detectors and minimizes the distance between the detectors and the emitting source. The space between the upper half of elliptical crystal design 104 and the lower half of elliptical crystal design 104 demonstrates the open hatch design of the 3D-CBS (3D Complete Body Scan), which can either be closed for greater photon detection efficiency or opened to accommodate the patient's claustrophobia or weight (further explained in FIG. 2).

FIG. 2 illustrates some of the functional blocks of the scanning system. A detector 200 includes two groups of sensors 202 and 204 for detecting photons. Sensors 202 further are vertically adjustable as indicated at 206. One element of the detector is shown at 208 and it is formed of many small crystals that are coupled to one sensor 210 (a photomultiplier or an APD). The sensor 210 generates a signal to processor 212. In the described embodiment, each sensor 210 is coupled to one processor 212 of a processor array shown generally at 214. In terms of physical configuration, each chip 216 has 16 processors. A board 218 includes 4 chips 216 that are connected to the sensors 210. Each chip is sequentially connected to 5 other chips that are on the same board as illustrated generally at 220. Accordingly, one board includes 24 chips. A seventh chip 222 is used to collect the results from the first 4 chips and generates the output result to patch panel number 114 of FIG. 1. The 14 boards of chassis 112 may be seen at 236 of FIG. 2.

The CT measures the density of body tissue by sending low-energy x-rays (60 to 120 keV) through the patient's body and computing their attenuation on the other side (see left side of FIG. 3).

Positron Emission Tomography (PET) uses radioactive substances injected into the patient's body that emit photons at higher energy (511 keV) and shows biological processes by tracking, at the molecular level, the path of the radioactive compound (see right side of FIG. 3). A PET examination detects cancer by using the body's consumption habits (metabolism) and it can monitor the blood flow and brain activity.

Figure 4:
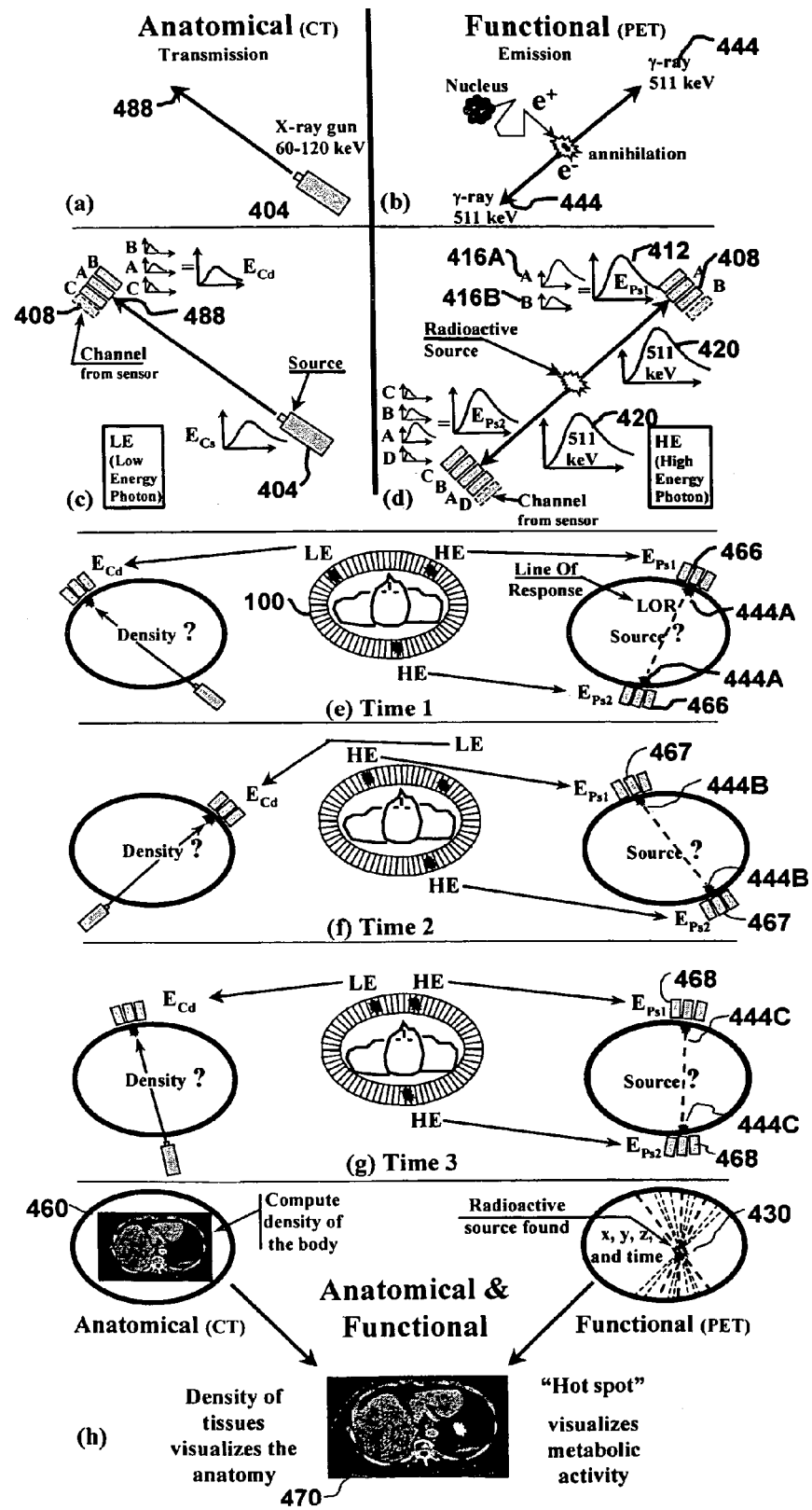

FIG. 4 illustrates the details of the paths of the x-ray (CT) and γ-ray (PET) photons and the technique used to compute the anatomical and functional images. Photons arrive at the detector 100 randomly at unregulated time intervals. When a short time interval of 2 to 3 ns is considered (e.g., as shown in section e, f, and g of the figure) there is a high probability of capturing not more than two high energy photons 444 (HE) in time coincidence from the same PET event and eventually one low energy photon 488 (LE) in the location where the x-ray gun 404 is shooting. The task of the detector and of the electronics is to recognize most of these PET and/or CT events and provide accurate information to the workstation that computes the anatomical and functional images. Each photon is recognized only if thorough measurements are performed on the signals as these photons are received from the sensors (the photomultipliers—PMT- or Avalance PhotoDiode—APD-) through the electronic channels. Among the most important measurements (see additional measurements in next section) is that of rebuilding the total energy of the incident photon. The total energy of an incident photons is the sum of the partial energies. Because a photon may strike the detector crystal in a location where it can produce signals in neighboring sensors, the sum of signals 412 is the sum of the primary detected signal 416A as well as the signals 416B from neighboring sensors must be computed. If a photon results in the three signals sent down three different channels, then all three of those signals would have to be appropraitely identified and accounted for. The sum of signals 412 are those detected signals that originated from the sources of signals 420. For example (see section c in the figure) the energy of a CT event measured at the detector $E_{Cd}$=A+B+C which should be equal to the source energy of the x-ray gun $E_{Cs}$ minus the attenuation caused by going through the body tissue. An example showing the process in PET, found in section d of the figure, shows the energy of one 511-keV photon that has been attenuated by its passage through the patient's body and has been measured as $E_{ps1}$=A+B; note that the matching 511-keV photon been measured as $E_{ps2}$=A+B+C+D. When the detector receives hits within 2 to 3 ns (e.g., during Time 1 in section e of the figure), the electronics separates the HE events from the LE event. It finds the location of the HE events and the line of response (the LOR is the line indicating where the annihilation of the electron occurred and where the two resulting photons, which leave the original event 180 degrees apart from each other, end up) passing through the two detectors that received the hits. During the first time increment, the incoming HE events 444A come arrive at sensor locations 466 and are "time stamped" (given a distinctive designation according to their time and the location as to where they "hit" the detector) and then a calculation is made as to determine which two HE events 444A came from annihilation of one electron (section (e) of FIG. 4). Sensors, such as 466, 467, and 468 of detector 100, receive the light of photons and then the photomultiplier coupled with the crystal detector converts the light into an electrical signal (similar to 416A and 416B). During the second time increment, the same process occurs, with an attempt to identify other HE events 444B at crystal detector 467 and confirm as to whether or not they came from the annihilation of the same electron (see section (f) of FIG. 4). During subsequent time increments, the same process occurs for identification of HE events 444C at sensor 468 and other LE events(section (g) of FIG. 4). The intersection of millions of LOR per second allow identification of the location of the emitting source 430 as shown in the right side of section h of the figure, while the computation of the attenuation of the x-rays 460 (LE) determines the density of the body and displays its anatomical image on the monitor. A combined image 470 is then created, which provided a 3D picture of the functional and anatomic views of the body, enabling health care professionals to identify where the emitting source is and that location relative to other parts of the body.

The patient receives a radioactive isotope (e.g., fluorine $^{18}$F) attached to a tracer (i.e., Fluorodeoxyglucose—FDG- or $^{15}$O-water) which is a normal compound used in the biological process of the human body. It is possible to reveal molecular pathways of the tracer because the radioactive fluorine isotope emits a positron that annihilates with an electron (after a path of about 1.4 to over 13 mm depending on the radioisotope used. See FIG. 4b on next page and Table 7-1 at page 26 of [7]) to produce two photons emitted in diametrically opposed directions. This phenomenon, the annihilation of a positron and an electron simultaneously producing two photons is called "event."

The two photons travel through and out of the body and are absorbed by the crystals in the detector rings of the PET machine (see FIG. 4e, f, g). The crystals are coupled with photomultipliers (sensors converting light into electrical signals. See shaded rectangles indicated with the letters A, B, C, D in FIG. 4d), which in turn send the electrical signals (see top of FIG. 8 and FIG. 9) to an array of 3D-Flow processors [8], [9], [10], [11], [12], [13]. The processor array analyzes and correlates the received signals with the nearest neighbors, measuring the amount of energy absorbed by the crystals and the arrival time and location of the photon. This information of the total energy of each incident photon and their arrival time will be used during phase II of the processing (described later) when the correlation between two far apart photons will be made. This will make it possible to identify the matching pair of photons.

The photons are emitted by the radioisotope inside the patient's body at a rate up to hundreds of millions per second. When the 511-keV γ-ray pair is simultaneously recorded by opposing detectors, an annihilation event is known to have taken place on a line connecting the two detectors. This line is called the "Line of Response" (LOR). (See FIG. 4e).

With a calculation, during phase I, based upon when and where the photons' energies were absorbed by the crystal detector, the electronics first identifies the "good photons." (See FIG. 4d). Good photons are those that originate from the same event and that arrived at the detector straight from the source without bouncing off in other matter (Compton scatter). Efficient electronics at the front end can identify some Compton scatter events by accurately measuring the energy and the time of arrival of the photons, however, other Compton scatter events can only be identified after acquisition during the image reconstruction phase. Missing good photons fails to provide a clear image to help the physician recognize subtle differences in normal anatomies. Second, each photon needs to find its companion emitted at the same time (or in time coincidence). Third, the pairs of photons are identified and the intersection of millions of LOR per second indicate the location of the source (x, y, z, and time) and its activity (see FIG. 4h) is translated into graphics on a computer screen.

There are areas, such as brain, kidney, and bladder wall, with normally higher metabolism activity than other areas of the body. The computer can subtract from each area the quantity of photons attributed to a normal activity and show only the abnormal metabolism by assigning different colors to level of activity (e.g. yellow for low abnormal activity and red for high). This is a standard techniques in image processing. The physician then look for abnormal metabolism "hot spots," in the body. The recorded timing information of the data (or their recorded sequential order) will allow the physician to display dynamically, for example, 4 minutes of recorded data in 10 seconds, or to expand one second of recorded data to one minute of dynamic display (e.g., slow motion to better appreciate the speed of the metabolism, or activity, of cancer).

The same electronics of the 3D-CBS also detects photons at low energy (LE) occurring concurrently with the high-energy (HE) photons but being received at the expected locations, according to where the x-ray gun is directed (see FIG. 4a, c). The electronics then calculates the attenuation of the signal, which is proportional to the type of body tissue it went through, and computes the anatomical image of the patent's body from this data (see left columns of FIG. 4e, f, g, h).

The main characteristic, difference, and value of the PET technology compared to other technologies is the uniqueness of the back-to-back emission of the two 511 keV photons, together with the high sensitivity of the 3D-CBS to uniformly detect the emission source, regardless of its location, offers a unique 3-D imaging capability.

The biochemical processes (e.g., metabolizing glucose) of the body's tissues are altered in virtually all diseases, and increased metabolism is indicated in PET by higher than normal photon emission.

Cancer cells, for instance, typically have much higher metabolic rate, because they are growing faster than normal cells and thus absorb more sugar (60 to 70 times more) than normal cells and emit more photons [14], [15]. Inflammatory diseases also absorb more sugar than normal cells.

Detecting these changes in metabolic rates with the PET enables physicians to find diseases at their very early stages, because in many diseases, the metabolism of the cells changes before the cells are physically altered. Similarly, a PET machine can use different radioactive substances to monitor brain or heart metabolism activity.

In general PET technology has already replaced multiple medical testing procedures with a single examination. In many cases, it diagnoses diseases before can be identified by their morphological changes in other tests or with other devices.

Combining different technologies in one device further assists physicians in clinical examinations. Viewing PET functional imaging data in conjunction with CT morphologic cross-sectional data is sometimes mandatory if lesions are found.

4.1 A Summary Showing the Evolution of the Improvements is Given in a Figure Taken from Article [16] and Reported Here in FIG. 5

Significant improvements the 3D-CBS offers over the PET are: (a) capturing more data from the emitting source and (b) processing the acquired data with a real-time algorithm which best extracts the information from the interaction between the photons and the crystal detector. A breakthrough in efficiency of the 3D-CBS, even if slow crystals are used, is achieved at least in part through the 3D-Flow architecture of the electronics, which can perform, with zero dead-time, pulse shape analysis with Digital Signal Processing (DSP) on each channel, with correlation with signals from neighboring channels as well as from channels far apart and with improvement of the signal-to-noise ratio (S/N) before adding them. In addition, the unique architecture of the electronics can accurately determine the photon's arrival time, resolve pile-up, perform several measurements requiring complex calculations (depth of interaction, clustering, signal interpolation to increase spatial resolution, etc.), and limit the detector dead time to the very small area where the incident photons hit the crystal, rather than a large portion of the detector as now occurs with current PET electronics.

If more data from a radioactive source used currently (or from a source with lower radiation activity) is captured by the detector, sent to the PET electronics, and processed correctly, then the examination time, radiation dosage, and consequently also the cost per examination can be significantly reduced.

In order to obtain more data, the axial field of view (FOV, the total length of the rings of crystals in the scanning detector) must be lengthened to cover most of the body. In order to process these data, the electronics must be designed to handle a high data input rate from multiple detector channels. The 3D-CBS can handle up to 35 billion events per second with zero dead time in the electronics (when a system with 1,792 channels as described in [8] is used), versus the 10 million events per second with dead time that current PET can handle [17], [18], [19], [20]. High input bandwidth of the system is necessary because the photons arrive randomly, at unregulated time intervals. (See Section 5.5 and 5.6).

The references [8], [21] describe (a) a novel architectural arrangement of connecting processors on a chip, on a Printed Circuit Board (PCB) and on a system, and (b) a new method of thoroughly processing data arriving at a high rate from a PET detector using the 3D-Flow sequentially-implemented parallel architecture [7], [9] (See Table I and FIG. 10).

The present invention is advantageous in that the efficiencies of the system allow for lower levels of radiation. For example, radiation levels in prior art machines typically exceeds 10 mCi of 18F-FDG. With the inventive system, however, the radiation level may be set to 1 mCi of 18F-FDG while obtaining scan images of a person.

4.1.1 In Layman's Terms

The processing of the electronics on the data arriving from the detector can be compared to a task of the reunion of families that were separated by a catastrophic natural event. The following analogy in human terms is made; the sequence of the events the family reunion example is one billion times slower than the sequence of events in the PET:

A catastrophic event separates on average 20 families every 50 seconds. During the attempt to reunite the families, unfortunately, only about 12% of the husbands and wives can arrive at a reunion center.

When a family was split, the husband and wife went in opposite directions, each with some of their children (similar to the back-to-back photons of the PET as shown in FIG. 4b). In the analogy, the children in neighboring channels the father (or mother) represent signals on neighboring sensors (or electronic channels) which have been generated by a photon striking the detector. The analogy lies in the fact that the total energy of the incident photon that was split among several neighboring channels (or wires; see FIG. 8 for an example showing channels, A, B, C, and D of FIGS. 4c and d, the top of FIG. 8 and the top of FIG. 9) must be rebuilt, just as the parent must be reunited with his children.

The family reunion takes place in two phases. During the first phase, the father and the children who went with him but followed a neighboring path (channel or wire) are reunited. The same process is followed independently, in a separate venue, by the mother with their other children, however, that will take place far apart from where the father is. During the second phase the two half-families are reunited.

Figure 8:
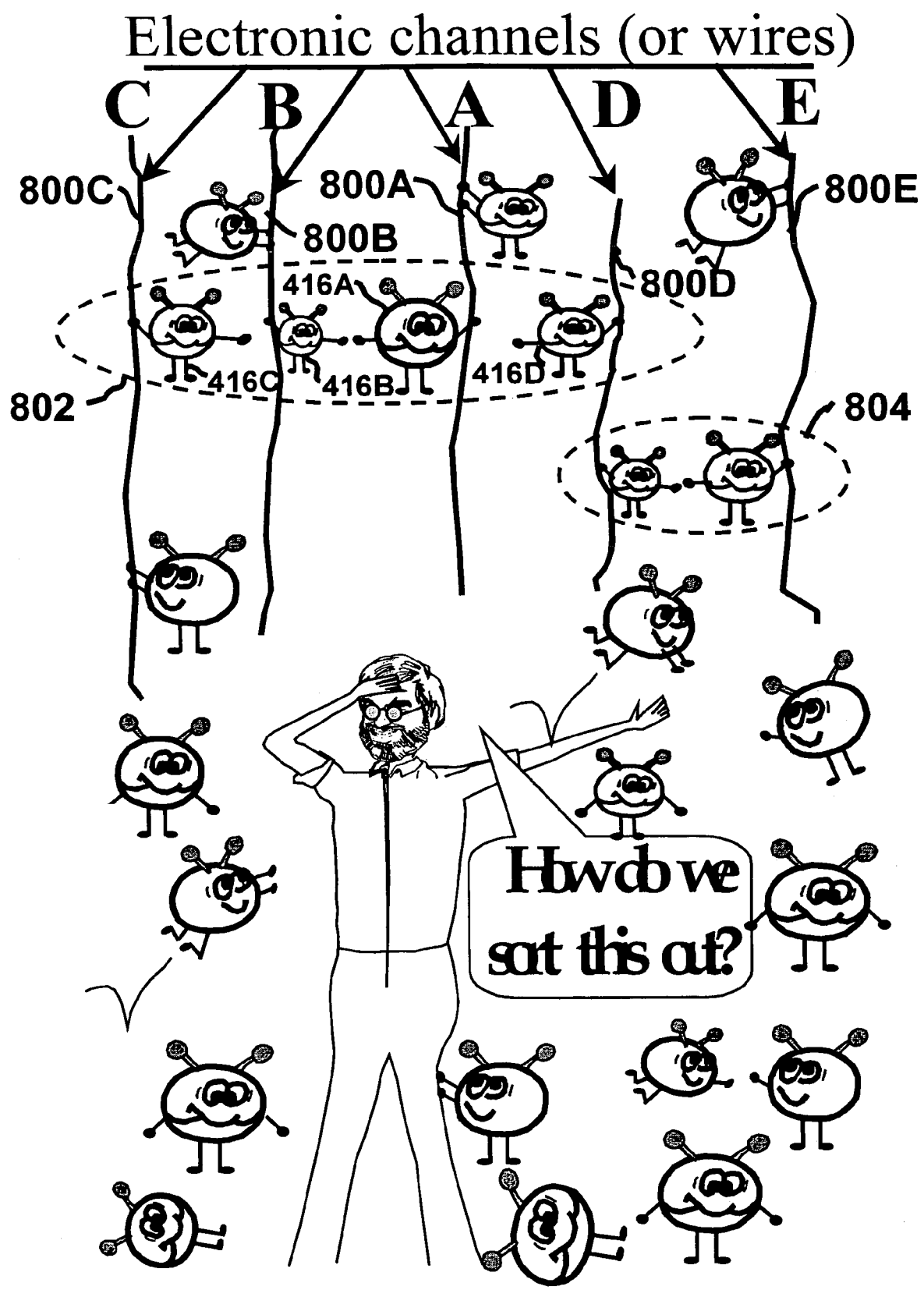

FIG. 8 shows an example of information split over several channels (or wires). A photon striking in such a way that its information is divided among several electronic channels is analogous to one parent with some children going down several channels (see on the second row the split of a family among four wires during time 802, and on the third row the split of a family between two wires during time 804). The signals for any one increment of time are represented as family members, meaning that the entire family which travels down different electronic channels must be identified and reunited for the machine to correctly process the data and ultimately create the correct pixel graphic on the computer screen. The top columns identified as A, B, C, D, E are the channels where the signals are arriving; the signals themselves are indicated with the smiling faces. Note that top end of the channels 800A, 800B, 800C, 800D, and 800E are connected to what was labeled as the tip of the sensors 466, 467, or 468 in FIG. 4. These channels are receiving electronic signals from the photomultipliers (sensors). As discussed briefly before, because a photon may strike the detector crystal in a location where it can produce signals in neighboring sensors, the sum of signals of different channels needs to be calculated for every increment of time. If this is not done, then signals going down parallel electronic channels would be inappropriately labeled as "nonphotons" because the individual energy of the photon would not meet the criteria of 511 KeV, even though in reality, these signals may actually represent a photon which hit the edge of more than one sensor (as represented in FIG. 11). In order to calculate the sum of the energy 412 (identified on FIG. 4), one would need to know the sum of the primary detected signals as well as the neighboring signals. In FIG. 8, similar numbers of 416A, 416B, 416C, and 416D represent signals coming down different channels, which were registered at the same increment of time (FIG. 4 only displays an example of two signals coming down similarly located channels, while FIG. 8 has the example of four signals coming down at one time 802, three during another increment of time 800, two during the time 804, etc.). The strength of signals 416A, 416B, 416C, and 416D, must be compared and calculated. The sum of the energy during any increment of time (represented as 412 in FIG. 4) must be computed and is represented by at least three consecutive increments of time of 800, 802, 804. Notice that signals from photons hitting the detector at time 802 are carried across four different channels and that the calculation of the strength of signals 416A, 416B, 416C, and 416D must be calculated to know how many photons came in during that time.

Because there are on rage about 5 groups of fathers with children (or mothers with children) arriving randomly, at unregulated time intervals every 50 seconds at any place in the approximately 2,000 channels at the reunion center, it is necessary to reunite the half-family (rebuild the energy of the incident photon) at their arrival site, before the children are mixed with millions of other people.

Phase I: Reunite the half-family (rebuild the energy of each incident photon, determine its exact arrival time, measure the exact position of its center of gravity, measure the DOI, and resolve pile-up).

Figure 9:
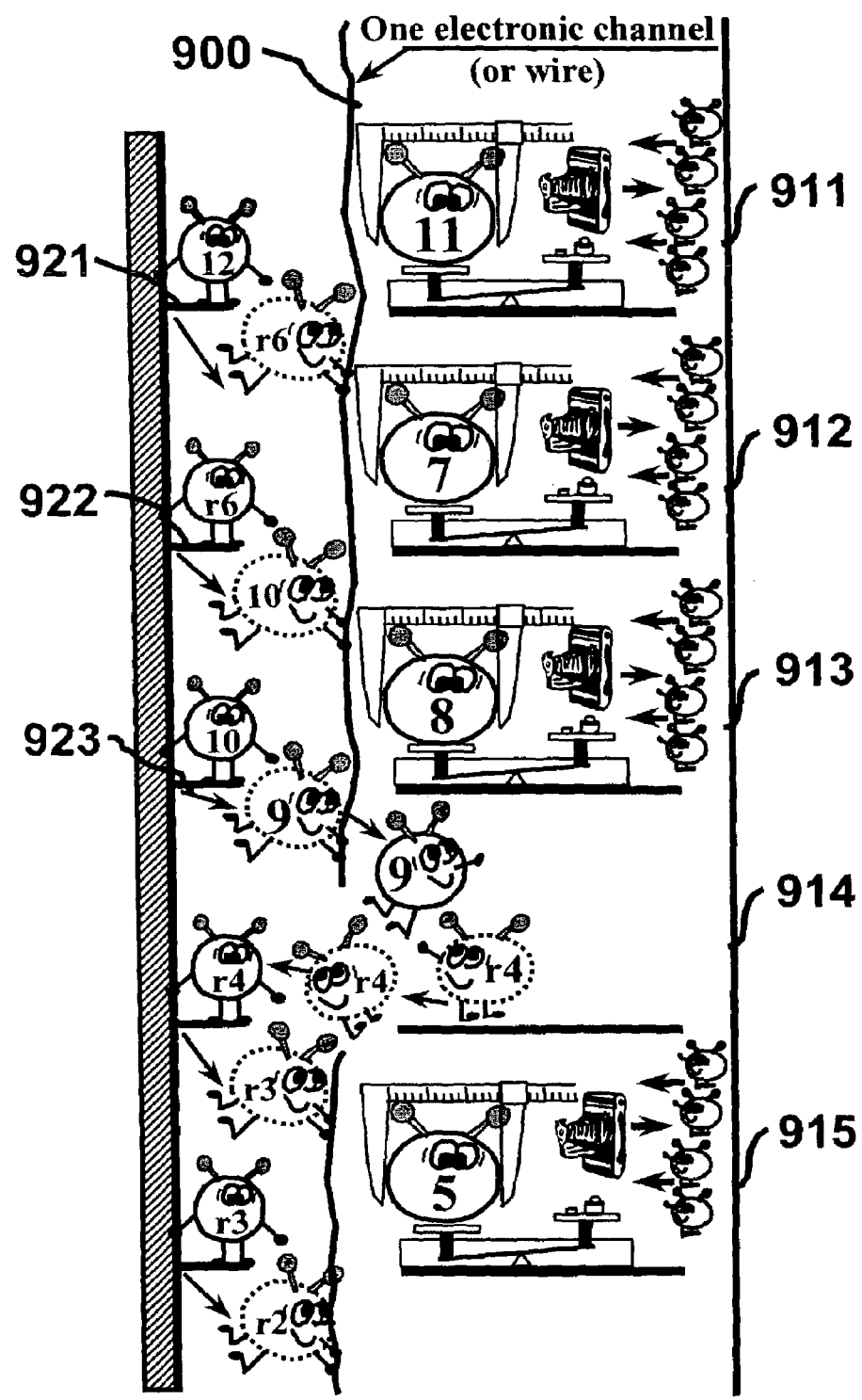

The solution to the problem of phase I, which is illustrated in a cartoon of the "family reunion" of FIG. 9, is mainly provided by the "bypass switch" (or multiplexer) of the 3D-Flow architecture (see Table I and FIG. 10). FIG. 9 demonstrates how one of the electronic channels or wires (such as 800E on FIG. 8), processes the information (signal) in order to identify the characteristics of the input data, calculate their arrival time, and compare signals to neighboring signals to ascertain whether they are related. FIGS. 9 and 10 should be viewed in conjunction to understand how the data is processed and how the bypass switch is optimally utilized to process data arriving at a high rate of input (currently, the input rate is faster than the time necessary to fully process each single data packet received; however, this sequentially-implemented parallel processing allows the data to be processed at a rate as fast as the input rate, even if the time to process any single data packet, is longer than the time between consecutive data input). Information concerning the father and children, that is, the signals generated by the photon, arrives at the top of the channel 900 (wire) and moves down one step each time new data arrives at the input. The numbers in FIG. 9 correspond to the position of the objects at time 14t of Table I. Objects outlined in dotted lines correspond to the status one instant before time "14t."

The 3D-Flow architecture allows a high throughput at the input because (a) each data packet relative to the information about the photon (or about the family member) has to move at each step only a short distance, from one station to the next, and (b) complex operations of identification and measurement can be performed at each station for a time longer than the time interval between two consecutive input data.

Every time a new data packet arrives at the top of the channel (or wire), all other data packets along the vertical wire move down one step, but the wire is broken in one position where the station is free to accept a new input data packet and is ready to provide at the same time the results of the calculations of the previous data packet.

In other words, at any time, four switches in "bypass mode" and one switch in "input/output mode" (or the wire broken at a different place) are always set on the vertical wire. This synchronous mechanism will prevent losing any data at input and will fully process all of them.

When a data packet relative to a photon enters a measuring station (that is, a 3D-Flow processor, or the station represented on the right side of FIG. 9), it remains in that station for its complete identification, measurements, and correlation with its neighbors. Five different stations are labeled as 911, 912, 913, 914, and 915. As is discussed later, the task done at station 914 appears different from stations 911, 912, 913, and 915 because it is simultaneously sending out the completed result labeled as r4 (the completed result is all the data revealing the correct identity, measurements, and location of a pair of photons) and doing the first step of the next task, which is to take in the next data from the electronic signals, labeled as 9, which has patiently been passed down by three other stations (911, 912, and 913) which were busy. During every increment of time, data is either being processed or passed along to the next platform; in this example, 9 has previously been on the platform 921 and 922 (it did not go to workstation 911 and 912, because they were performing calculations on other data), and was sent down to await the first available workstation. Every workstation is either processing data or revealing a result and taking in the next task. The number of stations is built in relation to the number of steps of execution of the algorithm; for instance, in FIG. 9, the electronic channel has five stations because the complex calculation and identification process requires five units of time to produce a result.

Every station can perform each of the required steps. Several operations are performed at each station (station 911 displays the calculations):

1. A "picture" is taken and sent along with the time of arrival to the neighbors, while "pictures" from the neighbors, along with their time of arrival are also received and checks are performed to see if there were any family members in the neighboring channels (similarly the energy and arrival time of photons are exchanged between neighboring elements to check if the energy of the incident photon was fragmented between several channels).

2. Local maxima (checking to see if the signal is greater than the neighbors) are calculated to determine if the parent arrived at that channel; this is equivalent to comparing the photon's energy and arrival time to similar information in the neighboring channels. If the parent did not arrive at that channel, the process at that channel is aborted to avoid duplication. The neighboring channel that finds the father will carry on the process.

3. Center of gravity is calculated (that is the point at which the weight of an object is equally distributed). This calculation will provide an accurate location where the half-family was found; this is equivalent to the spatial resolution of the incident photon.

4. Pile-ups, which occur when two half-families belonging to two different families arrive within a very short time interval, or when two events occur in a nearby detector area within a time interval shorter than the decay time of the crystal, are resolved. When this happens, the apparent integral of the second signal will show it riding on the tail of the previous signal. Digital Signal Processing (DSP) techniques of the 3D-Flow processor can detect the change of slope of the tail of the signal and separate the two signals.

5. The accurate arrival time of the half-family group is calculated and assigned to be carried for the rest of the trip; similarly, the accurate arrival time of the photon is calculated Other measurements are performed on the input data (half-family or photon), such as the depth-of-interaction (DOI) on the incident photon. DOI measurements solve the problem of identifying the affected crystal when the incident photon arrives at an oblique angle instead of perpendicularly to the face of the crystal. Several techniques [22], [7], [23], [24] of DOI measurements which allow for correcting the effect commonly referred as "parallax error" can be performed by the 3D-Flow processor.

6. Finally, the half-family is reunited (total energy of the photon is calculated), all measurements are performed and results are sent back to the channel for its propagation to the exit (See workstation 914 in FIG. 9, the object r4 in the fourth station from the top, which is the result of the input data No. 4).

7. Only some of the above processing is carried on in the current PET. The most important task of rebuilding the energy of the incident photon (equivalent to reuniting a half-family) is not performed.

Instead, the current PET adds analog signals before checking whether the signals belong to the same incident photon (equivalent of checking to see if a member belongs to the same half-family). In essence, the current PET would reject family members going down different wires if they were not in the electronic channels that are connected in a 2×2 detector block arrangement; data which should be reconstructed (i.e., two signals from the same time and location with a cobined energy of 511 KeV) is rejected if it is not close to the photon's expected 511 KeV. Additionally, this operation in current PET turns out to be very counterproductive at the next electronic stage because the analog signal (which is the sum of several signals) cannot be divided into its original components and the information on the single photons that is needed for several subsequent calculations is instead lost forever.

In the most advanced current PET, the electronics cannot complete the processing before the arrival of another data, and consequently dead-time is introduced and photons are lost.

FIG. 10 explains the same process as FIG. 9, but through the perspective of the importance of the bypass switch instead of the focus of how the workstations process the signals so quickly (additionally, as is detailed later, FIG. 10 shows how the 3D-Flow system extends the execution time in a pipeline stage beyond the time interval between two consecutive input data (sequentially-implemented, parallel architecture)).

A review of FIG. 9 and comparison with FIG. 10 notes that the workstations 911, 912, 913, 914, and 915 are doing the same tasks as in FIG. 10. Platforms 921, 922, 923, 924, and 925 are also indicated. While on a platform, data bypasses the workstation if it is busy and is passed along to be processed as soon as the next workstation is set to be open.

Table I. presents the sequence of the data packet at different times in the pipeline stage (See FIG. 10). One data packet in this application contains 64-bit information from one channel of the PET detector. The clock time at each row 1008 in the first column of the table is equal to $t=(t_1+t_2+t_3)$ of FIG. 10. The number in the lower position in a cell of the table is the number of the input data packet that is processed by the 3D-Flow processor at a given stage. In Table I, the values in the raised position, indicated as iX and rX, are the input data and the result data, respectively, which flow from register to register in the pipeline to the exit point of the system. Note that input data I remains in the processor at stage 1d for five cycles, while the next four data packets arriving (i2, i3, i4, and i5) are passed along (bypass switch 1004) to the next stage. Note that at clock 14t, while stage 4d is fetching 9 to workstation 914, it is at the same time, outputting r4 to platform 924. This r4 value is then transferred to the exit of the 3D-Flow system without being processed by any other d stages. In Table 1, note that clock 14t shows the status represented in FIG. 10 and that input data and output results are intercalated in the registers/platforms 921, 922, 923, 924, 925 of the 3D-Flow pipelined system.

| Time | Proc (1d) data # | Reg (1d) data # | Proc (2d) data # | Reg (2d) data # | Proc (3d) data # | Reg (3d) data # | Proc (4d) data # | Reg (4d) data # | Proc (5d) data # | Reg (5d) data # |
|---|---|---|---|---|---|---|---|---|---|---|
| 3t | 1 | | | | | | | | | |
| 4t | 1 | i2 | | | | | | | | |
| 5t | 1 | i3 | 2 | | | | | | | |
| 6t | 1 | i4 | 2 | i3 | | | | | | |
| 7t | 1 | i5 | 2 | i4 | 3 | | | | | |
| 8t | 6 | r1 | 2 | i5 | 3 | i4 | | | | |
| 9t | 6 | i7 | 2 | r1 | 3 | i5 | 4 | | | |
| 10t | 6 | i8 | 7 | r2 | 3 | r1 | 4 | i5 | | |

-continued

| Time | Proc (1d) data # | Reg (1d) data # | Proc (2d) data # | Reg (2d) data # | Proc (3d) data # | Reg (3d) data # | Proc (4d) data # | Reg (4d) data # | Proc (5d) data # | Reg (5d) data # |
|---|---|---|---|---|---|---|---|---|---|---|
| 11t | 6 | i9 | 7 | i8 | 3 | r2 | 4 | r1 | 5 | |
| 12t | 6 | i10 | 7 | i9 | 8 | r3 | 4 | r2 | 5 | r1 |
| 13t | 11 | r6 | 7 | i10 | 8 | i9 | 4 | r3 | 5 | r2 |
| 14t | 11 | i12 | 7 | r6 | 8 | i10 | 9 | r4 | 5 | r3 |

The conclusion is that the limitation of the electronics of the current PET (front-end and coincidence detection described later) does not detect many photons and the overall performance of the best current PET detects about 2 photons in time coincidence out of 10,000 emitted by the radioactive source. This should be compared to 1,000 photons out of 10,000 captured by the 3D-CBS, with its improved electronics and extended axial FOV. In addition, of the 2 out of 10,000 photons in coincidence captured by current PET, many will be discarded by subsequent processing, or will not carry accurate information. For example, the measurements of the center of gravity (which affect spatial resolution) cannot be accurate in current PET because the full energy of the incident photon was not rebuilt. Photons whose energy was split between two channels are lost.

Conversely, the advantage of the 3D-Flow architecture of the 3D-CBS is a result of the use of several layers of stations (processors) with the data flow controlled by the "bypass switches," allowing more than 50 seconds (50 ns for the photons) to weigh the subject, to take the picture, to exchange them with the neighbors, to calculate the local maxima, the center of gravity, etc. Five layers of stations (or processors at the same level) allow 250 seconds in each processor to perform all the above calculations. In the event this is not sufficient more layers are added. The bypass switches at each station will provide good synchronization of input data and output results at each station by simply taking one data package for its station and passing four of them along.

Using the scheme of FIG. 9 we can follow the path of a data packet of photon (i3) through the entire system. At time 5t shown in Table I, the data packet of photon i3 enters the channel at the top of FIG. 9. If it finds a busy station (processor) on the right, it rests for one cycle on the platform (or register, shown in FIG. 10 as a rectangle next the bypass switch).

During the next cycle (6t of Table I), this data packet of photon (i3) advances to the next station. If this station is also busy, then it will rest on the next platform, and so on until it finds a free station.

When the data packet of photon (i3) finds a free station (at time 7t in Table I), it enters the station and stays there for five cycles for measurements (processing). After the data packet of photon (r3, which contains the results of the processing performed on i3) leaves the station and goes to the platform on the left, adjacent to the station (at time 12t), another data packet of photon (i8) enters the station from the upper left platform.

The result from photon (r3) cannot go straight to the exit but can only advance one platform at a time until it reaches the exit.

Phase II: Reunite husbands and wives (the two half-families reunited in phase I) from locations far apart (or find the back-to-back photons in time coincidence).

The measurements performed during phase I have reunited the half-families (each parent with some children), creating good candidates for the final entire family reunion. The result of the previous process is that, at most, four new fathers (or mothers) are found every 50 seconds.

The approach used in current PET in the final reunion is that the fathers and mothers do not move from the location where they are and each location interrogates about half of all the other locations in order to find out whether there is a companion in that location. It is not necessary to test a Line of Response—LOR—which does not pass through the patient's body.

Because, as we have mentioned, there are about 2,000 locations (electronic channels) in the system, the total number of comparisons required to be performed in order to find the companion will be enormous. For instance, for a PET with 1,792 channels, the number of comparisons necessary would be: $(1,792*1,791)/4=802,368$ comparisons every 50 ns; that is equivalent to $1.6 \times 10^{13}$ comparisons/second. Although in our human analogy family events are one billion times slower, it would still require $1.6 \times 10^4$ checks of matching families per second.

In order to avoid making that many comparisons per second, manufacturers of current PET have reduced the number of locations (electronic channels). This has several drawbacks such as increasing dead-time, reducing resolution, etc. For example, with a reduction to 56 channels, the number of comparisons in current PETs is still $(56*55)/4=770$ comparisons every 250 ns, equivalent to about 3 billion comparisons/second, which are performed in seven ASICs (Application Specific Integrated Circuit) in the current GE PET [20].

The approach used in the proposed 3D-CBS is simple. It greatly simplifies the circuit and requires only 120 million comparisons per second for an efficiency equivalent to that of the PET with 1,792 channels, which, as noted above, would require instead $1.6 \times 10^{13}$ comparisons per second.

In layman's terms, the approach can be explained as follows: the husbands and wives should move from their location to the reunion center. At that location an average of 4 groups of parents with children arrive every 50 seconds, thus in order to make all possible combinations among 4 elements and avoid accumulation in the room, 6 comparisons every 50 seconds are necessary. This would still be manageable in the world of the family reunion, only 6 comparisons being required instead of $1.6 \times 10^4$ comparisons per second with the current PET approach) and it will also be manageable in the world of photons requiring only 6 comparisons every 50 nanoseconds, which is equivalent to 120 million comparisons per second.

4.1.2 In More Technical Terms

The technological innovations of the 3D-CBS design are the following:

1. Accurate time determination of the arrival of the incident photon to the detector and "time-stamp" assignment to the detected photon. The front-end circuit of the 3D-CBS accurately determines, by means of a Constant Fraction Discriminator (CFD), a Time-to-Digital converter (TDC), further improved with the DSP real-time algorithm and assigns of the time-stamp to each event. (See also Sections 5.5.4 and 5.5.10)

2. Digital processing of the front-end electronics versus analog processing. With the advent of fast analog-to-digital converters and new processors oriented toward digital signal processing (DSP), there arose the tendency to treat analog signals in digital form, thus using discrete algorithms instead of analog functions [25]. The advantages of the digital versus analog processing are principally perfect stability (no drift due to temperature or aging), repeatability (not dependent on component tolerance) easy design (programming an algorithm), lower cost of programming the same devices for different functions, absence of the need for component calibration while system calibration can be performed easily by reading parameters acquired during a calibration procedure, accuracy limited only by converter resolutions and processor arithmetic precision, low power consumption, testability, and high circuit density. In contrast, upper speed limits of DSP using the standard DSP architecture are inferior to those of analog processing. This is the reason why many applications are still using analog processing. The manufactures of current PET are among those still using analog processing as is described in detail in Section 5.6.7.1.1, or as can be found directly from the manufacturers documentation in [19]. However, this barrier has been overcome with the 3D-Flow sequentially-implemented parallel architecture described previously. With the 3D-Flow architecture using a clock of only 80 MHz (or at a speed that can be implemented with a low cost CMOS technology), it is now possible to have all the DSP advantages listed above in addition to special instructions for particles identification, while sustaining a high data input rate.

3. Elimination of the saturation at the input stage for any detector type and speed and for any simple or complex real-time algorithm. The implementation that satisfies the requirements of eliminating the saturation at the input stage is the use, for each electronic channel, of a number of cascaded 3D-Flow processors as shown in FIG. 10 which is proportional to the processor speed, the number of steps of the algorithm to be executed, and the data input rate. For example: sampling a PET detector at 20 MHz (see Section 5.5.3) with a 3D-Flow processor running at 80 MHz that requires the execution of a real-time algorithm of less than 20 steps, needs a 3D-Flow system of 5 layers. A layer is an array of 3D-Flow processors equivalent to the number of channels of the PET detector, where each processor is interconnected to its four neighbors through North, East, West and South ports. Although the entire PET electronic system can receive a data packet every 50 ns, each layer can executes an algorithm lasting up to 20×12.5 ns=250 ns, thus each layer takes one data packet from the detector and skips 4 sets of data packets that will be forwarded to the other processors, via the bypass switches (switch 1004 of FIG. 10), that are located in the other four layers (see FIG. 10). If the sampling rate of the detector increases or if the algorithm becomes more complex, one or more layers of 3D-Flow processors is added in order to reach a situation where the system will never saturate.

4. The implementation of a new concept that all signals within a defined view angle of the detector from the emitting source at the center of the detector are processed and correlated digitally. A programmable algorithm (see next section and references [7], [21], [11]) is executed in real-time on all signals received from a defined view angle, together with the signals of the neighboring detector elements in order to extract, directly from the raw data, all information of the interaction between the photon and the detector. In current PET, the approach is of extracting from a few signals one type of information, from other set of signals other information, and so on. The next level of the electronics combines the results of the first level of the processing of partial data. The reason for using that approach which provides less accuracy in the calculation of the parameters characterizing the incident photons, was because the electronics on current PET can handle only few operations on a few data at a high rate. The 3D-Flow architecture, on the other hand, can handle more data, performing complex real-time algorithms on them while receiving at high data input rate because of the sequentially-implemented parallel architecture described in the next section. The combination of the detector raw data received within a defined view angle is performed in a FPGA circuit (from PMT, photodiodes, time-to-digital converter, etc.) [11]. These data are then sent to the 3D-Flow processor in a formatted word of 32- or 64-bit (See reference [21], and Section 5.5.3).

5. The 3D-Flow sequentially-implemented parallel architecture (see Table I and FIG. 10) allows execution of complex, programmable real-time algorithms which include correlation with neighboring signals, and fully reconstruct the energy, extract the information of the type of interaction between the photons and the crystal, improve signal-to-noise ratio, measure accurately the depth of interaction, resolve photon pileup, and capture most of them (See example of the real-time algorithm for photon identification on Sections 5.5.11.2, and 5.5.11.3). Thus this architecture improves image quality, and leads to lower radiation dosage and to shorter scanning time. The reader who is not interested in the details of the novel unique technology, may skip the entire page of the 3D-Flow architecture and the references. The concept of the 3D-Flow architecture is described in simple terms in [26], while a more complete description of the concepts, implementation and application can be found in [7], [8], [9], [21], [10], [11], [12], and [13]. One of the differences is that in the standard pipeline a data moves at each clock from one stage to the next, while in the 3D-Flow system a data remains in the same stage for several clocks, until the entire algorithm is completed. The basic 3D-Flow component has been implemented in a technology-independent form and synthesized in 0.5 µm, 0.35 µm technology, and in FPGA's Xilinx, Altera and ORCA (Lucent Technologies). A cost-effective solution is to build the 3D-Flow in 0.18 µm CMOS technology @ 1.8 Volts, accommodating 16 3D-Flow processors with a die size of approximately 25 $mm^2$, and a power dissipation [gate/MHz] of 23 nW. Each 3D-Flow processor has approximately 100K gates, giving a total of approximately 1.7 million gates per chip. (See [7], [10], [13], [12] for more details). Among the features of the 3D-Flow architecture, the following are listed as are pertinent to advantages which suite this project:

Eliminates saturation on the input data, no deadtime, no bandwidth limitation (see Section 2.4 item 1.e and Section 3.1.2, item 3)

Allows execution of programmable, simple or complex real-time algorithms with an execution time of an uninterruptable sequence of operations which is longer than the time interval between two consecutive input data. The same 3D-Flow system can be used for different crystal detectors (slow and fast) and can be adapted to an optimal extraction of the information of the interaction of incident photon with the crystal detector by simply loading a different real-time pattern recognition algorithm in the 3D-Flow program memory Eliminates the boundaries with a convenient way to communicate with the neighbors (3×3, 4×4, 5×5, etc.) through North East, West, and South ports.

The 3D-Flow instruction set includes all typical DSP operations such as multiply-accumulate, arithmetic and logic operations, and in addition has operations to move data to/from the 10 input output ports and operations comparing the received data with the 8 or 24 neighbors in a single cycle (to check for local maxima). Up to 26 operations in different units (2 ALUs, 1 MAC/Divide, 64 registers, 5 input FIFOs, 32 comparators, 1 timer, 4 data memories, all connected via four internal busses) can be executed in a single cycle. This balance of operations of moving and computing data allow to execute all typical DSP filtering techniques, for signal-to-noise ratio improvement and algorithms for photon identification (see Section 5.5.11), all essential to improve PET efficiency. Among the operations performed are also those of digital signal-processing operations on the incoming bit string such as: (a) variable digital integration time (or pile-up identification/correction), which allows for the maximum count rate capabilities while preserving spatial resolution; (b) depth of interaction, which reduces the parallax error by performing calculation based on pulse shape discrimination (PSD), and/or pulse height discrimination (PHD); (c) local maxima, to avoid double counting, (d) centroid calculation to improve spatial resolution or/and techniques of most likely position given the statistical nature of the signals; (e) correlation with neighboring signals; and (f) improving the timing resolution from the information received from the time-to-digital converter (TDC) and pulse shape analysis.

Figure 43:
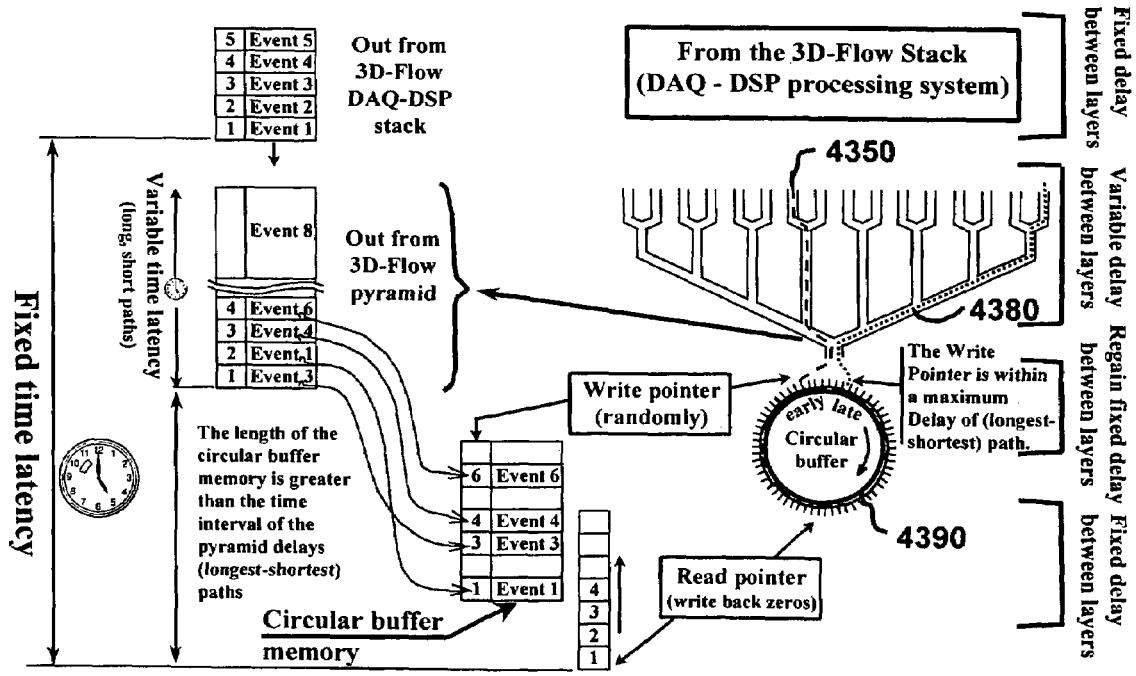

6. A simplified coincidence detection circuit. In the new design described in Section 5.5.14, only the detector elements (coupled to a PMT or APD), that are hit by a photon which was validated by a thorough real-time, front-end pattern recognition algorithm, are then checked for coincidence. This method is much simpler than the one used in the current PET, which compares all of the possible LOR even the ones connecting two detectors that did not receive a hit (see references [20], [18] or Section 5.5.14 for more details). The number of comparisons for finding the coincidences in the 3D-CBS is proportional to the radiation activity (e.g., for about 80 million hits per second into the detector, corresponding to a limit of the radiation dose to the patient, only 120 million comparisons per second are necessary) and not to the number of detector elements as in the current PET (See Section 5.6.8 for the implementation of the coincidence circuit with the 3D-Flow and the flow chart of the programs). In the new design, the coincidence detection problem is solved with simple electronic circuit that funnels all hits detected to a single electronic channel, sorts the events in the original sequence, as shown in FIG. 43, and compares all hits within a given time interval, for validation of time-stamp and location situated along an LOR passing through the patient's body. (See Section 5.5.14.1).

7. Elimination of the saturation at the output. The elimination of the saturation at the output stage is easily achievable by implementing a circuit that performs the number of comparisons corresponding to the highest radiation activity that a detector should ever receive. Assuming to have at most four hits at the detector during one sampling of 50 ns, (corresponding a rate of 80 million single photons per second hitting the detector), than because we can have at most 6 comparisons out of four data, the total number of comparison to avoid saturation will be 120× $10^6$ comparisons per second. (See section 5.5.14 for more details).

8. The new electronic design now makes the extension of the PET FOV cost-effective. One of the most important benefits of the use of the innovations set forth in this article is that of efficiently capturing more photons. This moves beyond the point where the current PET manufacturers erroneously thought that the benefits of capturing more photons and decreasing the examination time could not offset the significant increases in the costs associated with PETs with a longer FOV. In addition, these innovations allow to reduce the radiation dose to the patient permitting examination annually on asymptomatic people. The use of the 3D-Flow architecture described previously and the funneling circuit of the coincidence detection section described previously, allow to extent the FOV of the PET to any length and to any number of detector elements.

9. The incorporation of the Electron Beam Computed Tomograph (EBCT) and Positron Emission Tomograph (PET) in a single apparatus with a single detector eliminating completely the motion artifact in the image is facilitated by the use of the 3D-Flow DSP that can efficiently execute the calculation for identifying and separating from the same crystal detector the two types of incident photons (CT X-rays and PET γ rays).

10. The accurate measurement of the attenuation during CT x-ray transmission scanning will be used to calculate a more accurate attenuation correction coefficient for the PET examination.

Other innovations that provide benefits to the 3D-CBS machine are: hardware, software, cabling, system architecture, component architecture, detector element layout, data acquisition and processing, and detection of coincidences.

4.2 Limitations of Current PET Remedied by 3-D Complete Body Scan

In order to reconstruct an image of the metabolism of the cells of the patient's body, it is necessary to capture more than 20 million photons in coincidence emitted by the radioactive source within the patient's body during each examination. If the electronics is not rigorous in selecting the "good photons[2]", the image quality will be poor and the machine will require additional scanning time. This presents the disadvantages that (a) a particular biological process might be finished by the time the scan has accumulated more than 20 million photons; and (b) the "bad" photons acquired along with the "good" ones cannot be subtracted during off-line filtering algorithms without subtracting several good photons along with them.

The current PET imaging machines do not thoroughly analyze in real-time the data received from the detector which contains the information of the characteristics of the interaction between the incident photon and the crystal. The result is that many "good[2]" photons are missed and photons are captured that later in the process must be disregarded as "bad" photons. This fails to provide a clear image to help the physician to recognize subtle differences in normal anatomies. The innovations set forth in this article remedies the above in the following manner:

4.2.1 The Remedies Offered by the 3D-CBS to the Above Deficiencies

Figure 13:
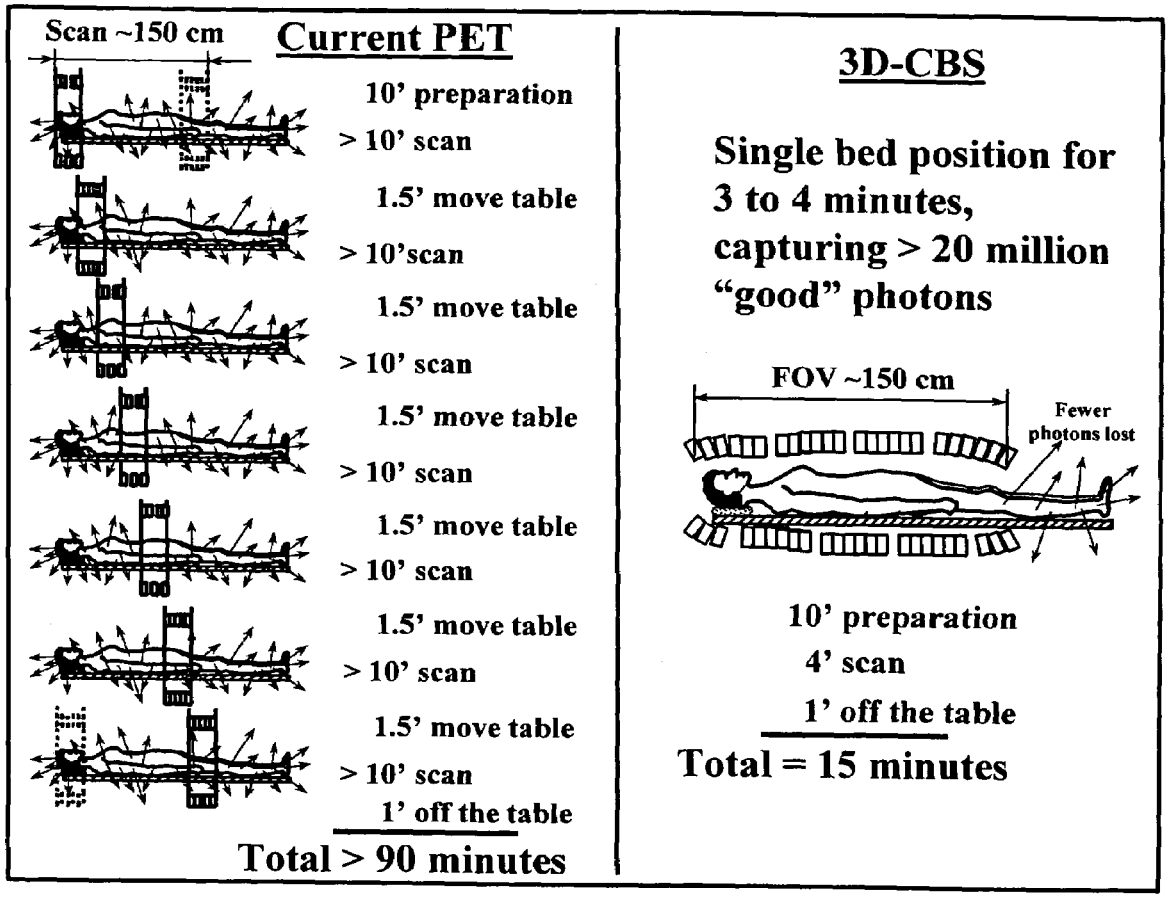

1. The image quality of current PET is improved with the following (see the same items listed as a problem in Section 2.4):

a) FOV longer than one meter, covering almost the entire size of the patient's body. The simpler, lower cost, more efficient electronics described in this article and in references [7], [8], [9], [21], [10], [11], [12], [13] allows to capture more "good" photons providing the benefit of improving the image quality, decreasing the radiation dose to the patient and shortening the examination time which allows to compensate the higher cost of the detector of a PET with a longer FOV b) accurate photon arrival time determination and assignment to the input data packet using the circuit described in Section 2.4, item 1 and in Sections 5.5.4 and 5.5.10. The determination of the accurate arrival time of the photon at the detector allows to better identify "good" events by the coincidence detection circuit;

c) digital signal processing on the front-end electronics at each electronic channel with neighboring signal correlation as described in Section 5.5.8. Using digital signal processing techniques, one can most efficiently extract the characteristics of the interaction between the incident photon and the crystal detector and improve the signal-to-noise ratio on each signal before adding them with other signals;

d) elimination of detector boundaries by means of the North, East, West, and South communication ports of the 3D-Flow architecture as described in Section 2.4, item 5 of this article and in Section 5.5.8. The possibility to exchange information, to/from neighboring detectors, in real-time during acquisition, allows to fully reconstruct the energy of the emitted photon which permits a better selection and classification of them;

e) elimination of the dead-time of the electronics. The analysis of bottlenecks on the electronics of current PET and the design of a dead-time free system with the 3D-Flow architecture is described in detail in Section 5.5 and 5.6;

f) elimination of the saturation of the electronics at the input stage. The bypass switches of the 3D-Flow architecture (see Table I and references [8], [21]) allow the electronics of the 3D-CBS to sustain, with zero dead time, a data input rate of 20 million events per second at each channel. (This is equivalent to a total system input bandwidth for 1,792 channels or about 35 billion events per second compared to the 10 million events per second offered by the current PET.) This capability eliminates electronic saturation when any type of (fast or slow) detector is used. Electronics saturation, which is one cause of inefficiency of the current PET, should not be confused with detector saturation of the slow crystals. For example, considering a BGO crystal with a decay time of about 300 ns and an over all recovery time of about 700 ns, one could conservatively consider that the crystal will saturate at about 1 MHz. Because detectors are made of many crystals cut in 2 mm×2 mm, or 4 mm×4 mm, only a small portion where the photon hits the detector and a few surrounding detector elements could be affected by crystal saturation if another photon should arrive during the same time interval of 1 μsec. However, the 3D-CBS electronics has the capability of detecting any other photon arrived in any other part of the detector during the same time, up to one every 50 ns (higher than 1 μsec in order to cope with fast crystals) at the same location, with a time difference resolution between two different detected photons of 500 ps (the 500 ps resolution of the electronics which is provided by the resolution of the Time-to-Digital converter in some cases may be higher than the time resolution of slow crystals. See Section 5.5.10);

g) a simplified coincidence detection circuit sensitive to the radiation activity rather than to the number of detector elements (see Section 2.4, item 6) captures more photons in coincidence more efficiently at a lower cost, improves image quality, allows lower radiation dosage, and leads to shorter scanning time;

h) elimination of the saturation at the output. Using the 3D-Flow coincidence detection approach, the elimination of the saturation at the output stage is relatively simple because after having set the maximum radiation dose that will ever hit the detector, it is sufficient to implement the circuit(s) that performs the number of comparisons necessary to detect the maximum number of expected photons in coincidence (See Section 2.4, item 7 and Section 5.6.2.4). This number, will always be lower and simpler than the coincidence detection circuit used in the current PET, which performs about 3 billion comparisons per second in seven ASICs. The circuit would be simpler because 3 billion comparisons per second corresponds to an isotope dose to the patient higher than 100 mCi, which will not be administered because is too dangerous for a patient;

i) reduction of the number of "Randoms" by means of the accurate determination of the arrival time of the incident photon hitting the detector. The accurate calculation (by means of a CFD, TDC and/or further improved with DSP real-time algorithm. See Section 2.4, item 1.b of this article and Section 5.5.10) and the assignment of the time-stamp to each event allow use of a shorter time interval between two detected photons when determining if they belong to the same event. Reducing randoms improves image quality, lowers radiation dosage and shorten scanning time;

j) very accurate calculation of the attenuation correction coefficients needed for PET image enhancement, using the information acquired during CT transmission scan. (See Section 6.4);

2. Reduction of the false positives and false negatives because of the improvements described above and in Section 3.1.2 in capturing more "good" photons and eliminating the "bad" photons at the front-end electronics during real-time processing. The main reasons that allow to acquire better images which would allow the physician to recognize subtle differences in normal anatomies are: (a) the presence of a 3D-Flow DSP on each electronic channel, with neighboring signal correlation capabilities (see FIG. 11 and FIG. 12), which extracts with zero dead time, the full characteristics of the incident photon and improves the S/N ratio on each signal before adding it to other signals, (b) good attenuation correction coefficients, (c) good, efficient, and simple coincidence detection circuit (see Section 3.1.2 item 6), and (d) having a sufficiently long FOV which allow capturing most photons as shown in FIG. 12 and FIG. 13.

3. Reduction of the radiation dose delivered to the patient to a negligible level (1/30 the radiation administered during current PET examination) that will permit annual screening and will permit several examination during the treatment of the disease with no hazard to the patient, allowing better monitoring it. This is possible because the 3D-Flow sequentially-implemented parallel architecture described in Section 3.1.2, item 5 and in Section 5.5, 5.6 and 5.7, allow to detect at a high data input rate, about 1,000 photons every 10,000 emitted, and capturing more than 20 million "good" photons in coincidence per examination in a short time. FIG. 14 shows the factors contributing to increase the deliver of higher radiation dose to the patients when current PET are used. See more details on Section 5.6

4. The fast scanning time of the 3D-CBS is because of the long FOV of its detector and of the highly efficient electronics. The high efficiency mentioned before of 1,000 out of 10,000 reduces acquisition to a short time. This allow the examinations be performed in 15 to 20 minutes with 3 to 4 minutes scan time (a) facilitating the capture of a specific biological process desired to observe, (b) without making the patient uncomfortable, and (c) at a cost that would be greatly reduced from the current one;

5. The factors that will reduce the cost are:
   a. the lower cost of the negligible dose of radioisotope required;
   b. the fast scanning time that allows to examine 40 to 50 patients per day; and
   c. the cost of highly paid personnel who must operate the slow machine will be divided over a larger number of examination per day instead of only 6 to 7 patients/day.

FIG. 12 shows detector 1200 with a short field of view (FOV) and a detector 1208 with double the field of view relative to detector 1200. For detector 1208, there are four times as many photon detection paths (lines of response—LOR) 1216. FIG. 12 further illustrates that a FOV angle 1220 for detector 1216 is twice as large as FOV angle 1224 for detector 1200.

FIG. 13 shows how the 3D-CBS can acquire over 20 million photons in a shorter time compared to the current PET. This is equivalent to scan more patients per hour, thus it lowers the examination cost.

4.2.2 List of the Innovations which Provide Additional Improvements to Medical Imaging Technology 1. A single detector assembly for PET and CT, covering most of the patient's body (current PET/CT use two detectors, one for each modality with a moving bed on which the patient goes through both). In addition to eliminating completely picture blurring, this feature improves the imaging capabilities allowing the superimposition of anatomical pictures with functional imaging, provides very accurate attenuation correction coefficients, and utilizes the synergy of the other innovations to decrease the cost per examination.

2. The use of a detector shape as close as possible to the size and shape of the human body (e.g. elliptical for the torso and a detector ring with a smaller diameter for the head), saves cost in the detector and improve photon detection capabilities which have to travel a shorter distance from the body to the detector, thus randoms can be reduced because a shorter time interval between two photons hits can be set. The 3D-Flow DSP capabilities can perform a good DOI measurement providing higher resolution at a lower cost than what would have been achieved by using a detector with wider diameter ring and no DOI measurements.

4.3 Technology Highlights of the 3D-CBS which Permit Annual Cancer Screening

A more detailed analysis of the deficiencies of current PETs, how those limitations are remedied by the 3D-CBS (with precise references to the distinctive innovative features of the 3D-CBS to which the improvements are attributed) can be found in Appendix C.

The 3D-CBS' breakthroughs in four areas allow improvements of: (a) quality and quantity of detection; (b) speed of detection; (c) lower radiation dosage requirements; and (d) lower costs.

4.3.1 Quality and Quantity

In the 3D-CBS system, there is a one-to-one correspondence between a processor cell and a detector channel (or sensor, or electronic channel. See details in FIG. 15). If a photon lands across the borders of detector channels (see FIG. 11; photon 1111 landed directly in the center of a sensor while photon 1155 landed between two sensors and was partially absorbed by both), the signals sent by each sensor to its corresponding processor need to exchange their information with the neighbors in order to be able to reconstruct the total energy of the photon. This operation increases the sensitivity by capturing more good photons which are essential to reduce the "false positives" and "false negatives." The exchange of signals between neighboring channels with no detector boundary, allow signals interpolation which also improves spatial resolution. (Both affect the image quality).

The need to increase the sensitivity that helps to reduce the false positives and false negatives is demanded by the users, while the sensitivity that also increase the noise which provide worst images is undesired. The DSP on each electronic channel allows improving S/N ratio on signals before adding them. An observation referring to the disadvantages of the increased sensitivity with an equivalent or more increase of noise in current new PET was made by Dr. Alan Waxman [27], director of the nuclear medicine Cedars-Sinai Medical Center in Los Angeles. He stated "The bad news is that the new systems [PET] are so sensitive to minute accumulations of fluorine-18 fluorodeoxyglucose (F-18 FDG) that it has become harder to tell the difference between malignancy and inflammation."

More photons emitted by a single organ can be captured if the FOV is increased. FIG. 11a shows that by doubling a short field of view the number of photons that can be captured is actually increased by a factor of four instead of two. FIG. 11b shows that also the image resolution is increased by increasing the axial FOV.

4.3.2 Speed

The fast scanning time of the 3D-CBS is because of the long axial FOV of its detector and the highly efficient electronics. The high photon detection efficiency (of 1,000 out of 10,000 compared to 2 out of 10,000) reduces the time needed for acquisition of the 20 million photons in coincidences (or the amount of photons which provide a sufficient statistic to yield a good image). This allows the examinations to be performed in 15 to 20 minutes with 3 to 4 minutes scanning time, (a) facilitating the capture of a specific biological process one desires to observe, (b) without making the patient uncomfortable, and (c) at a greatly reduced cost. (See FIG. 13).

4.3.3 Less Radiation to the Patient

The loss of efficiency in the current PET is not only due to shorter axial FOV and smaller solid angle as shown in FIG. 14; a great fraction is caused by the inefficiency of the electronics.

The current PET imaging machines do not thoroughly analyze in real-time the data received from the detector, which contains the information of the characteristics of the interaction between the incident photon and the crystal. The result is that many "good" photons are missed and photons are captured that later in the process must be discharged as "bad" photons. Conversely, the electronics of the 3D-CBS can perform a thorough analysis on the incoming data at high rate.

FIG. 14 shows the factors contributing to an increase in radiation dose to the patients when current PETs are used. Although the text cannot be read in the figure, the symbols in the picture show clearly the difference between the old approach used in current PET (left on the figure) and the new 3D-CBS approach (right in the figure) and where the great areas of inefficiency are. See more details on Section 5.6 and FIG. 14).

4.4 Measurements of the Inefficiency of Current PET

The measurements of the limited efficiency of the current PET devices have been reported in articles written by manufacturers. (See references [28], [29] and Sections 11.2.2.6.3.2 and 11.2.2.6.4.2 of [7]). The calculation of the improved efficiency over 400 times using the new 3D-CBS compared to the current PET is reported in [7] and is calculated as follows: the division between 10% divided by 0.014%=714 (see lower part of FIG. 14). The 0.014% is calculated as the division of the 0.2 million coincidences/sec detected divided by 1,424 million coincidences/sec emitted by the radioisotope. Both values are taken from FIG. 8 on page 1405 of the article by DeGrado et al. [29]. The improved efficiency of 10% in the 3D-CBS is due to its breaking of the barrier of the axial FOV by a novel simplified design of the electronics (which will also improve the performance of current PET with short axial FOV if the electronics are replaced). See Section 6.6 for more details.

4.5 The Novel Methodology and Apparatus of this Invention Compared to the Prior Art The usefulness of this invention can be measured as follow: During the past 20 years the focus of the designers of PET devices has been on improvement of the crystal detectors. For about 15 years, the fast lutetium orthosilicate (LSO) crystals, which are nearly ideal; have been available, however, the world-wide production capability of LSO is still far from what would be necessary for a development plan such as the one target with this invention (that is providing a low cost, low radiation medical instrument device to a large number of people in order to improve and lower health care cost by helping the physician in the prescription of the drugs and monitor their effect on the patients. If drug use were optimized, we will have a reduced mortality at lower cost). An ideal scintillating crystal should be not hygroscopic and would have the speed of the Barium Fluoride (BaF2), the density of Bismuth germanium (BGO) and the light of thallium-activated Sodium Iodide (NaI(Tl)), yttrium orthosilicate (YSO), or cesium Iodide (CsI). Lutetium orthosilicate (LSO) is nearly to ideal and has been incorporated in the most recent PETs. However, the search of economical new material which is dense and has a short decay time (or narrow light pulse) is still underway.

The efficiency increase in one giant step of the 3D-CBS, even when slow crystals are used, opens the door to a whole new area of applications by permitting (a) an annual whole-body screening for early detection of cancer and other systemic anomalies, (b) the monitoring of the drug's efficacy during diagnostic workup and staging of cancer[8][14], [15] and other diseases, (c) the development of new drugs and the study of their effects, and (d) its use in an emergency room.

If LSO becomes more available or less expensive in the future, the design of the 3D-CBS can accommodate for these fast crystal detectors as well by simply loading a different program (real-time pattern recognition algorithm) in the 3D-Flow processors program memory. (See Section 2.4). In order to achieve the very conservative projection of about 3,000 3D-CBS scanners by 2010, approximately 150 m$^3$ of scintillating crystals (see calculation in Section 6.10) will be needed during the next 9 years just for the U.S. market, and over 500 m$^3$ would be needed if the world-wide market would be considered. Because during the past fifteen years the overall worldwide production of fast LSO crystals was less than 5 m$^3$, it is difficult to imagine that the production capability for LSO crystals could increase to 500 m$^3$ during the next nine years.

The operating costs of the 3D-CBS shown in FIG. 15 include the capital cost of the machine amortized over 8 years, the capital cost of the building where the machine is located (estimate $1 million) amortized over 40 years, the operating cost, including the expenses of the radioisotope, the personnel, the maintenances, and the upgrades. Radiopharmaceutical costs, as well as building costs, may vary substantially depending on the location; figures in this article are conservative, using the figures toward the highest costs. Although the 3D-CBS will be scanning more patients per day and it will use a lower daily quantity of radioisotope, the daily cost for 18F-FDG radioisotope has been kept the same for the three scanners ($3,400/day). The cost of the 18F-FDG is higher in U.S. compared to Europe. This estimate is based on the higher U.S. cost for the amount of radioisotope needed by a ~25 cm axial FOV PET, which is $3,100 per day for scanning 4 patients/day, $3,400 per day for scanning 5 patients/day, $3,600 for scanning 6 patients/day, and $3,800 per day for scanning 7 patients/day. Personnel costs have been based on Table 5-2 on page 37 of [14]: ½ MD, 2 technologists/administrators for the >14 cm FOV; ½ MD, 2½ technologists/administrators for the ~25 cm FOV, 1 MD, 2½ technologists/administrators for the 3D-CBS. Annual maintenance costs has been assumed to be $60,000 for the <14 cm FOV PET, $100,000 for the ~25 cm FOV PET, and $200,000 for the 3D-CBS. Annual costs for the upgrade of the scanners have been assumed to be $60,000 for the <14 cm FOV PET, $100,000 for the ~25 cm FOV PET, and $150,000 for the 3D-CBS. Because the 3D-CBS has included all possible improvements, the costs for upgrades is relatively low and is mainly due to software upgrade, while for the short FOV PETs there is room for more improvements.

For purpose of comparison, let us use an examination price of $400. At this price, the revenues per year of the current PET with about 25 cm axial FOV (see left side of FIG. 15) are calculated based on a quantity slightly above the average [30] (about 1,250/year, or 5/day) as 1,250× $400=$500,000 per year. Because of the expenses of $1.75 million per year, the current PET would experience a loss of about $1.25 million per year. (This explains why the current PET exam cost is between $2,000 and $4,000).

The current PET with a shorter axial FOV (<14 cm) would have less expenses than the PET with about 25 cm axial FOV; however, because is also slower than the 3D-CBS, it can perform even fewer examinations (about 1,000/year, or 4/day), and the loss will still be about $1 million per year.

Conversely, the 3D-CBS with about 150 cm axial FOV (see right side of FIG. 15) can perform more examinations (about 7,500/year, or 30/day) providing net revenues of about $335,000 per year per scanner calculated as $400×7, 500 exams=$3 million, minus $2.665 million of costs.

The cases for these three different PET devices under the worst case scenario for the 3D-CBS is considered in Table IV of reference [31]; that is, assuming that the volume of patients per unit will not increase. The 3D-CBS will still be advantageous because it will perform the same number of examinations in fewer days per week, saving radioisotope and personnel costs. Table XII of reference [31] reports detailed study of the lowest price possible for an examination using 3D-CBS vs. other PET devices. It shows that the 3D-CBS could sustain a $300/examination price (compared to the current average price of $3,000/exam). The winner from the entire process will be the consumer (the patient) who will receive, thanks to the competition, a better examination with a better quality image, requiring lower radiation [32] at about 1/10 of its current cost. The recommended limits of radiation exposure (whole-body dose) are stricter in Europe (maximum 1.500 mrem per year) than in the U.S. (5.000 mrem per year) [321. However, it is recommended that everyone monitor his/her radiation exposure to keep it to the minimum level.

5. DESCRIPTION OF THE DRAWINGS

Further features and advantages will become apparent from the following and more particular description of the preferred and other embodiments of the invention, as illustrated in the accompanying drawings in which like reference characters generally refer to the same parts, elements of functions throughout the views, and in which:

FIG. 1. Layout for the hardware assembly of the 3-D Complete Body Scan (3D-CBS) for 1,792 channels.

FIG. 2. Logical and physical layout for a 3-D Complete Body Scan (3D-CBS) for 1,792 channels.

FIG. 3. Differences between CT (left in the figure) and PET technologies (right in the figure).

FIG. 4. Details of the paths of the x-ray (CT) and γ-ray (PET) photons and the technique used to compute the anatomical and functional images. Photons arrive at the detector randomly at unregulated time intervals. When a short time interval of 2 to 3 ns is considered (e.g., as shown in section e, f, and g of the figure) there is a high probability of capturing not more than two high energy photons (HE) in time coincidence from the same PET event and eventually one low energy photon (LE) in the location where the x-ray gun is shooting. The task of the detector and of the electronics is to recognize most of these PET and/or CT events and provide accurate information to the workstation which computes the anatomical and functional images. Each photon is recognized only if thorough measurements are performed on the signals as they are received from the sensors (the photomultipliers—PMT- or Avalance PhotoDiode—APD-) through the electronic channels. Among the most important measurements (see additional measurements in next section) is that of rebuilding the total energy of the incident photon. Because a photon may strike the detector crystal in a location where it can produce signals in neighboring sensors, the sum of signals from neighboring sensors must be computed. For example (see section c in the figure) the energy of a CT event measured at the detector $E_{Cd}$=A+B+C which should be equal to the source energy of the x-ray gun $E_{Cs}$ minus the attenuation caused by going through the body tissue. An example showing the process in PET, found in section d of the figure, shows the energy of one 511-keV photon that has been attenuated by its passage through the patient's body and has been measured as $E_{ps1}$=A+B; note that the matching 511-keV photon has been measured as $E_{ps2}$=A+B+C+D. When the detector receives hits within 2 to 3 ns (e.g., during Time 1 in section e of the figure), the electronics separates the HE events from the LE event. It finds the location of the HE events and the LOR passing through the two detectors that received the hits. The intersection of millions of LOR per second allow identification of the location of the emitting source as shown in the right side of section h of the figure, while the computation of the attenuation of the x-rays (LE) determines the density of the body and displays its anatomical image on the monitor.

FIG. 5. The evolution of positron imaging systems (original source of the FIG. [1]). Section (a) shows the evolution of the PET using past and current approach, while Section (b) shows the improvements achievable with the novel 3D-Flow approach describe in this document.

Figure 6:
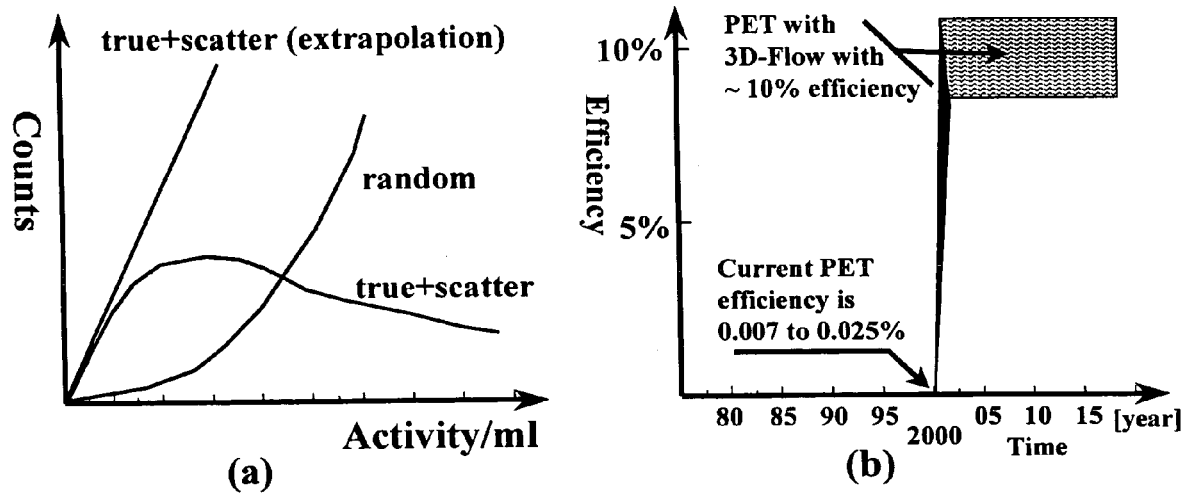

FIG. 6. (a) Typical sensitivity plots of current PETs, which are shown in articles of the past 25 years. The saturation of the electronics limits the capturing of the true events as the radiation activity increases. The randoms increase due to poor timing resolution. The "true+scatter" curve is not to be confused with the crystal's dead time because these days the crystals are cut in 2 mm×2 mm, or 4 mm×4 mm, and the dead time is confined to a small area of a few crystals out of the entire detector. A PET with non-saturating electronics should show a measurement of the type of "true+scatter (extrapolation)." Section (b) shows the change in PET efficiency with the improvements of the 3D-CBS described herein. The efficiency is increased from about 2 photons detected out of 10,000 to about 1 out of 10. (The 10% estimated efficiency could vary as shown in the top section of FIG. 6b, depending on the patient's weight, the FOV, and whether fast, expensive crystals or slow, economical crystals are used).

FIG. 7. Graphic view of the ideal vs actual coincidence detection of the current PET system and the solution to improce the efficiency.

FIG. 8. "Family reunion." A solution that identifies family members and checks in detail for their characteristics is needed for the reunion of related pairs of photons. The figure shows an example of the arrival of information of the particles from several electronic channels at one time. In the figure, several members of a family arriving at the same time on different electronic channels (e.g. see four members of a family in the second row from top) are compared to a photon that has its energy split among several channels FIG. 9. A "family reunion" cartoon for time 14t of Table I and FIG. 10. Each photon remains in the measuring station (processor) for a duration five times longer than the time interval between two consecutive input data. The result from any measuring station will not be an input to the next station (as it is in a typical pipeline system) but will be passed on with no further processing in the 3D-Flow sequentially implemented, parallel-architecture until it exits (see additional description on next page).

FIG. 10. The example shows how the 3D-Flow system extends the execution time in a pipeline stage beyond the time interval between two consecutive input data (sequentially-implemented, parallel architecture). An identical circuit (a 3D-Flow processor) is copied 5 times at stage d (the number of times the circuit is copied corresponds to the ratio between the algorithm execution time and the time interval between two consecutive input data). A bypass switch 1004 (shown as a dotted right arrow in the figure) coupled to each processor in each 3D-Flow stage 1d, 2d, 3d, 4d, and 5*d* sends one data packet to its processor and passes four data packets along to the next stage ("bypass switch"). Thus, the execution time at each substation d will be $t_p=4(t_1+t_2+t_3)+t_1$. The numbers in the rectangles below the switches identify the input data packets to the CPU of the 3D-Flow processor. (See also Table I for the sequence of operations during the previous clock cycles). A 3D-Flow processor is shown in the figure with the three functions of (a) a bypass switch (dotted right arrow in the rectangle), (b) an output register/platform such as 921, 922, 923, 924, 925(rectangle to the right), and (c) a CPU/workstations 911, 912, 913, 914, 915 (rectangle below).

FIG. 11. Inefficiency of current PET to detect photons when they strike the crystal in a location that it can produce signals in neighboring sensors. Case (figure at left) when a photon is detected because it strikes a detector which is coupled to a sensor (or a group of sensors such as photomultipliers, or APDs. Most of current PET have sensors organized in groups of 2×2 elements). Case (figure at right) when a photon is undetected in current PET because it strikes a detector that produce signals in neighboring sensors (or group of sensors). The 3D-Flow approach remedie this limitation by exchanging the information with processors receiving signals from neighboring sensors.

FIG. 12. A PET with an axial FOV that is twice as long as the FOV of current PET can detect four times the number of photons in time coincidence from an organ emitting photons from the center of FOV. Section (a): Doubling the axial FOV increases the Line of Response (LOR), thus the sensitivity increases four times when doubling a short axial FOV, this should enable the user to detect four times the number of coincidences when the electronics do not saturate and DOI measurements are performed. Section (b): Increasing the axial FOV increases the resolution.

FIG. 13. The current PET (figure at left) with short (<25 cm) axial FOV (the length of the detector) requires ≧7 scanning table positions, each longer than 10 minutes, to cover about 150 cm of the body and record more than 20 million data of photons in time coincidence. The 3D-CBS (figure at right) with a longer axial FOV (~150 cm) and with a more efficient electronics, can capture >20 million data from photons in time coincidence in <4 minutes.

FIG. 14. Comparison of the efficiency between the new 3D-CBS (right side) and the current PET system (left side).

FIG. 15. Differences in operating costs between the current PET and the 3D-CBS.

FIG. 16. Example of an assembly of a PET/SPECT/CT multimodality device (lead septa that should be placed inside the detector between the crystals and the transmission bar, are not shown in the figure).

FIG. 17. Example of the implementation of the CT section of the 3D-CBS (CT) using the proven technology of the Electron Beam Computed Tomography. The upper half of the detector cab be adjusted for positioning the patient in the bed and it can be left open for claustrophobic or overweight patients. (The closed position provides the highest efficiency). The arrows at 1775 indicate how the hatch will adjust to be open to accommodate claustrophobic or overweight patients.

Figure 18:
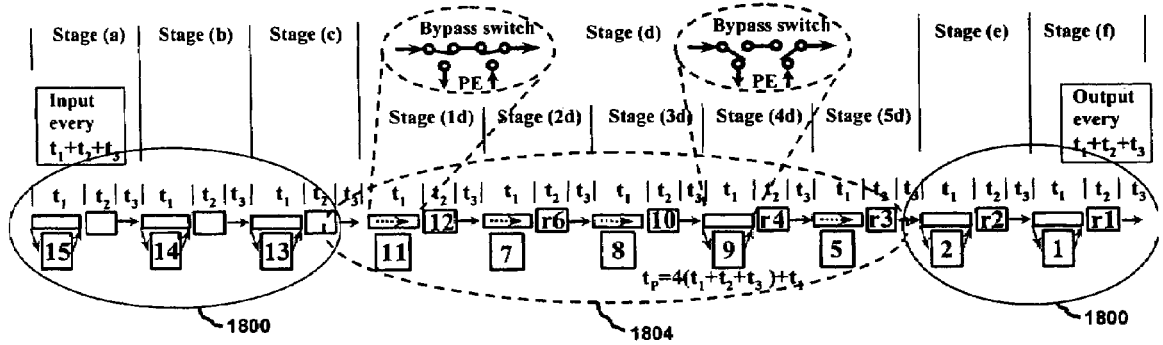

FIG. 18. The 3D-Flow system (inside the dashed line) nested into the well known pipeline technique. The example shows how the 3D-Flow system extends the execution time in a pipeline stage beyond the time interval between two consecutive input data (sequentially-implemented, parallel architecture). The standard pipeline system consists of six stages called a, b, c, d, e, and f. Each stage is executing for the time t1 a portion of the entire task in all stages with the exception of stage d, which requires the execution of a longer algorithm. At stage d, an identical circuit (or 3D-Flow processor) is copied 5 times (the number of times the circuit is copied corresponds to the ratio between the algorithm execution time and the time interval between two consecutive input data). A bypass switch (shown as a dotted right arrow in the figure) coupled to each processor in each 3D-Flow stage 1d, 2d, 3d, 4d, and 5d sends one datum packet to its processor and bypasses four data packets to the next stage. Thus, the execution time at each substation d will be $t_p=4(t1+t2+t3)+t1$. However, the result from any substation d will not be an input to the next station in d (as it is instead in a typical pipeline system such as the one at stage a, b, c, e, and f), but it will be passed on with no further processing in the 3D-Flow pipeline until it will exit and will encounter the next stage e of the standard pipeline system. The numbers inside the rectangles below the switch are the input data packets numbered in sequential order. Note that in the standard pipeline system in stages a, b, c, e, and f, the numbers are sequential, while in stages 1d, 2d, 3d, 4d, and 5d, the data remain in the same processor for five consecutive clock cycles. (See also Table 1 for sequence of operations during the previous clock cycles). Note that at stage 4d, while the processor is fetching a new datum i9, it is also sending the previous processed result r4 to the output.

Figure 19:
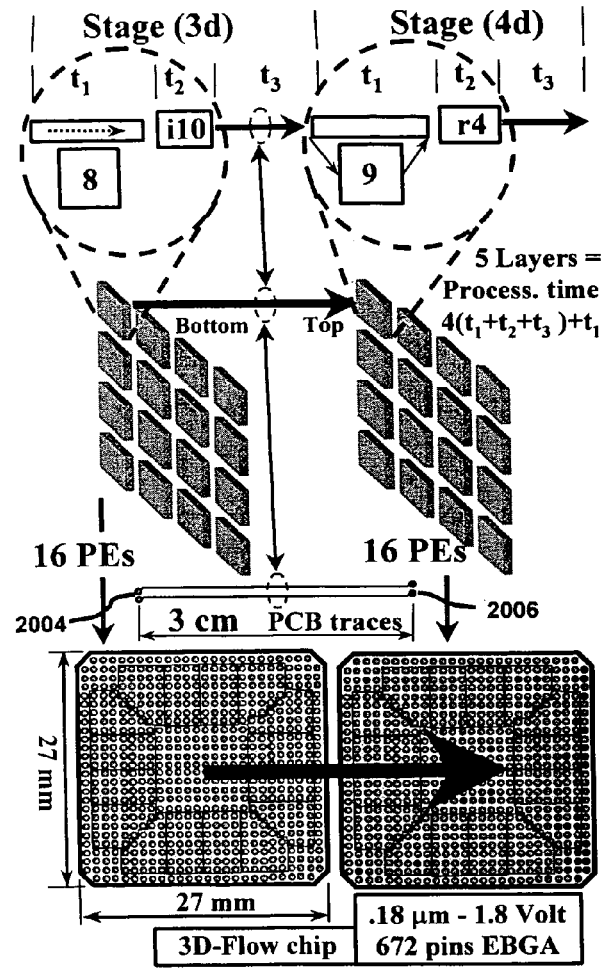

FIG. 19. Implementation merit of the 3D-Flow system The connection of the signals of the bottom port of one processor of the 3D-Flow architecture shown within the dashed line of FIG. 18 can be connected to the top port of the next processor (see solid horizontal arrow) with very short equal distance traces of 3 cm (See also bottom right of FIG. 2 and top left of FIG. 1 for the complete layout of 64 channels on an IBM PC board). All traces can be easily kept at the same length because during ASIC pin assignment design phase, to each pin carring an input for the top port, a signal of its equivalent bottom port has been assigned to its adjacent pin. The top section of the figure shows the detail of two stages of FIG. 18. (Note that one 3D-Flow processor consists of three units which are incorporated into the chip: a bypass switch, a register, and a processor). The middle section of the figure represents the logical layout of the 16 processors, which are accommodated into a single chip. The lower section of the figure shows how the connection is made between the bottom port of the processor in one chip and the top port of the processor on the adjacent chip via 3 cm PCB traces. Such component's layout and connections allow for a low power dissipation driver for a single load unit, reduced ground bouncing and noise, easy implementation of matched impedance PCB traces, reduced crosstalk and signal skew, easy construction of the PCB because of no crossing traces, and modularity that provides the advantage of using the same chip (by cascading them) for other configurations and/or applications with more complex algorithms, thus more layers of processors.

Figure 20:
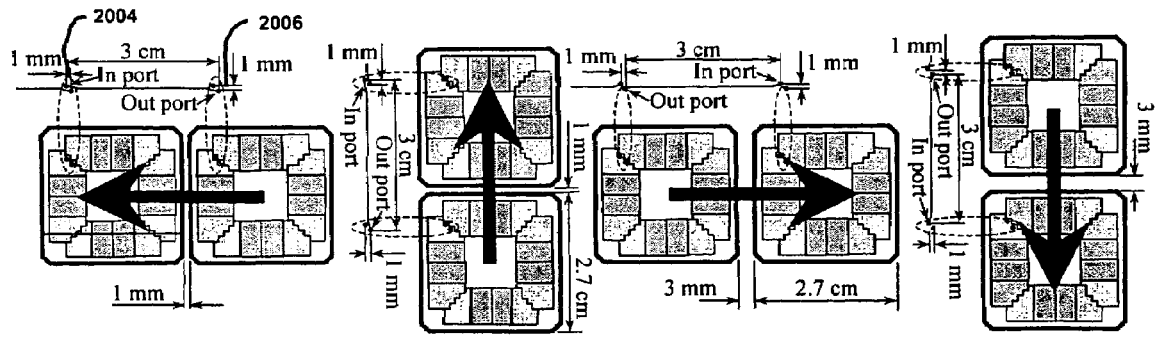

FIG. 20. Equal-length connections between bottom and top ports of two 3D-Flow processors located on adjacent chips. When input and output of a given port bit are assigned to adjacent pins, it is possible to obtain connections in any direction with uniform trace length as shown in the figure. (See the 3D-Flow components layout on the bottom right of FIG. 2). The 16 groups of input and output pins for each of the 16 processors in the chip are shown in the figure. The NEWS connections between on chip processors are not carried out to the pins.

Figure 21:
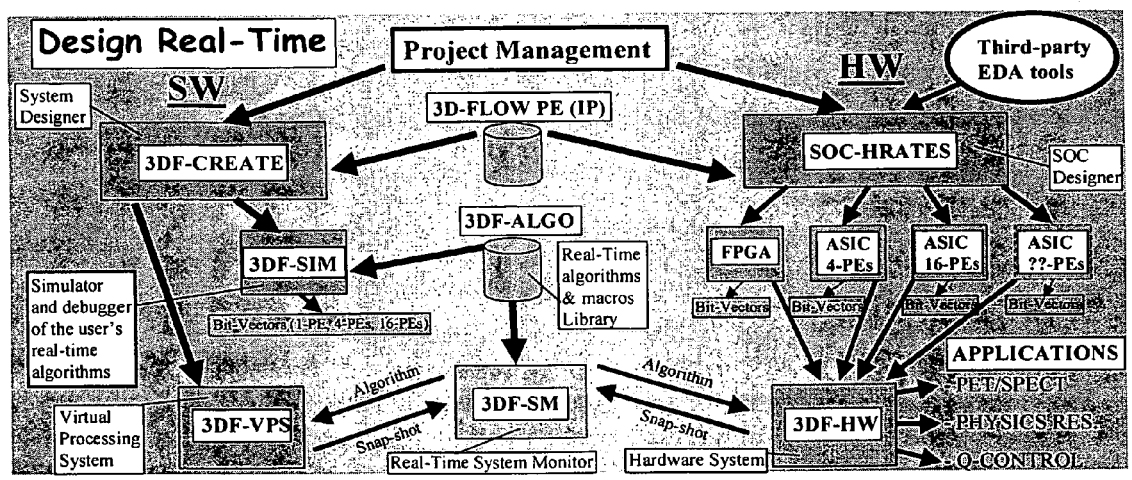

FIG. 21. Interrelation between entities in the Real-Time Design Process.

FIG. 22. Comparison between different implementation techniques with different throughput performance when executing real-time algorithms.

Figure 23:
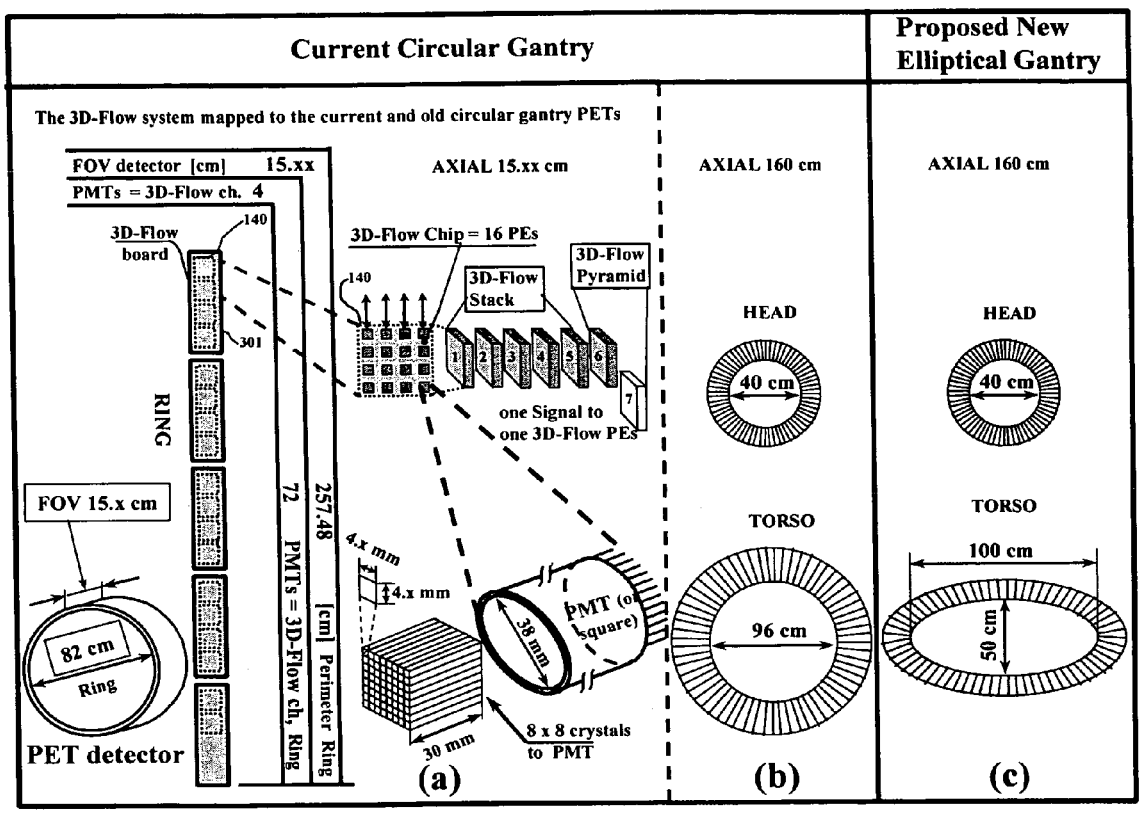

FIG. 23. Mapping the 3D-Flow system into PET imaging system. Section a) shows the layout of the 3D-Flow electronics for current and old PET devices, b) shows the dimensions of the PET rings using current circular gantry, and c) shows the dimensions of the PET rings using the proposed elliptical gantry.

Figure 24:
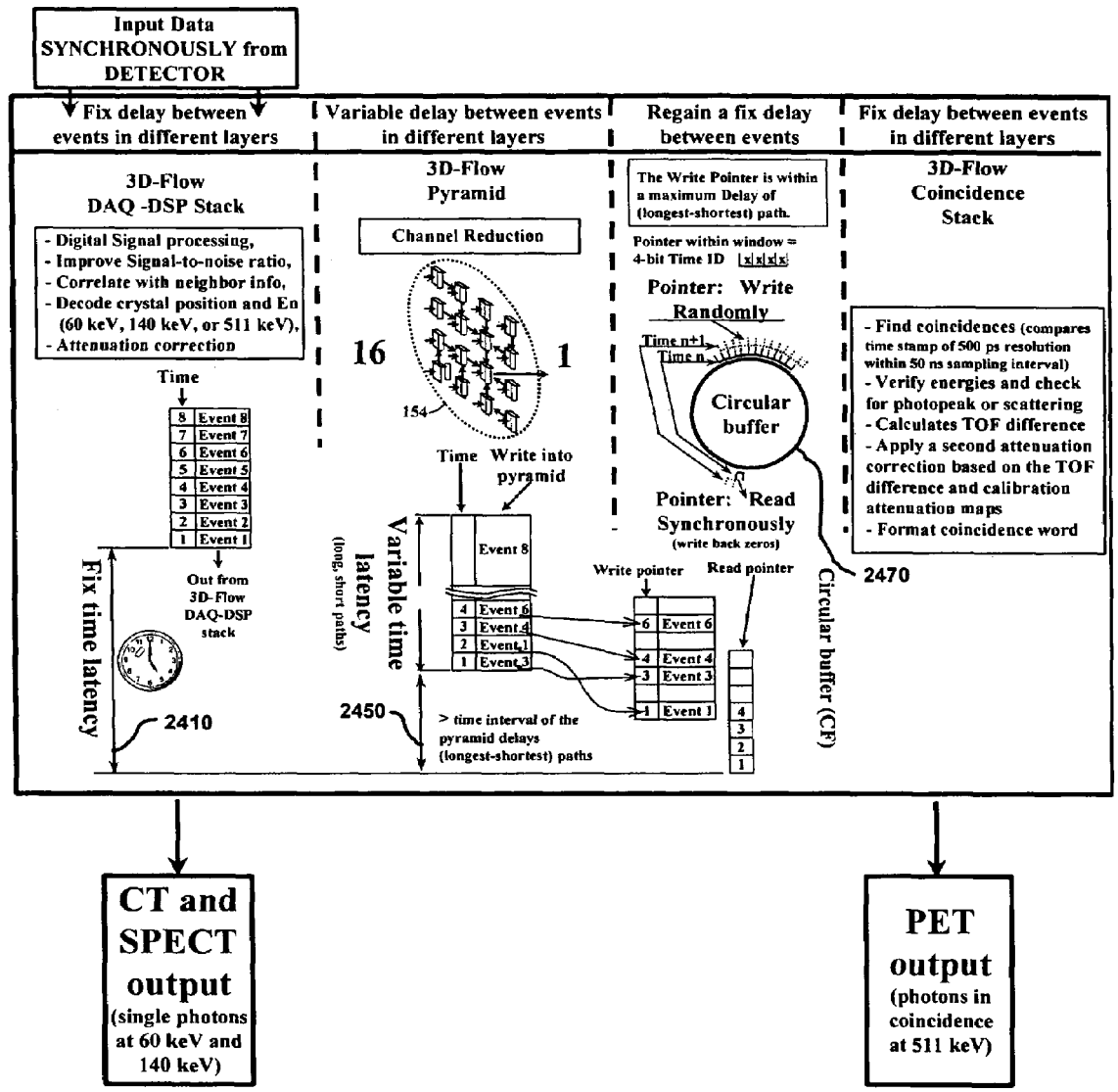

FIG. 24. Time latency between data at different layers of the 3D-Flow system.

Figure 25:
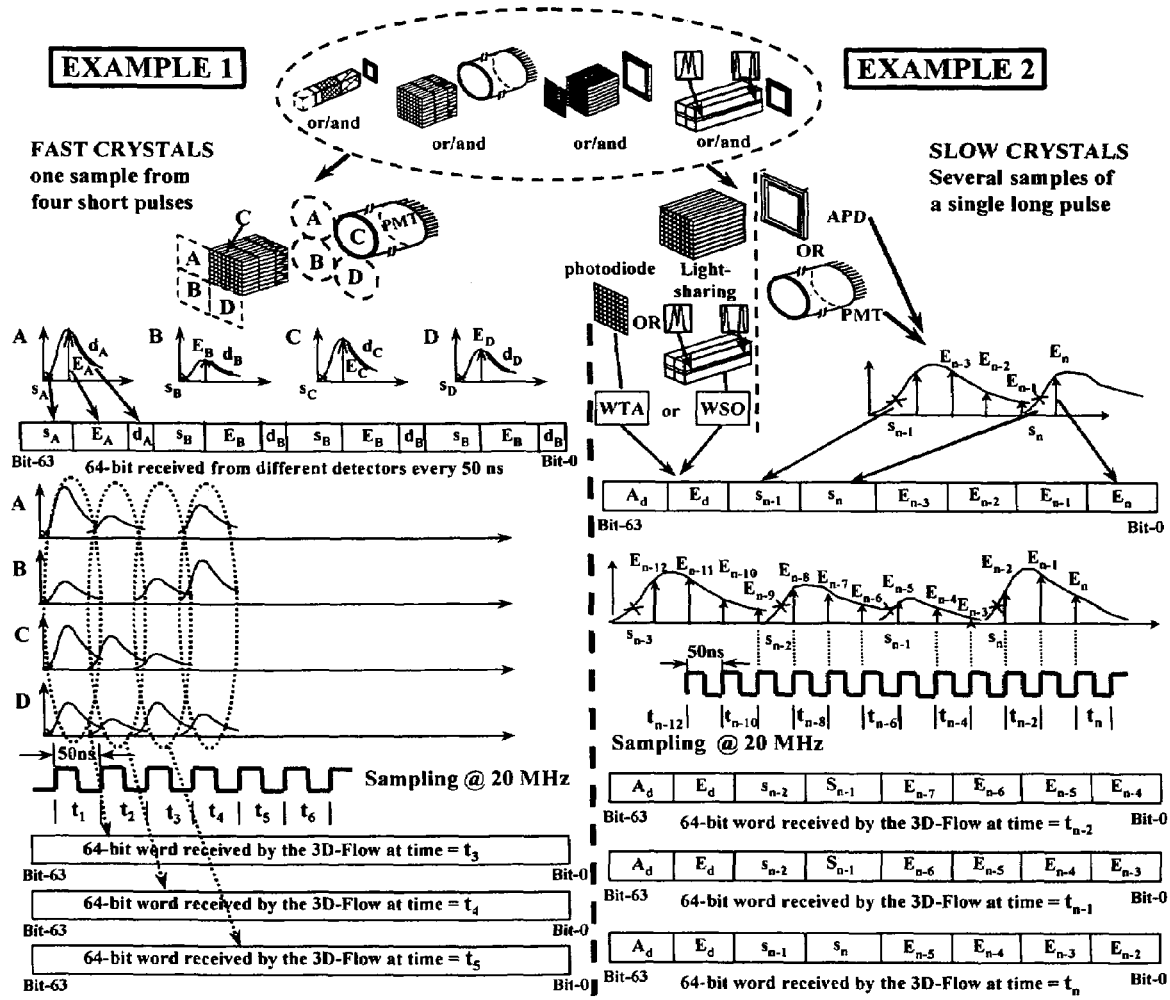

FIG. 25. Examples of acquiring data by the 3D-Flow system, from the detector.

Figure 26:
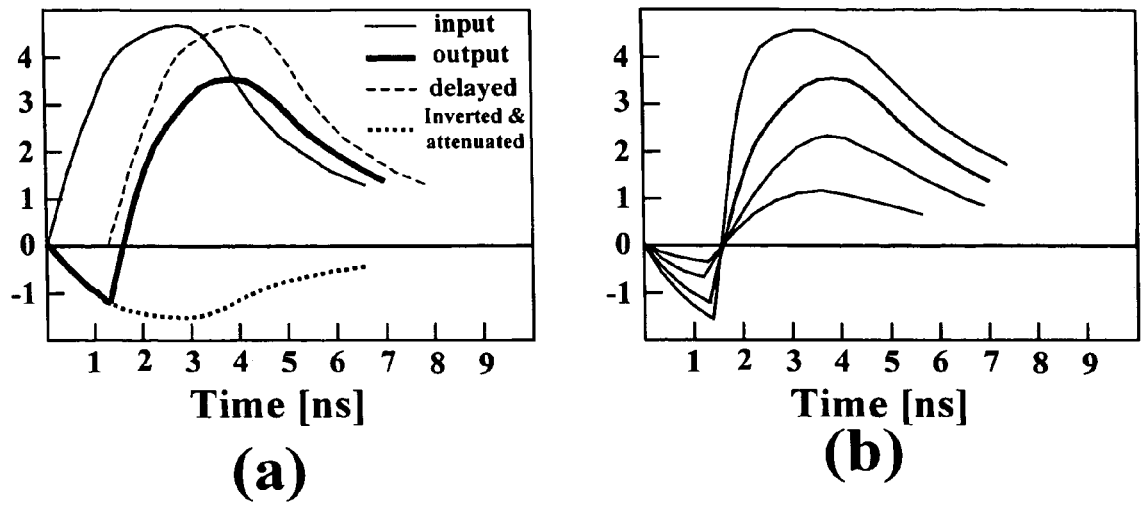

FIG. 26. Constant fraction discriminator (CFD). Section (a) shows the relation between the output signal and the input signal and the intermediate steps of the delayed, inverted, and attenuated signals. Section (b) shows the zero crossing of signals with the same shape but with different amplitude occurring at the same time.

Figure 27:
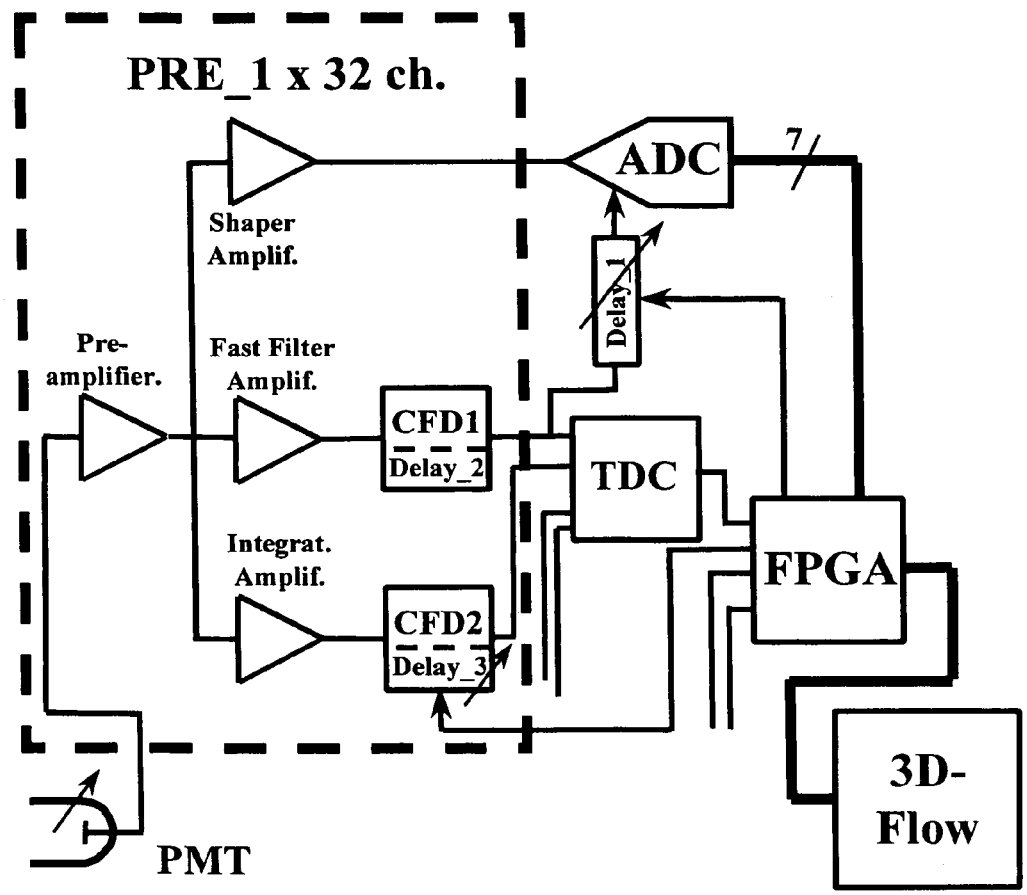

FIG. 27. Block diagram of the front-end electronics for the fast crystals.

Figure 28:
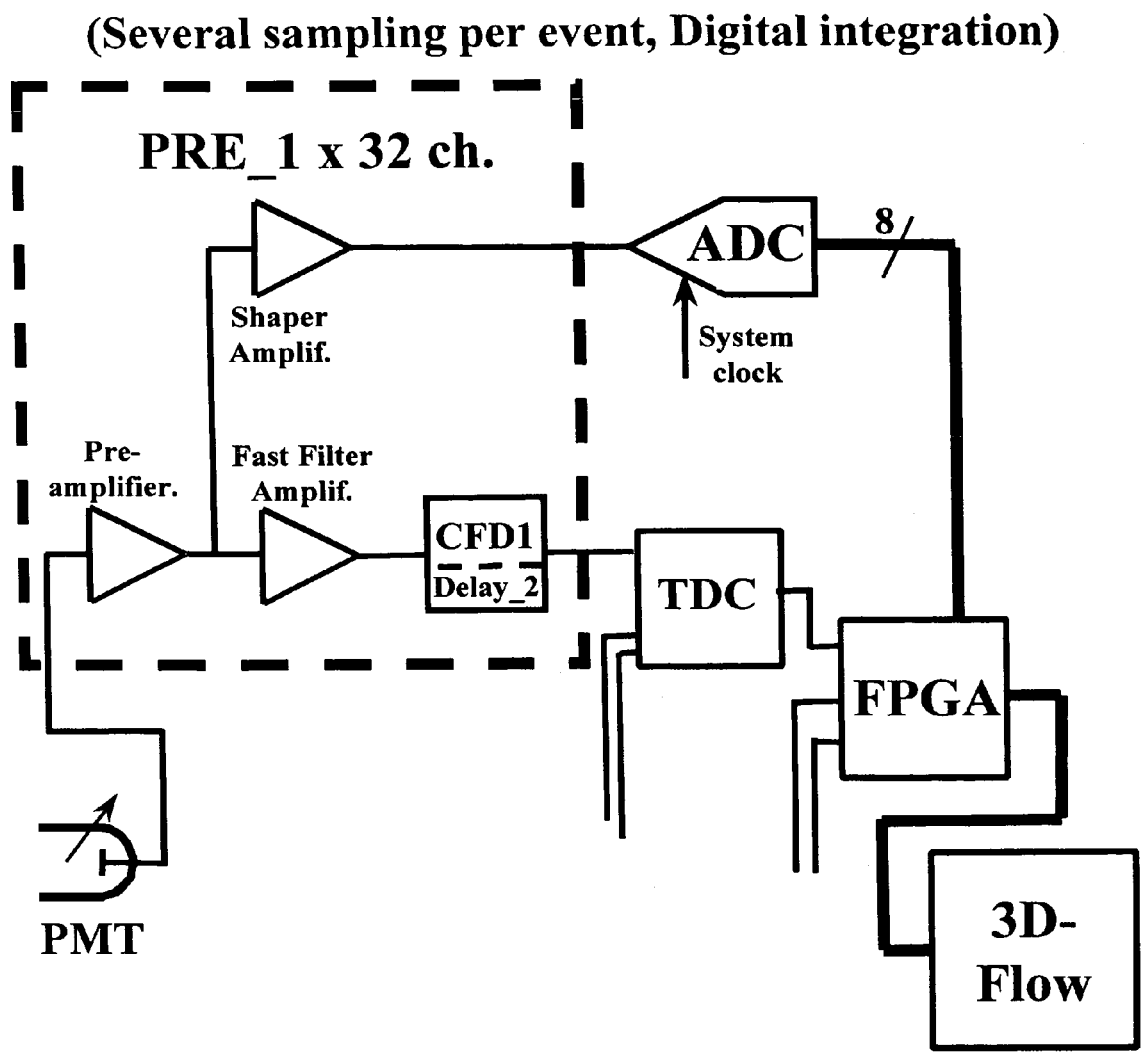

FIG. 28. Block diagram of the front-end electronics for the slow crystals.

FIG. 29. Randoms.

Figure 30:
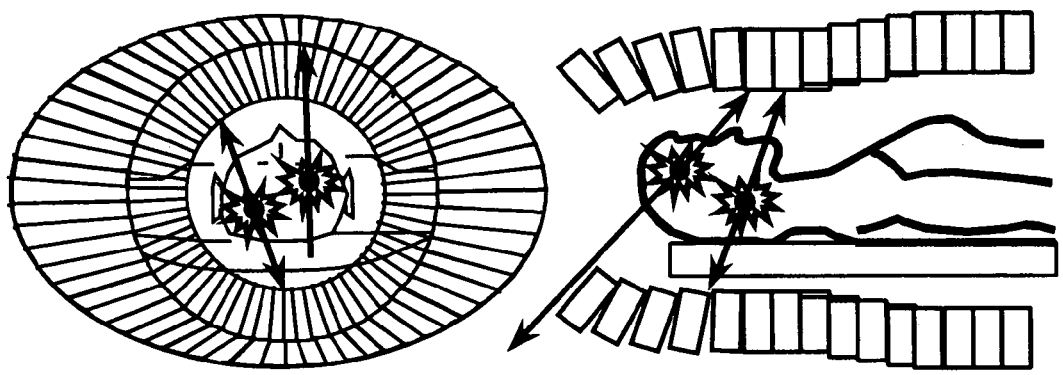

FIG. 30. Multiples.

Figure 31:
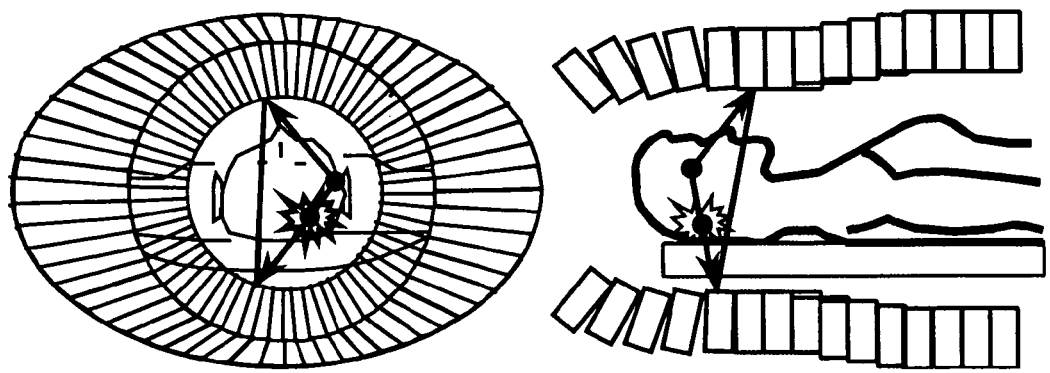

FIG. 31. Compton Scatter.

Figure 32:
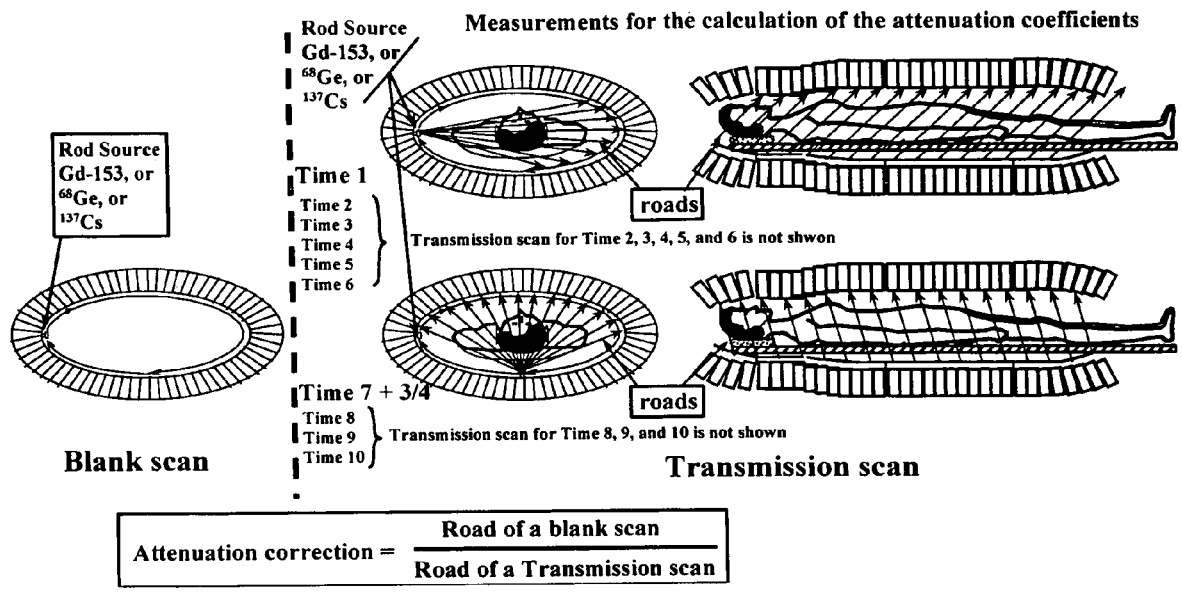

FIG. 32. Measurements of the attenuation correction for PET and determination of attenuation coefficients.

FIG. 33. Comparison of the centroid calculation method using the 3D-Flow and the current PET systems.

Figure 34:
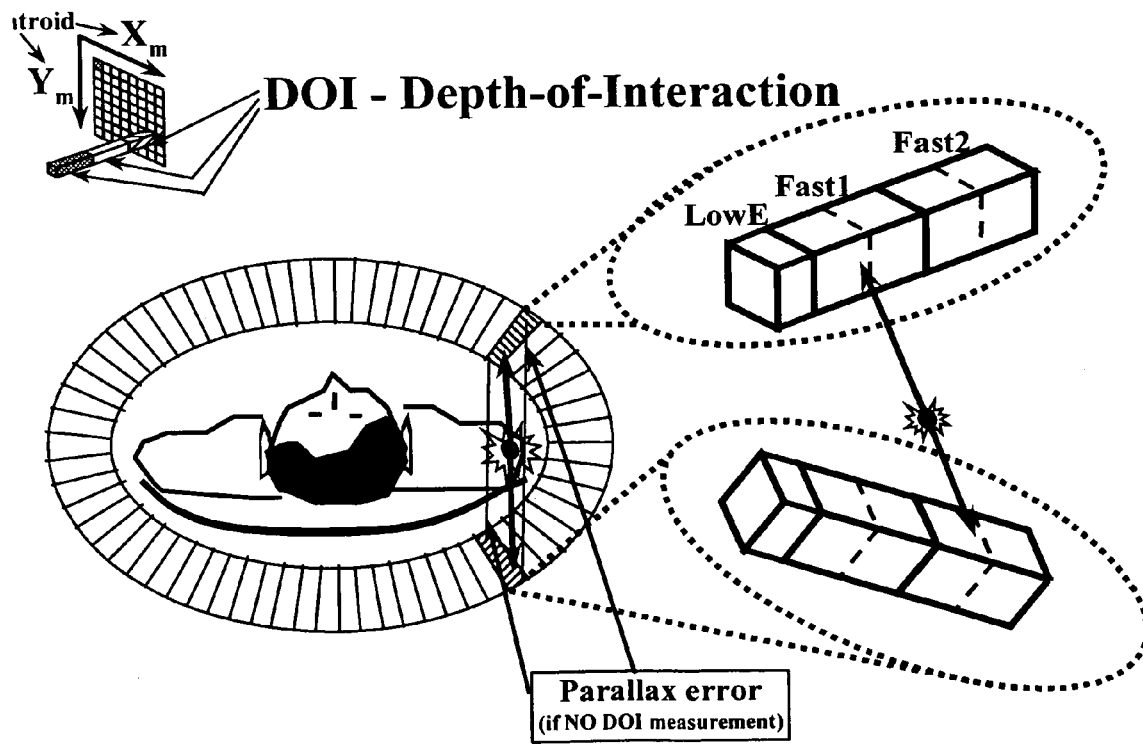

FIG. 34. Parallax error measured by the Depth of interaction.

Figure 35:
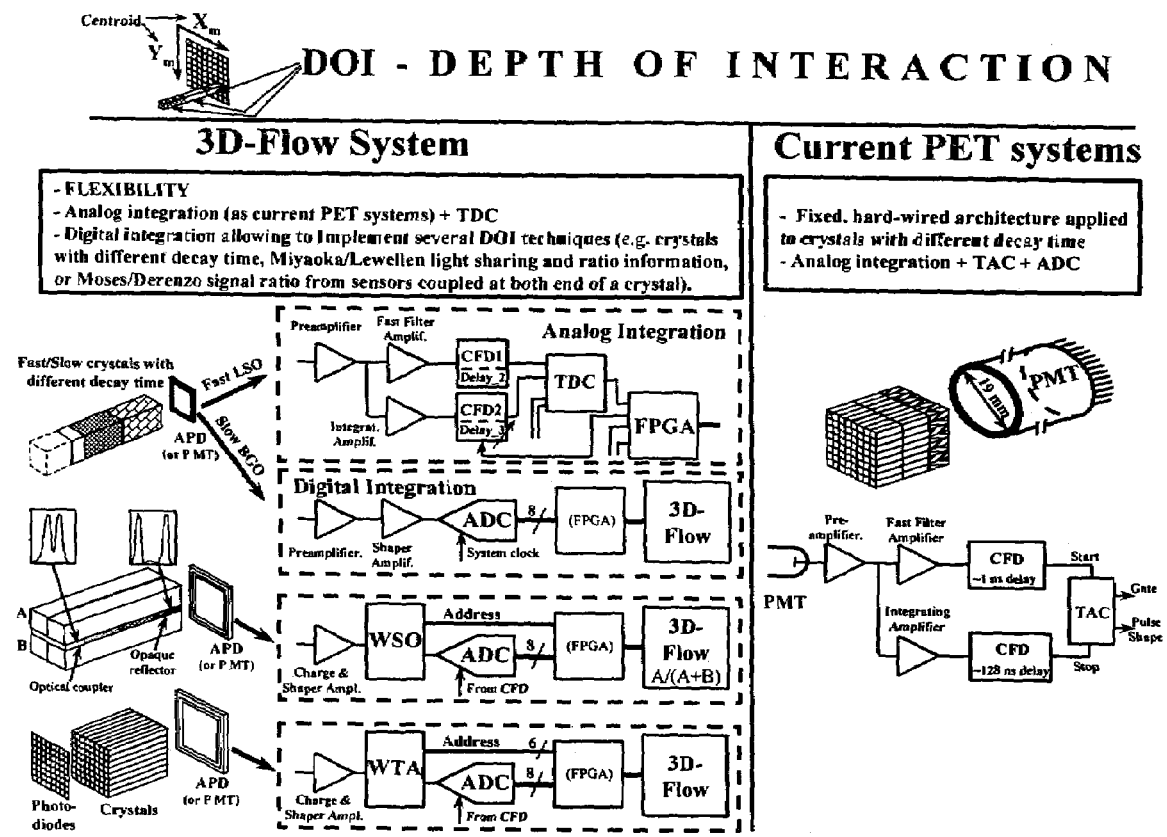

FIG. 35. Flexibility of DOI measurements with the 3D-Flow vs. fix technique used by current PET systems.

Figure 36:
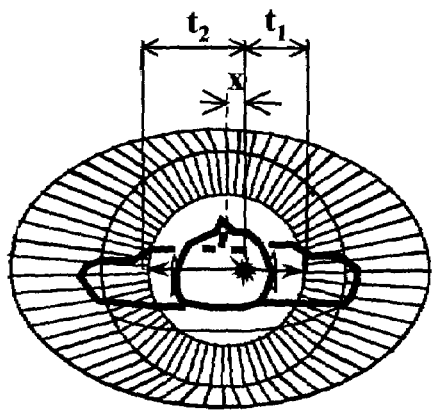

FIG. 36. Time resolution of 500 ps for PET devices assisted by TOF information.

FIG. 37. Calibration of the PET system.

FIG. 38. Photon detection detection algorithm simulation with the 3D-Flow for PET/SPECT/CT.

FIG. 39. 3D-Flow simulation of the 5×5 clustering algorithm in 9 steps.

Figure 40:
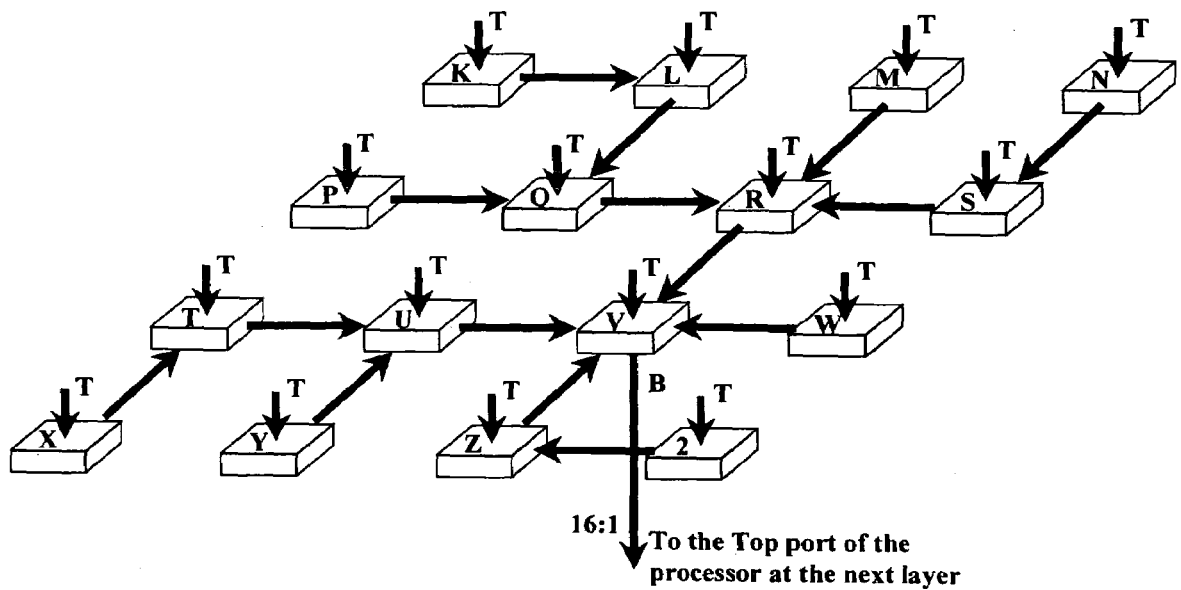

FIG. 40. Channel reduction scheme of the 3D-Flow pyramid.

Figure 41:
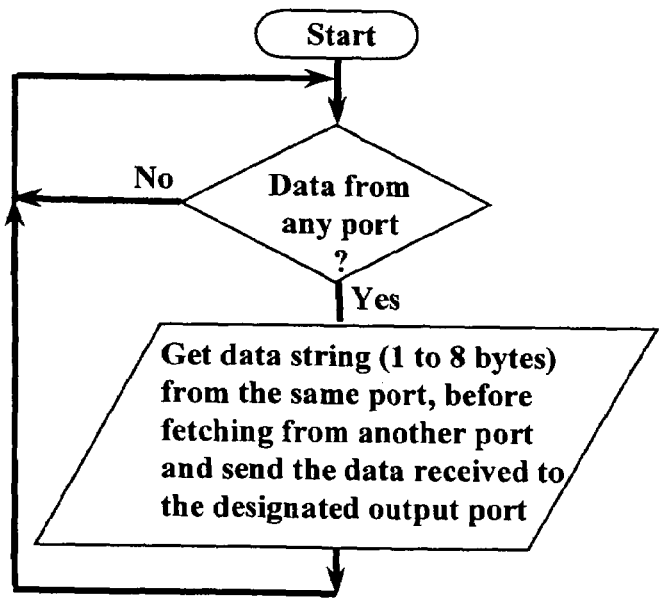

FIG. 41. Flow chart of the 3D-Flow program routing data in the pyramid.

Figure 42:
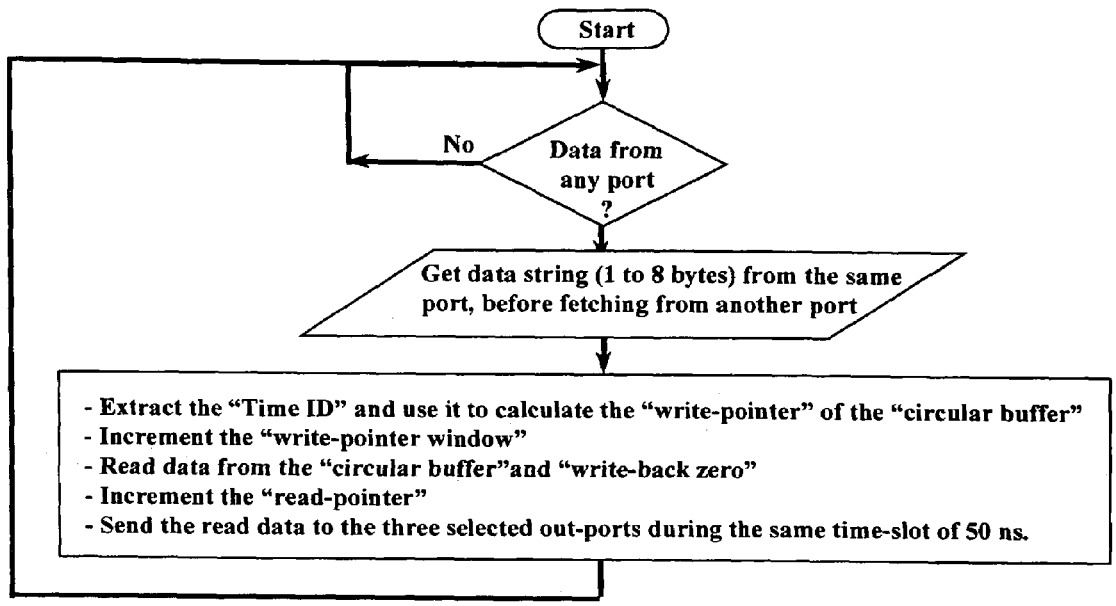

FIG. 42. Sequence of operations for the implementation of the circular buffer for sorting and regaining fixed latency of events.

FIG. 43. Sorting the events in the original sequence and regaining a fixed delay of the data between stages.

Figure 44:
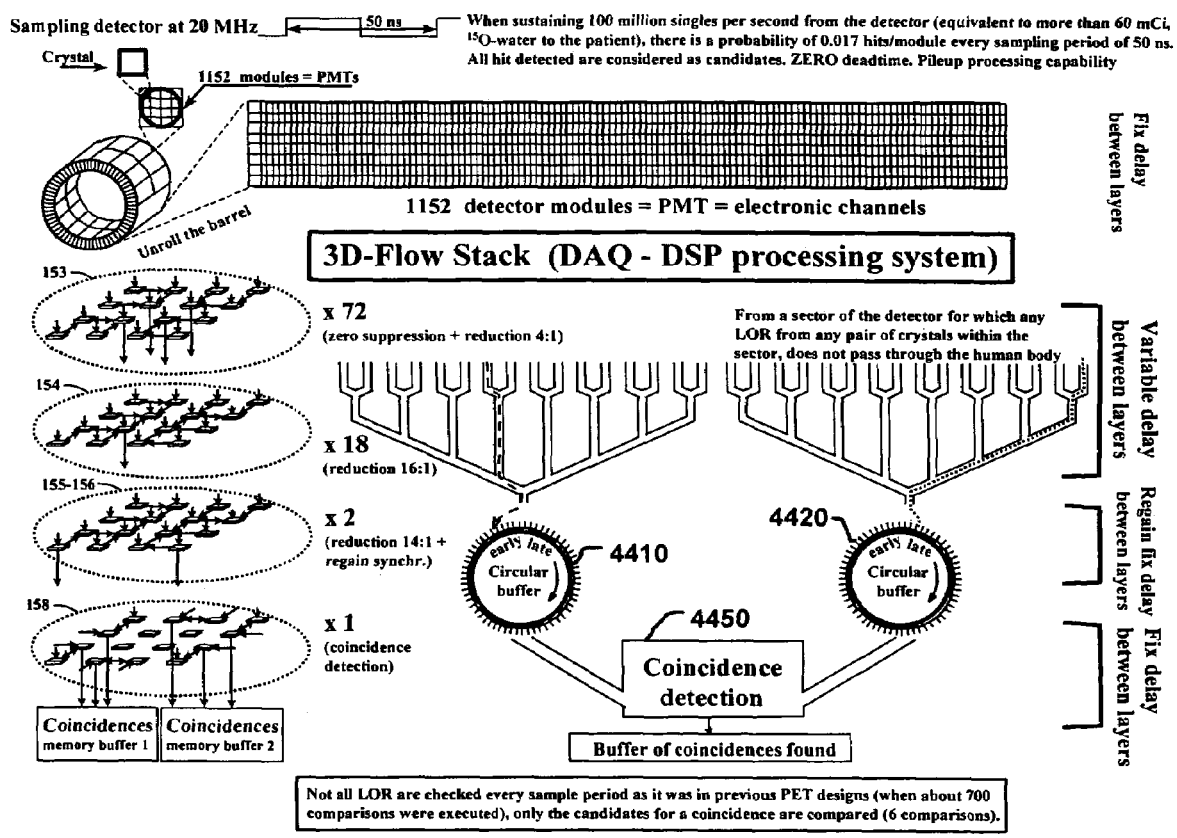

FIG. 44. Coincidence detection scheme with the 3D-Flow approach. Only the candidates found within a time of 50 ns are compared (no more than 4 are expected for a radioactive dosage not hazardous to the patient). The candidates from different detector blocks may require different numbers of clock cycles to reach the exit point; thus a sorting/resynchronizing circular buffer realigns the events in the original sequential order and within a fixed delay time from when they occurred. The left part of the figure shows how many types of 3D-Flow components are required to implement the different functions.

Figure 45:
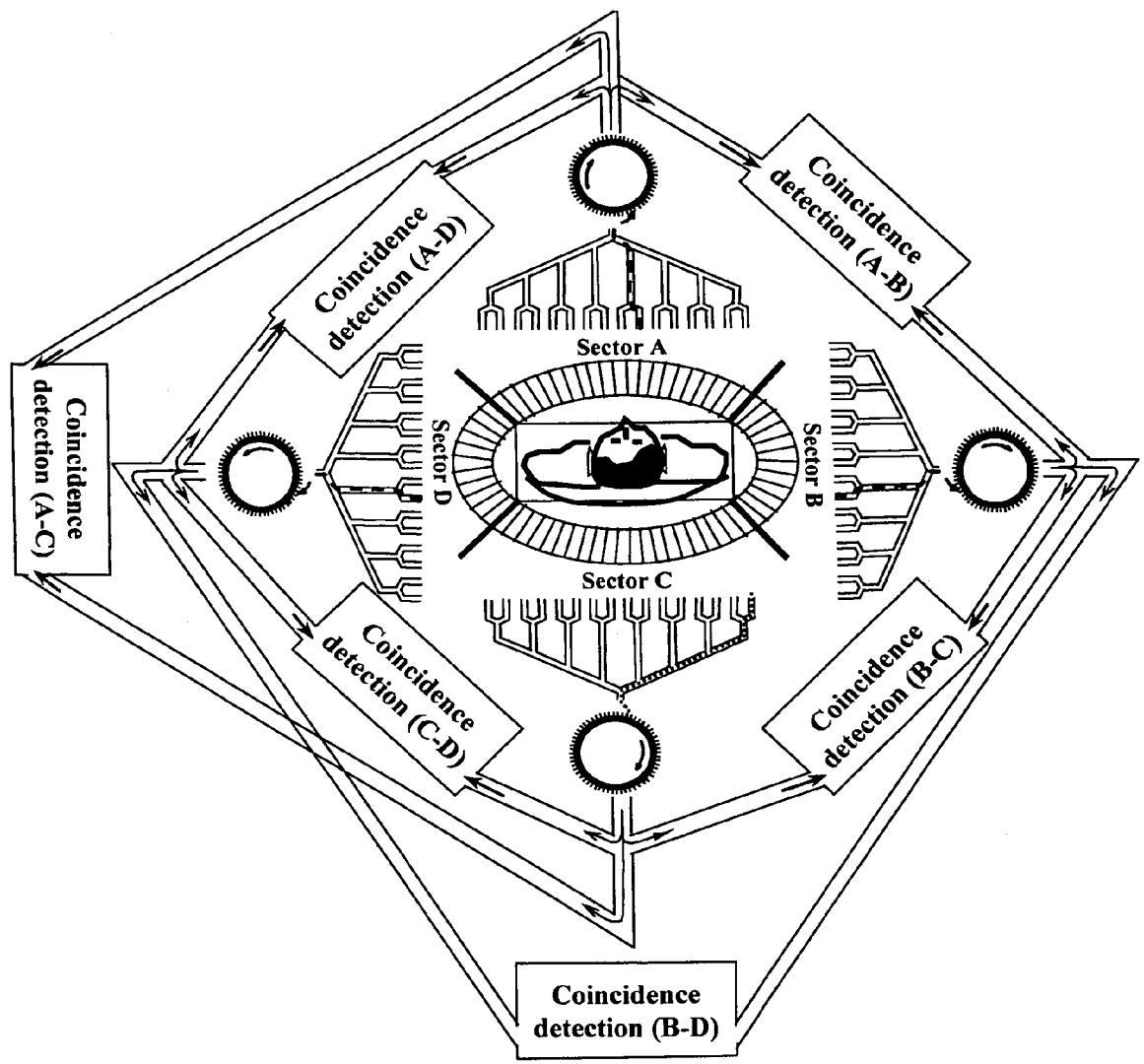

FIG. 45. Definition of sectors for the detection of coincidences in PET mode.

Figure 46:
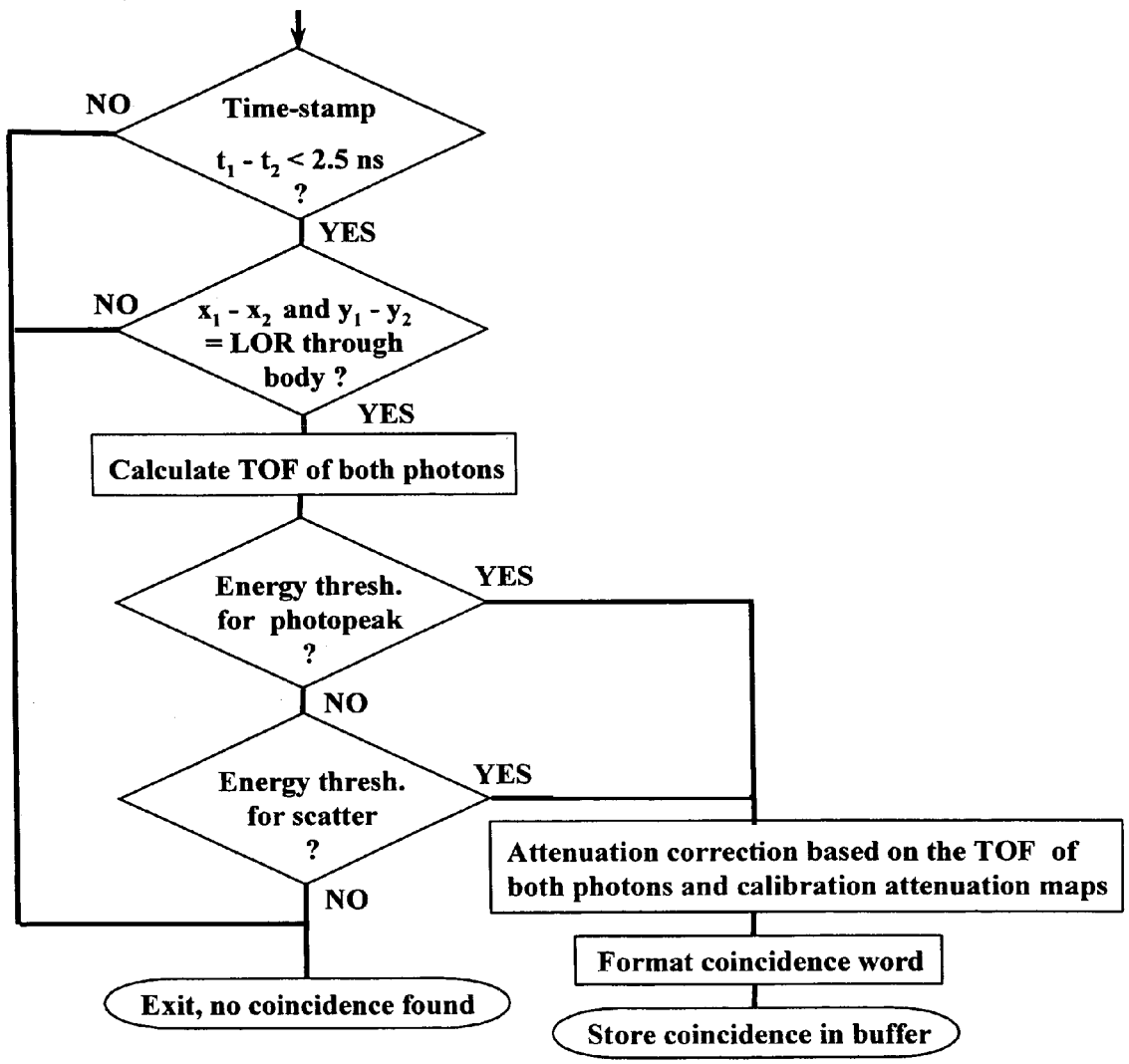

FIG. 46. List of operations performed in the processors of component 158.

Figure 47:
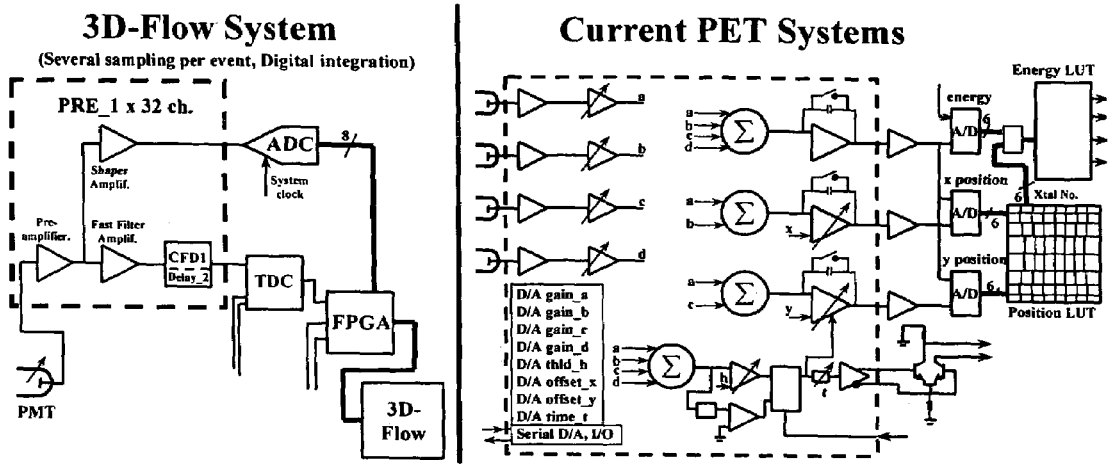

FIG. 47. Digital Signal Processing vs. Analog Signal Processing Front-End for PET with digital signal integration.

Figure 48:
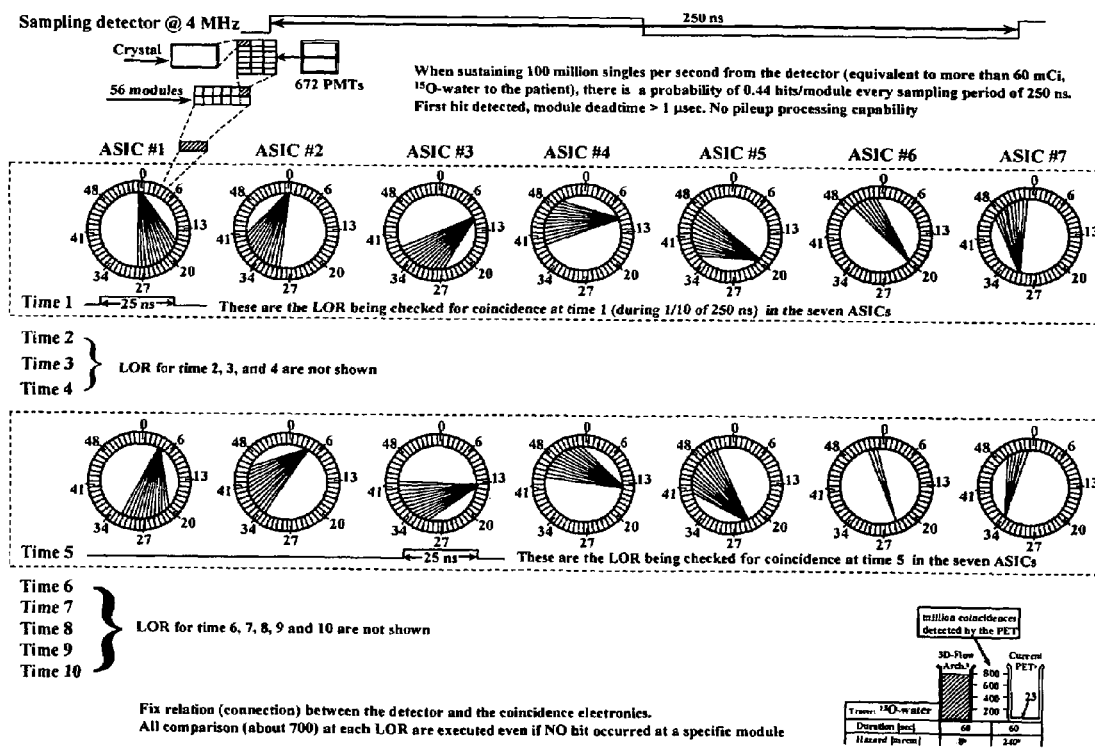

FIG. 48. LOR checked for coincidence as implemented on the GE Advance. Data from 56 detector modules are sent to 7 ASICs according to the connection scheme reported in Table 6-4. Each ASIC performs 13 comparisons each time slot of 25 ns. The first row of the figure indicated with "Time 1" shows the detector modules that are compared (e.g. at top left of Time 1, module 0 is compared with module 16, then with 17, and so on). The figure shows only the comparisons along the line of response LOR during Time 1 and Time 5.

Figure 49:
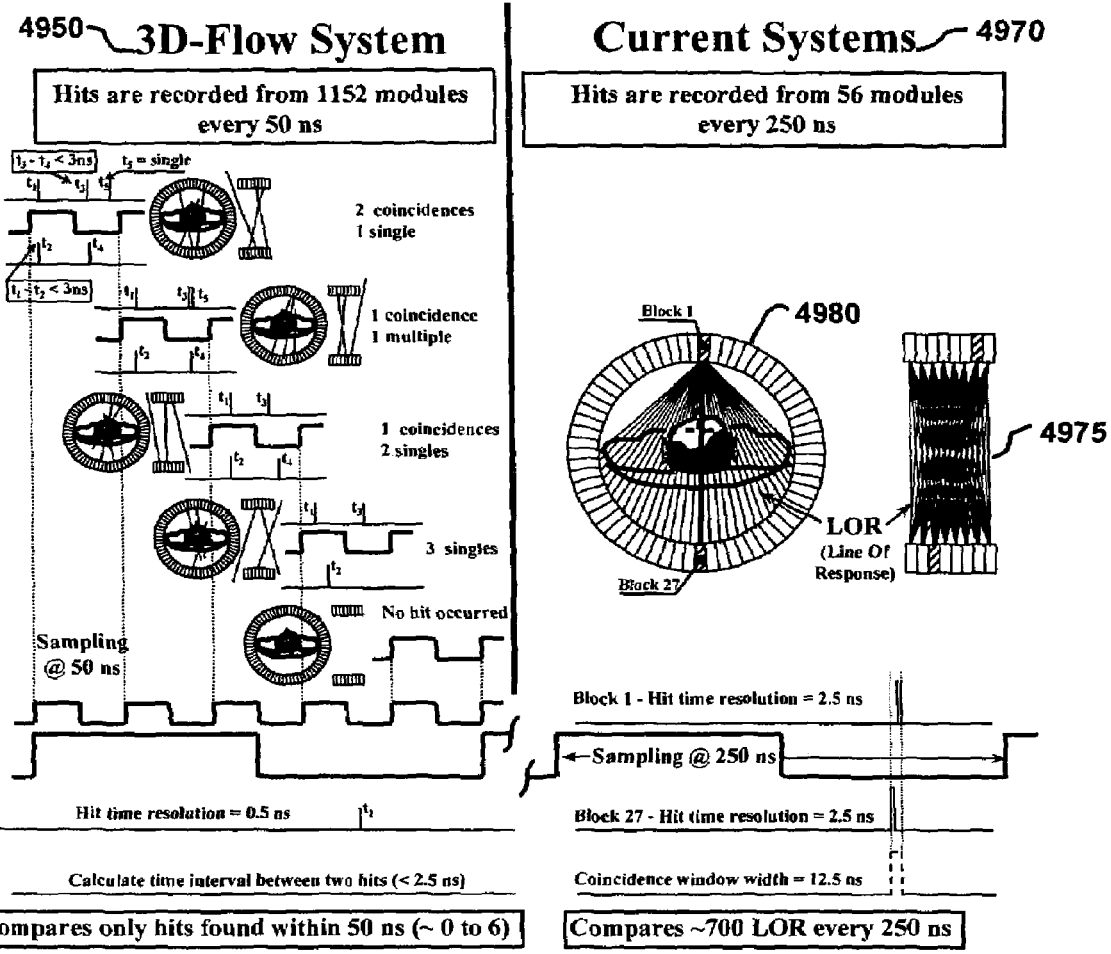

FIG. 49. The 3D-Flow PET coincidence detection approach vs. the current approaches to find coincidences in PET.

FIG. 50. 64 channels IBM PC compatible 3D-Flow board. One analog channel to one 3D-Flow processor.

FIG. 51. 256 channel IBM PC compatible board; four analog channels to one 3D-Flow processor.

Figure 52:
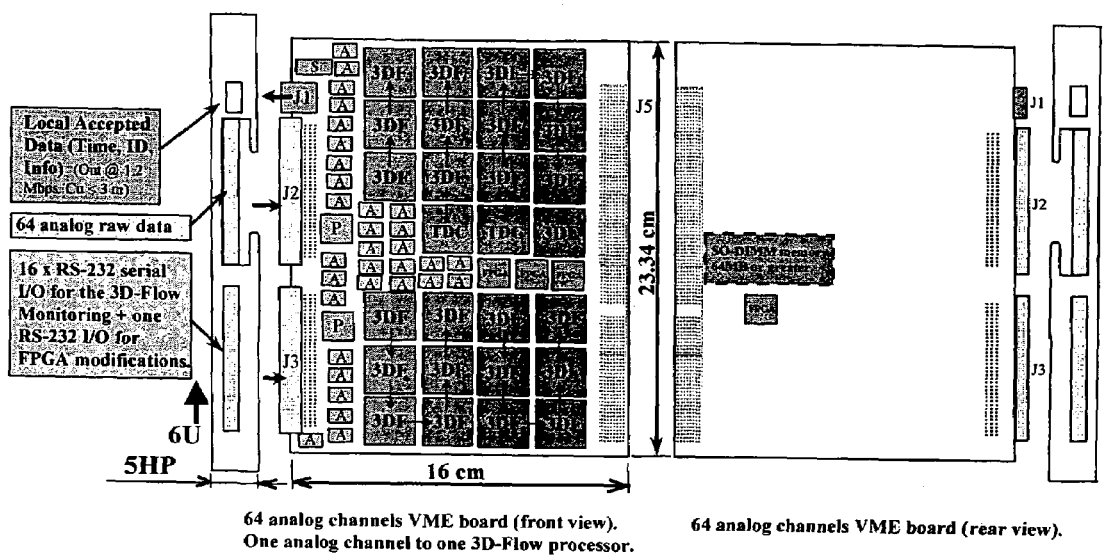

FIG. 52. 64 channel VME board; one analog channel to one 3D-Flow processor.

Figure 53:
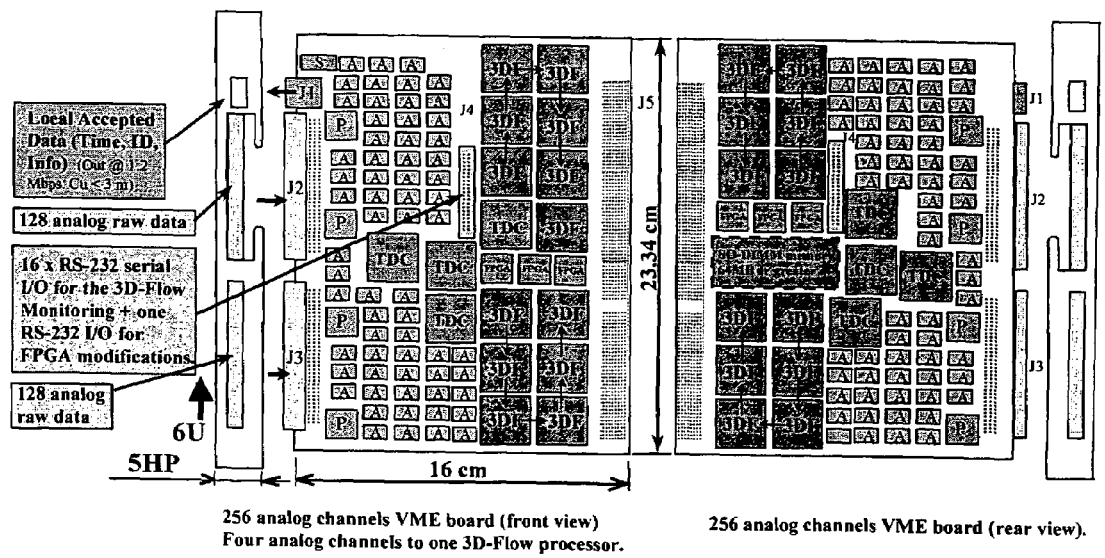

FIG. 53. 256 channel VME board; four analog channels to one 3D-Flow processor.

FIG. 54. IBM PC 3D-Flow Pyramid board for channel reduction, event sorting, and coincidence detection.

FIG. 55. VME 3D-Flow Pyramid board for channel reduction, event sorting, and coincidence detection.

FIG. 56. Backplane carrying the information to/from the neighboring 3D-Flow processors.

Figure 57:
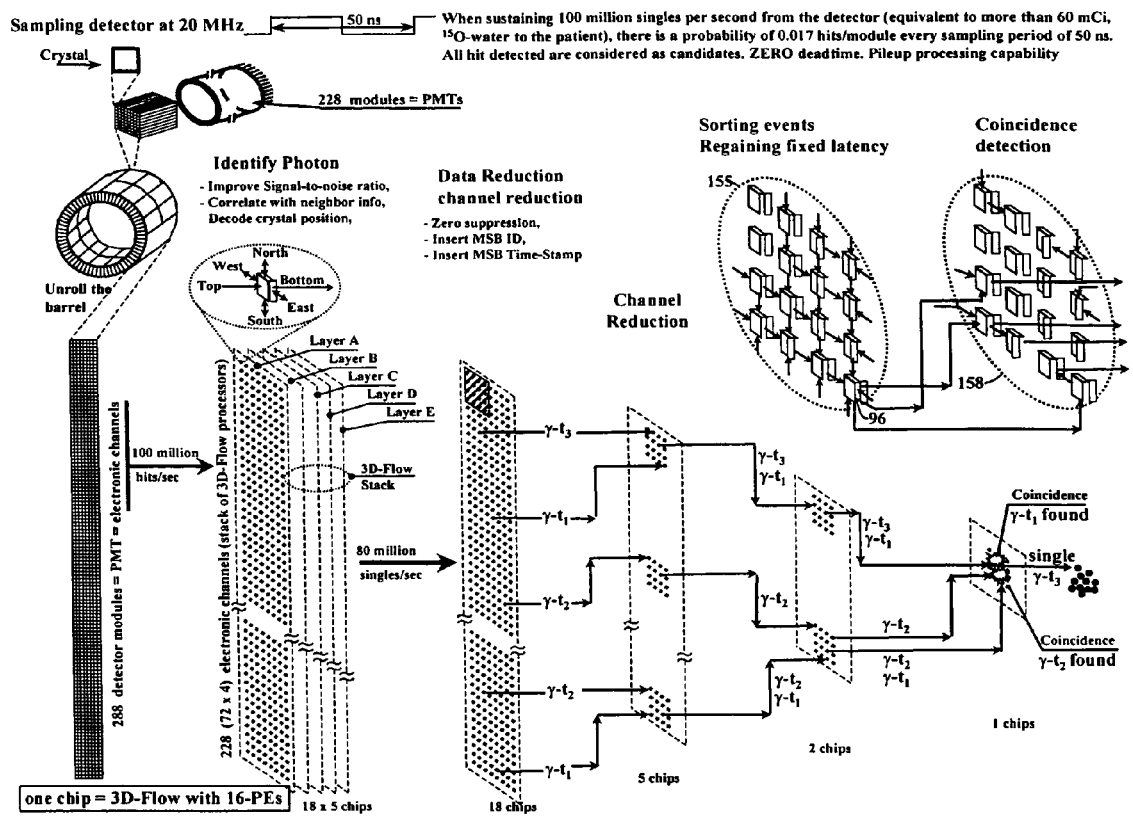

FIG. 57. Logical layout for a 3D-Flow system replacing the electronics of the current and past PET for lowering the cost and the radiation to the patient.

Figure 58:
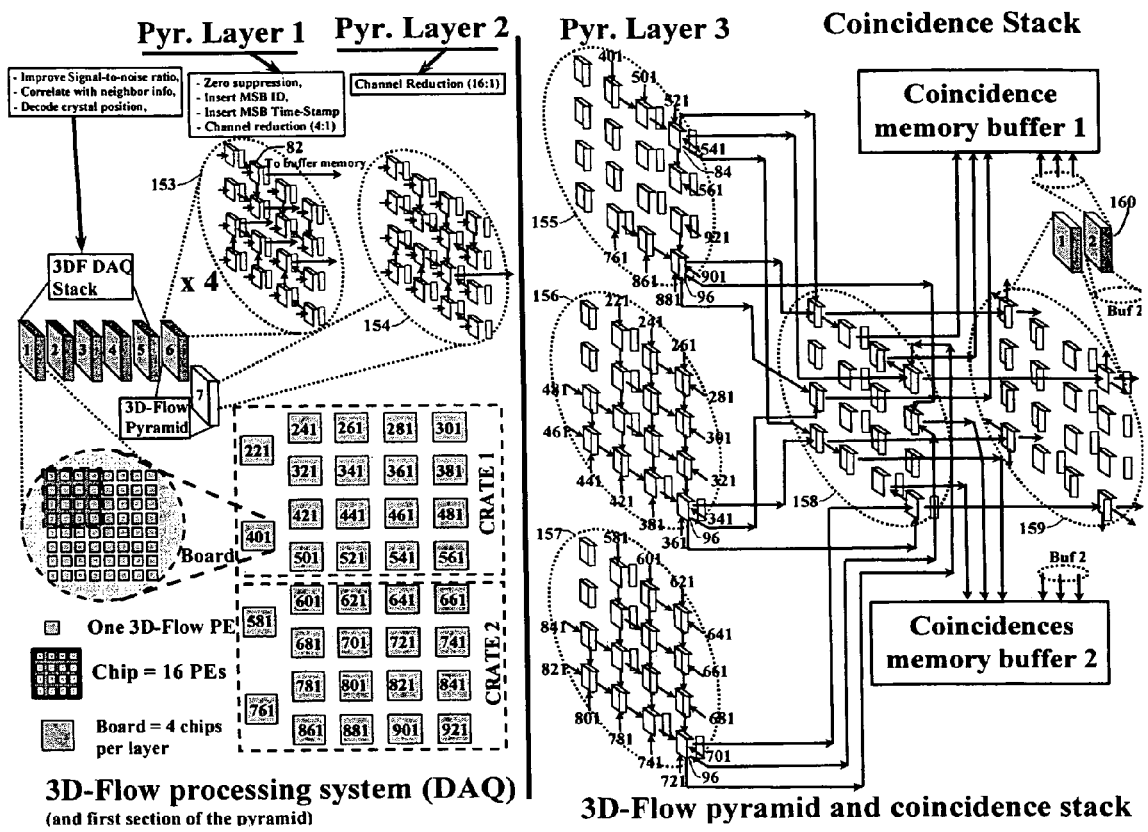

FIG. 58. Logical layout for a PET/SPECT/CT system requiring high performance for extracting photon characteristics from slow crystals.

Figure 59:
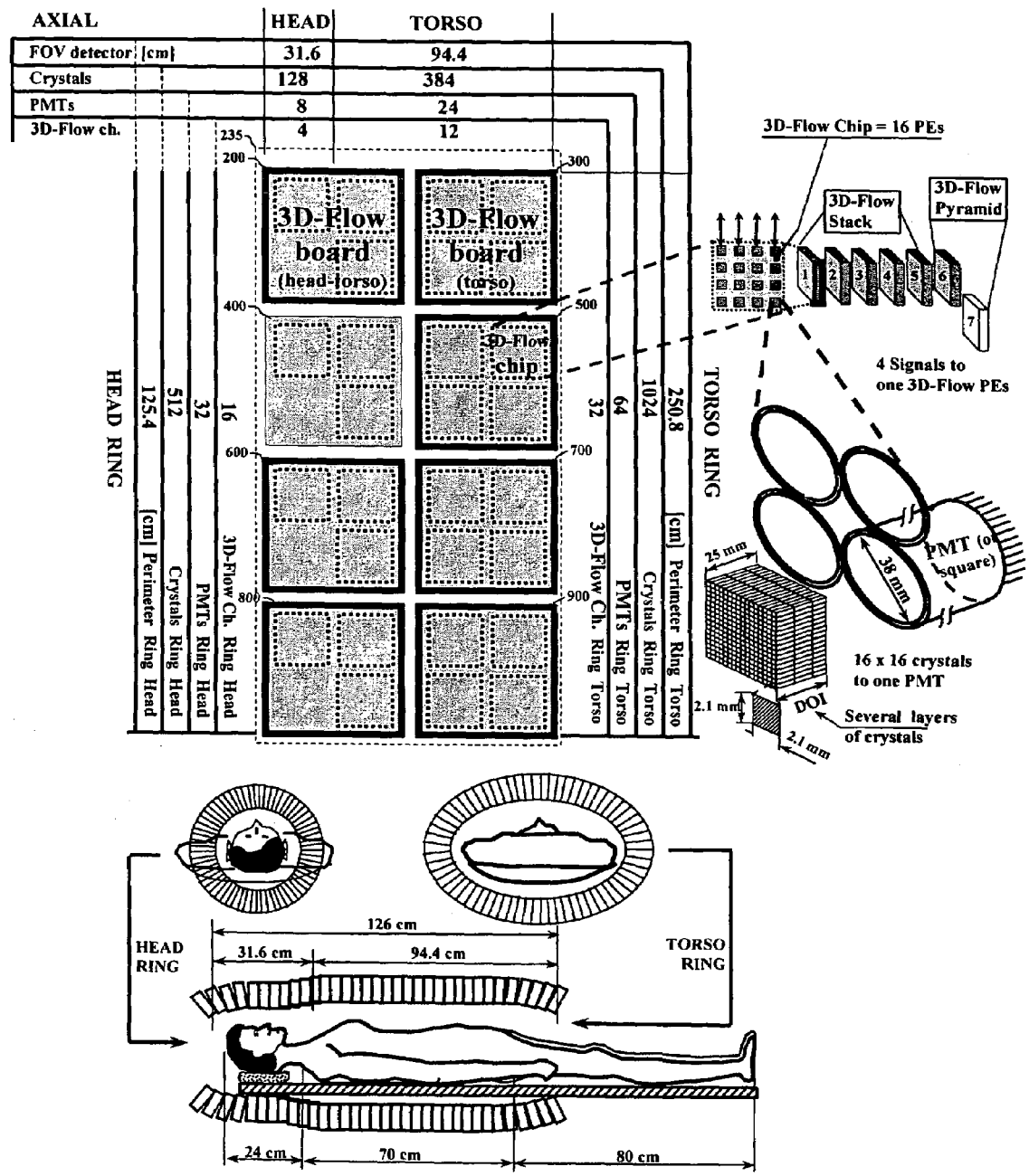

FIG. 59. Logical and physical layout for a PET/SPECT/CT system using fast crystals FIG. 60. Logical and physical layout for a 3-D Complete Body Scan (3D-CBS) for 2,304 channels FIG. 61. Layout for the hardware assembly of the 3-D Complete Body Scan (3D-CBS) for 2,304 channels.

Figure 62:
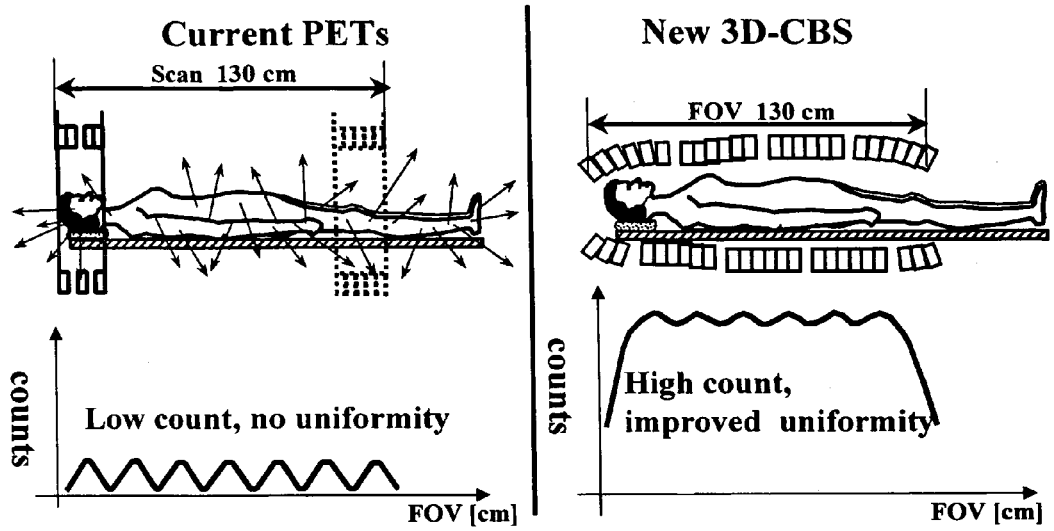

FIG. 62. Higher counts and improved uniformity of the 3D-CBS in detecting back-to-back pairs of photons in time coincidence from different areas of the body. Each small triangle at the bottom left of the figure is the sensitivity of the scanner without septa for a different position as measured by Karp et al. in FIG. 6 of [34].

Figure 63:
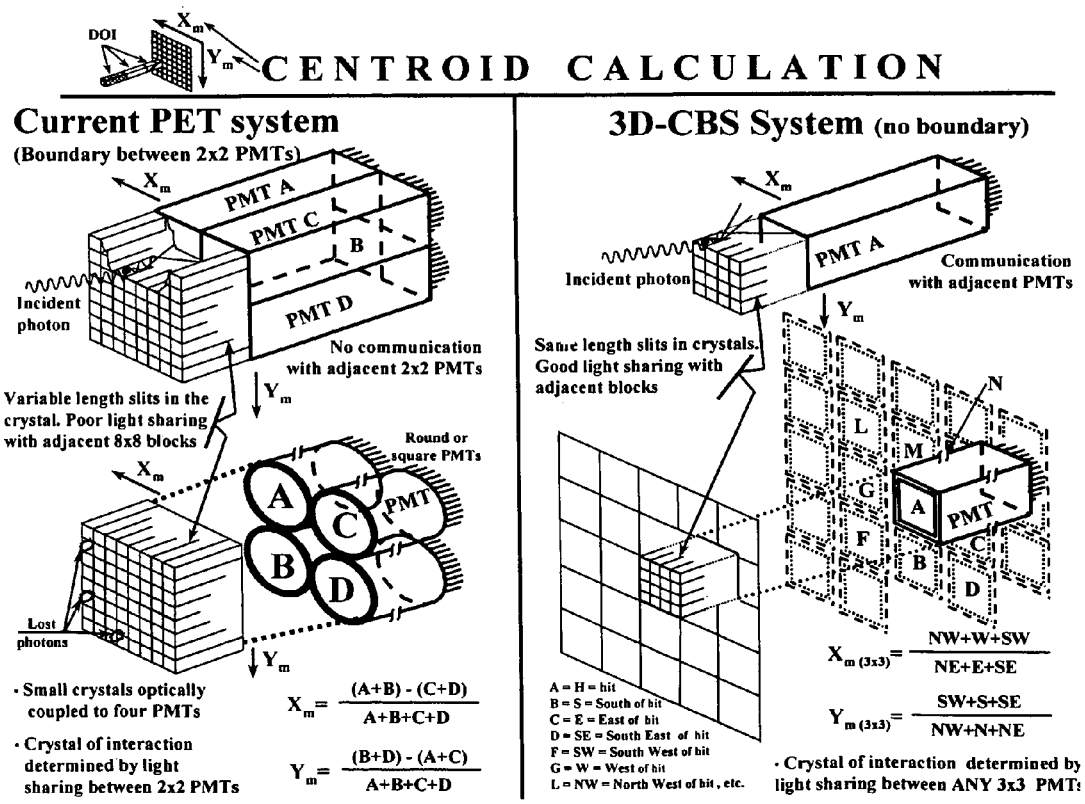

FIG. 63. Comparison of the assembly of the 3D-CBS crystals coupled to the PMT (or APD) sensors allowing centroid calculation with no detector boundary limitation vs. the detector assembly of current PET which has a 2×2 PMTs (or module) detector boundary limitation. The block detector of current PET (figure at left) consists of four 4 PMT tubes coupled to a set of crystals (64 in the example of the figure). The variable lengths of the slits (made of reflecting material) in the crystal act like a light guide that allows more or less light sharing between the four PMTs. The long slits of reflecting material at the edges of the 8×8 crystal block allow minimal or no light sharing between adjacent 8×8 crystal blocks (or 2×2 PMT blocks). The identification of the crystal of interaction in the 2×2 PMT block is made through the Anger logic shown at the bottom right of the figure. The crystals at the edges and corners of the 8×8 crystal block contributes a smaller signal compared to the inner crystals, making their identification more difficult (see measurements on FIG. 3 of [33]). The 3D-CBS assembly (figure at right) solves these problems by permitting all crystals to have the same degree of light sharing with adjacent crystals with slits of equal length. This allows for sharing the light with adjacent PMTs in the four directions with no boundaries. The interconnections in the North, East, West, and South directions of the electronic channels of the 3D-Flow system allow any PMT receiving the highest signal to be identified as the center of a 3×3 (or a 5×5) cluster which then rebuilds the total energy of the incident photon by summing all the adjacent signals and by calculating the centroid as show at the bottom of the figure (figure at right).

6 DETAILED DESCRIPTION OF THE INVENTION

6.1 Multimodality: Design of a Multimodal PET/SPECT/CT 3D-Flow Based System

6.1.1 Description and Requirements of a Multimodality PET/SPECT/CT Device

The combination of several medical imaging modalities in a single device is referred to as multimodality. It helps the physician in clinical examinations to see in a single image several pieces of information which before could only be acquired by having the patient go through several medical examinations.

The combination of the PET device with an x-ray-computed tomograph (CT) scan provides, by means of the CT, the anatomical information that helps to identify the organs in the body, and it provides, by means of the PET, the functional information that provides real-time imaging of the biological process at the molecular level. (In some area, such as the one showing increased brain activity caused by sensorimotor or cognitive stimuli, functional Magnetic Resonance Imaging (fMRI), shows image contrast in regions where oxygen is highly extracted from blood by using the property that oxyhemoglobin is a strongly paramagnetic molecule. However, MRI is mainly anatomical, while PET is only functional and the best for oncology studies [15]).

The Single Photon Emission Computed Tomography (SPECT) medical imaging device uses tracers emitting a single photon, and thus requires a collimator placed in front of the crystals that acts like a lens in an optical imaging system. One way to implement a collimator is to have multiple parallel (or converging) holes in lead material allowing the photons travelling with the desired acceptance angle to pass through the holes to interact with the crystals. The dominant factor affecting image resolution in SPECT is the collimator.

The PET functional device has clear advantages over the SPECT and the dual-head camera. A dual-head camera (which can have SPECT and PET capabilities), instead of a full ring of detectors, has only two modules of detectors (or heads) on the two sides of the subject (the body of the patient) who had received a radiotracer by injection or inhalation. Thus, the dual-head camera has a limited detector area capable of capturing the emitted photons. The comparison between PET, SPECT and dual-head cameras has been made in reference [35]). The advantages of the PET result from its technique of the electronic collimator detecting two photons emitted in opposite directions at the same instant, as opposed to the SPECT technique of the hardware lead collimator.

It is possible to combine PET and SPECT in a single multimodal device which has several parts in common (detector, mechanics, electronics) while the complexity of the electronics increases only slightly. However, the use of lead septa as collimator between the patient and the detector will require the construction of a PET system which is larger in diameter. This will introduce a longer path to the photons before reaching a detecting element, which, in turn, will require a longer coincidence time window. This increases the possibility of acquiring multiples (see Section 6.5.5.2), and thus lowers the device efficiency. The need to build a PET/SPECT detector with a larger diameter to accommodate the septa will also increase the cost, because it requires a larger volume of crystals and a larger number of photomultipliers (PMT), or avalanche photodiodes (APD) and electronic channels.

For the reasons stated above, the PET with CT capabilities should be the first choice and should be targeted to hospitals that will use the device for cancer screening. The only justification for using a SPECT would be the types of examination that require the use of a tracer (such as Technetium Tc 99 m Mebrofenin for hepatobiliary, Sestamibi, a myocardial perfusion for detecting coronary artery disease, Mertiatide renal imaging agent, or Albumin aggregated lung imaging agent) different from the ones emitting photons at 511 keV (such as $^{18}$F-FDG, $^{13}$N, $^{11}$C, $^{15}$O, and $^{82}$Rb), because the latter ones do not allow the physician to perform the kind of specialized examination that might be required for specific conditions. In that case, the choice of SPECT would be dictated not by the lower cost as is the case today, but because of the overriding need for some specialized examinations, even though it may require a higher radiation dose and a higher cost.

The same electronics described herein for PET/SPECT/CT could be used for the PET/CT. The 3D-Flow electronics system can detect all three photons during the same examination and separate them (60 keV from x-ray, 140 keV for SPECT and 511 keV for PET).

The PET/SPECT/CT imaging devices use the following techniques:

1. PET detects emission photons at 511 keV. There exist fast and slow crystals suitable to detect photons at this energy. The most commonly used crystal in past PET devices was BGO, while the most recent PET use, or plan to use faster crystals such as LSO and GSO. (Detection efficiency of 25 mm BGO and LSO is about 90%, while 10 mm GSO is about 57%.). "Emission photons" refers to the photons emitted from a radiotracer (e.g.: $^{18}$F-FDG $^{13}$N, $^{11}$C, $^{15}$O, and $^{82}$Rb for PET examinations, or $^{99m}$Tc for SPECT exams) delivered to the patient.

2. SPECT detects emission photons at 140 keV. Several crystals such as BGO, NaI(Tl), LSO provide a detection efficiency close to 100% with a smaller crystal thickness of only 10 mm, compared with the detection of 511 keV photons, which require 25–30 mm crystal thickness (5 mm of CdZnTe can detect 140 keV photons with an efficiency of at least 80%).

3. CT operates on transmission X-rays at 60 keV transmitted from a tube or a high-intensity radionucleide rod source which is placed on the gantry on the opposite side of the detecting element, across the patient's body. Several crystals are suitable to detect 60 keV photons. This document will refer to tests performed on 3 to 10 mm thickness CsI(Tl) crystal.

6.2 Detector Geometry: Example of Assembly of a PET/SPECT/CT Device

The 3D-CBS detector can have different geometry. One geometry could have an elliptical shape as proposed herein for the section along the body of the patient (instead of the current circular shape) in order to minimize the distance from the radiation source to the detector, and it could have a circular, smaller diameter for the section of the head.

6.2.1 Assembly of the Detector Elements (Crystals) for the Detection, Validation and Separation of events from Different Modalities (PET/SPECT/CT)

Three or more crystals can be assembled such as shown in the upper right side of FIG. 34 in a single detector which detects photons from the three modalities PET/SPECT/CT.

Reference [36] describes a detector module for multimodal PET/CT made of a multi-crystal detector CsI(TI)/LSO/GSO coupled to APD, capable of discriminating low-energy X-rays (60 keV), medium-energy (120 keV used for CT of overweight patients) and 511 keV γ-rays used with PET.

The authors [36] propose a thin (3 mm) CsI(TI) scintillator sitting on top of a deep GSO/LSO pair read-out by an avalanche photodiode (APD). A channel consists of all signals from all detectors coupled to sensors (APD, photomultiplers, photodiodes, etc.) within a given view angle of the detector seen from the radioisotope source located in the patient's body. In this application a channel is 64-bit. See also reference [9].

The article [36] also reports additional tests made on another phoswich detector that consists of YSO/LSO coupled to APD.

The GSO/LSO pair provides depth of interaction (DOI) information for the 511 keV detection in PET. Measurements (see Section 6.5.9) show that CsI(TI) [36] achieves the best energy resolution and largest time separation at all energies (60 keV, 140 keV, and 511 keV) and should have a thickness such that all x-rays will be absorbed in CT mode.

The medium γ-rays of 120 keV (measurements were made by the authors of [36] at 140 keV) will interact in the two front layers of the detector (CsI(TI) and LSO) and are not expected to reach the bottom GSO layer.

The measurements reported in [36] can be easily implemented in the real-time algorithm executed by each 3D-Flow processor (see Section 6.5.9). First, the energy of the photons are validated by summing and comparing with the neighbors and then the CT photons are separated from the PET photons as described in detail in Section 6.5.

6.2.2 Assembly of the Entire Medical Imaging Detector

6.2.2.1 Example 1: Assembling a Multimodal Detector with Maximum Coverage Area FIG. 16 visualizes the example of an assembly for the two modalities, PET and CT, in a single device that offers maximum coverage of detector sensitive to capture most of the photons in the FOV. The separation of the blade 1600 that holds the x-ray source 1604 is minimal. Conventional x-ray gun (60 keV to 120 keV) can be place and rotate around the patients body in spiral mode (or up-left-down-left-up, and so on, or any direction to cover the entire body). The additional SPECT functionality requires a lead collimator to be placed between the horizontal bars (holding the X-ray transmission source) which rotate along the elliptical torso ring and along the circular head ring and the detector 1608 (crystals). By changing slightly the size of the crystals 1608, the entire gantry can become smaller (increasing the resolution and efficiency of the entire device), or larger in order to accommodate thicker lead collimators; however, the ratio between the number of crystals and the number of electronic channels should be kept as is because of its optimal match between channels per board and board per detector ring. In the entire document the additional provision of SPECT functionality is described and anticipated in the hardware implementation, although some figures may display only the PET/CT devices (e.g. not displaying the lead collimator). The most important outcome of using only PET/CT devices, besides the lower cost in requiring a smaller detector, is the lower radiation dose to the patient, permitted by the higher efficiency of smaller detectors.

In the example, the top part of FIG. 16 shows a longitudinal section (cut vertically) of the PET device. The inner crystals are 50 cm apart from top to bottom and 100 cm apart from left to right in the elliptical torso section (top right in the figure) and 40 cm apart in all directions in the circular head section (left in the figure). The longitudinal section of the brain and neck measures 31.6, cm accounting also for the sawcut of 2 mm in between the central rings of the head (as shown in the figure) to accommodate the movement of the X-ray transmission bar (128 rings times 2.45 mm of the crystal, which is the sum of 2.1 mm crystal plus 0.35 mm of material between crystals). The longitudinal section of the torso measures 157.4 cm, accounting also for the sawcut of two 2 mm in between the rings of the torso section (as shown in the figure) for the movement of the X-ray transmission bar (512 rings times 2.45 mm of the crystal, which is the sum of 2.1 mm crystal plus 0.35 mm of material between crystals).

The crystals 1608 at the extremities of the entire detector (which consist of a cylindrical barrel attached to an elliptical barrel) have an orientation of their longitudinal axis which minimizes their angle with the incident photons received from the patient's body. This is in order to facilitate the depth of interaction measurement. The two bars holding the X-ray transmission tube (or high-intensity radionucleide) shown on one side of the patient (the position called "garage") and on the bottom of the detector are attached to a support (similar to a metal blade of about 1.5 mm×20 mm, see detail in the middle of the figure) and requires a cut of about 2 mm in between two rings of the gantry. The bar positioned along the length of the elliptical torso is attached in two places (as shown in the figure) by means of the metal blades described above to an apparatus at the external side of the gantry that provides the movement of the X-ray tube around the body of the patient of the elliptical torso and of the circular head detector ring.

Similarly, in the circular head detector ring, a metal blade, only one in this section, supports the X-ray transmission bar. In order to reduce the number of x-ray tubes required in the complete assembly, an angular movement (shown with the letter α in the details of the X-ray transmission bar in the middle of FIG. 16) of the tube allowing the transmission of X-rays to opposite detectors of the side rings can be provided. Alternatively, in the event a high-intensity radionucleide is used, the source is encapsulated in a source holder with a collimator and a shutter to control the transmission. The several rotations of the transmitting X-ray tubes (or high-intensity radionucleide) at several angles will cover the entire volume of the body.

Several solutions could accommodate the insertion and removal of a lead collimator for SPECT functionality. The solution of having a sector of lead collimator rotating inside the gantry, as it is proposed in some SPECT designs, is not advisable for two reasons: first, the elliptical gantry of the torso section will make rotation along the entire ring difficult, and second, the efficiency in detecting photons is very low in the event a lead collimator covers only a sector of the entire detector at any given time. The removal or insertion of the lead collimator will depend upon the overall assembly of the detector.

There are several ways the PET/SPECT/CT devices can be assembled. The detector can open along a lengthwise separation like the cover of a box; it can separate between the head and torso sections, pivoting at one short segment of the perimeter; or it can be a solid variable tube-like structure with a sliding bed used to position the patient, such as are used in current imaging devices (e.g., CT scan. PET, MRI).

The combination of more than one medical imaging capability in a single device, is advantageous not only in providing the physician with the anatomical information together with the functional information about biological processes at the molecular level. In addition, it also provides a) a cost advantage in using the same electronics, mechanics, photomultipliers or APD, and most of the detector parts (adding the CT will only require to add about 3 to 5 mm of crystal thickness); b) the non-negligible advantage of improving the efficiency and the accurateness of the measurements; c) accurate identification of the anatomical image of any region of the body; d) precise patient positioning; e) accurate geometrical information to PET measurements for scatter correction; f) accurate attenuation correction factors based on the CT acquired images in very short scan time. The attenuation factor can be used by the PET imaging to improve S/N ratio and quality of the image.

6.2.2.2 Example 2: Assembling a Multimodal Detector with Gaps in Between Crystal Detector of the Passage of an x-ray Beam Another type of CT scanner can be integrated into the 3D-CBS device. This section describes the integration of the fastest CT scanner (often referred to as a fifth-generation CT system) with a design to enhance its features by eliminating the patient's bed motion.

The principle of operation of the electron-beam fast CT scanner was first described in [37]. Later, in 1983, Imatron Corporation developed the scanner and commercialized it. It is now a proven technology (see also [38, 39, 40, 41]).

Current designs of the Electron Beam Computed Tomograph scanner (EBT) consist of an electron gun that generates a 130 keV electron beam. The beam is accelerated, focused, and deflected by the electromagnetic coils to hit one of the four stationary tungsten target rings, which emit x-ray photons. The x-ray beam is shaped by collimators into a fan beam that passes through the patient's body to strike a curved stationary array of detectors located opposite the target tungsten rings. A few rings of detectors covering an arc of about 210°, made of crystals coupled to sensors which convert light into current, detect the signal, of the incident photons and send them to the data acquisition system. The patient's bed moves through the x-ray fan beam for a whole-body scan.

The system of FIG. 17 eliminates the patient's bed movement by increasing the number of tungsten target rings above and below the patient. One electron beam (or two, one sweeping the lower half of the detector and one sweeping the upper half) is accelerated, focused, and deflected by the electromagnetic coils at a desired angle to strike one of the tungsten rings. The collision of the electron beam with the target tungsten ring 1712 generates the x-ray fan beam (shaped by collimators), which passes through the patient's body to strike the opposite detectors (lower or upper half). One or two electron beams, sweeping at different deflections and hitting different target tungsten rings, will scan the patient's entire body in the FOV, with high resolution. The patient's body is surrounded by crystal detectors with apertures shown generally at 1700 for the x-ray beam going from the tungsten rings to the detectors beyond the patient's body and having only the patient's body as an obstacle as shown in FIG. 17 (The PMT and crystals close to the apertures are shielded from receiving the x-ray fan beam from the back of the detector). The same crystal detectors (see Section VII) used for detecting the photons from the emission technique of the PET at 511 keV with one energy criterion are also detecting the lower energy levels of the transmission technique of CT with a second energy criterion (60 keV to 120 keV depending on the settings, which are related to the patient's size).

The attenuated x-rays detected by the CT, besides being used to display the anatomy of the body, will also serve as very accurate information for determining the attenuation correction coefficients for PET scanning.

The geometry of the CT of FIG. 17 lends itself to multi-slice acquisition to an even greater extent than the 16-slice-scanner presently under design by some manufacturers because it has several rings of detectors covering over one meter of FOV.

FIG. 17 further illustrates that the plurality of detectors forming a group of detectors that reside above the patient are vertically adjustable. The adjustability of the detectors is advantageous in that larger patients and patients that require space can be accommodated. Similarly, the upper detectors may readily be lowered to improve efficiency for smaller patients. The capability of adjusting the top half or hatch of the machine is indicated by 1775. Accordingly, the present design does not require the creation of a chamber that fits patients of all types and sizes.

When specific studies for high resolution using the sole CT are needed, the technique of using one, four, or more positions of the patient's bed (not to exceed 34 cm in distance) will increase the resolution. If two scans are performed 17 cm apart from each other, that section of the patient will receive the x-rays from one side of the body and in the next position will receive them from the other side from a different angle at the extremity of the 17 cm segment and from the same angle at the center (see FIG. 17). If four scans are performed at 8.5 cm bed distances in one direction, the entire body will receive x-rays from both sides and from more angles.

Gated techniques (a technique in which the heartbeat is synchronized with the scan views) or other techniques currently used with EBT can be easily implemented with this new design because they are facilitated by the stationary position of the patient.

6.2.3 Eliminating Motion Artifacts

The difference between the PET/CT devices introduced recently in the market and the ones currently under design as compared to the device described in this article, is that the latter completely eliminates the motion artifacts of the sliding bed and uses the same detector to detect both CT and PET photons. The complete elimination of the artifact is possible because the scan is done in a single bed position by the two machines integrated in a single unit with a long field of view.

The EBT with extended FOV incorporated into the 3D-CBS provides additional advantages compared to the conventional CT. With the EBT, each organ is scanned in a fraction of a second by two electron beams hitting the two tungsten target semi-rings (top and bottom of the detector) that emit x-rays, while at the same time the PET emission photons from inside the patient's body are detected as described in Section VII. The problem of blurring images, or poor spatial resolution associated with imaging moving organs, such as the heart (as well as motion resulting from breathing) is overcome.

The recording of the 511 keV photons of the PET functionality with the timing information allows the software to replay the paths of the biological process at the molecular level in fast or slow motion on the physician's monitor.

6.3 Electronics 6.3.1 The Technological Improvements which Avoid Saturation of Electronics, Improve Efficiency of Current PET, Allow the Extension of the FOV and Increase Patient Throughput FIG. 18 is a functional schematic diagram that illustrates one configuration of sequentially implemented parallel processor (SIPP) architecture as nested within a traditional pipeline system. More specifically, a traditional pipeline system 1800 includes the embedded or nested SIPP configuration 1804 as is described herein. System 1800 is one in which data progresses from stage to stage with every clock cycle. SIPP 1804, however, keeps a piece of data for N defined clock cycles while it performs a defined algorithm for that data. During the processing for a given piece of data, any data that is received is merely passed through to a subsequent stage.

FIGS. 18, 19 and 20 illustrate physical relationships, and more particularly, measurements between components in one embodiment of the invention. The present invention is advantageous in that trace and line lengths are made in constant lengths to add predictability and control to timing issues for the large amounts of data that are processed by the inventive system. As may be seen from the Figures, the spacing between output port pins and input port pins is a constant value in the range of 1 mm. The overall layout is one in which any output pin 2006 to an adjacent input pin 2004 of another processor is constant. While the method of designing pin layouts on a board is well known, such a design has not been possible before because of variations in processing requirements for a particular calculation. The SIPP architecture herein, however, facilitates creating a pin layout that has equal length traces to enjoy the benefits therefrom.

The improvement in the efficiency of PET and CT is achieved by accurately measuring the properties of most photons that escaped from the patient's body (PET) and that went through the patient's body (CT) and hit the detector. After measuring and validating the "good" ones, a circuit should identify those coming from the same PET event. This requires electronics and algorithms, which are both fast and advanced.

Designers of the electronics of past and current PET, or CT (and designers of the electronics for particle identification in High Energy Physics [42], [43]), have approached the goal of the single photon validation requirement by making compromises between (a) a high or low sampling rate, (b) a large or small number of bits of information to handle from each input channel at each sampling clock, (c) thorough (with subdetectors and/or neighboring signal correlation operations) or approximate real-time algorithms, and (d) complex or simple circuits. Within these limitations, conventional thought was that performance improvement would most likely come from a faster processor, FPGA, ASIC, or circuit provided by advances in technology.

Because of the solution described in this article, it is no longer necessary to sacrifice one (high sampling rate) for the other (a good, thorough, real-time, unpartitionable algorithm). This solution does not require the use of faster electronics, but instead, is based on the advantages provided by the 3D-Flow architecture [12, 21] and in its implementation.

The concept of this unique 3D-Flow architecture is shown in FIG. 18 and the synchronous data flow through the 3D-Flow system is shown in Table 2. FIG. 18 and FIG. 20 shows the detail of the hardware implementation allowing the use of low-power consumption drivers that solve the problem of ground bounce, noise, cross-talk, and skew between signals. An example of the implementation of the 3D-Flow architecture that clarifies the new concept in simple terms, can be found in Cunningham's statement [26] (director of the largest Montessori school in the U.S): "in learning the theoretical ideas through the practical activities."

6.3.2 Design of a System with High Throughput and an Efficient Photon Identification, Real-Time Algorithm for a Higher Sensitivity PET A 3D-Flow system samples the detector at 20 MHz (equivalent to taking 20 million pictures per second) and processes the data (1,792 channels with different location IDs as shown in the example of FIG. 2, each containing 64 bits of information relative to the energy, DOI, location and timing) every 50 ns (which is equivalent to recognizing the objects in the picture.) The conceptual approach to solve the above problem is the following:

First, one should design a complete, real-time algorithm that extracts the information from various detectors for the best identification of photons. This algorithm may even require the execution of a irreducible number of operations for a time longer than the time interval between two consecutive input data. One example of such an algorithm is the need to correlate information from several subdetectors, or neighboring detectors. In the event that information from neighboring detectors is needed, each processing element sends the information received from its detector element to the neighboring processors, waits to receive information sent by the neighbors, and then processes the data (to reduce their number), before sending them to the next pipeline stage. Processing elements may need hundreds of nanoseconds ("ns") to complete processing but they also need to cope with data arriving at the input every tens of ns. The current design based on the well-known pipelined techniques cannot fulfill these requirements because it prevents the use of operations (uninterruptable and lasting hundreds of ns) correlating information from neighboring signals, and this information is essential for better photon identification. Additional processing by the photon identification real-time algorithm is described in Section VI.

Second, the design must satisfy the need to execute an unpartitionable algorithm longer than the time interval between two consecutive input data. This is accomplished by duplicating several identical circuits working in parallel and out of phase of the time interval between two consecutive input data. The ratio of execution time to input data period determines the number of circuits required.

Third, these identical circuits must be implemented in a physical architecture for optimal efficiency, with an arrangement designed to provide a uniform time delay of the signal propagation between them, regardless of their number. The design must focus around the concept that no signal of the data flow (bottom to top port) of the programmable hardware will be transmitted a distance longer than that between two adjacent circuits (See FIG. 18 and FIG. 19 and FIG. 20).

Fourth, the 3D-Flow architecture must work in a synchronous operation mode with registers in between circuits, as shown in FIG. 18, to assure maximum throughput. This is because at each cycle, all signals through the system should travel only through short, equal-distance paths.

Different from the well-known pipelining technique shown in stages a, b, c, e, and f of FIG. 18, data to the novel 3D-Flow system architecture shown in the dashed lines of the same figure for stations 1d, 2d, 3d, 4d, and 5d are input at one of the 5 stages d (the one that is free) during every unit of time (for example 50 ns, and each processing unit can process the received data for 250 ns). The merit of the 3D-Flow architecture is provided by the hardware implementation of the connection between the bottom port on one chip and the top port of the adjacent chip with minimal distance between components, as shown in FIG. 19 and FIG. 20 of the concept described in the dashed lines of FIG. 18.

6.3.3 Design Verification of the Technique Providing Higher Throughput

In order to verify the validity of a design, one can describe the behavior of each unit of the design, and the interrelations between the units, and then have the data flow through them. A detailed simulation from top level to the silicon gate level has been performed as described in [12, 10, 21]. The simulation of the concept has also been performed by young students in a "hands on" practice where each student implements the behavior of his unit as described in [26].

The behavior of each unit (represented in FIG. 18, FIG. 19, and FIG. 20 with a symbol) is the following:

1. The long rectangle with the dotted arrow inside means "bypass switch." The behavioral model of the example of FIG. 18 can be explained as repeating forever the operations: (a) move ("I/O") one data packet from input (called "Top port") to processor while simultaneously moving one result data packet of the previous calculation from processor to output (called "Bottom port"), and (b) move ("bypass") four data packets in succession from input to output, taking time $t_1$ to move each packet. The bypass switch is not interpreting the content of the message but instead utilizes a preprogrammed functionality counting the number of data packets to send to the processor and the number to bypass. Because the entire system is synchronous, the flow of the input data packets and output data packets result will be as shown in Table 2.
2. The square is a register (or storage element during one clock cycle) that sends out a data packet and receives a new one when the time-base clock advances one step. The propagation time of this stage is $t_2$.
3. The rectangle below switch is the symbol of the process execution task, or function on the input data. Each process on a new set of data during any of stage d is executed from beginning to completion. For the example shown in FIG. 18, the execution time is: $t_p=4(t_1+t_2+t_3)+t_1$.
4. The solid right arrow means the delay of the signal on the Printed Circuit. Board (PCB) trace connecting the pin of the bottom port of the 3D-Flow processor in one chip to the pin of the top port of the 3D-Flow processor on the adjacent chip. For the example shown in FIG. 18, FIG. 19 or FIG. 20, $t_3$ is the delay provided by the signal on a 3 cm PCB trace. The 3 cm length is due to the example of this application using a 672-pin EBGA component of 27 mm per side. A smaller component will allow a shorter PCB trace.

6.3.4 The 3D-Flow Design Real-Time Tools.

Design Real-Time is an integrated high-level design environment for the development, verification, and implementation of scalable high-speed real-time applications for which commercially available processors fail because of throughput requirements.

The Design Real-Time software tools allow the user to design fast programmable real-time 3D-Flow systems [9], [10] of different sizes, topologies, and performance (8-bit, or 16-bit wide internal buses). The steps are: a) to create a system and simulate it in software, b) using the Electronic Design Automation (EDA) tools, to create a component in hardware, simulate, and verify each feature against the requirements of each section of the software system (e.g. stack, pyramid, real-time monitoring).

Features of the Design Real-Time:

- interfaces with third-party EDA tools;
- is based on a single type of replicated component, the 3D-Flow (PE in the form of an IP block);
- is technology independent because the PE, IP block can be targeted to the latest technology;
- takes the user to a higher level of abstraction and productivity gain during the design phase because of the simplicity of the 3D-Flow architecture, and the powerful tools, the set of predefined macros and the real-time algorithms available to the user;
- allows for implementation of the user's conceptual idea into the fastest programmable system at the gate level.

The 3D-Flow Design Real-Time tools allow to:

1. create a new 3D-Flow application (called project) by varying system size, throughput, filtering algorithm, and routing algorithm, and by selecting the processor speed, lookup tables, number of input and output bits for each set of data received for each algorithm execution;
2. simulate a specified parallel-processing system for a given algorithm on different sets of data. The flow of the data can be easily monitored and traced in any single processor of the system and in any stage of the process;
3. monitor a 3D-Flow system in real-time via the RS232 interface, whether the system at the other end of the RS232 cable is real or virtual; and
4. create a 3D-Flow chip accommodating several 3D-Flow processors by means of interfacing to the EDA tools.

A flow diagram guides the user through the above four phases. A system summary displays the information for a 3D-Flow system created by the Design Real-Time tools.

6.3.4.1 Interrelation Between the Entities in the Real-Time Design Process

FIG. 21 is separated into two sections. On the left is shown the flow of the software design and simulation process to create and simulate a 3D-Flow system, on the right is shown the System-On-a-Chip for High-speed Real-time Applications and TESting (SOC-HRATES) hardware design process. The center of the figure shows the common entities of the system:

1. the IP 3b-Flow processing element as the basic circuit to which has been constrained the functionality required by different applications;
2. a set of 3D-Flow real-time algorithms and macros organized into a library;
3. the System Monitor software package that allows the user to monitor each 3D-Flow processor of the 3D-Flow system (hardware or VPS—Virtual Processing System—), via RS-232 lines. The System Monitor (SM):
a. performs the function of a system-supervising host that loads different real-time algorithms into each processor during the initialization phase;
b. detects malfunctioning components during run-time. (A sample of data is captured at the processor speed of 80 MHz at a preset trigger time for 8 consecutive cycles (called snap-shot), and is transferred at low speed (at the RS-232 speed of 230 KBaud) to the System Monitor for debugging and/or monitoring);
c. excludes malfunctioning processors with software repair by downloading into all neighbors a modified version of the standard algorithm, instructing them to ignore the offending processor The "3DF-CREATE" software module allows the user to:
1. define a 3D-Flow system of any size; interconnect processors for building a specific topology with or without the channel reduction stage ("pyramid");
2. modify an existing algorithm or create a new one. The complexity of the real-time algorithms for identifying particles arriving from multiple channels at high rate at the input of the 3D
3. Flow system, such as the ones reported in [12], [21], [44], [45], have been examined and fewer than 10 layers (corresponding to 20 steps, each executing up to 26 operations) of 3D-Flow processors are required;
4. create input data files to be used to test the system during the debugging and verification phase.

The "3DF-SIM" module allows for simulation and debugging of the user's system real-time algorithm and generates the "Bit-Vectors" to be compared later with the ones generated by the third-party silicon foundry tools.

The "3DF-VPS" module is the Virtual Processing System that emulates a 3D-Flow hardware system.

The right side of FIG. 21 shows the flow of the hardware implementation of the 3D-Flow system in a System-On-a-Chip (SOC). The same common entity, the IP 3D-Flow processing element (PE), shown in the center of the figure and previously used as the behavioral model in the simulation, is now synthesized in a specific technology by using the same code.

The number of chips required for an application can be reduced by fitting several PE's into a single die. Each PE requires about 100K gates and the gate density increases continually. Small 3D-Flow systems may fit into a chip. For this reason, it is also called SOC 3D-Flow. However, when an application requires the building of a 3D-Flow system that cannot be accommodated into a single chip, several chips each accommodating several 3D-Flow PEs can be interfaced with glueless logic to build a system of any size to be accommodated on a board, on a crate, or on several crates [9].

6.3.4.2 Design Real-Time Verification Process

The verification process of an entire 3D-Flow system can be performed down to the gate-level in the following steps:
The 3DF-SIM: a) extracts from the system the input data for the selected 3D-Flow processor(s) for which an equivalent hardware chip (which was targeted to a specific technology has been created, and b) generates the Bit-Vectors for the selected processor(s);
The same input data and the same real-time algorithm are applied to the hardware 3D-Flow model, and the simulation is performed using the third-party tools;
Bit-Vectors generated by the third-party tools using the hardware model are compared with the Bit-Vectors obtained by the previous software simulation (3DF-SIM);
Discrepancies are eliminated.

6.3.4.3 Results from the Use of Design Real-Time

The use of the Design Real-Time tools has made it possible to determine the parameters that led to design the data acquisition and processing system for pattern-recognition (particles in HEP experiments) described in [21] and [8], providing:
1. simulation and implementation results of a real-time system for the Level-0 trigger of LHCb [44], [45] experiment at the Large Hadron Collider at CERN [46]; and
2. the simulation and verification of the LHCb HEP Level-0 system trigger algorithm simulated using 3DF-SIM vs. the results (test pattern in the form of bit-vectors) obtained from the EDA tools from the design of
a) a single 8-bit wide internal bus 3D-Flow PE version synthesized for different FPGAs,
b) a 3D-Flow ASIC chip containing four PEs with 16-bit wide buses synthesized into a 0.5 µm technology, and
c) the same four PEs into a 0.35 µm ASIC technology.

Simulation has been performed, and Bit-Vectors have been compared between the system simulator (3DF-SIM) and a 3D-Flow chip implemented with 0.35 µm Cell Based Array (CBA) technology at 3.3 Volts. The CBA ASIC EDA design tools show dissipation of 884 mW @ 60 MHz and a die size of 63.75 mm$^2$ for a chip with 4 3D-Flow processors.

Implementation with the current technology of 0.18 µm which has a gate count of ~65K gates per mm$^2$ requires about 1.5 mm$^2$ of silicon per PE. A chip accommodating 16 PEs dissipates 23 nW Gate/MHz, and requires a silicon area of about 25 mm$^2$ in 0.18 µm technology (leading to a chip @ 1.8 Volts, 676-pin EBGA, 2.7 cm×2.7 cm).

6.3.5 Implementation Merits the 3D-Flow Design

The 3D-Flow system open new doors to a way of accurately measuring photon properties in real-time by providing the supporting architecture to execute thorough algorithms with zero dead time. The possibility of executing such algorithms in real-time was not envisioned before by the user, because it would have required electronics that were too costly and complex. For some applications with demanding performances, the current approach would not provide a solution at all. For those applications demanding high performance, the 3D-Flow architecture provides a solution because of its simple implementation.

The 3D-Flow implementation allows achievement of high-speed input data throughput at a very low power consumption, which minimizes the problems of ground bounce and cross-talk.

The modularity of the 3D-Flow system permits the implementation of scalable systems, where the complexity of the algorithm or the throughput of the system can be increased.

When an unpartitionable, real-time algorithm needs to execute a longer and more complex task, several programmable, 3D-Flow chips can be cascaded.

One of the key features of the 3D-Flow architecture is the physical design of the PCB board.

During the pin assignment phase of the ASIC design, each pin carrying a 3D-Flow bottom port output is placed adjacent to a pin carrying the input of the relating top port bit.

This allows for uniform trace length when connecting processors of adjacent, cascaded 3D-Flow chips and also allows traces that do not cross each other.

This regular pattern of the PCB traces eliminates crosstalk and signal skew and easily allows impedance matching and a simple low cost PCB construction.

Table 2. Sequence of the data packet at different times in the pipeline stage of solution No. 4 (See FIG. 18 and FIG. 22). One data packet in this application contains 64-bit information from one channel of the PET detector. The clock time at each row in the first column of the table is equal to $t=(t_1+t_2+t_3)$ of FIG. 18. The lower number in a cell of the table is the number of the input data packet that is processed at a given stage. The upper values, indicated as ix and rx, are the input data and the result data, respectively, which are flowing from register to register in the pipeline to the exit point of the system. Note that the input data 1 remains in the processor at stage 1d for five cycles, while the next four data packets arriving (i2, i3, i4, and i5) are bypassed to the next stage. Note that at clock 8t, while stage 1d is fetching i6, it is at the same time, outputting r1. This r1 value then walks to the exit of the 3D-Flow system without being processed by any other d stages. Note that clock 14t is reporting the status of FIG. 18 and that input data and output results are intercalated in the registers of the 3D-Flow pipelined system.

level that will be difficult or impossible to overcome. The high power consumption of the generic I/O driver will be too high for the number of I/O ports needed on a Printed Circuit Board (PCB) or in the system. For example, in our case the need to drive 672 bottom-to-port connections at 640 Mbps on the PCB board (see FIG. 1 and FIG. 2) consuming 50 mW each, results in a total of 33.6 Watts. This needs to be added to the power dissipation of the other electronics on the board and to that of the North, East, West, and South links going out of the board, which will create serious system problems.

The above implementation merits of the 3D-Flow architecture allow for:

1. The construction of a very high performance system that can execute n consecutive instructions on a system having an input data rate equal to the fastest implementation of the 3D-Flow processor. Although the latency of the result provided by such a system is longer than the time interval between two consecutive input data, the resulting processing capability of the system on the incoming data is equivalent to that of a processor running n times the speed of the fastest implementation of the 3D-Flow processor (where n is the number of layers of the 3D-Flow system). For example, a 20-layer

| Time | Stage (a) data # | Stage (b) data # | Stage (c) data # | Proc (1d) data # | Reg (1d) data # | Proc (2d) data # | Reg (2d) data # | Proc (3d) data # | Reg (3d) data # | Proc (4d) data # | Reg (4d) data # | Proc (5d) data # | Reg (5d) data # | Stage (e) data # |
|---|---|---|---|---|---|---|---|---|---|---|---|---|---|---|
| 3t | 4 | 3 | 2 | 1 | i2 | | | | | | | | | |
| 4t | 5 | 4 | 3 | 1 | i3 | | | | | | | | | |
| 5t | 6 | 5 | 4 | 1 | i4 | 2 | i3 | | | | | | | |
| 6t | 7 | 6 | 5 | 1 | i5 | 2 | i4 | | | | | | | |
| 7t | 8 | 7 | 6 | 1 | r1 | 2 | i5 | 3 | i4 | | | | | |
| 8t | 9 | 8 | 7 | 6 | i7 | 2 | r1 | 3 | i5 | | | | | |
| 9t | 10 | 9 | 8 | 6 | i8 | 2 | r2 | 3 | r1 | 4 | i5 | | | |
| 10t | 11 | 10 | 9 | 6 | i9 | 7 | i8 | 3 | r2 | 4 | r1 | | | |
| 11t | 12 | 11 | 10 | 6 | i10 | 7 | i9 | 3 | r3 | 4 | r2 | 5 | r1 | |
| 12t | 13 | 12 | 11 | 6 | r6 | 7 | i10 | 8 | i9 | 4 | r3 | 5 | r2 | |
| 13t | 14 | 13 | 12 | 11 | i12 | 7 | r6 | 8 | i10 | 4 | r4 | 5 | r3 | 1 |
| 14t | 15 | 14 | 13 | 11 | | 7 | | 8 | | 9 | | 5 | | 2 |

The need to carry unidirectional signals on short PCB traces with equal distance as described above, requires simple, low-power (a few mW) I/O drivers and receivers with a differential signal voltage of a few hundred mV. The driver needs to drive only one load at 3 cm (or less, if the 3D-Flow component is smaller, it will need to drive a PCB trace a few millimeters longer than the side of the component). On the contrary, implementations different from the 3D-Flow architecture attempting to build a system with similar performance, as described in solution No. 3 of FIG. 22, will need to make use of a generic I/O driver (e.g., Low Voltage Differential Signaling (LVDS) driver dissipating 35 mW and a LVDS receiver dissipating 15 mW). These generic drivers provided by ASIC manufacturers, designed to drive distances of a few meters, will create problems of high power consumption, ground bouncing, etc., at system 3D-Flow system with the processor running at 250 MHz provides a system with the resulting processing capability on the incoming data equivalent to that of a 5 GHz processor. The bits on the I/O bus will be transferred from the input of one chip to the input of next chip with a delay of $t_1+t_2+t_3$. The system throughput limitation is calculated as the sum of the time $t_1$ of the bypass switch to commute, (plus) the propagation time $t_2$ of the D register, and (plus) the propagation time $t_3$ of the signal on the 3 cm PCB trace (see FIG. 18 and FIG. 19). Advanced technologies allow for the implementation of the above functions ($t_1+t_2+t_3$) with a total propagation time of hundreds of picoseconds, providing a throughput of several GHz.

2. The construction of a low-cost system with a high throughput. The designer selects the technology and processor speed that he/she can afford to build with a given budget. For example, assume that the maximum chip-to-chip speed that one would like to handle is 640 Mbps (or 320 Mbps), the processor speed 80 MHz, and the system throughput with a word of 64 bits at 20 MHz. A 3D-Flow system, with 5 layers, with the above characteristics will provide the capability to execute on each processor a programmable unpartitionable real-time photon identification algorithm of 20 steps (which will include neighbor's data exchange). This will require only two communication channels, each with 32-to-1 multiplexing (or four communication channels, each with 16-to-1 multiplexing) for the communication between the bottom port of the 3D-Flow processor of one chip and the top port of the 3D-Flow processor on the adjacent chip. All the above parameters are achievable with straightforward implementation of electronics that do not present difficulties of a particular type. For example, the board shown at the bottom right of FIG. 2, or top left of FIG. 1 (see more details of the 3D-Flow DAQ-DSP board in Section 5.7.1.1.1 would require one to implement 672 bottom-to-top PCB traces (calculated as 5 cascaded chip-to-chip times 16 processors per chip times 2 lines per port times 4 chips per board, plus 32 traces to the 3D-Flow pyramid chip), 3 cm in length, matched in impedance and carrying signals at 640 Mbps from drivers implemented in the 3D-Flow ASIC with a voltage on a differential signal of a few hundred mV and power consumption of a few mW. (In the event the designer had set the maximum chip-to-chip speed at 320 Mbps, 1,344 bottom-to-top PCB traces will be needed). Considering that (a) there are Printed Circuit Boards (PCB) developed for telecommunication applications with data speeds at several GHz, on much longer traces than 3 cm, and (b) that the LSI Logic G12 ASIC Cell-Based technology provides up to 33 million usable gates on a single chip (~65,000 gates/mm$^2$) at the power consumption of 22 nW/MHz/Gate (1.8 Volt supply, 0.13 μm L-effective CMOS technology), the required 1.7 million gates of the 3D-Flow chip with 16 processors is not among the largest chips built, nor is it a relatively "high risk" chip to build.

The architecture of the 3D-Flow system enables it to provide the significant advantages of both high performance and simplified construction at a low cost.

6.3.6 Comparisons Between the 3D-Flow System and Other Techniques.

For better understanding of the advantages of this novel architecture, a comparison is made with other techniques:

1. The simplest approach to the solution of the execution of a task (see solution No. 1 in FIG. 22) is to build a circuit or processor that executes in sequence all necessary operations and does not fetch new input data until the processing of the previous data has been completed.
2. Another approach which increases efficiency is the well-known pipeline technique used in many applications (e.g., computer architecture) for more than half a century. This technique allows an increase in the throughput by splitting the processing of a task in "n" smaller operations, each executing an nth subdivision of the global task (see solution No. 2 of FIG. 22).
3. When a stage of the pipeline of the previous technique requires the execution of an unpartitionable algorithm longer than the time required by the other stages, the circuit at that stage can be copied and connected by means of a "Generic Switch" to the previous and following stages as shown in solution No. 3 of FIG. 22. Because the designer has to lay the components on a PCB, he will face a limit in keeping the distance short. When a signal is going from one component to several components, the path will necessarily be longer for some with respect to others, increasing the signal skew. This will create timing problems. The split from one data point to several data points ("fanout") should drive more than one unit, requiring high power consumption, which creates spikes, noise, and "ground bounce," when several outputs switch at the same time. There is no modularity in the implementation, and when the algorithm needs to be increased and more circuits are required, the fanout may not be sufficient, requiring additional buffers for each line. As circuits need to be added, the PCB board territory (PCB real estate) increases with the consequence that the components will be further apart from each other, thus requiring additional circuits in parallel to make up for the lost efficiency in communication speed. Soon the limit of the throughput becomes the power consumption and the distance between components, making this solution undesirable.
4. The 3D-Flow system solution No. 4 of FIG. 22 copies the circuit (or processor) coupled to a bypass switch and a register at the stage where it is necessary to execute an unpartitionable algorithm longer than the time required in the other stages. This simplifies the construction because it requires short point-to-point connections that need only a very low power driver. The hardware can achieve better performance at a lower cost, because any added circuit will not increase the power consumption on other circuits, require additional drivers or more powerful buffers, or increase the length. The only parameter increase is the latency.

6.3.7 Increasing Sensitivity Improves Resolution, Data Quality and Detection Ability, and Requires Lower Radiation The previous sections described the architecture that allowed an increase of the throughput in a Data Acquisition system (DAQ) and also described how it could be possible to execute a fast, unpartitionable, thorough, real-time algorithm on each input data packet. Now that we have the supporting architecture, in this section, a short description (with more details in references) will be made of the type of the calculations that are performed in the thorough, unpartitionable, real-time algorithm in order to improve the accuracy, sensitivity and capture more "good" photons. Section VI-D describes (and provides references for more details) how the coincidence detection circuit used in current PET can be simplified, reduced in cost and designed to meet the requirements of zero dead time for the maximum radiation that a detector should ever handle.

The programmability of the 3D-Flow system at each detector channel provides the flexibility to execute any user defined real-time algorithm.

A few examples of real-time algorithms that extract the information from the signals received from the detector and accurately measure the properties of the incident photons are described herein in Section 6.5.8, 6.5.9, 6.5.10, and 6.5.11. However, the user can execute his real-time algorithm that he had tested off-line on some detector data. One example of such an algorithm is the one tested off-line in some universities on single photon emission data. This algorithm aims to determine the direction of the incident photon of a known energy, when the information of a single scatter+absorption or the information of three scatters are provided. Achieving the result of successfully translating such off-line algorithms into 3D-Flow real-time algorithms would allow one to consider the construction of a SPECT without the need of a lead collimator.

One of the important features added to the 3D-CBS design is the accurate calculation and assignment of a "time-stamp" to the incident photon.

By calculating the differences between the accurate time-stamp of different incident photons, it is possible to isolate data packets belonging to a PET event or to a Compton scatter event. After this separation, the 3D-Flow processing system routes the data packets' information about a specific event to a processing unit for extracting and measuring the particle's properties (e.g., its incoming direction and energy.)

Other examples of operations performed by the 3D-Flow during the execution of the real-time algorithms are the following: (a) measuring the spatial resolution using interpolation, or centroid calculation as described in Section 6.5.8, (b) calculating the local maxima, which avoids double counting of the photons (see Section 6.5.11 for more details). (c) measuring the energy resolution as described in Section 6.5.11, (d) improving the time resolution (see Section 6.5.11), (e) event integration from slow crystals using digital signal processing techniques (DSP) (see Section 6.5.4); (f) resolving signal pileup by using DSP techniques when slow crystals are used (see Section 6.5.11), and (g) measuring the Depth of Interaction (DOI). DOI measurements solve the problem in identifying the crystal when the incident photon has an oblique penetration (instead of being perpendicular) to the face of the crystal looking toward the emitting source. The effect commonly referred as "parallax error" occurs when DOI is not measured. (See Section ~6.5.9+for more details).

All the above contribute to increasing the sensitivity of the 3D-CBS scanner, which allows for recording better data quality and increased detection ability, avoids erroneous readings (false positives) and allows the reduction of the radiation delivered to the patient to $\frac{1}{30}^{th}$ that of current PET. (See Section FIG. 14] for a more complete estimate of the loss of PET emission photons at all stages).

The improvement of the electronics in capturing PET emission photons will also result in capturing more CT transmission photons, thus lowering the radiation required during a CT scan. By solving the saturation problem of the electronics of the current PET and being able to process even more photons at low cost, it is possible to increase the FOV dramatically.

6.3.8 Digital Signal Processing at Each Detector Channel

Signals from each detector channel are converted to digital by flash analog-to-digital converters and processed in real-time by programmable 3D-Flow processors. Examples of the sequence of 3D-Flow instructions of a real-time algorithm for photon identification can be found in Section 5.5.11.2 and Section 5.5.11.3. A 3D-Flow processor executes the typical arithmetic and logic operations, the multiply accumulate operations and those of moving data from input ports to output ports.

This programmability allows the user to execute on each channel a customized program for every detector, in order to take into account small variations in crystal properties. Some examples of programs that can be executed are the following:

1. Event integration. When slow crystals are used, DSP techniques are used to digitally integrate the signal and extract better spatial, energy and timing resolution. By analyzing the pulse shape of a signal digitally it is possible to detect with greater accuracy the start of an event and to assign it a precise time-stamp.
2. Pileup separation. When two events occur in a nearby detector area within a time interval shorter than the decay time of the crystal, the apparent integral of the second signal will show it riding on the tail of the previous signal. DSP techniques can detect the change of slope of the tail of the signal and separate the two signals. This technique can improve existing PET just by changing the electronics without costly hardware detector upgrade.
3. Normalization. Recording of photons at different energies and correcting them for displaying a good image with the right contrast can be achieved by normalizing the input data through the 3D-Flow look-up tables or through corrections obtained with data processing.
4. Signal-to-noise ratio improvement. The DSP functionality of the 3D-Flow processor can execute on each channel standard techniques of signal processing to improve S/N ratio.

6.3.9 Higher Accuracy in Spatial Resolution

Increasing the Field of View also increases the spatial resolution because more pairs of photons in time coincidence can be captured, and those intersecting at 90° allow for better spatial resolution. (See FIG. 12).

Spatial resolution is also improved by the centroid calculation algorithm which is now possible because of the exchange of data between neighboring processors without boundary limitation described in the next section and in FIG. 33.

6.3.10 Higher Accuracy in Energy Resolution

With the 3D-Flow sequentially-implemented, parallel architecture, it is now possible to increase the energy resolution of each incident photon in the detector by more accurately measuring it with the execution of a longer, thorough algorithm (see FIG. 33).

FIG. 33 shows the difference between the electronics of current PET, which does not extract the particle properties accurately and the technique used in the 3D-CBS device.

The 3D-Flow system provides the capability to exchange information relative to 2×2, 3×3, 4×4, or 5×5 detector elements in a cost effective manner, after raw data have been fetched from the detector by an array of 3D-Flow processors (see Section 6.5.11 for details).

In addition, this neighboring information exchange feature allows for many photons to be captured which "Compton scattered" in the crystals. These photons are lost by the electronics of the current PET devices because the communication among PMTs is limited to 2×2 elements and photons that are "Compton scattered" in the crystals might spread the energy throughout a larger area.

6.3.11 Higher Accuracy in Time Resolution

Achieving a better time resolution reduces randoms. The capability to assign a time-stamp to each photon detected is achieved by using the DSP technique, or by using the Constant Fraction Discriminator (CFD) at the front-end, which generates a signal edge, which is digitized in time by the Time-to-Digital converter (TDC) with a resolution of 500 ps. (Higher time resolution could be achieved, however 500 ps are sufficient for a PET device assisted by Time of Flight (TOF) information as it is intended to be. This will avoid the need to use expensive fast electronics. Other techniques aiming to determine the location of the interaction by measuring the time-of-flight, require more expensive electronics with a resolution of the order of 50 ps.

The digitized time information is sent and further improved in resolution by the 3D-Flow DSP (See Section 6.5.4.3 for more details). A very important phase of the process for improving timing accuracy is the calibration that is described in some details in Section 6.5.10.

In order to find photons in coincidences, the electronics calculate the time interval between the time-stamp of two photons that hit the detector (see bottom left of FIG. 49). An accurate time-stamp will allow one to set a maximum time interval between two hits for which the photons will be accepted. This interval will be related to the maximum difference in distance that the two photons traveled before striking the detector.

Thus, if the maximum time interval for accepted coincidence photons is small there is lower probability of recording randoms (or photons belonging to two different events).

6.3.12 Simpler, Efficient and Lower Cost Coincidence Detection Circuits

In the new coincidence detection design, only the detector elements coupled to a PMT or APD, hit by a photon which was validated by a thorough real-time, front-end pattern recognition algorithm, are checked for coincidence. This method is much simpler than the one used in the current PET, which compares all of the possible LOR (see reference [20], or Section 5.5.4.14 for more details). The number of comparisons for finding the coincidences is proportional to the radiation activity and not to the number of detector elements as they are in the current PET. The advantage of the new approach requiring simpler electronics is that with only $1.2 \times 10^8$ comparisons per second, the new approach described herein achieves the efficiency equivalent to that of a current PET that would perform $2.6 \times 10^{13}$ comparisons per second (see Section 3.6.8 for more detail).

In the new design, the coincidence detection problem is solved with simple electronics as described in Section 5.5.14.1. A simple implementation funnels all hits detected to a single point, sorts the events in the original sequence, as shown in FIG. 43, and compares all hits within a given time interval for validation of time-stamp and location situated on an LOR passing through the patient's body.

6.4 Mapping the Electronics of the 3D-Flow system into the Geometry of the PET/SPECT/CT Imaging System.

Detectors of PET/SPECT/CT devices of different sizes and of different components (crystals coupled to PMT or APD, photodiodes coupled to crystals, solid state detectors, etc.) can be mapped to the 3D-Flow system.

The ratio of 256 crystals (or a single crystal of equivalent size in a "continuous" detector) coupled to a photomultiplier of 38 mm in diameter has been selected based on the promising results by the tests performed by Andreaco and Rogers [47] in decoding 256 BGO crystals per block and not indicating that they had reached a limit in the number of crystals that could be decoded. The limit would be determined a) by the light emitted by the crystal, b) the S/N ratio, and the 3D-Flow capability to improve the S/N ratio with DSP processing.

based on the number of photomultipliers per detector area used in several PET built by Karp and co-workers on the "continuous" detectors (e.g., 180 PMTs were used in the HEAD PENN-PET with the ring of 42 cm in diameter and 25.6 cm FOV). Each of the 2,304 PMT of the new PET proposal with 3D-Flow is coupled to an equivalent detector area.

In the event the light emitted by a certain type of crystal adopted in a particular PET design is not sufficient, or the S/N ration does not allow to decode 256 crystals, than the number of PMT and electronic channels can be multiplied by four and the 256 channels 3D-Flow DAQ-DSP board can be used at the place of the 64 channels. (The computation by the 3D-Flow DSP required for decoding 64 channels in place of 256 will be reduced, allowing each 3D-Flow to handle four electronic channels).

The Table 6-4 provides an example of the coupling of "block" detectors for PET/SPECT/CT with different FOV based on 64 crystals 4.55 mm×4.55 mm coupled to a PMT of 38 mm in diameter, and 256 crystals 2.1 mm×2.1 mm coupled to a 38-mm diameter PMT (about 0.35 mm is accounted for the space taken by the opaque reflector or the optical coupler placed in between the crystals). Slight increases or decreases in the size of the entire PET/SPECT/CT device should preferably change the dimension of the crystals and the ratio between the number of crystals, while the number of electronic channels should be kept constant because of its optimal match between channels per board, and board per detector ring.

On Table 6-4, first the comparison is made between the current whole-body PET detectors made of about 12,000 to 18,500 crystals in a circular gantry to an elliptical gantry with the same field-of-view which shows a reduction in volume of crystals (thus reduction in cost) of about 12%. If the electronics proposed herein were to be installed in current PET with circular gantry, only 288 PMT 38 mm in diameter coupled to 288 electronic channels of five 3D-Flow DAQ-DSP and one 3D-Flow pyramid of IMB PC compatible boards would be necessary (see FIG. 23). In the elliptical version of the same detector, only 256 PMTs would be required, coupled to four 3D-Flow DAQ-DSP boards and one 3D-Flow pyramid board.

Comparison has been made also between a PET detector with 157.4 cm FOV with a circular gantry of 96 cm in diameter versus one with the same FOV but with an elliptical gantry for the torso section 100 cm wide by 50 cm high. The elliptical shape of the torso section would save 20% in volume of the crystal.

The total number of crystals required for the elliptical version (each crystal having the dimensions of 2.1 mm×2.1 mm) for a 157.4 cm FOV is 589,824; that for a crystal 25 mm thick is equivalent to a crystal volume of 65,028 $cm^3$. Considering that crystals with slow decay time such as BGO have a cost of about $10/$cm^3$, the cost of the main components for the elliptical version of a PET (100 cm wide by 50 cm in height) is about $650,280 for the crystals and about $460,800 for the 2,304 PMTs 38 mm in diameter (assuming about $200/PMT). Thus the elliptical version would require only 36 3D-Flow DAQ-DSP boards. This is to be compared with the cost for the circular version of the same PET, with a circular gantry (96 cm in diameter), which would cost about $794,787 for the crystals and about $563,200 for the PMTs, and would require 44 3D-Flow DAQ-DSP boards.

One implementation with a smaller FOV of 126 cm shown in Section 6.9.2 and FIG. 25, using the elliptical implementation, requires only 458,752 crystals (2.1 mm×2.1 mm) for a volume of 50,577 $cm^3$ crystal (for 25 mm crystal thickness), and 1,792 PMTs. This implementation would cost about $505,770 for the crystals and about $358,400 for the PMTs.

Another implementation that should demonstrate the significant advantages offered by the 3D-Flow architecture is the implementation of the PET/SPECT/CT device with a "continuous" detector with several layers of crystals arranged in annular rings of different types of crystals, one inside the other. Each layer would have a different decay time so that the 3D-Flow system could measure the depth of interaction. The "continuous" type of detector has proven to be a viable solution. Moreover, the 3D-Flow architecture, because of its additional capability of detecting the head of a cluster corresponding to the location of the incident photon with great precision, allows reconstruction of the whole energy of the incident photon due to its elimination of the boundary limitation. This feature offers advantages compared to the electronics currently used and might greatly simplify the construction of PET/SPECT/CT detectors and save cost also in that area FIG. 23 shows the 3D-Flow system mapped to a PET detector, similar to those currently operating, with a ring of about 82 cm in diameter (or 56 cm in diameter of the patient's port) and with a FOV of about 15 cm. Only five 3D-Flow DAQ-DSP boards and one 3D-Flow pyramid board would be required here. Section b) of the same figure refers to the column of the current circular gantry with 157.4 cm FOV of Table 6-4, and Section c) refers to the columns of the proposed new elliptical gantry with a FOV of 157.4 cm.

TABLE 6-2

Mapping the 3D-Flow system to current PET devices and future PET devices of different sizes with circular and elliptical gantry.

| | Current Circular Gantry[a] (PMT diameter = 38 mm) | | | | Proposed New Elliptical Gantry Head Ring $d_h$ = 40 cm (circular) Torso Ring $d_{t1}$ = 50 cm; $d_{t2}$ = 100 cm (ellipt.) (PMT diameter = 38 mm) | | | |
|---|---|---|---|---|---|---|---|---|
| | 15.6 cm FOV Ring d = 82 cm | | 157.4 cm FOV Head Ring $d_h$ = 40 cm Torso Ring $d_t$ = 96 cm | | 15.6 cm FOV | | 157.4 cm FOV | |
| x and y dimensions of crystals are in [mm] (about 0.35 mm of opaque reflector or optical coupler is used between crystals) | [number of crystals/PMT in a ring, PMT axial, crystals per PMT/total PMT] | IBM PC boards [3D-Flow DAQ 64 ch./ pyramid] | [number of crystals/PMT in a ring, PMT axial, crystals per PMT/total PMT] | IBM PC boards [3D-Flow DAQ 64 ch./ pyramid] | [number of crystals/PMT in a ring, PMT axial, crystals per PMT/total PMT] | IBM PC boards [3D-Flow DAQ 64 ch./ pyramid] | [number of crystals/PMT in a ring, PMT axial, crystals per PMT/total PMT] | IBM PC boards [3D-Flow DAQ 64 ch./ pyramid] |
| (4.55 × 4.55) head | | 5[a]/1 | 16,348 cryst./ (32 × 8 × 64)/256 PMTs | 44/1 | | 4/1 | 16,348 cryst./ (32 × 8 × 64)/256 PMTs | 36[b]/1 |
| (4.55 × 4.55) torso | 18,432 cryst./ (72 × 4 × 64)/288 PMTs | | 163,840 cryst./ (80 × 32 × 64)/2,560 PMTs | | 16,384 cryst./ (64 × 4 × 64)/256 PMT | | 131,072 cryst./ (64 × 32 × 64)/2,048 PMTs | |
| (2.1 × 2.1) head | | | 65,536 cryst./ (32 × 8 × 256)/256 PMTs | 44/1 | | | 65,536/ (32 × 8 × 256)/256 PMTs | 36[b]/1 |
| (4.55 × 4.55) torso | | | 163,840 cryst./ (80 × 32 × 64)/2,560 PMTs | | | | 131,072/ (64 × 32 × 64)/2,048 PMTs | |
| (2.1 × 2.1) head | | | 65,536 cryst./ (32 × 8 × 256)/256 PMTs | 44/1 | | | 65,536/ (32 × 8 × 256)/256 PMTs | 36[b]/1 |
| (2.1 × 2.1) torso | | | 655,360/ (80 × 32 × 256)/2,560 PMTs | | | | 524,288/ (64 × 32 × 256)/2,048 PMTs | |

[a]see in FIG. 23 the layout of 3D-Flow DAQ-DSP boards for current and old PET devices, the dimensions of the PET rings using current circular gantry, and the dimensions of the PET rings using the proposed elliptical gantry.
[b]see layout of 3D-Flow DAQ-DSP boards in FIG. 1, and FIG. 2.

6.5 Solutions Provided by the 3D-Flow System to the PET/SPECT/CT Requirements

Electronics can be subdivided into two sections: one section, applicable to PET, SPECT, and X-ray instruments, identifies the particle and its characteristics (energy, position, timing, type, etc.) by means of a thorough analysis of the signal(s) produced by the incident photon. Another section, applicable to the PET device only, detects the coincidences.

6.5.1 Latency Time Through the Entire System

An overview of the entire electronic system with the functionality of the different sections, the flow of the data through all of them from the input from the detector to the output for CT, SPECT and PET is shown in.

The entire electronic system is synchronous and has a fixed time latency from the input data to the output results. While the time latency between data at different layers of the 3D-Flow system remains fixed during the photon identification operation (executed in the 3D-Flow DAQ-DSP boards, see Section 6.5.11) which is the only operation required by the CT and SPECT functionality, the additional coincidence detection function required by the PET functionality of the device, with the flow of the data through different paths of the pyramid (see in the second column from the left) introduces a variable time latency between data at different layers. The fixed time delay is regained before the data reach the coincidence circuit, as described in Section 6.5.14.1 and shown in the third column from the left in FIG. 24.

The coincidence circuit stage is operating in synchronous mode on data sorted at a fixed latency time and in the same sequence as they were when received from the detector, just as it was operating the previous stage of the photon identification of Section 6.5.11. As before, at this stage also it is offered the provision to implement a second stack (with fewer channels) of 3D-Flow processors similar to the one implemented for the photon identification, in the case where the algorithm (comparisons and photons parameters checking) requires an execution time longer than the time interval between two consecutive input data at that stage.

The last column to the right of FIG. 24 shows the operation performed for the coincidence detection required by the PET operation mode.

6.5.2 Ascertaining that the 3D-Flow System Provides Sufficient Input Bandwidth The sampling rate of the detector signals every 50 ns seems reasonable for a maximum rate of about $105 \times 10^6$ single photons that can potentially hit the detector at start of scanning, 20 seconds after an injection of 5 mCi radioactive source dose is delivered to the patient (e.g., $^{15}$O-water which is equivalent to 21 mrem effective dose equivalent to the patient. See Section 6.6.3 and FIG. 14 for the calculation of the input data rate of photons to the detector for a specific delivered dose of radioactive source to the patient).

The calculation of the maximum rate of single photons hitting the detector for 5 mCi $^{15}$O-water, 20 seconds after injection, is the following: The $^{10}/_{12}$ of $(5 \times 37 \times 10^6 \times 2)$ single photons per second activity, 20 seconds after delivery of 5 mCi of $^{15}$O-water, reduced to 39% single photons (equivalent to about 15% pairs of photons in coincidence as shown in FIG. 14) leaving the patient's body, reduced to 95% FOV efficiency and 92% solid angle efficiency, provides $(^{10}/_{12} \times 370 \times 10^6 \times ^{39}/_{100} \times ^{95}/_{100} \times ^{92}/_{100}) = \sim 105 \times 10^6$ single photons per second hitting the detector. A higher rate of photon emission by the radioactive source would require delivery to the patient more radiation. This is not recommended for even a short half-life radioisotope such as $^{82}$Rb or $^{15}$O-water, which have half-life times of 75 seconds and 124 seconds respectively.

At the above maximum rate, each crystal out of the total of 589,581 crystals of the detector would have a 0.00089% probability of being hit by an incident photon every sampling period of 50 ns. Each PMT out of the total 2,304 PMTs of the detector will have a 0.22% probability of receiving the signal of an incident photon to the detector every sampling period of 50 ns.

The architecture of the 3D-Flow (See Section 5.3) with the capability of extending the processing time beyond the time interval between two consecutive input data, allows each processor to execute the entire real-time algorithm (See Section 6.5.11) at each of the PMT channels thus providing zero dead-time with 100% capability to sustain one signal per channel every 50 ns.

This calculation should be persuasive evidence that the 3D-Flow system has been dimensioned with sufficient bandwidth at the input stage so that bottlenecks will not occur at the predicted radiation activity.

6.5.3 Two Examples of Detectors: Crystals with Fast and Slow Decay Time

The following section describe all the functionality required by a PET/SPECT/CT system and the requirements are addressed one by one and a solution provided by the 3D-Flow system is described.

Two examples are presented for two different types of applications (see FIG. 25):
1. one which makes use of more expensive, faster crystals with short decay time, for which analog integration would seem to be appropriate; and
2. one which makes use of more economical crystals with a longer decay time, for which a digital signal integration would be appropriate.

The analog integration of the signal for example 1 using fast crystals (with a decay time shorter than 40 ns) has been suggested in this application in the event it is intended to use the 3D-Flow processor at the relatively low speed of 80 MHz. This avoids exotic and more expensive electronics which would be required at higher speed.

However, if it is desired to solve all problems digitally, the speed of the 3D-Flow processor in example 1 can be increased by a factor of 2. In this way the 3D-Flow processor clock period of 6.25 ns will guarantee the execution of a few instructions and a few samplings during a 40 ns detector signal. By doing so, the same approach described for example 2 could be applied for example 1.

Along with the signals from the photomultipliers (or APD) coupled to the crystals (or, more generally, any gamma converter), the 3D-Flow system can acquire and process signals from any other sensors, such as photodiodes, VLPC, etc.).

FIG. 25 shows two examples of the 64-bit word received by each 3D-Flow processor of one layer of the stack every 50 ns.

6.5.3.1 Example 1: Interfacing Between Detectors with Fast Crystals and the 3D-Flow Example 1 shows a 64-bit word carrying the information from four detector blocks made of fast crystals with short decay time (about 40 ns). Each detector provides three pieces of information: the time-stamp, the energy and the decay time.

The time-stamp (e.g., $s_A$ in FIG. 25) is the detection of a hit by the constant fraction discriminator CFD1 with short delay (see also FIG. 26, Section 6.5.4.2, and FIG. 27), which sends a logical signal to the time-to-digital (TDC) converter (see Section 6.5.10). The TDC produces a 7-bit time-stamp mapped in the 3D-Flow input word in bits 57–63.

The energy (e.g., $E_A$ in FIG. 25) is the peak of the analog signal from the shaper amplifier (see FIG. 27), which is converted to digital and mapped into the 3D-Flow input word in bits 50–56.

The decay-time (e.g., $d_4$ in FIG. 25) is the difference between the time detected by the CDF2 after integration of the signal from the PMT (this time is proportional to the decay time of the crystal) and the previously detected time-stamp. The TDC produces the second time-mark, which is subtracted from the time-stamp of CFD1 and mapped into the 3D-Flow input word in bits 48–49 by the FPGA (see also Section 6.5.4.2, and FIG. 27).

Similarly the information from the other three detector blocks are mapped into the remaining sections of the 3D-Flow input data word.

The data received by the front-end electronics during a given 50 ns sampling time period (e.g., $t_3$), are sent in a pipeline mode, e.g., two sampling periods later, in order to allow the analog and digital electronics to propagate and convert to digital the signals (e.g., at time $t_5$) to the 3D-Flow electronics (see bottom left of FIG. 27).

6.5.3.2 Example 2: Interfacing Between Detectors with Slow Crystals and the 3D-Flow Example 2 shows a 64-bit word carrying the information from one or more transducers (PMTs, APDs, and/or photodiodes), coupled to a detector block made of slow crystals. Slow crystals have a long decay time of about 230 ns, which can be shortened to 200 ns. (Alternatively, the 3D-Flow CPU clock could be stretched). The detector provides the raw information of the ADC counts of the signals received every 50 ns, the time-stamp of the last two hits detected, and the position/DOI through photodiode and/or light sharing information.

All characteristics of the incident photon are extracted from the raw data received by means of the 3D-Flow digital signal processing capabilities (see Section 6.5.8, 6.5.9, 6.5.10, 6.5.6, 6.5.11).

Since the sampling time is 50 ns and the crystal decay time is expected to be on the order of 230 ns (shortened to 200 ns using the technique described in [48]), a buffer memorizes the last three samples. Each time a new sample of the input signal is acquired, the last value is grouped to the previous three samples and sent to one 3D-Flow DSP. The buffering function is implemented in the FPGA (see Section 6.5.4.3, and FIG. 28).

The bottom right of FIG. 25 shows that the amplitude of the signals $E_{n-3}$, $E_{n-4}$, $E_{n-5}$, and $E_{n-6}$, are sent at time $t_{n-1}$ to the 3D-Flow and that the amplitudes of the signals $E_{n-2}$, $E_{n-3}$, $E_{n-4}$, and $E_{n-5}$, are sent at time $t_n$ to the 3D-Flow. The above four 8-bit values of signal amplitude information (ADC counts) are mapped to the 3D-Flow input word in bits 0–31. Data are sent to the 3D-Flow system in a pipeline mode, e.g. two sampling periods later than the receiving time from the detector. This allows the analog and digital electronics to propagate, convert to digital, and align the time of signals belonging to the same event. Signals belonging to the same event are produced at different times because the transducers have different response times. (See reference [49] for the conceptual design down to the circuit description in graphic form and in VHDL form of the interface that aligns signals between different detector/transducer types with different response times.)

The rising edges of the signal from the PMT (or APD) above a certain threshold are detected by the CFD1 with short delay (see Section 6.5.4.3), and a logical signal is sent from the CFD1 output to the time-to-digital converter (see Section 6.5.10). This, produces a 9-bit time-stamp (e.g., $s_n$ in FIG. 25), which is mapped in the 3D-Flow input word in bits 32–40. More bits for the time-stamp are needed in example 2 with respect to example 1, because, while the 500 ps resolution of the TDC is the same, the duration of the decay is longer (from 40 ns to 200 ns), and the longer time measurements require more bits. The previously recorded time-stamp (e.g., $s_{n-1}$ in FIG. 25) in the FPGA buffer is mapped in the 3D-Flow input word to bits 41–49.

Either technique—ratio of signals from photodiode and PMT [50] or the light sharing technique [23]—can be used in the 3D-Flow system.

In the case of the use of a scintillator crystal coupled to the PMT at one end and at the other end to 64 photodiodes (PD), the following observations can be made:

a) the crystal o interaction can be identified by the PD with highest signal;
b) the sum (PD+PMT) contributes to calculate the total energy, and
c) the ratio PD/(PD+PMT) determines the depth of interaction.

The 3D-Flow can perform the operations of addition and division to extract the photon's characteristics from the raw data that are provided by the "winner-take-all chips" (WTA) [51]. These are interfaced to the 64 PD and which produce one analog signal of the highest PD and its relative 6-bit address. The analog signal converted to 7-bit digital (e.g., $E_d$ in FIG. 25) can be mapped into the 3D-Flow input word at bits 50–56 and its relative address (e.g., $A_d$ in FIG. 25) at bits 57–62. Thus, one spare bit of the 64-bit 3D-Flow input data word remains.

In case the light-sharing technique is used, then the information can be mapped into the 3D-Flow input word at bit 50–56 for the maximum+partner and bits 57–63 for their address. This technique makes use of the "winner-select-output" (WSO) [52] chip, which provides the analog signal with the highest amplitude called "maximum," and second highest signal called "partner.")

6.5.4 The Front-End Electronics

The 3D-Flow system is synchronous with a proposed sampling time of 50 ns. The sampling time can be changed to best match the decay time of the crystal used.

Any rising edge detected within the 50 ns sampling time by the fast constant-fraction discriminator (CDF) causes a digital time-stamp with a dynamic range of up to several microseconds and with the resolution of 500 ps to be generated and memorized by the time-to-digital (TDC) component. In this application only 9-bit will be used.

A preamplifier (called PRE on the figure of the printed circuit boards for IBM PC or VME), accommodates 32 analog channels as described in Sections 6.5.4.3, and 6.5.4.2.

6.5.4.1 Constant Fraction Discriminator

A constant fraction discriminator provides a logical output when the input amplitude reaches a certain fraction of its maximum amplitude, eliminating the time jitter caused by variable pulse heights.

FIG. 26a and FIG. 26b showss how the technique is used by the CFD for a zero crossing time, which is independent of the amplitude of the signal. The technique is to send the input signal to two amplifiers. One amplifier delays the original signal by a fixed time (dashed line), the other one attenuates it by a fixed fraction and inverts it (dotted line). Then the two pulses from the two amplifiers are added together.

6.5.4.2 Front-End Electronics for Fast Crystals

The front-end electronics for fast crystals, samples each channel of the detector at its peak amplitude every 50 ns using a delayed pulse generated by the CFD1 as described above.

The 7-bit amplitude of the sampling at time $t_n$, together with the converted amplitude of the samplings at time $t_n$ from three adjacent PMTs (which form a 2×2 block), will be formatted in the FPGA with their timing and DOI information and will be sent to the 3D-Flow processor at time $t_{n+2}$.

FIG. 27 shows the block diagram of the front-end electronics for fast crystals. The signal generated by the PMT and sent to the preamplifier is optimized by controlling the high voltage power supply to the photomultiplier.

The integrating amplifier generates an output pulse proportional to the decay time of the input pulse. The output of the integrating amplifier is sent to CFD2 and uses a delay_3, long enough to be able to integrate enough signals from the crystal with the slowest decay times and also sufficiently long to be able to measure the different decay time of the different crystals. On the other hand, the delay should be shorter than 50 ns, if possible to avoid system dead time A pulse shortening technique [48] could be used if the crystal decay time is too long. However, sufficient light from the incident photon should be provided to be able to distinguish the signal from the noise.

The logical output generated by CFD2 is sent to the TDC, which generates a time-stamp of 7 bits. The FPGA reads from the TDC the information of the time-stamp generated by CFD1 and CFD2, and computes the difference, which is proportional to the decay time of the crystal that detected the incident photon.

This DOI information of 2 bits (allowing up to four crystals with different decay times to be used for DOI measurements) is formatted by the FPGA with the 7-bit time-stamp information (within the 50 ns sampling time period) and with the 7-bit photon energy converted by the ADC connected to the shaper amplifier. The information of four 16-bit channels is then sent to the 3D-Flow by the FPGA every 50 ns.

6.5.4.3 Front-End Electronics for Slow Crystals

The front-end electronics for slow crystals samples each channel of the detector every 50 ns using the system clock.

The 8-bit amplitude of the current sampling, together with the converted amplitude of the past three samplings as memorized in the FPGA, are sent to the 3D-Flow processor together with the last two time-stamps (9 bits each) read from the TDC.

A different set of information for DOI measurements could be used for a total of 64 bits, which are then sent to the 3D-Flow processor every 50 ns. For instance, a 6-bit address from a WTA chip [51] and its analog amplitude pulse converted to digital for DOI technique with photodiode [51], could be used. Alternatively, the address bit from a WSO [52] chip and the analog amplitude pulse converted to digital for DOI technique with light sharing [23] can be used The high-voltage control of the PMT, the preamplifier, and the fast filter amplifier are identical to the previous case in Section 6.5.4.2, and, therefore, are not described. In fact, a single chip of this type could be developed and used for both applications. This application will not use some of the pins and functions which have been developed for the other application.

FIG. 28 shows the block diagram of the front-end electronics for slow crystals. Once the output of the preamplifier is sent to a shaper amplifier and then through the ADC, its digitalized amplitude is collected by the FPGA for packaging with other bits and is sent to the 3D-Flow.

The other output of the preamplifier is sent to a fast filter amplifier and then to CFD1, which uses a very short delay_2 and generates a prompt CFD logical output to the TDC.

The TDC generates a time-stamp of 9 bits which is read by the FPGA. The FPGA formats a 64-bit word of information at each clock cycle and sends it to the first 3D-Flow processor in the first layer of the stack.

6.5.5 Definition and how to Deal with Randoms and Multiples

Simultaneous annihilations (or pairs of photons generated by the source) can cause erroneous coincidence detection. This document makes a distinction between what are generally referred to in literature as Randoms and Multiple. Provisions are given on how to eliminate or account for them.

6.5.5.1 Randoms

Figure 29:
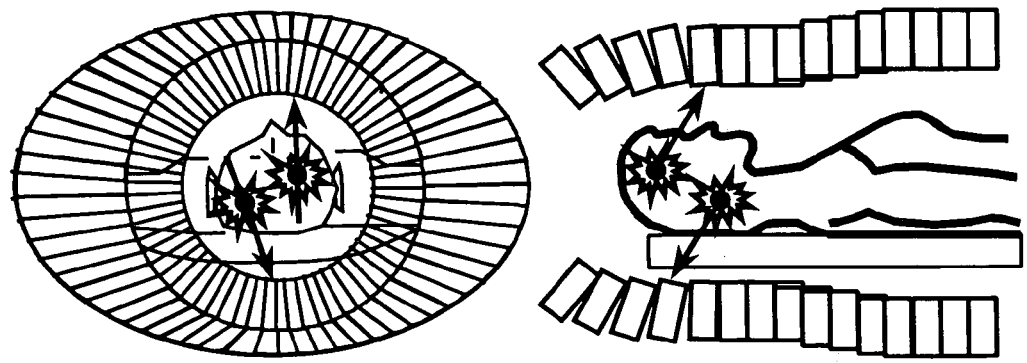

Random coincidences occur when two unrelated photons hit two detectors (see FIG. 29) within the time window used to detect true coincidences.

6.5.5.2 Multiples

Multiple coincidences occur when more than two photons hit more than two detectors (see FIG. 30) within the time window used to detect true coincidences.

6.5.5.3 How to Identify Randoms and Multiples, Correct, and/or Reject them

Random and Multiple rates are proportional to the rate of hits (or singles) to each detector and to the time coincidence window with the following relation:

$$(\text{Random}+\text{Multiple}) = \text{Rate}_1 \times \text{Rate}_2 \times 2\Delta t$$

Where $\text{Rate}_1$ is the rate of a single at detector 1, $\text{Rate}_2$ is the rate of singles at detector 2, and $\Delta t$ is the time coincidence window. They are reduced by reducing the rate of the singles at the detector and the time window coincidence. Both parameters are reduced by the proposed design with the 3D-Flow because a) the increased FOV of the detector reduces the percentage of singles (see FIG. 7) with respect to the total radiation activity (and an increased FOV requires also a lower radiation dose to be delivered to the patient); and b) the time window coincidence is reduced by the accurate time measurement, which is improved by the CFD, TDC, the front-end operations in the FPGA, and the DSP functionality of the 3D-Flow, which can improve accuracy of the time stamp assigned by the TDC with the digital signal analysis of the PMT pulse received from the shaper amplifier. This increased efficiency made merely with the improvement in the electronics. A further improvement in the time resolution can be effected by the use of faster crystals with shorter decay time; however, this strategy will entail additional cost.

6.5.5.4 Compton Scatter: How to Detect these Events, and/or Correct and/or Reject them.

Compton scattering is the collision between a photons and a loosely bound outer shell orbital electron of an atom. Because the energy of the incident photon is much greater than the binding energy of the electron to the atom, the interaction looks like a collision between the photon and a free electron. The incident photon in a Compton scattering deflect through a scattering angle θ. Part of the energy of the incident photon is transferred to the electron and the energy loss is related to the scattering angle of the scattered photon at lower energy. It is a photon-electron interaction and the energy transferred does not depend on the density, atomic number or any property of the absorbing material.

Events of this type have one of the pair of photons at 511-keV that "Compton scatters" in the patient but still interacts in the detector ring. (Some others Compton scatter in the detector ring.) The result is a coincidence event because it satisfies the coincidence time window; however, the line connecting the detectors which sensed the hits is invalid.

Better energy resolution improves Compton scatter correction and rejection. The 3D-Flow system has the capability of improving the energy resolution by:

a) handling the detector as a single large array of signals received from PMTs or other transducers or a combination of them, rather than by defining boundaries in the detector, as is the case in current detectors, b) having the capability of identifying, anywhere in the detector array, the head of the cluster (the sensor absorbing the highest scintillating light of the incident photon compared to its neighbors; see local maxima detection in Section 6.5.11.2) and then reconstructing the energy of the incident photon by adding the energy value of its neighbors (3×3, 4×4, or 5×5, etc., according to the size of the array). This calculation corrects for events which scatter in the detector c) applying the attenuation correction when the photon is identified in the stack of the 3D-Flow. This attenuation correction is for the SPECT operation mode, based on attenuation maps obtained with septa-in, and the calibrating parameters are obtained using the transmission source rotating around the patient's body.

A more accurate attenuation correction can be obtained when the device is operating in PET mode. When the coincidence is detected at the exit of the 3D-Flow pyramid, the x and y position of the crystals within the array are known, and the time-of-flight is known. The time-of-flight provides an accuracy of ±7.5 cm because of 500-ps resolution, so it is possible to calculate more accurately the attenuation of the photonsand, consequently, the energy of the pair of photons hitting the detector.

Further scatter correction and/or rejection can be calculated off-line during image processing, using the parameters of the incident photons provided by the 3D-Flow during their characterization.

6.5.6 Attenuation Correction

The importance of the mass absorption effect of the body in PET and SPECT examination requires the use of an attenuation correction technique in order to improve quantification, quality image, and specificity.

In PET operation mode there is the advantage that the attenuation is less because the photons have higher energy (511 keV) compared to SPECT (140 keV), and accurate attenuation measurements on several lines through the patient's body can be performed. This provides a precise attenuation correction factor for different organs and sections of the patient's body.

In SPECT operation mode, attenuation maps are acquired with the transmission scan in order to correct for attenuation for the different organs.

Several techniques for attenuation correction have been developed with or without transmission scan and with or without septa. Many of them have the main goal of reducing the time required for calibration and of providing at the same time an accurate attenuation correction. The 3D-Flow architecture allows us to implement the methods providing highest accuracy while still requiring a very short overall time to run the attenuation correction because of its capability of sustaining continuously an input data rate of 20 MHz at each electronic channel (PMT, or APD, and/or photodiode, etc.).

Although only two examples are provided herein (one for SPECT and one for PET), several other techniques described in the literature can also be implemented with the 3D-Flow.

The attenuation coefficient for SPECT can be acquired from a rod source in transmission mode with septa-in at an acquisition rate of up to 20 million photons per second per PMT channel. It is then stored in the look-up table memories of each 3D-Flow processors in the stack.

A more precise attenuation coefficient for PET can be acquired from a rod source in transmission mode with septa-out and stored into a 512 MB (or greater) DIMM memory installed on the 3D-Flow pyramid-buffer board (see Section 6.7.2) This is accomplished in the following manner:

A blank scan is measured using rotating rod sources (e.g., $^{137}$Cs emitting 662 keV γ rays) as shown in FIG. 32a (see also FIG. 16). The acquired coefficients are stored temporarily in the memory lookup tables of each front-end 3D-Flow processor in the stack.

A second transmission scan with the patient in place (see FIG. 32b) measures the transmission attenuation coefficients with the same rotating rod source at different angles (e.g., about 10 rotations at 10 different angles requiring about one second for each complete rotation). The ratio of the coefficients from the "blank scan" with the acquired attenuation coefficients of the transmission scan (e.g., about 524,288, corresponding to 524,288 "roads" of attenuation coefficients) is sent to the PET attenuation coefficients look-up table memory on the 3D-Flow pyramid-buffer memory (see Section 6.7.2).

When a coincidence is found by the circuit described in Section 6.5.14 and implemented as described in Section 6.7.2, the position of the two crystals identifying the line on which the annihilation occurred allows the calculation of the address of the corresponding attenuation coefficient stored in the "PET attenuation coefficient look-up table memory." The time-of-flight information of each photon with a resolution of 500 ps (corresponding to 7.5 cm spatial resolution of the annihilation occurring along the line connecting the crystals that detected the hit), which has been calculated by subtracting the time-stamp of the two photons in coincidence, allows the accurate calculation of the attenuation coefficient correction factor for the two photons in coincidence. Finally, the two calculated coefficients, which are related to the time-of-flight information for the photons and to the specific attenuation as a result of the mass encountered during their journey to the scintillation crystal detector, are used to correct the energy of the two photons in coincidence.

6.5.7 Difference Between True Event Efficiency and Coincidence Efficiency

The efficiency referred to in this document is the capability to detect photons in time coincidence (events) lying on a line connecting two detectors which passes through the patient's body. Included among these events are also all events that are not true events (such as Compton scatter and Randoms), which could not be rejected at this stage by the electronics.

The reason for using this type of measurement of efficiency based on the count rate of the coincidences and not based on the count rate of the true events is that:

1. it is not possible to separate out the non-true events until they are processed off-line during the phase of reconstruction of the image and their location in the patient's body is determined;

2. it is a parameter easy to calculate and for that reason the count rate of the coincidences is used by manufacturers and designers in the performance measurements.

The real efficiency of the device is then the ratio of the number of real events divided by the number of total events (or disintegrations) created by the radioisotope.

The total number of coincidences found should be reduced in some cases by up to 50% to obtain the count rate of the true events.

6.5.8 No Detector Boundaries for the Centroid Calculation with the 3D-Flow

In the PET implemented with the 3D-Flow system, the geometry of the PET sensors are mapped to the a 3D-Flow processor array in a manner that allows the exchange of information among the adjacent PET sensors through short signal delay.

The entire 3D-Flow system is a single array with no boundary limitation. The neighboring of sensors in the PET detector array is reflected with an identical neighboring scheme in the 3D-Flow processor array. Each channel (defined as all signals, from all subdetectors within a given view angle) in the 3D-Flow processor array, sends its information to, and receives their information from, its neighbors. This is equivalent to the exchange of information among adjacent channels (or sensors) in the PET detector array. The practical implementation of the data exchange between neighbors is shown in detail in FIG. 56.

Once all data from each channel and its neighbors are moved into a single processing element, any pattern recognition-algorithm, and/or signal-to-noise filtering algorithm well known in the literature can be applied by using the DSP functions of the 3D-Flow processor. This is achieved with the instructions of arithmetic and logic operation including multiply-accumulate and divide.

These operations are accomplished in parallel on each channel In the example of the application of Section 6.9, for instance, each of the 2,304 processors of one layer of the 3D-Flow stack executes in parallel the real—real time algorithm, from beginning to end, on data received from the PET detector, while processors at different layers of the 3D-Flow stack operate from beginning to end on different sets of data—or events—received from the PET detector.

In the current PET system, on the contrary, if a photon hits the detector at the border of a 2×2 PMT block, releasing its energy partly in one block and partly in the neighboring block, then both might reject the photon as having failed to pass the energy threshold.

The centroid calculation with the 3D-Flow is straightforward after having gathered the information of 3, 8, 15, or 24 neighbors in a single processor, as is described in Section 6.5.11.2 for a 3×3 centroid calculation and in Section 6.5.11.3 for a 5×5 centroid calculation.

One example of a more accurate centroid calculation compared to the 2×2 example show on FIG. 33b is for the calculation of $\Delta_x$ the ratio of the sum of the energies of all sensors at the west of the central element, divided by the sum of all sensors at the east of the central element ($\Delta_x = \Sigma E_W / \Sigma E_E$). Similarly for the calculation of $\Delta_y$ the ratio of the sum of the energies of all sensors at the north of the central element, divided by the sum of all sensors at the south of the central element ($\Delta_y = \Sigma E_N / \Sigma E_S$). Accuracy and algorithm execution speed will determine whether a ratio or a subtraction is needed (the subtraction algorithm is a faster hardware operation).

Another important advantage provided by the elimination of the boundaries within the detector array is the resulting increase in the accuracy of the energy resolution calculation of each incident photon.

The complete energy of the incident photon can be rebuilt by adding to the channel with the highest energy (head of a cluster), the energy values of the 3×3, or 4×4 surrounding the channels. Alternatively, when larger areas of 5×5 or 6×6 are added, the complete energy of photons which went through crystal scatter can be rebuilt.

Increasing energy accuracy will improve spatial resolution, scatter rejection/acceptance, and attenuation correction.

FIG. 33b shows the limitation introduced by the presence of 2×2 PMT block boundaries of the current PET systems. The bottom section of the figure shows one of the several figures available in several publications [53, 47]. Although on Section II.C of [54] it is stated that " . . . Detector boundaries may form any appropriate shape to account for nonlinearities in the positioning response . . . ," the much lower thresholds (see FIG. 3 of [54]) used for the corner and edge crystals of the 2×2 block compared to the thresholds of the center crystals (which are also corner crystals of PMTs) indicates that the energy of the incident photons detected by the corner/edge crystals is much lower than that detected by the center crystals. This is because part of the energy of the incident photon is detected by the adjacent 2×2 block and is lost when using the approach of the current PET, because there is no communication between 2×2 PMT blocks. The center crystals (which are also corner crystals of the PMTs) have instead higher thresholds since the Anger logic [55] can account for the energy of the incident photon which was split among the four PMTs).

The proposed architecture of the 3D-Flow with no boundary between 2×2 PMTs provides a platform where all corner crystals will be like the ones currently located at the center of the 2×2 PMT block, or providing even higher accuracy by means of 3×3, or 5×5 neighbor clustering. Thus all measurements will be like the four crystals in the center of the 2×2 PMT block; no such difference of lower thresholds as the ones used in the current PET will be required, and the complete energy of the corner/edge crystals could be rebuilt as it is for the center crystals.

In the current PET, the fact of having blocks with 2×2 boundaries (the 2×2 boundary is provided by the grouping of the 2×2 PMTs) causes different signals in different positions of the 64-, 144-, or 256-crystal block (see the crystal-region boundary lines in FIG. 3 of reference [47]) change the geometrical segmentation of the crystals into the layout of the crystal region boundary lines similar to the one shown in the bottom right of FIG. 33b. The signal at the corner of the 2×2 PMT block (see FIG. 33b1) has a high component of noise and only a fraction of the signal (about 50 ADC counts. See measurements performed in [53] on the left of FIG. 3) of the incident photon. The other part of the signal is in the adjacent 2×2 PMT block and is lost because there is no communication among the two blocks. FIG. 33b2 shows a much higher signal (about 150 ADC counts) corresponding to the crystal directly over the PMT photocathode (see measurements performed in [53] on the right of FIG. 3). FIG. 33b3 shows the estimated signal (as described from measurements in several articles) at the center of the 2×2 PMT block, which corresponds to a corner crystal in between 4 PMTs.

6.5.9 Flexibility in Measuring the Depth of Interaction with the 3D-Flow System.

An oblique penetration of a incident photon into a crystal generates a parallax error if the depth of interaction (DOI) is not measured.

FIG. 34 shows the effect of the parallax error and the technique of using different layers of crystals with different decay times in order to be able to identify at which depth the scintillation light occurred.

During the past 14 years, different techniques have been used to measure the DOI. The digital signal processing capabilities of the 3D-Flow system offer the possibility of implementing several of them. FIG. 35 shows the block diagram of the logic to implement some of them. (See also the photon detection algorithm with the 3D-Flow in Section 6.5.11.2).

The different depth of interaction techniques shown in FIG. 35 can be implemented with the 3D-Flow system because all necessary information from the detector needed for the calculation of the DOI are fetched from the detector as shown in Section 6.5.3. The operations among them can be executed by the DSP functionality of the 3D-Flow processor (arithmetic an logic operation typical of a DSP) during an execution time that can be extended as necessary, thanks to the bypass switches of the 3D-Flow (as described in reference [56]).

6.5.10 Time Resolution of 500 ps for PET Devices Assisted by TOF Information The measurement of the time-of-flight in the proposed design is used for improving the signal-to-noise ratio of images, for the DOI measurement, and for narrowing the time window in order to eliminate multiples. It is not intended to directly use the TOF information in source positioning. The choice is dictated by economic consideration and the desirability of avoiding exotic and expensive electronics that need skew control at tens of ps.

The position of annihilation can be determined from the difference between the time-of-flight of the y-rays. The relationship between time difference ($t_1-t_2$) and the source position from the center of opposite detectors, x, can be expressed by x=(t2−t1)*c/2, where c is the light velocity. (See FIG. 36).

Before the digital TDCs were on the market, only analog TDCs which normally have a better accuracy (<50 ps), were available. They have a very long dead time, however, and usually can record only one hit. These TDCs cannot be used in high-rate data acquisition. Most recently, however, digital TDCs have been developed that can record multi-hits with a resolution of 50 ps. The cost of such digital TDC will be too high and will also increase the cost of the associated electronics. For the above reasons, a multi-hit digital TDC with a resolution of only 500 ps and 24 or 32 channels per chip is the most appropriate for the proposed project. The TDC, costs about $2 per channel.

At any time during the time interval of 50 ns between the acquisition by the 3D-Flow system of two consecutive sets of digital input data, the TDC can memorize a signal received from the detector by the CFD on the analog interface with a time resolution of 500 ps (see Section 6.5.4).

The simplified operation of the TDC can be described as a continuous running counter (a single counter for each group of 32-channels in a chip). When a signal is received from one of the 32-inputs, the current value of the counter is copied into a buffer. More hits could arrive within 50 ns, thus more values are copied into the TDC buffer. Typically, the actual rate of hits at a single channel of the detector is much lower than 20 MHz.

While there is no problem of relative time measurement between channels within the same chip (because there is only one counter), there might be a problem of counter alignment between different chips residing on the same board or on different boards. This problem can be overcome by making an accurate distribution of the signal of the reset of the counters of the TDC. The skew of the signal at the different locations of the components should be minimal as described in reference [56] Section 9, page 377.

A calibration of the system will correct all discrepancies from the different channels. A possible calibration of the system could be the following: a radioactive source is placed at the center of a collimator as shown in FIG. 37 and moved longitudinally along the center of the detector barrel. The time measurement on one end of the detector (TDC counter value) should correspond to the time measurement of the sensor along the line passing through the radioactive source and located in the opposite side of the detector. Any count difference between the two counters should be memorized and used as a counter offset during subsequent measurements.

6.5.11 Photon Identification: The PET/SPECT/CT Real-Time Zero Dead-Time Algorithms for Fast or Slow Detectors Using the 3D-Flow system.

The detector should be made of at least three different crystals with different decay times and one with good stopping power for 60 keV, another of 140 keV and another for 511 keV (See reference [36]). The 3D-Flow real-time algorithm with digital signal processing and correlation with neighboring signals will decode the energy, time information, and spatial information and will identify the type of incident gamma ray.

The capability of the 3D-Flow system to apply any digital-signal-processing (DSP) filtering algorithm on the complete set of data relative to an incident photon (the head of the cluster of an incident photon with all its neighbors, including its timing information) can extract all relevant information of the incident photon (energy, position, timing and type of event, e.g. PET, SPECT, x-ray, scattered or photopeak) and enhance them.

6.5.11.1 Format of the Input Word from the Detector to the 3D-Flow System Stack Two input words to the 3D-Flow processor are described, one for example 1 for slow crystals, and another for example 2 for fast crystals (see also Section 6.5.3):

input word to the 3D-Flow processors for example 1 (fast crystals):

bit 0–1 DOI of PMT_D, bits 2–8 amplitude of PMT_D, bits 9–15 time-stamp PMT_D;

bit 16–17 DOI of PMT_C, bits 18–24 amplitude of PMT_C, bits 25–31 time-stamp PMT_C;

bit 32–33 DOI of PMT_B, bits 34–40 amplitude of PMT_B, bits 41–47 time-stamp PMT_B;

bit 48–49 DOI of PMT_D, bits 50–56 amplitude of PMT_D, bits 57–63 time-stamp PMT_D. input word to the 3D-Flow processors for example 2 (slow crystals):

bit 0–7 amplitude (n) of PMT, bits 8–15 amplitude (n−1) of PMT, bit 16–23 amplitude (n−2) of PMT, bits 24–31 amplitude (n−3) of PMT;

bit 32–40 time-stamp (n), bits 41–49 time-stamp (n−1)

bit 50–56 amplitude highest PD, bits 57–62 PD address.

6.5.11.2 Photon Detection Algorithm Simulation with the 3D-Flow for PET/SPECT/CT The 3D-Flow system is synchronous.

Every 50 ns, upon reception of the 64-bit word from the FPGA, all processors of one layer of the 3D-Flow stack execute the following steps in parallel:

- Get data from detectors, convert ADC counts into energy value through look-up-table.
- Fetch four signals from fast crystals, TOF/decay time information, calculate DOI, or integrate signals from slow crystals, calculate DOI (signal decay time) and check for pileup.
- Calculate attenuation. Calculate time-stamp.
- Send data to North, East, West and South neighbors and save energy photon in R46. Increment time stamp.
- Save first 3×3 data into Sum1, route 3×3 corner values.
- Get energies from four NEWS neighbors, add them, and save into registers R0, R16, R32, and R48 for local maxima calculation.
- Get energies from four corner neighbors, add them, and save into registers R1, R17, R33, and R49 for local maxima calculation.
- Compare 9 energy values for "Local Maxima" tests to determine whether the energy of the central cell is larger than any of its neighbors. (This operation is executed in one CPU cycle). Compute the total energy sum of 3×3 array by adding the partial sums, Sum1 and Sum2. Check for "photopeak" and "scattered." Calculate 3×3 "centroid" compute the energy asymmetries, for subsequent determination of the point of impact ($\Delta_x = \Sigma E_W - \Sigma E_E$ and $\Delta_y = \Sigma E_N - \Sigma E_S$.) Format output word, or reject event.

At this stage there is much information computed that allows conclusions to be drawn, whether the photon is a 60 keV (x-ray), 140 keV (SPECT), or 511 keV (PET), and if the attenuation, DOI, timing, spatial information are available. Any further operations can be executed upon the 9 data (the one received from the detector and its 8 neighbors) by the CPU of the 3D-Flow processor, which can, in a single cycle, execute up to 26 operations, including all normal arithmetic and logic operations of a standard computer.

Each processor gathers the information from the neighbors and acts like the head of a cluster without boundary limitations. The calculation of the "local maxima" prevents duplication in the detection of photons because only one cluster can be larger than the neighbors.

FIG. 38 shows the flow of the operation on each processor in a graphical form. In the event a 5×5 clustering calculation is desired in place of the 3×3 clustering, steps 7 through 10 must be replaced by the program of Section 6.5.11.3

6.5.11.3 Simulation of the 5×5 Clustering Algorithm in 9 Steps with the 3D-Flow Simulation of the 5×5 algorithm has been performed with the 3D-Flow real-time design and software tools [57].

Nine steps (each step corresponding to the 3D-Flow clock period of 12.5 ns) are required to send and receive the data to and from 24 neighbors while adding them.

Two 3D-Flow cycles are required to propagate signals from the internal bus of one processor to the internal bus of an adjacent processor.

During step 7, the data of one channel is sent to the North, East, West, and South ports. All processors are executing the same operation; thus the values from the neighbors, which were sent at the same time, are ready to be fetched two cycles later at step 9.

In order to move the data from the corner of a 3×3 and of a 5×5 and the value of the outer 5×5 ring to the inner ring during steps 8 to 12, the operation of moving data from one input to one output is performed.

The moving operations performed by each processor are identical (aside from the processors at the two sides of the array with no neighbors) and are performed in such a way that at each 3D-Flow clock cycle there are four new neighboring values at the North, East, West, and South ports to be fetched by each processor.

The move operations are performed according to the instructions listed in step 8 such as: North to East, West to North, South to West, East to South.

At step 9 through 12 the moving operations are different. The summaries of the path of each single datum going from an external position to the four North, East, West, and South processor neighbors of the central processor, are shown with thin lines in the graphic section of FIG. 39. The starting processor is indicated with a black square, a line indicates the path from processor to processor at each 3D-Flow clock cycle, the four arrows indicate when the datum is fetched by the central processors.

This scheme can be applied to any processor of the 3D-Flow array; and at each step, the relative position of the central datum with respect to its neighbors in the process of being fetched is the same.

6.5.11.4 Format of the Output Word of the "singles" Identified by the 3D-Flow "Stack"

The format of the output word of the "singles" that passed the photon identification criteria of the real-time algorithm in the 3D-Flow stack, is the following:

bit 0–19 crystal spatial ID; bits 20–23 depth of interaction, bits 24–31 photon energy;

bits 32–43 time-stamp; bits 44–50 for the type of photon, bits 51–63 not used.

The 20-bit field for spatial ID allows for coding up to 1,048,575 crystals. The 4-bit DOI field allows for a depth of interaction with up to 1.56 mm resolution when crystals 25 mm thick are used. The energy of the photon is coded in 256 intervals from the smallest to the highest energy value. The 12-bit field for the time-stamp allows a maximum latency of 4 us from when the photon hits the detector to when it reaches the coincidence circuit. Several types of photons could be coded such as: 60 keV for x-ray, <60 keV for attenuated x-ray, 140 keV for SPECT, <140 keV for attenuated SPECT, 511 keV for photopeak PET, and <511 keV for scatter PET, and PET Randoms).

6.5.12 Output of the Identified Photons: Memory Buffer and/or 3D-Flow Pyramid The 3D-flow DAQ-DSP board provides the possibility of installing a memory buffer for accumulating the single photons found during scanning time (see the SO-DIMM buffer memory indicated with dashed lines on the physical layout of FIG. 50, FIG. 52, or FIG. 53, and its dimensions, characteristics, and size in Table 6-5, and Table 6—6).

The 3D-Flow DAQ-DSP memory buffer can be used:

1. to store the single photons that passed the criteria of the real-time algorithm in the 3D-Flow stack and were recognized either as 60 keV x-ray of the CT scan, or 140 keV of the SPECT (including the ones attenuated) during the SPECT and CT operation mode. The buffer memory on each 3D-Flow DAQ-DSP board will provide a large buffering capability of several hours (or Gbyte) of data taking.
2. to store the single photons found during PET operation mode for the verification of the efficiency of the coincidence circuit operating in real-time. The circuit for real-time coincidence identification has the advantage of requiring less storage space and less computing power during successive processing phases of the data. The presence of the memory buffer on each 3D-Flow DAQ-DSP board will make possible a test on the efficiency of the real-time coincidence detection circuit when the PET is operating under different conditions. This test can be performed by spying and saving in the memory buffer the single photons acquired during a PET examination before they go through the circuit detecting the time coincidences among them in real-time. The photons in time coincidences could then be extracted from the raw data stored in the memory buffer by a slow algorithm running on the IBM PC CPU. The coincidences found using the circuit executing the algorithm in real-time and the slow off-line algorithm could be compared, and any discrepancies, could be investigated for the improvement of the real-time coincidence circuit.

In the event the output data rate never exceeds a few tens of MHz for the three modalities, PET, SPECT, and CT, then the memory buffer is not needed. All results found in the three modalities could be funnelled through the 3D-Flow pyramidal circuit and stored in the pyramid buffer memory located in the pyramid boards shown in FIG. 54, and FIG. 55.

6.5.12.1 Separating the Single Photons Found by the 3D-Flow Stack

Based on the reduction rate of photon activity at different stages of the PET acquisition detection system, as shown in FIG. 14 and Section 6.5.2, only about $80 \times 10^6$ single photons per second are expected at the start of scanning, 20 seconds after delivery of about 5 mCi of $^{15}$O-water tracer to the patient.

The processors at the first layer of the 3D-Flow pyramid will find no data from most of the 2,304 channels (see Example in Section 6.9) of the 3D-Flow stack. Only approximately four processors will find data during a sampling period of 50 ns.

Then, 1. in the event the memory buffer on the 3D-Flow DAQ-DSP board is installed, the data will be interpreted by checking the "type" bit-field of the output word received from the stack (see Section 6.5.11.4), and then routed to the DAQ-DSP memory buffer if 140 keV (and attenuated single photons) of SPECT modality are found or if 60 keV (and attenuated single photons) of CT modality are found;

2. in the event the memory buffer on the DAQ-DSP boards were not installed, the processors in the first layer of the pyramid will filter only the zero data and forward all single photon information found to the exit point of the 3D-Flow pyramid. The check of the content of the "type" bit-field will be performed only at the exit point of the pyramid. The single photons tagged as 140 keV (and attenuated single photons) of SPECT modality, or the 60 keV (and attenuated single photons) of CT modality, will be stored into the pyramid buffer memory (see Section 6.7.2, FIG. 54, and FIG. 55). Single photons tagged as 511 keV (or lower for Compton scattered events) PET events will be sent to the circuit that sorts the data in the same sequence as they were in the original sequence when they were created in the detector. The data flow will regain the fixed latency time with respect to when the event occurred in the detector, and the information will be sent to the time coincidence detection circuit.

6.5.12.2 Simulation of the channel reduction in the 3D-Flow pyramid The pyramid is a series of 3D-Flow processor layers that has a reduced number of processors between the first layer of the pyramid adjacent to the last layer of the 3D-Flow processor stack and the next adjacent layer that carries out the information. Again between this layer, the number of processors is reduced, and so on, until the number of processors per layer reduces to one ASIC (equivalent to sixteen 3D-Flow processors).

The direct synchronization between instructions and I/O ports allows efficient routing of data in an array. It is possible to route data efficiently from n to m channels by a 3D-Flow layout arranged in set layers with a gradual reduction in the number of processors in each successive layer.

It is important to calculate the data rates and make sure that data reduction matches the reduction in the number of channels. Most of the data reduction by zero suppression is accomplished at the first layer of the pyramid, which is attached to the output of the stack of processors that execute the digital filter and pattern recognition algorithm. Each processor in the first layer of the pyramid checks to determine if there is a datum at the top port (from the last layer of the 3D-Flow stack that has executed the digital filter and pattern recognition algorithm) and forwards it toward the exit. Only valid information along with their ID and time stamp are forwarded. All zero values that are received are suppressed, thus reducing the amount of data.

In the event the buffer memories on the 3D-Flow DAQ-DSP are not installed, all photons of the three modalities, PET, SPECT, and CT, validated by the real-time algorithm in the 3D-Flow stack are moved through the 3D-Flow pyramid to the pyramid buffer memory. For the PET mode of operation, instead, the data of the photons candidate for coincidence will be moved to the circuit which regains the fixed time delay between data at different stages, and then finds coincidences.

The data are moved from many channels to fewer channels (reducing by a factor of 4 or 16) in the 3D-Flow pyramid in the way shown in FIG. 40.

The 3D-Flow processors in the pyramid, as in the stack, work in data-driven mode. A FIFO at the input of each 3D-Flow processor derandomizes data and buffers them when more than one neighbor is sending data to one processor during the same clock cycle.

Data in the example shown in FIG. 40 flow from 16 processors of one layer to one processor of the next layer in the pyramid. The flow chart of the programs loaded into the processors of the channel reduction layers of the pyramid is shown in FIG. 41.

The 3D-Flow instruction of the program routing data into the pyramid without the buffer memory on the 3D-Flow DAQ-DSP board is shown in Table 6-4.

The same program should be modified for use with the buffer memory installed on the DAQ-DSP board. The 3D-Flow processor for this use, which has the bottom output port connected to the DAQ-DSP memory buffer, as shown in FIG. 58, requires additional instructions to check the field of the "event type" in the output word received (see Section 6.5.11.4) and send the received data either to the DAQ-DSP memory buffer through the bottom port in the event of a SPECT/CT datum, or to the designated output port in case of a PET datum.

Table 6-4. 3D-Flow instructions to move data in the 3D-Flow pyramid from several input ports of one processor to the designated output port of the same processor (depending on the location of the processor in the 3D-Flow array. The data received are sent to different output ports. Five programs contemplating the cases of the five ports of the processor are necessary. The following example contemplates the case of sending the input data to the output port East. Similar programs will send the received input data to North, West, South, and Bottom).

| | | |
|---|---|---|
| Next_event | ANYPORT TO C, C TO EAST | The 3D-Flow processor in data-driven mode operation executes the instruction when a datum at one port is present at its input FIFO. The received datum is sent to the East output port. |
| | SAMEPORT TO C, C TO EAST | Depending on the size of the word of the message, additional words are fetched from the same port until the message is complete. The received data are sent to the East output port. |
| | SAMEPORT TO C, C TO EAST | Same as above. |
| | SAMEPORT TO C, C TO EAST | Same as above. |
| | BRA Next_event | GOTO fetch another event |

Besides routing the data from several input channels to fewer output channels, each processor in the pyramid has 1 Kbyte of memory that can be used during the data flow through the pyramid to buffer high bursts of data for a short period of time or in case there is a concentration of input data in a restricted area.

6.5.13 Choice of an Output Bandwidth and Design of the Output Stage to Meet it.

Although the input bandwidth of the 3D-Flow system could sustain up to $40.08 \times 10^9$ single photons per second (calculated as 20 MHz×2,304 PMTs), a radiation dose delivered to the patient of 5 mCi of $^{15}$O-water (equivalent to 21 mrem of effective dose equivalent to the patient) was selected. This provides a rate of about $105 \times 10^6$ single photons per second to a detector with a FOV of 157.4 cm as described in Section 6.9. (See Section 6.5.2, ascertaining that the 3D-Flow system provides sufficient input bandwidth).

The above consideration shows that the overall bandwidth of the system is determined by the design of the output stage of the pyramid and of the coincidence logic. The capability of the 3D-Flow system to sustain $40.08 \times 10^9$ single photons per second in input, will never impose a bandwidth limitation at the input stage for any reasonable level of radiation dose delivered to the patient, and will provide also the means to meet increased future requirements.

The above estimated $105 \times 10^6$ photons per second activity at the detector, corresponds to about $80 \times 10^6$ signals per second of single photons that are candidates for a coincidence and that produce a signal to the DAQ-DSP electronics. (The reduction from $105 \times 10^6$ to $80 \times 10^6$ is caused by the stopping power, photofraction, and crystal scattering, as described in Section 6.6.6). Statistically it is estimated that only $20 \times 10^6$ coincidences per second are expected out of $80 \times 10^6$ single photon per second generating a valid signal to the electronics.

Thus, from the above calculation and estimates, it is required to design the output stage of the pyramid and of the coincidence detector circuit with the capability of accepting in input about $80 \times 10^6$ single photons per second and the capability of finding $40 \times 10^6$ coincidences per second in the event that all photons at the input are good candidates for a coincidence.

The example of the design presented in Section 6.5.14.2, is a comprehensive way of describing a problem and a solution for it. However, for the actual implementation, a scheme that makes use of the same approach is introduced, with the difference that it accounts for the highest possible extraction of coincidences from the single photons and provides the flexibility to modify the design at a future time, in the event the user will desire to increase the output bandwidth (which in this case corresponds also to the overall system bandwidth. See Section 6.5.14.3).

6.5.14 Coincidence Identification Functions Implemented in the 3D-Flow Pyramid 6.5.14.1 Sorting Events in the Original Sequence and Regaining Fixed Delay Between Data at Different Stages The original sequences of the events as they were acquired by the detector, as well as their latency time from a location in a layer of the pyramid with respect to the time when they were created, are lost at the last stage of the pyramid. The reason is that events have followed different paths (short and long) when moved through the pyramid.

The task of this stage (or vertex of the pyramid) which is implemented with a layer of 3D-Flow processors (one component is sufficient for the applications described herein), is that of sorting the events in their original sequence and regaining the fixed latency time between data at different stages.

FIG. 43 shows the flow of results (photons identified by the real-time algorithm in the 3D-Flow stack) from the 3D-Flow stack to the coincidence circuit.

The right side of the figure shows the flow of results from one stage of the 3D-Flow system to the next stage with the relation of the time delay of the data in different stages.

Figure 60:
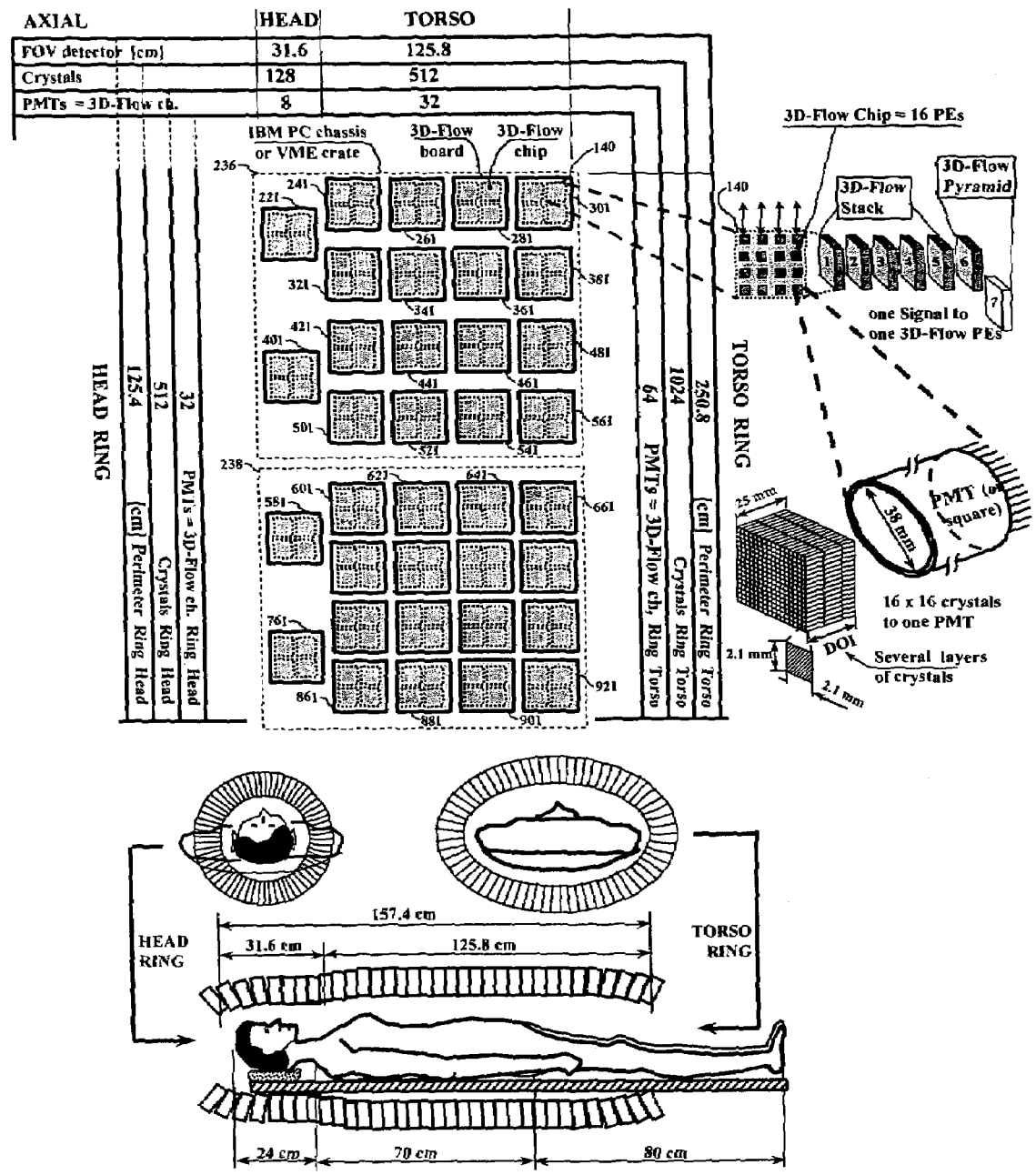

The real-time algorithm and its implementation with the 3D-Flow providing the results, shown on top left of FIG. 43 as output from the 3D-Flow DAQ-DSP stack, is described in Section 6.5.11, FIG. 38, and its implementation is shown in the left section of the logical layout of FIG. 58, on the right section of the logical and physical layout of FIG. 60, and on the physical board layout of FIG. 50, FIG. 51, FIG. 52, and FIG. 53.

The 3D-Flow program for the funnelling of the data through the pyramid, shown in the center left of FIG. 43, is described in Section 6.5.12.2, FIG. 40, Table 6-4; and its implementation is shown on the same figures mentioned in the previous paragraph.

The sequence of operations performed in the circular buffer shown in the center of FIG. 43 are described in FIG. 42, and their implementation is shown in the logical layout on the center section of FIG. 57 (see processor 84 of chip 155, and processor 96 of chips 156 and 157), and on the IBM PC board layout of FIG. 54, and FIG. 55.

FIG. 42 details the task of the computer program. It should be reviewed in conjunction with FIG. 43 and FIG. 24, which explain how the program functions with the logic detailed in the right half of FIG. 44 and the hardware in the left half of FIG. 44. Note that in FIG. 24, for CT x-rays, there is a fixed time for receiving the results and calculating for a single photon at 2410 (the same is true for the SPECT). For PET, the calculations occur at variable time latency, because creating a data set requires two photons and the location of the photons could be anywhere over a larger number of detectors as noted in 2450 of FIG. 24. Photons arriving at the same time but in positions far apart, may take paths that are longer than the other's path to get to the comparison station. An additional calculation must be made to accommodate for signals representing photons whose time of processing (comparing their time stamp) may be later than other photons that arrived at the same time, because of the distance that the data must travel until it is paired up. In FIG. 44, 4350 indicates the path of an event that occurs and is processed more quickly than event 4380 which has to go a greater distance to be processed. If nothing is done to accommodate the variable processing times, then the wrong result would come out. A circular buffer, such as 2470 of FIG. 24 solves this problem. The buffer is also represented in 4390 of FIG. 43. This buffer 4390 evaluates the time stamp and then reorders the data according to the true arrival time. After the data is reordered according to its true arrival time, in circular buffers 4410 and 4420 of FIG. 44, then the time stamped photons are ready for coincidence detection 4450.

FIG. 43 illustrates a process for sorting and realigning photon measurements into the sequential order of the radiations that created the photons. In general, the photons are assigned a time stamp. The known good photons are then funnelled to a single channel and produced to a buffer where they are rearranged according to the time stamp values.

The circular buffer memory in the center of FIG. 43 receives the data from the last layer of the pyramid. The program loaded into the 3D-Flow processor implementing the circular buffer, reads the field of the time-stamp of the event received from the pyramid and uses the value of its content to calculate the address (write pointer) of the circular buffer where the event just received should be stored.

This operation has the effect of sorting and regaining the fixed latency delay between data.

At the system speed of 20 MHz the circular buffer is read out when all photons with a given time stamp have been stored in the circular buffer. (The reading should allow the data of the photon from the channel that follows the longest path of the pyramid being stored in the circular buffer).

The reading of the circular buffer(s) at any given time (50 ns period) will provide all photons that occurred n time periods before in the detector. Not more than 4 are expected on average for each 50-ns period for a 5 mCi of $^{15}$O-water radiation dose delivered to the patient for a PET with a FOV of 157.4 cm.

The task described in the next section will be that of executing all possible comparisons (6 comparisons) among the 4 photons found, in order to identify those in time coincidence that satisfy a certain set of criteria identifying the location of the radioactive source.

6.5.14.2 Example of a Coincidence Detection Implementation with the 3D-Flow

There are several ways of using the scheme of the circular buffer described above for detecting all possible photons belonging to a specific time period n of 50 ns (or, any sampling time period of the system). One simple example is described in this section, while an example for a more general application requiring maximum photon detection with the possibility of increasing the output bandwidth of the system is described in Section 6.5.14.3.

In order to find a coincidence, a signal from a detector block needs to be compared with the signal from another detector block. For the sake of convenience, the detector blocks are grouped in sectors, and only 4 sectors are defined in this example. All detector elements connected by lines that do not pass through the body of the patient are grouped together in a sector (see top right part of FIG. 44).

This scheme requires the implementation of 4 circuits of the type shown in FIG. 43. An example of an implementation for 1,152 channels is shown in FIG. 44(see chips 155 and 156), and for 2,304 channels is shown in FIG. 58 (processor 96 of chip 156 and 157, and processor 96 and 84 of chip 155).

For each sampling time period of 50 ns, the single photon detected in each of the sectors will be compared with the photon detected in the other sectors in the 3D-Flow processors of the chip indicated with the number 158 in FIG. 44, and FIG. 58. (In the very unlikely case that more than one photon is detected, the memory cell of that location is overwritten and the last value written is the one that will be compared). The operations performed on the data relative to the single photons received during a specific sampling time period in those processors are listed in FIG. 46.

FIG. 44 shows the coincidence detection scheme with the 3D-Flow requiring only one component instead of seven ASICs. FIG. 45 shows the circuit, which requires only six comparisons amongst 4 photons (A–B, A–C, A–D, B–C, B–D, and C–D) every 50 ns, as opposed to approximately 700 comparisons every 250 ns, in current PET, and provides a rate of coincidences found up to 40 million coincidences per second instead of 4 million coincidences per second, as is the limitation of the current PET (see references [20, 18]).

6.5.14.3 General Scheme for Implementing a System with Higher Bandwidth and Maximum Coincidence Detection Efficiency The following is a general scheme, based on the requirements of the maximum radiation dose delivered to the patient and the complexity of the coincidence detection algorithm, for implementing the circuits at the output of the 3D-Flow pyramid for sorting the photons (or events) in the original sequence, regaining a fixed latency time with respect to when the event occurred in the detector, and for identifying all coincidences.

The basic idea of the approach is very simple. There is no segmentation of the detector in sectors as was done before. If the radiation delivered to the patient creates $80\times10^6$ single photons per second, the circuit described above for sorting and realigning the latency needs to run also at $80\times10^6$. A single circular buffer is implemented at the speed equal to or higher than the rate of the single photon created.

Each photon detected within the sampling time window of 50 ns is compared with all other photons of the same time window (e.g., 6 comparisons for 4 photons, 10 for 5 photons, 15 for 6 photons, (or $(n\times(n-1))/2$), regardless of whether or not the x, y position of the two photons being compared lie along a line passing through the patient's body.

A 3D-Flow processor can be used for implementing the comparison circuit. A set of 3D-Flow processors working in parallel could perform all comparisons of detecting coincidences within a sampling period. For example, one 3D-Flow chip would be sufficient for a 5 mCi dose to the patient corresponding to about $80\times10^6$ single photons per second activity of a PET with about 150 cm FOV. The number of comparisons are so limited, compared to the approach used in the current PETs, which instead require more than 1 million comparisons every 250 ns for a FOV of about 150 cm, that it is not a problem to perform all of them.

In the event the real-time algorithm required to execute the comparison program listed in FIG. 46 is longer than the time interval between two consecutive input data, a stack of 3D-Flow (for one chip in x and y dimensions) similar to the stack implemented in the first stage of photon identification, can also be implemented at this stage, since all operations are synchronous and the latency of the data received are identical and are referred to the same event acquired at a specific time in the detector. The combination of the two circuits, a) the sorting and realigning latency circuit running at the speed higher than the single photons acquired by the detector and b) the real-time coincidence algorithm implemented with the 3D-Flow architecture (which allows the execution of an algorithm longer than the time interval between two consecutive data) will guarantee the identification of all possible coincidences, and will calculate the TOF of the pair of photons and apply to them the attenuation correction.

6.5.14.4 Format of the Output Word of the "Coincidences" from the 3D-Flow Pyramid to the Buffer Memory The format of the output word of the "coincidences" (pair of photons) from the 3D-Flow pyramid to the buffer memory is the following:

bits 0–19 crystal spatial ID (hit1); bits 20–23 Depth of interaction (hit1); bits 24–29 photon energy (hit1);

bits 30–33 time-of-flight (hit1 and hit2);

bits 34–53 crystal spatial ID (hit2); bits 54–57 Depth of interaction (hit2); bits 58–63 photon energy (hit2).

Two 20-bit fields for spatial ID of hit1 and hit2 allows for coding up to 1,048,575 crystals. Two-4 bit DOI fields allow for a depth of interaction of both hits with up to 1.56 mm resolution when 25 mm thick crystals are used. The energy of the two photons is coded in 64 intervals from the smallest to the highest energy value. The 4-bit field for the time-of-flight makes it possible to locate within 7.5 cm resolution the point of interaction along the line which connects the two crystals, and to measure up to 75 cm the distance in any direction inside the patient's body. The maximum measurement could be increased by changing the coincidence time window parameter. For instance, a 3-ns coincidence time window parameter will allow the measurement of any interaction that had travelled up to about 90 cm inside the patient's body).

6.5.15 Device Operation in PET SPECT and CT Mode

Simultaneous operation in PET/SPECT/CT mode can be performed. The instrument can detect and separate the photons acquired during transmission of 60 keV (CT scan), and during emission of 140 keV (SPECT), and emission of 511 keV (PET) mode (see Section 6.5.1. The real-time algorithm identifying and separating the three types of photons is described in Section 6.5.11, and the output word carrying the information of the photons identified for the three modalities is described in Section 6.5.12).

If the memory buffer is not installed on the 3D-Flow DAQ-DSP board, all photons from the three modalities are forwarded to the pyramid buffer memory.

Buffer memories of different sizes can be installed up to a maximum of two DIMM memories of 4 GB each, making it possible to accumulate up to 1 billion coincidences. This is equivalent to 50 seconds of scanning at the acquisition rate of 20 million coincidences per second, (or equivalent to 13.8 hours scanning buffering at the rate of the current PET devices of 20,000 coincidences per second).

6.5.16 Reading Results from the Event Buffer Memory and Packing for Transmission in the PETLINK Digital Interconnect Standard The IBM PC reads the data from the two DIMM buffer memories of the pyramid (or from the buffer memories of the DAQ-DSP boards when installed). The format may be changed by a program in C++ on the IBM PC CPU if it is desired to conform with the PETLINK [58] digital interconnect standard. However, the user might consider using the format described above in Section 6.5.14.4, because it provides information on the energy of the photon and the TOF, which is useful information for improving the signal-to-noise ratio of the image during reconstruction.

6.6 Comparison of the 3D-Flow Approach vs. Current Approach

The PET with the 3D-Flow system differs from the current PET systems by providing the capability of delivering to the patient a very low radiation dose and of performing the examination in a shorter time, thus at lower cost, making the device suitable for cancer screening instead of being used only with patients with higher risks.

FIG. 14 summarizes the differences between the two systems. The analysis of the performances have been made based on measurements made on the current PET manufactured by GE as reported in [2]. PET from other companies do not have performance very different from GE Advance, and in several models the performance is even worst.

The efficiency of the current PET instrument was expressed as the ratio of coincidences detected to the radioactivity delivered to the patient, or 0.014%. This was calculated as $200 \times 10^3$ coincidences per second found, divided by $1.424 \times 10^9$ disintegration per second of the source activity, at half the scanning time period of 60 seconds, which started 20 seconds after injection of 66 mCi of the tracer $^{15}$O-water. Based upon this finding, the efficiencies of the other intermediate stages were calculated or estimated with the purpose of discovering which stages are least efficient and most in need of improvement. It is in those stages that we find the greatest opportunity to improve overall efficiency, and that is where the effort involved will provide best results.

The efficiency of the PET of this proposal with the 3D-Flow (see bottom-right of FIG. 14) is 10% (calculated as $4.75 \times 10^6$ coincidences/sec found, divided by $47.4 \times 10^6$ disintegration/sec of the source activity, at half the scanning time period of 60 seconds, which started 20 seconds after injection of 2.2 mCi).

The number of coincidences per second found by the PET with the 3D-Flow system ($4.5 \times 10^6$) is 22.5 times greater than that found by the GE Advance PET ($200 \times 10^3$). The radiation dose to the patient required by the PET using the 3D-Flow system is on 2.2 mCi. That required by the GE Advance PET is 66 mCi, 30 times greater.

The total difference in efficiency between the two systems for this type of measurement is 22.5×30=675 times, which is well above the factor of 400 claimed in the preface of this book.

The values in the third column from the left in FIG. 14 report the efficiency for the GE PET (and similar machines) at the different stages. Low efficiencies spotlight stages needing improvement, and at only 8.1%, the electronics stage shows the greatest need.

(The estimate of 8.1% efficiency of the electronics is even optimistic. In reality it might be worse than that, because the particular examination described in [2] was made on the brain, where the radioisotope concentration is higher than many other parts of the body. The computations have been done with the assumption of an average equal distribution of the radiation over the entire body and to account for 8.5% FOV over the entire body. Accounting for a higher concentration of radiation in the brain compared to the feet would give an efficiency for the electronics of even less than 8.1%.).

The next lowest efficiency stage is the field of view (FOV), which provides only 8.5% efficiency and is also dependent, in the current PET, upon the electronics. The detector design used in the current PET presents an absolute limitation on the size of the FOV, a "brick wall," for the following reasons:

1. The current technical approach to comparing for coincidences every sampling period all possible lines of response between pairs of detectors located where the line connecting them (LOR) passes through the patient's body requires a very large number (e.g., over a million comparisons every 50 ns when 2,304 PMT are used. See Section 6.6.8.1.3) number of comparisons to be made if the FOV is increased. This approach is not practical, nor is it cost effective.
2. To find a solution to the problems of limitation and cost versus complexity in changes in the hardware is not possible. The circuit and cabling required by the current technical approach of the LOR as well as the poor efficiency in the photon identification circuitry at the front end, preclude achieving enough of an improvement in efficiency to justify building larger PET detectors. This puts a higher return on investment out of reach, because the goal of performing more examinations per day is unattainable The third area, with a low efficiency of 18% of the solid angle will automatically increase with the extension of the FOV as shown in row (2) of the same figure.

In summary, two "brick walls" and two "bottlenecks" have been identified in the electronics of the current PET systems (they are common also to the other PET such as the ones manufactured by CTI/Siemens) that are the cause of the low efficiency. The removal of them will improve the overall efficiency over 400 times.

Two sets of inventions remove them: group A removes "brick wall A" and "Bottleneck C" (see row (5) of FIG. 14), while group B removes "brick wall B" and "bottleneck D," (see row (6) of FIG. 14. The removal of "brick wall B" with a much simplified hardware electronics allows the increase of the FOV shown in row (2) of the same figure.)

The following subsections of this chapter describe in detail the limits of the current PET electronics and the details of the solution that overcomes each one of them can be found in Section 6.1.

6.6.1 Requiring $\frac{1}{30}$ the Radiation to the Patient with the 3D-Flow System.

The top of FIG. 14 shows the radiation dose delivered to the patient with the current PET systems and with the PET of this proposal using the 3D-Flow architecture. The radiation dose of 66 mCi of $^{15}$O-water delivered to the patient for an examination with the GE Advance PET [2] (corresponding to an effective radiation dose of 227 mrem, which is approximately equivalent to what a person in Seattle (WA) [59] receives during one year from all other sources), is 30 times more than the 2.2 mCi radiation dose required to be delivered to the patient with a PET of this proposal incorporating the 3D-Flow design. (2.2 mCi of $^{15}$O-water, corresponds to an effective dose of 9.2 mrem. This is equivalent to radiation received on a one-way flight at high altitude between the United States and Europe or Japan).

6.6.2 Identifying from 14 to 40 Times More Photons than the Current PET

The PET using the 3D-Flow system finds 22.5 times the number of coincidences found per second by the GE Advance PET (calculated as 4.5×10$^6$ coincidences/sec found by the PET with the 3D-Flow system, divided by 200×10$^3$ coincidences/sec found by the GE Advance PET). Similar performance differences occur in the case of CTI/Siemens PET models.

6.6.3 Photons Scattered and Absorbed in the Body of the Subject

The first reduction in photons from the original activity of the source of radiation (the tracer of imaging agent carrying the isotope) internal to the body of the patient is the Compton scatter and absorption inside the patient's body. The larger the volume of the matter encountered by the photons in their journey, the more chances there are that they will be scattered or absorbed. Thus depending on the weight of the subject, this stage should account for a loss of photons in time coincidence from a 75% to 93%.

(A simulation indicating more precisely the number of photons lost here with respect to a subject of a given weight can be performed with software packages from Stanford Linear Accelerator Center and Los Alamos National Laboratory referenced in [60]. See also the definition of the term "Monte Carlo" in the glossary of this document. The simulation by Tumer reported in [61] shows in FIG. 71 that 1.2×10$^8$ photons/sec leave the phantom out of 2.3×10$^8$ photons/sec created. This corresponds to an efficiency of 52%. Since PET technique requires two photons in coincidence, the percentage of the photons in time coincidence is the square of the percentage of the single photons, thus 27%. The phantom used by Tumer was a cylinder 20 cm×20 cm in diameter that could be compared to the head of a human, while the estimate of the photons in time coincidence leaving a whole body is only from 7% to 25% depending on the person's weight. While the previous software simulation package is for more general use, the SimSET [62] software package developed by the University of Washington, Division of Nuclear Medicine, is more specifically for the simulation of PET, SPECT and X-ray events).

At this stage, for either case, assuming only 15% of the photons in coincidence leave the body of the subject, the original 1,424×10$^6$ pairs of photons emitted per second by the radiotracer, as shown in row (1) of FIG. 14 are reduced to 214×10$^6$ pairs of photons per second. In the case of the PET with the 3D-Flow, which has an activity of 47.4×10$^6$ pairs of photons per second, this stage reduces them to 7.1×10$^6$ pairs of photons per second.

6.6.4 Field-of-View (FOV)

The field of view (FOV) of current PET devices is 15 cm to 25 cm. As mentioned above, the impracticability of the current approach of the electronics, where all lines of response (LOR) are checked for coincidences, requires an exorbitant number of comparisons. When it is desired to increase the FOV, an impasse, "brick wall B," (see row (2) of FIG. 14 is encountered. This reason, together with the low increase in efficiency provided by the PET advances in the last 25 years, has not encouraged investors to manufacture PET devices with larger FOVs. The increase in the number of crystals required in doing so would not repay their cost.

On the other hand, the two- to three-fold increase in cost of the proposed PET device with a greatly enlarged FOV would be capable of performing up to ten times as many examinations per day as current PET because of the reduced duration of an examination. Furthermore it extends the prospective market to include use of the device as a screening implement in addition to its current use as a diagnostic tool for patients at high risk for cancer. Thus, investors can expect a return of their investment in a shorter time and the possibility of realizing greater returns in an extended market.

Row (2) of FIG. 14 shows that for an increase from 15 cm FOV to 157.4 cm, the efficiency of the detected photons by the PET is increased from about 8.5% to about 95%. Only a minor number of photons are lost in the lower part of the legs and the feet. The "singles" generated from the section adjacent to the detector FOV are also greatly reduced (see also FIG. 7) because most of the activity is within the FOV of the detector.

The use of an examination protocol as described will further capture more photons, leaving less dispersion in the legs, thus increasing the efficiency even if the field of view is shorter than the actual height of the patient. This protocol manipulates the tracer kinetics by occulting blood circulation to the legs with cuffs in order to maintain the difference between activation and baseline signals longer than standard protocols.

The $214 \times 10^6$ pairs of photons per second for the examination with GE PET are reduced at this stage to $18 \times 10^6$ pairs of photons per second, while for the proposed 3D-Flow PET the $7.1 \times 10^6$ pairs of photons per second are reduced to $6.7 \times 10^6$ pairs of photons per second.

6.6.5 Solid Angle

Having increased the FOV, the solid angle will also increase as shown in row (3) of FIG. 14 from about 18% to about 92%. The $18 \times 10^6$ pairs of photons per second for the examination with GE Advance PET are reduced at this stage to $3.2 \times 10^6$ pairs of photons per second, while for the proposed 3D-Flow PET the $6.7 \times 10^6$ pairs of photons per second are reduced to $6.2 \times 10^6$ pairs of photons per second.

6.6.6 Crystal Stopping Power, Photofraction, and Crystal Scatter

Ideally when a 60 keV, 140 keV, or 511 keV photon interacts with a crystal, all energy would be deposited and converted to light. However, that is not the case for many crystals even if the thickness of the crystal is increased. Semiconductor detectors [63, 64] will have a better stopping power and a much more efficient detection of x and y rays, however, they requires to operate at low temperature (T=– 196° C.).

Photons in crystal detectors undergo Compton scatter (see Section 6.5.5.4), and some of the secondary photons leave only a portion of the 511 keV of the incident photon in the detector. Part of the energy leaves the crystal in the form of another photon. Different crystals have different characteristics, but if the electronics had the capability to analyze thoroughly the signals created by an incident photon, then the useful information could be extracted from its energy spectrum, and some events with crystal Compton scatter would be captured.

The 3D-Flow design with digital signal processing capabilities at this stage, would be very useful for extracting the energy spectrum [65] by processing the signal from each channel, and these signals can also be integrated with the information from their neighbors. The flexibility of the 3D-Flow allows the designer to choose and combine different detectors, each one aiming to provide the essential information at the lowest possible cost. The processing capability of the 3D-Flow system can process the information from different detectors of a given view angle of the source.

An efficiency for both designs (old and new) of 80% has been assumed at this stage (see row (3) of FIG. 14.

The estimate acceptance of 80% of the photons in time coincidence at this stage, provides a reduction from $3.2 \times 10^6$ pairs of photons per second in time coincidence to $2.5 \times 10^6$ pairs of photons per second in time coincidence. The same efficiency was also calculated for the 3D-Flow PET which provides a reduction from $6.2 \times 10^6$ pairs of photons per second in time coincidence to $5 \times 10^6$ pairs of photons per second in time coincidence.

6.6.6.1 Crystal Stopping Power

Crystals with high density provide a good stopping power. The PET built in the years 1990–1996 used mainly 30 mm BGO crystals which are reported in Table 1 of [16] to have 91% efficiency for 511 KeV when 25 mm thickness is used and 100% efficiency for 140 keV photons.

In part due to the cost and in part due to the limitation of the current electronics for PET, during the most recent years the crystal thickness has been reduced from 30 mm to 10–15 mm. (The 3D-Flow architecture of the novel approach presented herein overcomes the electronics limitation.) Most recent PET from 1996 to 2000 and the ones on the drawing board are using crystals with a thickness of 10 mm for the 57% crystal efficiency claimed for the GSO PENN PET) and 15 mm.

The crystals used in the GE Advance PET, the measurements of which are used in FIG. 14, have BGO crystal thickness of 30 mm, which provides a stopping power efficiency close to 100%, and their proposed new design projects a crystal thickness of 25 mm, which provides about 90% efficiency in stopping power.

6.6.6.2 Photofraction

The measure of the capability of a scintillation detector to absorb photons is the photofraction. Several factors such as: attenuation coefficient, crystal density, effective Z, and detector size affect the photofraction that can be measured as:

$$\text{Photofraction} = \frac{\text{Number of Photopeak Events}}{\text{Total number of Events}}$$

A photopeak event is that which occurs when most of the photoelectric interaction results in full deposition of the gamma-ray energy in the detector.

The photofraction of a BGO crystal 5.6 mm×30 mm×30 mm is about 65%, and less for GSO, and $BaF_2$.

6.6.6.3 Crystal Scatter vs. Scatter in the Patient's Body

Although one cannot distinguish between the crystal scatter and scatter in the patient's body, the digital signal processing of the 3D-Flow can capture the useful crystal scatter by summing the energy from neighboring detectors and applying DSP filtering algorithm. With the use of graded absorbers, it can also recognize most of the events reaching the detector that were scattered within the patient's body. With a DSP at each channel, the efficiency at this stage should not be calculated as the reduction provided by the stopping power minus the reduction factor of the photofraction, because the digital signal processing can capture some useful crystal scatter.

The body scatter which cannot be rejected by the electronics at this stage will be rejected by the off-line image reconstruction algorithm, while the crystal scatter events recognized by the real-time 3D-Flow DSP processing will contribute to improve the image quality.

6.6.7 Comparison on the Electronics

The reason for the poor efficiency of the electronics (8.1% or lower in the current PET; see row (5) of) is to be attributed first to the poor identification of the photons and their characteristics (this operation is common for the three modalities: PET, SPECT, and CT). Because identification of the good photon candidates at the first stage was not optimized, the following stage, the detection of coincidences (see row (6) of FIG. 14), becomes meaningless. If one of the pair of photons has already been discharged, the device obviously cannot find coincidences.

6.6.7.1 Identification of Photons and Extraction of Their Characteristics

Several factors responsible for poor particle identification are a consequence of the approach taken to the electronics of the current PET. Attempting to improve improving the photon identification by trimming and fine-tuning the electronics in the PETs using the current approach has definite limits, "brick wall A."

No matter how much analog signal processing is put into the current PET design, the problem remains that the complete sources of information and the hardware platform to handle them are missing.

The information to the north, east, west, and south of the signal from the incident photon are missing; thus it is impossible to reconstruct the total energy of the incident photon. The positioning is also difficult to calculate. As long as there is a fixed segmentation of a 2×2 detector module, there will always be an incident photon that will hit the edges or corners of the block and some information on one side of the hit will be missing (see Section 6.5.8).

Unless a drastic change in the overall approach (in detector block segmentation, analog processing, processing for increased timing, spatial resolution, and signal-to-noise improvement) is made, it will be impossible to effect significant improvement.

In order to tear down this "brick wall A," the data acquisition system of the PET should acquire data from all channels of the detector, and then the electronics should provide a method to evaluate each channel to determine if it is the head of a cluster of the incident photon (2×2, 3×3, 4×4, 5×5, etc., depending on the energy of the photon and the area covered by one channel). This can only occur if no boundaries are set a priori, and if each channel can have on its own processing unit all the information (including signals from its neighbors) necessary to determine if it is the head of a cluster of an incident photon.

The 3D-Flow overcomes this "brick wall" with its architecture. Data from each channel (PMT, or more generally, any sensor within a given view angle) are acquired, converted to energy through a look-up table before summation, exchanged with the neighbors, and processed for photon characteristic extraction. Each individual channel is analyzed at a rate of 20 MHz to determine if it is the head of a cluster of an incident photon with respect to all its neighbors.

Most of the PETs used in hospitals nowadays operate on a time window of about 12 ns over signals with a time resolution of about 2.5 ns when attempting to separate one event from the other. Considering that in 2.5 ns the photon travels a distance of 75 cm, and that in 12 ns it travels 3.6 meters, the timing resolution provided is not of great help in identifying the coincidence event. It is so broad that many events could have occurred during that time; and the resolution is so poor that it does not help to separate the photon of one event from the photon of another event. In other word, more to the point, it cannot tell for sure if two detected photons belong to the same event.

The 3D-Flow system can achieve better timing resolution by acquiring for each signal rising edge the timing information (time-stamp) of the photon absorbed by the detector. The signal is sensed by the CFD which passes the logical output on to a time-to-digital converter (TDC), which produces a 500 ps resolution time-stamp. The time-stamp is then processed by the FPGA and the 3D-Flow for best timing resolution determination. (The 3D-Flow can also extract timing information by means of the DSP on the acquired PMT signals).

6.6.7.1.1 Front-End Electronics of the 3D-Flow System vs. Current PET FE Electronics In FIG. 47a, at left, is shown the Digital Signal Processing (DSP) of the 3D-Flow system with digital signal integration functionality as opposed to the analog signal processing implemented in the current PET systems in FIG. 47b.

The specific circuit shown at right in FIG. 47b is used in several models of PET devices manufactured by CTI/Siemens [66]. Although it has the merit of being able to remotely control 8 parameters to fine-tune each channel (the gain of the 4 preamplifiers, the constant fraction discriminator threshold, the x and y offset, and the time alignment of the system clock), those variables still place a limit on the processing of the analog signal compared to the flexibility of digital signal processing.

In the same circuit used in the current PET, the signals received from 4 photomultipliers (PMTs) are then combined and integrated over a period of the order of 1 μs to form an energy signal and two position signals (axial and transaxial).

Any attempt at processing of the above signals will encounter a brick wall, because they carry the information of 4 PMTs and cannot be decomposed for further enhancement of energy, spatial resolution, or timing resolution. The attempts made in the current PET, with its mix of look-up tables and analog processing to decompose the signals and decode the position and energy information absorbed by the crystal that was hit, will never be able to achieve good performance, because the neighboring information to the 4 PMTs (2×2 array) is missing.

The gain control of the preamplifier is good; however, if the PMT does not deliver an optimum signal, it does not help to be able to increase the gain of it. A better control would be that of the power supply to the PMT as in the 3D-Flow system.

The sum of 4 analog signals used in current PET may be critical because it adds in the noise as well, while the 3D-Flow converts the ADC counts of each individual channel through the internal look-up tables and subtracts individually the noise of each channel, by means of its DSP functionality, before summing them.

The position and energy lookup tables shown on the right of FIG. 47b encounters the difficulties and limitations in identifying position and energy of the incident photon as explained in Section 6.5.9.

Using a look-up table immediately after receiving, from each channel and not from each group of four, the ADC counts from the analog-to-digital converter (as is projected in this new proposal) provides the possibility of including all specific corrections for each channel (gain, non-linear response of the channel, pedestal subtraction, etc.).

The 3D-Flow can extract much more information (area, decay time, etc.) from the signal received performing digital signal processing on the last four or five received signals from the direct PMT channel and on the 3, 8, 15, or 24 signals from the neighboring PMTs via the North, East, West and South ports of the 3D-Flow.

The tuning of each channel with a digital look-up table is also convenient, because the calibrating parameters can be generated automatically from calibration measurements.

6.6.7.1.2 Elimination of the Detector Blocks Boundaries

The fixed cabling in current PET of the 2×2 PMTs is another limitation. When a photon hits the detector at the edge of the 2×2 block and the energy is split between the two blocks, both may reject it because they do not see enough energy.

This is solved with the 3D-Flow system where each signal (PMT with a group of crystals associated with it) is checked to see the local maximum of a cluster against its 3, 8, 15, or 24 neighbors without any boundary limitation. Details on how this functionality is achieved in the hardware implementation is shown in FIG. 56.

With the 3D-Flow approach, the entire PET system is seen as a single large array instead of several 2×2 blocks that, introduce boundaries. There is no difference in efficiency in event identification between the crystals in the center and those on the edge of a 2×2 block because there is no block definition, but each channel is a block that receives the information from all its neighbors.

6.6.7.1.3 Elimination of the Incoming Data Bottleneck

There is a bottleneck, shown as "Bottleneck C" in FIG. 14 (See also Section 6.5.2), in the incoming data in the current PET for the following reasons:

a) The detector in current PET is segmented into 56 modules [2] (or a number not very different for PET from other companies. Each module covers a large detector area; and when crystals with slow decay time are used, the entire module is unable to acquire data (dead time) for 1 to 2 μs when a hit is detected. (This corresponds to a capability of receiving photons continuously from the same module only at a maximum rate of 0.5 to 1 MHz.). For an activity of about $100 \times 10^6$ single photons per second received from a detector with 56 modules, there is a 44% probability that a photon will hit a module during a sampling time period of 250 ns. This has to be compared with 0.43% probability that one of the 1152 detector elements of the 3D-Flow implementation will be hit by an incident photon every 50 ns when the activity at the input is the same, $100 \times 10^6$ single photons per second. (See also Section 6.8).

b) The coincidence electronics in the current PET cannot handle the 1,344 acquisition channels, but an arbitrary reduction is made to 56 channels. The reduction is based on a simple check to find out if a signal received from the sum of 4 channels is within a certain energy window. To avoid this bottleneck, a more thorough check of all the characteristics of the incident photon, to see if it conformed to the ones expected, would be required.

The 3D-Flow system overcomes the above "bottleneck C" because it has a sampling rate of 20 MHz for a 64-bit word received individually on each of the 1,344 channels, sustainable continuously on all detectors. A real-time algorithm that checks thoroughly all parameters characterizing a photon is executed on the data of an entire event and each channel is investigated to determine if it could be the head of a cluster. The 3D-Flow feature of extending the processing time in one pipeline stage, allows the execution of real-time algorithms longer than the time interval between two consecutive input data. In the event the rate of 20 MHz cannot be sustained for other reasons not dependent upon the electronics, such as crystal slow decay time, having the 3D-Flow handle each single channel of the 1,344 channels means that only one channel out of 1,344 (and not one out of 56 as is in the current PET) will be dead for the duration of the decay process in the crystal.

6.6.8 Coincidence Detection Logic

6.6.8.1.1 The Approach of Coincidence Detection Used in the Current PET

The approach to detecting coincidences in current PET machines installed in hospitals is similar. I will describe only the General Electric Advance, and I will provide the references to a similar one implemented by CTI/Siemens. Together, the above-mentioned manufacturers have the largest section of the PET market in the world.

Their approach requires the electronics to compare all pairs of signals from crystals which are points on a line passing through the patient's body.

Using this approach, for a system with n channels, all possible comparisons between all channels are: (n×(n−1)) divided by 2. Since in the PET application only the crystals which are a point on a line passing through the patient's body are useful, the number obtained for all possible combinations further divided by 2, will be approximately equal to all LOR of a PET.

Current PET [2, 20] for a 15-cm FOV have about 56 modules and perform about 700 comparisons along all LOR passing through the patient's body. This implies that ALL comparisons (about 700) are executed every 250 ns at each LOR, even if NO hit occurred at a specific module. The number of 700 comparisons is calculated by applying the above formula as follows: (56×55)/2=1540 provides all possible combinations, and since not all LOR pass through the patient's body, approximately half are the total LOR which need comparison.

The use of this approach on a PET with an increased field of view runs into "brick wall B." (See FIG. 14). The number of LOR to be checked and compared will increase enormously, the complexity of the consequent circuitry will also increase, and the time available to execute all the comparisons will not be sufficient. If a larger number of channels are arbitrary dropped as is done now from 1,344 to 56 channels, additional inefficiency will be introduced. Any decision to perform the coincidence detection task using the current approach has a drawback which introduces inefficiency, becomes very costly, or is impossible to execute within a short sampling time period.

On the left of row (6) of FIG. 14, bottleneck C at the front end is shown. This problem, as described above, also affects the coincidence detection efficiency, because the arbitrary reduction of the number of photons detected by the 1,344 channels to 56 channels lowers the probabilities that a photon will find its companion in time coincidence.

The entire hardware system of the current approach by GE Advance and the coincidence electronics is described in the patent [20]. The 1,344 blocks are reduced in number and grouped into 56 modules with 24 blocks per module, for the reason that the cost of a circuit testing all possible combinations (LOR) of 1,344 blocks would be exorbitant Every 250 ns, all 56 modules (see FIG. 14) acquire the information from a set of 24 crystal blocks. The first "single" satisfying the energy requirements received in one of the 24 blocks of a module prevents other "singles" in the same module from becoming coincidence candidates. This arbitrary selection of the first single among all the possible candidates introduces dead time. For an activity at the detector of $100 \times 10^6$ photons per second, the probability that a module is hit during the 250-ns sampling time period is 0.44 hits per module. The calculation is: during an activity of $100 \times 10^6$ singles per second hitting the detector (which requires an estimated dose of more than 60 mCi of $^{15}$O-water to be delivered to the patient for a PET with a FOV of 15 cm.), then each of the 56 modules has the probability of receiving, during every 250 ns, the number of incident hits divided by the number of modules multiplied by the sampling rate $(100\times10^6)/(56\times4\times10^6)=0.44$.

FIG. 48 shows the line of response tested by each of the seven ASICs of the GE PET during time slots 1 and 5 of the 10 time slots of 25 ns each within the sampling time of 250 ns. Table 6-4 provides the interconnection between the 56 modules and the seven coincidence ASICs, and FIG. 44 show the layout of the 56 modules and the 7 coincidence ASICs. The entire circuitry can detect one coincidence during the sampling time of 250 ns, providing a maximum coincidence rate of $4\times10^6$ per second (see reference [2]). However, measurements performed have shown a rate of $200\times10^3$ coincidences per second at half the scanning time period of 60 seconds starting 20 second after injection of the patient with 66 mCi of $^{15}$O-water radiotracer [2].

CTI/Siemens uses the same approach which is described in [54], and its ASIC implementation is described in [67]. The coincidence detection circuit is based on the same approach as for the General Electric PET, but the CTI/Siemens device detects coincidences among 16 modules instead of 56 modules (see [18]. Note that the 3D-Flow with its novel approach detects coincidences among 1,344 or more modules requiring only six comparisons). In 1993, a subsequent VLSI implementation [68] of the coincidence circuit by the same group presents an improvement by optimizing the silicon area.

TABLE 6-4

Connection of each of the 7 ASIC detecting coincidences to the 56 detector modules.

| ASIC # | Detector module to ASCI column | Detector module to ASCI row |
|---|---|---|
| 1 | 0–9 | 16–37 |
| 2 | 0–9 | 29–49 |
| 3 | 10–19 | 26–47 |
| 4 | 10–19 | 39–55 |
| 5 | 20–29 | 36–55 |
| 6 | 20–29 | 49–55 |
| 7 | 30–39 | 46–55 |

6.6.8.1.2 Elimination of Need to Compare an Extremely Large Number of LOR when the FOV Increases The novel approach that tears down "brick wall B," the comparison of all LOR used in current PET, is based upon the principle that the ONLY photons compared are those whose characteristics show them to be a candidate for coincidence.

Using this approach, the performance requirements of the electronics drop considerably. The number of comparisons to be made are very few and are mostly related to the radiation concentration (or activity) delivered to the patient and not as much to the size of the detector, as is the case in the approach of the current PET.

The 3D-Flow approach to finding coincidences in a PET system is to identify all possible candidates within the sampling time of 50 ns (no more than 4 candidates are expected for a radioactive dose of 5 mCi delivered to the patient, see also Section 6.5.2, and Section 6.5.13) and to look for a coincidence only among those candidates. It is not necessary to test all LOR as is done by the current approach; it is more efficient to move the fewer (less than 4) photon candidates for coincidence to a coincidence circuit through a pyramidal funnelling structure such as the 3D-Flow.

For example, a radiation activity of 5 mCi (radiotracers with short half-life, such as $^{15}$O-water or $^{82}$Rb, provide the highest activity) generates about $30\times10^6$ "singles" per second that create a signal to the electronics for a PET with a FOV of 30 cm. For a PET with a FOV of 157 cm, that same radiation activity generates about $80\times10^6$ "singles" per second that create a signal to the electronics.

The entire electronics runs at 20 MHz. Thus, every sampling period of 50 ns an average of 4 singles are candidates for coincidences ($80\times10^6$ singles per second that create a signal to the electronics for a FOV of 157 cm, divided by 20 MHz=4).

In the above case, it will be required to implement a circuit with only 6 comparators, comparing all possible combinations of the four singles. (See Section 6.5.14.2).

Simulation results show that only two photons out of four will turn into a coincidence, thus the maximum expected rate for a 5 mCi radiation dose will be $20\times10^6$ coincidences per second This is to be compared with the approach used in the current PET which performs about 700 comparisons of the timing and characteristics of the "singles" made by 7 ASICs operating at 40 MHz for a 15 cm FOV [20] for the determination of coincidences on LOR among only 56 modules which decode, at most, 12,096 crystals.

6.6.8.1.3 3D-Flow Coincidence Detection Circuits vs. GE's Advance Coincidence Circuit In summary, the innovative concept described herein for detecting coincidences requires only 6 comparisons where current PET devices require about 700 and one ASIC instead of seven, and it provides a detection rate of up to 40 million coincidences per second as opposed to only 4 million coincidences per second provided by current PET devices. This coincidence circuit would remain the same, 6 circuits comparing every 50 ns all possible combinations of the 4 singles, as long as the radiation dose does not exceed 5 mCi.

It would be impossible to match this performance in a PET with a 157.4-cm FOV and 2,304 PMTs (as described in Section 6.9) using the approach of the current PET without an unacceptable reduction in efficiency. With the coincidence detection approach used in the current PET, it would be necessary to execute 1,326,528 comparisons every 50 ns (calculated with the above formula (n×(n−1))/4, that is (2,304×2,303)/4=1,326,528). It is obvious that building such a circuit performing all those comparisons every 50 ns, besides being prohibitively costly, would be impossible.

Using the approach which is implemented in the current PET operating in the hospitals, it will be required to execute 1,326,528 comparisons every 50 ns (calculated with the above formula (n×(n−1))/4, that is (2,304×2,303)/4=1,326, 528. It is obvious that building such a circuit performing all those comparisons every 50 ns, besides being costly, would be impossible.

FIG. 49 shows the 3D-Flow coincidence detection 4950 vs. the current approach to finding coincidences in PET 4970. The first thing to notice is that the approach used in the current PET systems, shown at right, entails many line of responses 4975 even though the FOV is only 15 cm. For example, on PET ring of detector 4980, a successful identification of a photon pair striking Block 1 and 27 would require a comparison of data received by every single detector in the ring, even though almost all of these detectors did not receive any photons; the data is not sorted out on the front end, and so detector blocks where no photons were received are unnecessarily compared with those where photons were received. For the current PET, the number of coincidence detections performed is defined by the number of detector elements. In short, the current PET systems attempt to perform coincidence detection by reviewing and comparing all of the possible lines of response, while the 3D-Flow only makes comparisons based upon photon hits and very likely actual lines of response.

With the 3D-Flow or the 3D-Flow approach, presented at the left of FIG. 49, the lines of response are very few and they are proportional to the activity of the radiation and not to the number of crystals, PMTs, or modules in a detector. Since the radiation to the patient should not be increased, but rather should be decreased, the coincidence circuit for a larger number of detectors should either remain the same or should decrease, even if the number of detectors increases.

6.6.8.1.4 Elimination of the Outgoing Data Bottleneck

The current PET system has a limitation of about 4 MHz on the output throughput, as stated for General Electric Advance in [20] and for CTI/Siemens in [18]. This is referred to in FIG. 49 as "Bottleneck D."

In practice, the performance of detecting 4 million coincidences per second is never achieved and measurements on CTI/Siemens model ECAT EXACT HR using phantoms show (in FIG. 14 of [6] a saturation in detecting true+scatter of about 400,000 coincidences per second. The GE Advance shows in [2] saturation in detecting true+scatter of about a half million coincidences per second. One reason for such low efficiency is the front-end circuit, Bottleneck D, that has reduced the channels from 1,344 to 56 by checking only the energy value and without performing a thorough check of the characteristics of a photon.

The elimination of outgoing "bottleneck D" with the 3D-Flow design is achieved by increasing the level of saturation of the outgoing detection of coincidences to 40 million coincidences per second. The design parameter of sustaining coincidence detection up to 40 million coincidences per second has been set as described in Section 6.5.14.2. The output of 40 million coincidences per second is provided by having four independent detection of single photons at 20 MHz in the four sectors of the detector. When each sector has found a single photon that is in coincidence with a photon of another sector, then at most two coincidences can be found, providing a maximum throughput of 40 MHz. Section 6.5.13 provides the scheme to choose a specific output bandwidth of the entire system, while Section 6.5.14.3 provides a general scheme for its implementation with maximum efficiency.

6.7 Modular Hardware Implementation in IBM PC or VME Platform for Systems of any Size The modularity, flexibility, programmability and scalability of the 3D-Flow system for the electronics of PET/SPECT/CT apply to all phases of the system, from the components to the IBM PC chassis, (or crate(s) for the VME implementation).

The same hardware can be used to replace the electronics of current PET as well as for building new systems of different sizes, making use of different detectors that provide analog and digital signals. The programmability of the 3D-Flow system can acquire, move, correlate, and process the signals to best extract the information of the incident photons and find the coincidences.

Two examples of implementation are described herein.

One, based on the IBM PC platform, has the advantage of providing the latest and most powerful CPUs and peripherals at the lowest price because of the large volume of its market. However, it has the disadvantage that particular care must be taken in the connectors and cables carrying the information between processors located on different boards.

The other, based on VME, has the advantage of a robust and reliable construction with the signals between processors on different boards carried through a secure backplane. However, the market for the latter is smaller, the prices are higher, and the boards with the latest components take more time to get into production.

For each platform, IBM PC, or VME, two systems have been designed. For applications requiring less processing, a system with 4 channels for each 3D-Flow processor is presented. For applications requiring higher computational needs, such as when detectors with economical crystals having slow decay time are used, a system with one channel per processor is presented.

6.7.1 A Single Type of DAQ Board

Having selected a platform (IBM PC, or VME) and the processing needs (4 channels per processor, or one channel per processor), only one type of DAQ-DSP board is necessary for the entire application. The following section will describe the boards for the four-channel application: IBM PC 64 channel, IBM PC 256 channels, VME 64 channels, or VME 256 channels.

6.7.1.1 IBM PC DAQ Boards 6.7.1.1.1 IBM PC Board with 64 Analog Channels and 32 Digital I/O The 64 analog signals from the PET/SPECT detector are converted into digital and formatted to be interfaced to the 3D-Flow system via ADC and FPGA. One additional element, the time-to-digital converter (TDC) chip/function, is described in Section 6.5.10.

FIG. 50 shows the front and rear views of a mixed-signal IBM PC-compatible board accommodating 64 channels processed by a stack of 5 layers of 3D-Flow processors with a 2-layer filtering and channel funneling in a partial 3D-Flow pyramid (see Section 6.5.12.1, Section 6.5.12.2, FIG. 58, and reference [56]). Each channel of 3D-Flow processor stack handles one analog input data (see Section 6.5.3.2).

All dimensions of the components and connectors shown in FIG. 50 are scaled to the real sizes of boards. The analog-to-digital converter from Analog Devices AD9281 has two ADC per chip @ 28 MHz, in a package of 9×9 mm, it dissipates only 225 mW, and it has a low cost of $4.5 per chip. The need of carrying 64 analog channels with some digital channels through the small back panel of an IBM PC compatible board is not a problem because there exists on the market a PCI board with 64 analog inputs (e.g., CYDAS 6400 from 2HR from CyberResearch has 64-channels A/D with 16-bit resolution, 8 digital inputs and 8 digital outputs in a single connector).

The power dissipation estimated in Table 6-5, shows that it requires about 20.47 Watt per 3D-Flow board.

The interconnection between processors residing on different boards is implemented by using connectors and cables on the top of the boards (e.g., AMP MICTOR, Matched Impedance Connector System having characteristics for carrying signals with 250 ps rise time. See FIG. 56).

The control of the 3D-Flow processor (program downloading into the 3D-Flow processors, real-time algorithm initialization, processing and system monitoring) is performed via the RS232 ports as described in [56, 57]. Each 3D-Flow DAQ-DSP board implements 16 Serial I/O ports which are directly controlled from the IBM PC CPU via the PCI bus. One additional serial port downloads the circuits into the FPGAs.

Figure 61:
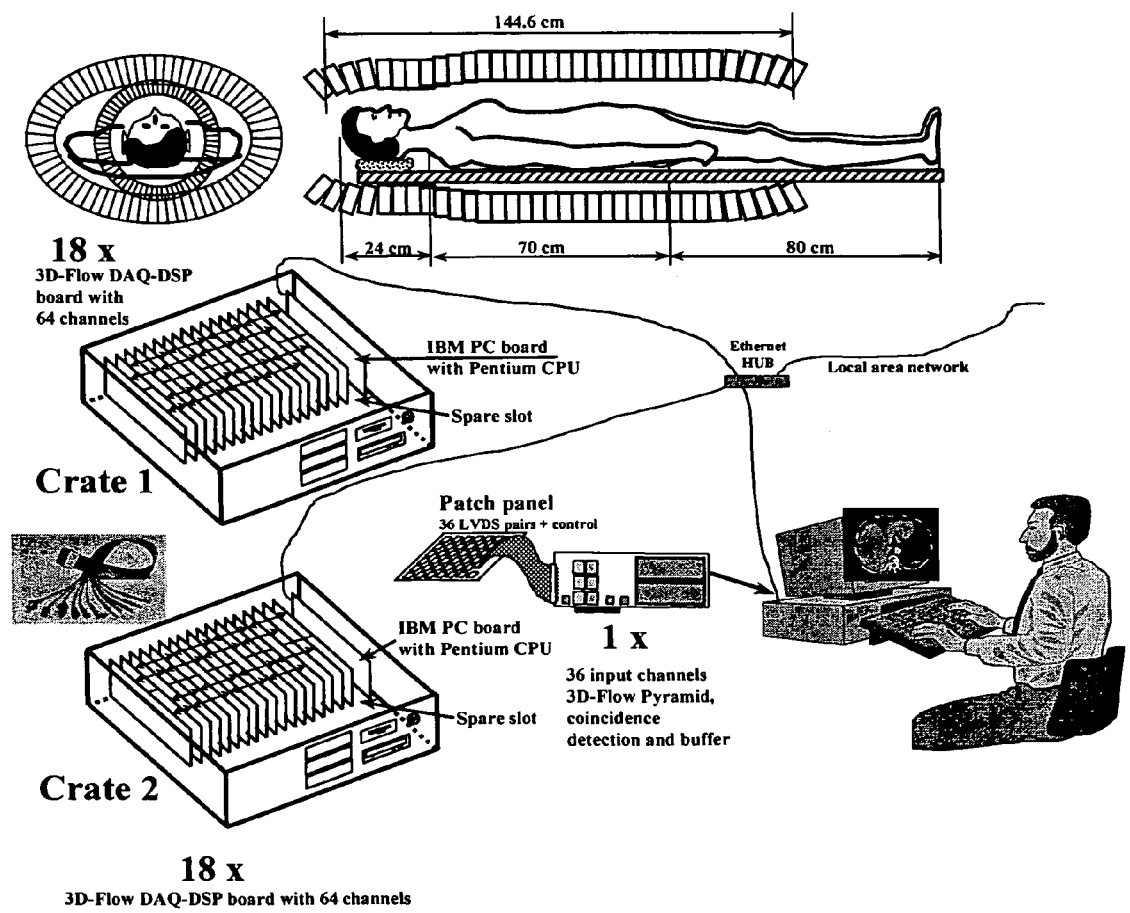

The coincidence candidates found among the 64 channels of the board are sent out from chip 154 of FIG. 58 through two wires carrying LVDS signals to the connector on the back panel of the IBM PC board. (A single connector on the back panel similar to the one assembled on the CYDAS 6400 board from CyberResearch carries analog and digital signals. Wires are separated as shown in FIG. 61 and sent to the detector and to the patch panel connected to the pyramid board.) The two wires carrying the LVDS signals are sent to the pyramid board of FIG. 54 through the patch panel shown in FIG. 61.

A SO-DIMM buffer memory can be installed on the back of the board to acquire a high rate and a high volume of single photons during SPECT or CT scanning.

LVDS DS92LV010A. See reference [56]). Control signal distribution can be implemented with several technologies.

6.7.1.1.3 IBM PC Board with 256 Analog Channels and 32 Digital I/O

FIG. 51 shows the layout of a 3D-Flow IBM PC board handling 256 electronic input channels. Each channel of the 3D-Flow processor stack handles four analog input data (see Section 6.5.3.1). A special assembly consisting of a cable,

TABLE 6-5

3D-Flow IBM PC board component list and power dissipation estimate for 64 channels.

| # | Type | Device | Package [mm] | IC power [Watt] | total power [Watt] |
|---|------|--------|--------------|-----------------|--------------------|
| 32 | A | AD9281 | 28-pin SSOP (10.3 × 7.9) | 0.225 | 7.2 |
| 2 | P | 32-channel preamplifier | 256-pin FineLine BGA (17 × 17) | 0.5 | 1 |
| 2 | TDC | Time-to-Digital Converter | 225-pin BGA MO-151 (27 × 27) | 0.5 | 1 |
| 25 | 3DF | 3D-Flow | 672 FineLine BGA (27 × 27) | 0.35 | 8.75 |
| 4 | FPGA | Altera-Xilinx-ORCA | 484-pin FineLine BGA (22.8 × 22.8) | 0.3 | 1.2 |
| 1 | SO-DIMM | Synchronous DRAM (64 MB) 3.3 volt @ 400 mA | 144-pin module (28 × 67) | 1.32 | 1.32 |
|  |  |  | Total | | 20.47 |

6.7.1.1.2 Timing and Synchronization Issues of Control Signals in the 3D-Flow System The 3D-Flow system is synchronous. This makes it easier to build and to debug. The most important task is to carry the clock, reset, clear, and control signals to each 3D-Flow component pin within the minimum clock skew.

This task can be accomplished without using special expensive connectors, delay lines, or sophisticated, expensive technology because the processor speed required to satisfy the design runs at only 80 MHz. The expected worst clock skew for the distribution of one signal to up to 729 chips (equivalent to a maximum of 11,664 processors) is a maximum of 450 ps (e.g., by using three stages of the PECL component 100E111L that has 50 ps worst case within-device skew for the first stage and 200 ps worst case part-to-part skew for the subsequent two stages. Or using printed circuit and connector is required to carry the 256 analog signals. Components are assembled on both sides of the board.

The power dissipation estimated in Table 6-6, shows that about 47.35 Watt per 3D-Flow DAQ-DSP board is required. The other sections of the board are similar to the one previously described in Section 6.7.1.1.1 for the 64 channels.

TABLE 6.6

3D-Flow IBM PC board component list and power dissipation estimate for 256 channels

| # | Type | Device | Package [mm] | IC power [Watt] | total pow. [Watt] |
|---|------|--------|--------------|-----------------|-------------------|
| 128 | A | AD9281 | 28-pin SSOP (10.3 × 7.9) | 0.225 | 28.8 |
| 8 | P | 32-channels preamplifier | 256-pin FineLine BGA (17 × 17) | 0.5 | 4 |
| 8 | TDC | Time-to-Digital Converter | 225-pin BGA MO-151 (27 × 27) | 0.5 | 4 |
| 25 | 3DF | 3D-Flow | 672 FineLine BGA (27 × 27) | 0.35 | 8.75 |
| 6 | FPGA | Altera-Xilinx-ORCA | 484-pin FineLine BGA (22.8 × 22.8) | 0.3 | 1.8 |
|  |  |  | Total |  | 47.35 |

6.7.1.2 VME DAQ Boards

A system analogous to the 3D-Flow for IBM PC, such as the one described in Section 6.7.1.1.1, can be implemented with VME boards shown in FIG. 52, and FIG. 53. The interconnection between processors residing on different boards is implemented through a VME backplane as shown at the bottom of FIG. 56.

The control of the 3D-Flow processor (program downloading into the 3D-Flow processors, real-time algorithm initialization, processing, and system monitoring) is performed via the RS232 ports as described in [56, 57].

The coincidence candidates found among the 64 channels (or 256 channels) are sent out from chip 154 of FIG. 58 by means of LVDS signals through the connector J1 located on the top part of the front panel of the boards shown on FIG. 52, and FIG. 53. Local accepted data on each board are then sent to the pyramid board shown in FIG. 55 through a patch panel similar to the one shown in FIG. 61.

6.7.1.2.1 VME Board with 64 Analog Channels and 32 Digital I/O

FIG. 52 shows the layout of the 64 channels 3D-Flow DAQ-DSP VME board. Components are installed only on one side of the board. It would be possible to install a SO-DIMM buffer memory on the rear of the board (indicated with dashed line) for applications with high-rate, high volume of data during SPECT and CT scanning.

Each channel of the 3D-Flow processor stack handles one analog input data (see Section 6.5.3.2).

6.7.1.3 VME Board with 256 Analog Channels and 32 I/O

FIG. 53 shows the layout of the 256-channel 3D-Flow DAQ-DSP VME board. Components are installed on both sides of the board. It is possible to install a SO-DIMM buffer memory (indicated with dashed line) for applications with high-rate, high volume of data during SPECT and CT scanning.

Each channel of the 3D-Flow processor stack handles four analog input data (see Section 6.5.3.1)

6.7.2 A single Type of Pyramidal & Buffer Board

A single type of pyramidal, coincidence detection and buffer board implements in IBM PC or VME platform the logical circuits described in the right section (indicated with "Pyr. Layer 3" and "Coincidence Stack") of FIG. 57, in the three right-most columns of FIG. 24, and in FIG. 44.

The pyramidal board receives the data relative to the photons validated by the real-time algorithm executed on the 3D-Flow DAQ-DSP boards through a patch panel shown in FIG. 61. It then, performs the functionality attenuation correction described in Section 6.5.6, separating the photons found into the three modalities (PET, SPECT, and CT), the channel reduction in Section 6.5.12, and the coincidence identification in Section 6.5.14. The board stores results, the coincidences found (or the single photon validated by the algorithm for SPECT and CT when the buffer memories on the DAQ-DSP boards are not installed), in the two DIMM buffer memories, which can have a capacity up to 4 GB each for a total maximum of 1 billion events accumulated (one event or coincidence is in the 64-bit format described in Section 6.5.14.4), during a single study session.

An additional DIMM module memory of 512 MB stores the coefficients for the attenuation correction acquired during calibration scan as described in Section 6.5.6.

Results are read from the buffer memories by the IBM PC CPU via the PCI bus (or VME CPU via the VME bus) and sent to the graphic workstation via a standard high-speed local area network.

6.7.2.1 IBM PC Pyramidal and Buffer Board

FIG. 54 shows the layout of the IBM PC pyramid, attenuation correction, and coincidence detection board. Components are assembled on only one side of the board, and there are three 168-pin slots for synchronous DIMM memories. @ 100 MHz. Two slots are designated as buffer memories storing events (single photons from SPECT and/or CT modality and photons in coincidence for PET modality) and one slot is designated as a memory module storing the attenuation correction coefficients.

Data are received from the connector on the backpanel and are read by the IBM PC CPU via the PCI bus.

6.7.2.2 VME PC Pyramidal and Buffer Board

FIG. 55 shows the layout of the VME pyramid, attenuation correction, and coincidence detection board. Components are assembled on only one side of the board, and there are three 168-pin slots for synchronous DIMM memories @ 100 MHz. Two slots are designated as buffer memories storing events (single photons from SPECT and/or CT modality and photons in coincidences for PET modality) and one slot is designated as a memory module storing the attenuation correction coefficients.

Data are received from the connector on the front-panel and are read by the VME CPU (e.g., VMIVME 7587 from VMIC Co.) via the VME bus.

Table 6-7 shows the power dissipation estimated by the IBM PC, or VME pyramid board.

TABLE 6-7

3D-Flow IBM PC pyramid board component list and power dissipation estimate.

| # | Type | Device | Package [mm] | IC power [Watt] | total power [Watt] |
|---|------|--------|--------------|-----------------|--------------------|
| 6 | 3DF | 3D-Flow | 672 FineLine BGA (27 × 27) | 0.35 | 2.1 |
| 3 | FPGA | Altera-Xilinx-ORCA | 484-pin FineLine BGA (22.8 × 22.8) | 0.3 | 0.9 |
| 3 | DIMM | Synchronous DRAM (1 GB) 3.3 volt @ 650 mA | 168-pin module (133.35 × 31.75) | 2.145 | 6.435 |
| | | | | Total | 9.435 |

6.7.3 3D-Flow Neighboring Connection on the Edge of the IBM PC Board, or on the Backplane of the VME Crate.

The backplane carrying the information to/from the neighboring processors is built, in the IBM PC compatible implementation, with cables/connectors carrying LVDS signals located at the opposite edge of the PCI edge connector of the board. FIG. 56 shows the assembly of the interconnection between 3D-Flow processors on different boards.

The following details of inter-board communication are very important and show the feasibility of the implementation of the detector without boundaries. All information (including the example of one type of connector with suitable characteristics for this application) is provided.

Each board has 64 channels and 5 layers of 3D-Flow processors. 64 channels is equivalent to: 8 processors per side, multiplied by 2 ports per processor (connections between processors are point-to-point, thus one port for input and one port for output) comes to 16 ports per side per layer. Five layers have a total of 80 ports. Each port transmits/receives in LVDS on two wires, totalling 160 wires per side. Speed up to 1.2 Gbps can be easily achieved with the current LVDS drivers from several vendors (e.g. LSI logic). Matched impedance connectors such as AMP MICTOR can provide good a connection with the ground bar at the center of the connector for a 250 ns signal rise-time characteristic. There is a discrete ground bus every half inch of the connector length, which can be assigned to either power or ground in any combination. The connector with 190 positions is only 76.2 mm×5.2 mm which makes it feasible to implement the processors interconnecting buses on one side of the board. Each board needs four such connectors at most to provide the communication of the 3D-Flow processors in all four directions North, East, West, and South ports.

The interconnection of the processors assigned to the border between the head and the torso of the detector where the side processors of the torso are connected to the side processors of the head which are half in number, requires only 80 wires: the processor of the torso which does not have a direct connection with the processor of the head, moves its data through the neighboring torso-processor connected to the head).

The mother board (see center left section of FIG. 56 for the physical implementation of the logical interconnection shown on the center right of the figure) accommodating 18+1 DAQ-DSP 3D-Flow board, in the version IBM PC compatible, could be accommodated on a standard motherboard PBPW 19P18 from CyberResearch (this motherboard has 18 PCI+1 slot for CPU, or one ISA and 17 PCI) or from Industrial Control. Both companies offer chassis with power supplies up to 800 Watts; Industrial Control also offers chassis series 7100 with up to 1600 Watts.

The 3D-Flow inter-chip communication on the VME 6U platform is implemented on a printed circuit board backplane as shown at the bottom of FIG. 56. The same number of connections are required as the ones described in the previous case for the IBM PC.

A magnified area of the interconnection between a section of the connectors 361 to 461, to 541 is shown at the bottom right of FIG. 56. Five layers of printed circuit board (PCB) are required in order to facilitate routing of traces with no crossing. The pattern of the connections on the backplane is regular, thus requiring only short PCB traces as shown at the bottom right of FIG. 56 (the example of the connection pattern for three layers is shown in the figure). The distance between the connectors is 20.32 mm providing traces length less than 10 cm. The distance between two pins of 2 mm with two traces between pins permits construction of only 5 layers PCB reaching speed of hundreds of MHz with differential LVDS signaling.

6.8 Application: Replacing the Electronics of the Current and Past PET for Lowering the Cost and the Radiation to the Patient.

68.1 Logical Layout for a 3D-Flow System Replacing the Electronics of the Current and Past PET for Lowering the Cost and the Radiation to the Patient Following is the scheme of how to build a flexible, higher performance DAQ-DSP system that can be interfaced to different existing PET devices. A specific real-time program for each different PET device can be downloaded into the 3D-Flow system to tune the photon identification and coincidence detection to a specific detector.

FIG. 57 shows the logical layout for a 3D-Flow system replacing the electronics of the current and past PET.

The interface to the current or older PET devices can be located at the PMT level by taking the analog signals from the photomultipliers of the old or current PET devices and sending them to the 3D-Flow system. The left side of FIG. 23 shows the physical layout of the use of the 3D-Flow system in a typical whole-body PET currently used in hospitals. Only five 3D-Flow DAQ-DSP boards and one 3D-Flow pyramidal board will be required if, in addition to replacing the current electronics, the small photomultipliers (19 mm in diameter) are also replaced with larger photomultipliers (38 mm in diameter). However, if this change would present a practical problem in disassembling the blocks and in coupling the larger photomultipliers with the crystals, then one could simply multiply the number of input channels of the 3D-Flow system by four and use the current detector hardware. In the latter case eighteen 3D-Flow DAQ-DSP boards should be used in place of five, and the scalability of the 3D-Flow system will allow the processing of the signals from the detector as in the case shown in FIG. 23.

The occupancy of each detector module every sampling period of 50 ns using the new approach is only 0.017 vs. the 0.44 of the GE Advance implementation. (For the same 100 million "singles" events per second from the detector in a 15 cm FOV PET, the occupancy of each of the 288 modules is $(100\times10^6)/(288\times20\times10^6)=0.017$. The occupancy of each of the 56 modules every sampling period of 250 ns for the GE Advance is calculated as $(100\times10^6)/(56\times4\times10^6)=0.44$).

FIG. 57 shows on the left a detector of a size (18,432 crystals) similar to that of the current whole-body PET operating in hospitals (the PETs operating today in hospitals have a number of crystals ranging from 12,000 to 27,000.

In the figure, 64 crystals are coupled to a PMT of 38 mm in diameter, giving a total of 288 PMTs or detector modules, or electronic channels. (It should be pointed out here that, as mentioned above, if problems arise in replacing the existing small PMTs with the larger PMTs, the electronic channels of the 3D-Flow system can be increased.)

For the estimated highest activity of $100\times10^6$ photons per second that the detector should ever sustain (the highest activity is limited by the maximum radiation dose that can be delivered to the patient), the 288 processors per layer of the 5 five layers of the 3D-Flow stack system execute the programmable photon identification algorithm as described in Section 6.5.11.

The estimated reduction of photons to $80\times10^6$ is processed by the first layer of the pyramid as described in Section 6.5.12.1. Zero data are suppressed, insertion of the MSB of the ID and time-stamp is done before the data is funneled into the pyramid.

The photons with different time-stamp $t_1$, $t_2$, $t_3$, etc. indicated in FIG. 57 with $\gamma\text{-}t_1$, $\gamma\text{-}t_2$, and $\gamma\text{-}t_3$ travel through the pyramid, which performs the channel reduction function. All these operations are still executed on 3D-Flow chips residing on the 3D-Flow DAQ-DSP board as described and simulated in Section 6.5.12.2.

The fixed time latency of the data with respect to its origin, which was lost through the different paths followed in the pyramid, is regained in the functionality of the next board (see Section 6.5.14.1, and Section 6.7.2). Photons which occurred at the same time $t_1$, with an ID showing that they originated from the patient's body, are identified by the coincidence detection circuit as described in Section 6.5.14.2. Singles are discharged.

6.9 Application: Design for the Construction of a PET with 400+ Fold Efficiency Improvement PET detectors with fast crystals with a short decay time offer better time resolution, require electronics with simple real-time algorithm, can detect more photons at a high rate of radiation activity produced by the isotope without incurring pileup effects. However, they are more expensive and are subject to the licence of one manufacturer.

In order to provide more flexibility in the possible implementations of PET/SPECT/CT devices, following are provided examples with both slow and fast crystals.

The ratio of 256 crystals (or a single crystal of equivalent size in a "continuous" detector) coupled to a photomultiplier of 38 mm in diameter has been selected.

In the event the light emitted by a certain type of crystal adopted in a particular PET design is not sufficient, or the S/N ration does not allow decoding of 256 crystals, then the number of PMT and electronic channel can be multiplied by four and the 256 channel 3D-Flow DAQ-DSP board can be used in place of the 64 channel board. (The computation by the 3D-Flow DSP required for decoding 64-channels in place of 256 will be reduced, allowing each 3D-Flow to handle four electronic channels).

6.9.1 PET/SPECT/CT Application Using Slow Crystals

The first crystal with slow decay used in nuclear medicine, single photon and positron, was the NaI(TI); later, BGO was used. Their cost is relatively low compared to the fast crystal with short decay time such as LSO.

A 3D-Flow system for a PET/SPECT/CT with a field of view of 157.4 cm is described in this section. Given the one-to-one ratio between 3D-Flow processors and detector electronic channels and the high capability of the system of executing complex real-time algorithm on each detector channel (a channel consists of all electrical signals provided by the sensors within a view angle of the detector), this example is more suitable for PET with slow crystals where it is more difficult to extract the photon characteristics information. However, it can also be used for other types of detectors, even if the electronics might seem over dimensioned. The example of the 3D-Flow electronics requiring lower performance, because better, faster crystals are used and four detector channels can be assigned to one 3D-Flow processor, is shown in Section 6.9.2. The electronics in that case is reduced and less costly, while the fast crystals cost more.

6.9.1.1 Logical Layout of the Electronics for a PET/SPECT/CT System Requiring High Performance for Extracting Photon Characteristics from Slow Crystals FIG. 58 shows the logical layout of the electronics for a PET/SPECT/CT system with 157.4 cm FOV and 2,304 electronic channels.

The system has a one-to-one coupling between an electronic channel and one 3D-Flow processor stack, providing high performance digital signal processing on each channel for extracting the photon characteristics information from low cost slow crystals with long decay time.

The section on the left of the figure shows the functionality and the arrangement of the 38 DAQ-DSP boards. The DAQ-DSP boards are indicated by the number from 221, 241, 261 . . . through 921.

Each board consist of a 5-layer stack implementing the function of photon identification (see Section 6.5.11) and a 2-layer pyramid. One, layer of the pyramid, indicated by the number 6 in the figure, implements zero suppression (see Section 6.5.12.1); and the second, indicated by the number 7, implements channel reduction (see Section 6.5.12.2). During SPECT and CT modes of operation at high-rate and high-volume of coincidences created by the source, processor 82 of chip 153 collects the data (single photon of SPECT and CT energies) and sends them to the buffer memory installed on the 3D-Flow DAQ-DSP board. Each layer of the stack consists of four 3D-Flow chips having a total of 64 processors. The first layer of 64 processors is interfaced to the 64 detector electronic channels via the FPGAs (see Section 6.5.4.3).

The 36 boards are accommodated in two crates.

On the right section of the figure we have three 3D-Flow chips numbered 155, 156, 157 which receive the photon candidates for coincidence (one pair of LVDS wires per 3D-Flow DAQ-DSP board of the system) and route them to the processor indicated by the number 96 for chips 156 and 157, and to processors 96 and 84 for chip 155.

The 3D-Flow program at processor 84 and 96 (see flowchart in FIG. 43) sorts the events in the original sequence and regains the fixed time latency with respect to when they were originated.

The four sets of data are realigned in time at this stage to the original event and corresponding to the four sectors of FIG. 45. They are received from the three processors indicated by the number 96 and from processor 84 and are sent to chip 158, which performs the six comparisons A–B, A–C, A–D, B–C, B–D, C–D as described in Section 6.5.14.2.

Photons in coincidence are sent to coincidence memory buffer 1 and buffer 2. Three comparators are connected to buffer memory 1 and the other three are connected to buffer memory 2. Unmatched photons are discarded at this stage. The list of operations to be performed by the 3D-Flow processors of chip 158, which performs the comparisons, are listed in FIG. 46.

In the event the operation at this stage needs to be increased beyond the time interval between two consecutive input data, the 3D-Flow architecture implemented at the photon identification stage (see Section 6.5.11) and indicated in the figure as chip 159 and chip 160 can also be implemented at this stage, since the incoming data are synchronous and have a fixed latency time from when they were created.

6.9.1.2 Logical and Physical Layout for a PET/SPECT/CT requiring High Performance for Extracting Photon Characteristics from Slow Crystals.

FIG. 58 shows how the logical layout of the electronics for a PET/SPECT/CT system with 157.4 cm FOV and 2,304 electronic channels relates to the detector elements. In the center of the figure are shown the 36 DAQ-DSP boards from 221 to 921 accommodated in two chassis (or crates for VME implementation) indicated by the numbers 237 and 238.

Each board consists of four chips per layer, indicated by the number 140, for 5 layers of stack, one full layer of the pyramid and ¼ layer for the next layer of the pyramid (see top right of FIG. 60).

Each chip consists of 16 processors. The 64 processors of the first layer are connected to the photomultipliers and other sensors that receive data from the detector. (The ratio of 256 crystals to one photomultiplier can be changed to 64 to one and the 3D-Flow DAQ-DSP boards with 256 channels can be used in place of the 64 channels). The segmentation and mapping of the detector to the 3D-Flow system is also described in Section 6.4 and Table 6-2.

The bottom of FIG. 60 shows the physical layout of the detector consisting of an elliptical gantry of about 100 cm wide and 50 cm tall on the torso section, and 40 cm in diameter at the head section. These dimensions correspond to all other parameters shown at the left, top and right of the array of boards in the center of the figure.

Any parameter can be calculated from the numbers reported in the side of the board array. For instance, the number of PMTs for the head are easily calculated as the 32 PMTs shown at the left of the figure, multiplied by 8 PMT for the head section of the axial view. Similarly, the number of crystals for the head and for the torso can be calculated. The field of view can also be calculated by knowing the crystal dimensions increased by approximately 0.35 mm per side for the material between crystals.

At the joint between the head section and the torso section where four boards (221, 401, 581, and 761) are connected to eight boards from 241 to 861, the connection of the processors on the right side of 221 in the figure are alternately connected one to every other processor on the left side of 241 and 321. The processor that is not connected physically to the processor of the head will move its data to that neighboring processor that has a connection).

6.9.1.3 Physical Layout for a PET/SPECT/CT system Requiring High Performance for Extracting Photon Characteristics from Slow Crystals.

FIG. 61 shows the implementation on the IBM PC platform of the electronics for a PET/SPECT/CT system with 157.4 cm FOV and 2,304 channels.

The entire electronics consists of two IBM PC chassis, such as that commercially available from CyberResearch or Industrial Control, accommodating 36 DAQ-DSP boards as described in Section 6.7.1.1.1 and one 3D-Flow pyramid board of the type described in Section 6.7.2.1.

The list of the hardware needed and the estimated power dissipation is shown in Table 6-8.

Each of the 36 DAQ-DSP boards has a connector on the back panel carrying the signals from the detector and the results of the coincidence candidates (or single photons for SPECT and PET mode) to the pyramid board through the patch panel shown in the center the figure. (The center left of the figure shows the connector type, which at one end plugs into the back of the IBM PC board and then the wires are split to go to the detector and to the patch panel).

A local area network provides easy communication between the chassis. Each chassis has a Pentium CPU or similar with Unix, Linux or NT Windows operating system which allows supervision and monitoring of the activity of the 3D-Flow system as described in [56, 57] and collection of the results.

6.9.2 Logical and Physical Layout for a PET/SPECT/CT System Using Fast Crystals

FIG. 59 shows how the logical layout of the electronics for a PET/SPECT/CT system with 126 cm FOV and 1,792 electronic channels relates to the detector elements.

In the center of the figure are shown the 8 DAQ-DSP boards from 200 to 900 accommodated on one chassis (or crates for VME implementation) indicated with the number 235.

Each board consists of four chips, indicated by the number 140, per layer for 5 layers of stack, one full layer of the pyramid and ¼ layer for the next layer of the pyramid (see top right of FIG. 59).

Each chip consists of 16 processors. The 64 processors of the first layer are connected to the photomultipliers and other sensors that receive data from the detector. (The ratio of 256 crystals to one photomultiplier can be changed to 64 to one, in which case the number of 3D-Flow DAQ-DSP boards should be multiplied by four).

The bottom of FIG. 59 shows the physical layout of the detector, consisting of an elliptical gantry for the torso of about 100 cm wide and 50 cm tall at the torso section, and 40 cm in diameter at the head section. These dimensions correspond to all other parameters shown at the left, top, and right of the array of boards in the center of the figure.

Any parameter can be calculated from the numbers reported in the side of the board array. For instance, the number of electronic channels for the head are easily calculated as the 16 shown at the left of the figure, multiplied by 4 for the head section of the axial view. Similarly, the number of crystals for the head and for the torso can be calculated. The field of view can also be calculated by knowing the crystal dimensions increased by approximately 0.35 mm per side for the material between crystals.

The list of hardware needed and the estimated power dissipation is shown in Table 6-9

TABLE 6-8

3D-Flow IBM PC base system for a whole-body PET with 157.4 cm FOV and 2,304 channels.

| # | Type | Device | Package [mm] | IC power [Watt] | total power [Watt] |
|---|---|---|---|---|---|
| 36 | 3D-Flow DAQ-DSP | 64 channels. (one analog channel to one 3D-Flow ch) | IBM PC board (333 × 114) | 20.47 | 736.92 |
| 2 | SBC | e.g. from CyberResearch 2 serial RS232 ports, one USB, 400 MHz CPU, PCI SVGA controller, 768 MB RAM, IDE I/O for floppy and HD, SCSI, Ethernet, mouse, keyboard, | IBM PC board | 25 | 50 |
| 1 | 3D-Flow Pyramid | | IBM PC(333 × 114) | 7.29 | 7.29 |
| 2 | Passive backplane | CyberResearch model PBPW 19P18 (18 PCI + 1 slot for CPU) | | | |
| 2 | IBM PC Rack-Mount | Cyber Research RWFD 19P18-8 (fault-tolerant rack-mount PC with 800 W power supply, 9 drive bays, room for 20 full-length PCI-Bus cards) | 800 Watt power supplies for each chassis | | |
| | | | | Total | 793.29 |

TABLE 6-9

3D-Flow IBM PC base system for a whole-body PET with 126 cm FOV and 1792 channels.

| # | Type | Device | Package [mm] | IC power [Watt] | total power [Watt] |
|---|---|---|---|---|---|
| 8 | 3D-Flow DAQ-DSP | 256-channels. (one analog channel to one 3D-Flow ch) | IBM PC board (333 × 114) | 47.35 | 378.96 |
| 1 | SBC | e.g. from CyberResearch 2 serial RS232 ports, one USB, 400 MHz CPU, PCI SVGA controller, 768 MB RAM, IDE I/O for floppy and HD, SCSI, Ethernet, mouse, keyboard, | IBM PC board | 25 | 25 |
| 1 | 3D-Flow Pyramid | | IBM PC (333 × 114) | 7.29 | 7.29 |
| 2 | Passive backplane | CyberResearch model PBPW 19P18 (18 PCI + 1 slot for CPU) | | | |
| 1 | IBM PC Rack-Mount | Cyber Research RWFD 19P12-8 (fault-tolerant rack-mount PC with 800 W power supply, 9 drive bays, room for 12 full-length PCI-slots and 6 ISA slots) | 800 Watt power supplies | | |
| | | | Total | | 411.25 |

6.10 Cost for a PET/SPECT/CT System of Different Sizes and Using Fast or Slow Crystals Table 6-10 shows the cost of the main components of a whole-body PET of recent development such as the CTI/Siemens 966/EXACT3D with slow crystals and 23.4 cm FOV. The cost of the main components is shown to be about half a million dollars.

The volume of the BGO crystals and the number of photomultipliers used are based on the layout of the PET Siemens 966EXACT3D.

The duration of the examination is over 15 times that of the PET using the new 3D-Flow approach. This is because, in the current PET, in order to cover 157.4 cm of FOV, 7 bed positions are required. The FOV is in effect less than 23.4 cm because each bed-position scanning must include some overlap of the previous one. Furthermore, the lower efficiency of the device in capturing photons, require delivery of a higher radiation dose to the patient and at least 10 minutes of scanning for each position, while the new 3D-Flow PET accumulates a larger amount of photons in less than 4 minutes scanning.

Table 6-11 shows the cost of the main components of a future whole-body PET of future development, based on the current approach such as the CTI/Siemens 966/EXACT3D, but with 157.4 cm FOV and slow crystals.

The cost of the main components is shown to be about three and half a million dollars.

The volume of the BGO crystals and the number of photomultipliers used are based on the layout of the PET Siemens 966EXACT3D multiplied by 6.7 which is the multiplication factor of the larger FOV.

The cost of the electronics has also been multiplied by 6.7. However, as discussed in Section 6.6.8.1.3, the 1.3 million comparisons every 250 ns required by this approach, used in the current PET, form a "brick-wall" difficulty. The cost to overcome this difficulty would be prohibitive, unless an inefficient solution is adopted.

TABLE 6-10

Cost of the main components of a current whole-body PET, 23.4 cm FOV, of recent development with slow crystals.

| model | crystals volume/cost [cm³/$] | Photomultipliers number/cost [#/$] | Estimated cost of the electronics | Estimated total cost |
|---|---|---|---|---|
| Current PET 23.4 cm FOV CTI/Siemens 966/EXACT3D | 13,602/~$136,020 (BGO~$10/cm³) | 1,728/~$276,480 (¾"~$160 each) | ~$100,000 | ~$512,500 |

TABLE 6-11

Estimated cost of the main components of a future whole-body PET, 157.4 cm FOV, with slow crystals based on the approach used in current PET.

| model | crystals volume/cost [cm³/$] | Photomultipliers number/cost [#/$] | Estimated cost of the electronics | Estimated total cost |
|---|---|---|---|---|
| Future PET 157.4 cm FOV based on the approach used in the PET CTI/Siemens 966/EXACT3D | 91,493/~$914,937 (BGO~$10/cm³) | 11,577/~$1,852,320 (¾"~$160 each) | ~$670,000 | ~$3,437,257 |

Table 6-12 shows the cost of the main components of a whole-body PET with slow crystals, 157.4 cm FOV, proposed here for future development, based on the new approach of the 3D-Flow described herein.

The cost of the main components is shown to be about 1.37 million dollars.

The volume of the BGO crystals and the number of photomultipliers used are based on the layout of the PET shown in FIG. 60.

The ratio between the number of photomultipliers and the detector area to readout has been based on the number of photomultipliers per detector area used in several PET built by Karp and co-workers and on the promising results by the tests performed by Andreaco and Rogers [47] in decoding 256 BGO crystals per block (See also Section 6.4).

The DSP capability at each channel of the detector should facilitate and improve position, energy, and timing resolution. In the event it will be necessary to use a different ratio between PMT and detector area because of low performance of the PMT or the crystals, than the 256 channels 3D-Flow board (see Section 6.7.1.1.3) should be used, or the number of 3D-Flow boards with 64 channels should be multiplied by four.

The cost of two IBM PC chassis of electronics and one 3D-Flow pyramid board has been generously estimated at $260,000.

The lower cost advantage is provided by the geometric elliptical shape of the new proposed gantry requiring a smaller volume of crystals and the higher performance electronics with no detector boundary, which can extract more photons from 25 mm thickness crystals (compared to the 30 mm crystals), can use fewer photomultipliers (because the DSP capabilities on each channel improves the S/N ratio), and can improve the energy resolution and the crystal decoding.

The shorter scanning time allows the examination of more patients per day, thus leading to earlier return of the invested capital as well as lowering the cost of examination to the patient or insurance company.

Table 6-13 shows the cost of the main components of a whole-body PET with slow crystals, with a 126 cm FOV, proposed here for future development, based on the new approach of the 3D-Flow described herein.

The cost of the main components is shown to be about 1 million dollars, and this implementation still provides many advantages in lower scanning time, lower radiation, better image quality, and lower examination cost.

TABLE 6-12

Estimated cost of the main components of a future whole-body PET, 157.4 cm FOV, with slow crystals based on the new approach of the 3D-Flow described herein.

| model | crystals volume/cost [cm³/$] | Photomultipliers number/cost [#/$] | Estimated cost of the electronics | Estimated total cost |
|---|---|---|---|---|
| Future PET 157.4 cm FOV based on the new approach of the 3D-Flow (see Section 6.9.1) | 65,028/~$650,280 (BGO~$10/cm³) | 2,304/~$460,800 (1½"~$200 each) | ~$260,000 | ~$1,371,080 |

TABLE 6-13

Estimated cost of the main components of a future whole-body PET, 126 cm FOV, with slow crystals based on the new approach of the 3D-Flow described herein.

| model | crystals volume/cost [cm³/$] | Photomultipliers number/cost [#/$] | Estimated cost of the electronics | Estimated total cost |
|---|---|---|---|---|
| Future PET 126 cm FOV based on the new approach of the 3D-Flow | 50,577/~$505,770 (BGO~$10/cm³) | 1,792/~$358,400 (1½"~$200 each) | ~$200,000 | ~$1,064,170 |

Table 5-14 shows the cost of the main components of a whole-body PET with fast crystals, 126 cm FOV, proposed here for future development, based on the new approach of the 3D-Flow described herein.

It is difficult to estimate the cost of the LSO crystals because the patent is owned by a single company; however, the cost of all other components is lowered (see Section 6.9.2), because fewer photomultipliers are required. In addition the real-time computation of the electronics is simpler due to the fact that the faster crystals provide better signals.

TABLE 6-14

Estimated cost of the main components of a future whole-body PET, 126 cm FOV, with fast crystals based on the new approach of the 3D-Flow described herein.

| model | crystals volume/cost [cm³/$] | Photomultipliers number/cost [#/$] | Estimated cost of the electronics | Estimated total cost |
|---|---|---|---|---|
| Future PET 126 cm FOV based on the new approach of the 3D-Flow (see Section 6.9.2) | 50,577/$_??? patent is owned by a single company (LSO~$??/cm³) | 1,792/~$358,400 (1½"~$200 each) | ~$120,000 | ~$_? |

Acronyms:
3-D Complete Body Scan (3D-CBS); Aritmetic Logic Unit (ALU); Avalanche Photo Diode (APD); Bismuth Germanium Orthosilicate (BGO); European Center for Nuclear Research (CERN); Constant Fraction Discriminator (CFD); Central Processing Unit (CPU); Cesium Iodide (CsI); Computed Tomography (CT); Depth of Interaction (DOI); Digital Rectal Examination (DRE); Digital Signal Processing (DSP); Electronic Design Automation (EDA); Food Drug Administration (FDA); Field Programmable Gate Array (FPGA); Fluorodeoxyglucose (FDG); First-In-First-Out (FIFO); Field Of View (FOV); Gallium Arsenic (GaAs); General Electric (GE); Gross Domestic Product (GDP); Health Care Financing Administration (HCFA); Health Maintenance Organization (HMO); Intellectual Property (IP); Line of Response (LOR); Lutetium orthosilicate (LSO); Multiply Accumulation Unit (MAC); Magnetic Resonance Imaging (MRI); Thallium-activated Sodium Iodide (NaI(Tl)); National Health care Expenditures (NHE); Positron Emission Tomography (PET); Printed Circuit Board (PCB); Pulse Height Discrimination (PHD); Prostate Specific Antigen (PSA); Pulse Shape Discriminator (PSD); System-On-a-Chip (SOC); Superconducting Super Collider (SSC); Time-to-Digital converter (TDC); United States of America (USA); Yttrium Orthosilicate (YSO).

[1] Wienhard, K., et al.: The ECAT EXACT HR: Performance of a New High Resolution Positron Scanner. JCT, vol. 18(1):110–118, 1994.

[2] DeGrado, T. R., et al.: Performance Characteristics of a Whole-Body PET Scanner, Juournal of Nuclear Medicine, vol. 35(8):1398–1406, August 1994,

[3] Jones, W. F. et al.: Next generation PET data acquisition architectures," IEEE TNS, vol NS-44, pp. 1202, (1997).

[4] Huber, J. S., and Moses, W. W.: Conceptual Density of a High-Sensitivity Small Animal PET Camera with 4 p Coverage. IEEE TNS, vol. 46, No 3, June 1999.

[5] Cherry, S. R., et al.: MicroPET: A High ResolutionPET scanner for imaging small animals." IEEE TNS, vol. NS-44, pp. 1161 (1997).

[6] Wienhard, K., et al.: The ECAT EXACT HR: Performance of a New High Resolution Positron Scanner. Journal of Computer Assisted Tomography, vol. 18(1): 110–118, 1994.

[7] Crosetto, D. "400+ times improved PET efficiency for lower-dose radiation, lower-cost cancer screening." ISBN 0-9702897-0-7 (2000). Available at Amazon.com

[8] Crosetto, D.: A modular VME or IBM PC based data acquisition system for multi-modality PET/CT scanners of different sizes and detector types. Presented at the IEEE Nuclear Science Symposium and Medical Imaging Conference, Lyon, France, 2000, IEEE-2000-563, submitted to IEEE, Trans. Nucl. Science. http://3d-computing.com/pb/IEEE2000-563.pdf.

[9] Crosetto, D.: Real-time, programmable, digital signal-processing electronics for extracting the information from a detector module for multi-modality PET/SPECT/CT scanners. Presented at the IEEE Nuclear Science Symposium and Medical Imaging Conference, Lyon, France, 2000, IEEE-2000-567, submitted to IEEE, Trans. Nucl. Science. http://3d-computing.com/pb/IEEE2000-567.pdf.

[10] Crosetto, D., "System Design and Verification Process for LHC Programmable Trigger Electronics" IEEE NSS-MIC Seattle (WA) Oct. 24–30, 1999.

[11] Crosetto, D.: Detailed design of the digital electronics interfacing detectors . . . LHCb 99-006, 5 May, 1999 CERN-Geneva

[12] Crosetto, D. "High-Speed, Parallel, Pipelined, Processor Architecture for front-end Electronics, and Method of Use Thereof." LHCb 96-2, TRIG 96-1. CERN, Geneva.

[13] Crosetto, D., "Real-Time system design environment for multi-channel high-speed data acquisition system and pattern-recognition" IEEE Real Time Conference, Santa Fe, (NM) Jun. 14–18, 1999.

[14] Von Schulthess, Gustav K.: Clinical Positron Emission Tomography (PET) Correlation with Morphological Cross-Sectional Imaging. University hospital, Zurich, Switzerland. Published by Lippincott Williams & Wilkins. 2000.

[15] Bar-Shalom, R., Valdivia, A. Y., and Blaufox, M. D.: PET Imaging in Oncology. Seminars in Nuclear Medicine, Vol. XXX, No. 3 (July), 2000: pp 150–185.

[16] Phelps, M. E., et al., The Changing of Positron Imaging System. Clinical Positron Imaging, vol. 1(1):31045, 1998

[17] Jones, W. F. et al.: Next generation PET data acquisition architectures," IEEE TNS, vol NS-44, pp. 1202, (1997).

[18] Dent, H. M., et al.: A real time digital coincidence processor for positron emission tomography. IEEE Trans. Nucl. Sci., vol. 33(1):556–559, 1986

[19] Binkley, D. M. et al.: A custom CMOS Integrated Circuit for PET tomograph front-end applications. IEEE, conf. rec. pp. 867–871, 1993.

[20] Mertens, J. D., et al.: U.S. Pat. No. 5,241,181. "Coincidence detector for a PET scanner." Assignee: General Electric Company, Aug. 31, 1993.

[21] Crosetto, D.: LHCb base-line level-0 trigger 3D-Flow implementation. Nuclear Instruments and Methods in Physics Research, Section A, vol. 436 (November 1999) pp. 341–385

[22] Saoudi, A., and Lecomte, R.: A Novel APD-based detector module for multi-modality PET/SPECT/CT scanners. IEEE Conf. Rec. Nucl. Sci. Symp. and Med. Imag., pp. 1089–1093, 1998.

[23] Miyaoka, R. S., et al.: Effect of Detector Scatter on Decoding Accuracy of a DOI Detector. IEEE Conf. rec. of the Nucl. Sci. Symp. and Med. Imag. M3–34, Seattle, Oct. 24–30, 1999

[24] Huber, J., et al.: Development of a 64-channel PET detector module with depth of interaction measurement. IEEE presentation at the Nucl. Sci. Symp. and Med. Imag., M4–6, Seattle, Oct. 24–30, 1999.

[25] Crosetto, D.: Digital Signal Processing in high energy physics. Lecture before the CERN School of Computing at Yesermonde, Belgium 2–15 September 1990. Publ. by CERN 91-05. 14 May 1991.

[26] Crosetto, D.: Understanding a new idea for cancer screening. ISBN 0-9702897-1-5, Available at Amazon.com.

[27] Rollo, F. D.: It's here, and it's for real. Diagnostic Imaging. ISSN 0194-2514. January 2001, pp. 36–43 and 63.

[28] Wienhard, K. et al.: The ECAT EXACT HR: Performance of a New High Resolution Positron Scanner. IEEE Trans. Nucl. Scie., 1997, pp. 1186–1190.

[29] DeGrado, T. R. et al.: Performance Characteristics of the Whole-Body PET Scanner. Journal of Nuclear Medicine, vol. 35(8):1398–1406, August 1994.

[30] Rollo, F. D.: It's here, and it's for real. Diagnostic Imaging. ISSN 0194-2514. January 2001, pp. 36–43 and 63.

[31] Crosetto, D. Saving lives through early detection: Breaking the PET efficiency barrier with the 3D-CBS. 3d-computing.Inc., available at www.3d-computing.com/pb/3d-cbs.pdf.

[32] Barnet, R. M. et al.: Review of particle physics. American Institute of Physics (AIP). Physical review D54, 1 (1996).

[33] Cherry, S. R., et al.: A comparison of PET detector modules employing rectangular and round photomultiplier tubes. IEEE Trans. Nucl. Sci, vol. 42(4): 1064–1068 (August 1995).

[34] Karp, J. S., et al.: Performance Standard in Positron Emission Tomography. J Nucl. Med. 1991; 12:2342–2350

[35] Paans, A. M. J., et al.: The imaging of positron emitters in single photon and coincidence mode: evaluation of SPECT and PET systems. 18th annual International Conference of IEEE Engineering in Medicine and Biology Society, Amsterdam 1996, pp. 846–847.

[36] Saoudi, A., and Lecomte, R.: A Novel APD-based detector module for multi-modality PET/SPECT/CT scanners. IEEE Conf. Rec. Nucl. Sci. Symp. and Med. Imag., pp. 1089–1093, 1998.

[37] Boyd, D. P., et al.: A proposed dynamic cardiac 3D densitometer for early detection and evaluation of heart disease. IEEE TNS, 2724–2727, (1979).

[38] Boyd, D. P., and Lipton, M. J.: Cardiac computed tomography, Proceedings IEEE, 198–307, (1983).

[39] Rumberger et al.: Electron Beam Computed Tomographic Coronary Calcium Scanning: A review and guidelines for use in asymptomatic persons. Mayo foundation for Medical Education and Research, vol. 74, pp. 243–252, (1999).

[40] Lehmann, et al.: First results of Computerized Tomographic Angiograph using EBT. Journal of Radiology, vol. 9, pp. 525–529, (1999).

[41] Teigen, et. al.: Pulmonary Rmbolism: Diagnosis with Electron Beam CT. Journal of Radiology, vol. 188, pp. 839–845.

[42] Lackey, J., et al.: CMS Calorimeter Level 1 Regional Trigger Conceptual Design. CMS note 1998/074, Nov. 13, 1998.

[43] Beigbeder, B., et al.: An Update of the 2×2 Implementation for the Level 0 Calorimeter Triggers. LHCb 99-007, CERN, 29 Apr. 1999.

[44] S. Conetti and D. Crosetto, "Implementing the Level-0 Trigger," IEEE Trans. Nucl. Sc. 43 170 (1996).

[45] G. Corti, B. Cox, and D. Crosetto, "An Implementation of the L0 Muon Trigger Using the 3D-Flow system." LHCb 98-13.

[46] http://www1hc01.cern.ch (Large Hadron Collider Project at CERN, Geneva, Switzerland).

[47] Rogers, J. G., et al.: Testing 144- and 256-crystal BGO block detectors. IEEE. Conf. Rec. Nuclear Sci. Symp. and Med. Imag., vol. 3, pp. 1837–1841, 1993.

[48] Karp, J. S., et al.: Event localization in a continuous scintillation detector using digital processing. IEEE Trans. Nucl. Sci., vol. 33(1):550–555, February 1986,

[49] Crosetto, D.: Detailed design of the digital electronics interfacing detectors . . . LHCb 99-006, 5 May, 1999 CERN-Geneva.

[50] Huber, M. H., et al.: Characterization of a 64 channel PET detector using photodiodes for crystal identification. IEEE. Trans. Nucl. Sci., vol 44(3): 1197–1201, June 1997.

[51] Moses, W. W., et al.: A "winner-take-all" IC for determining the crystal of interaction in PET detectors. IEEE Trans. Nucl. Sci., NS-43, pp. 1615–1718, 1996.

[52] Yu, H., et al.: A high-speed and high-precision Winner-Select-Output (WSO) ASIC. IEEE, conf. rec. Nucl. Sci. Symp. and Med. Imag., pp. 656–660, 1997.

[53] Cherry, S. R., et al.: A comparison of PET detector modules employing rectangular and round photomultiplier tubes. IEEE Trans. Nucl. Sci., vol. 42(4): 10641068 (August 1995).

[54] Cutler, P. D., et al.: Use of digital front-end electronics for optimization of a modular PET detector. IEEE Trans. Nucl. Sci., vol. 13, pp. 408–418, 1994.

[55] Anger R. T.: The Anger scintillation camera, Rao D. V., Ed.: Physics of Nuvlear Medicine, Recent Advances, New York, American Institute of Physics, 1984.

[56] Crosetto, D.: LHCb base-line level-0 trigger 3D-Flow implementation." Nuclear Instruments and methods in physics research, Section A 436 (1999) 341–385.

[57] Crosetto, D.: Real-time system design environment for multi-channel high-speed data acquisition system and pattern recognition. 11th IEEE Real time conference, Santa Fe, N. Mex., USA, 14–18 June 1999. pp. 329–336.

[58] Jones, F. Williams, PETLINK, CTI System, Inc. 810 Innovation Dr. Knoxville, Tenn. 37932-2571. www.cti-pet.com/bjones.nsf.

[59] Huges, G.: Special report: Radon in Washington. June 1994, Division of Radiation Protection Airdustrial Center, Building 5 P.O. Box 47827 Olympia, Wash. 94504-7827.

[60] Hughes, H. G., et al.: MCPNPX-The LAHET/MCNP Code Merger. XTM-RN(U) 97-012, Los Alamos National Laboratory; 1997.

[61] Tumer, O. Tumay, U.S. Pat. No. 5,821,541. Method and apparatus for radiation detection.

[62] http://depts.washington.edu/~simset/html/simset_main.html (SimSET: "Simulation System for Emission Tomography", a simulation package that uses Monte Carlo techniques to model the physical processes and instrumentation used in emission imaging.

[63] Armantrout G. A.: Principles of semiconductor detector operation, in Semiconductor Detectors in Future of Nuclear Medicine. New York, The Society of Nuclear Medicine, 1971.

[64] TerPogossian M M, Phelps M E: Semiconductor detector system. Semin. Nucl., Med., 3:343–365, 1973.

[65] Birks, J. B.: The theory and practice of scintillation counting. New York, MacMillan Co., 1964.

[66] Binkley, D. M., et al.: A Custom CMOS Integrated Circuit for PET Tomograph Front-End Applications. IEEE, conf. rec. pp. 867 871, 1993.

[67] Newport, D. F., and Young, J. W.: An ASIC implementation of digital front-end electronics for a high resolution PET scanner. IEEE Trans. Nucl. Sci., vol. 40(4), August 1993.

[68] Young, J. W., et al.: Optimum Bandwidth Usage in Digital Coincidence Detection for PET. IEEE conf. rec., Nucl. Sci. Symp. and Med. Imag., pp. 1205–1208, 1993.

The invention claimed is:

1. A detector, comprising:
a crystal having a body, a first surface on one end of said body, and a second surface at an opposite end of said body, said second surface substantially parallel to said first surface;
an array of sensors comprising a first sensor and a plurality of neighboring sensors interfacing with the second surface of said crystal, each of said sensor and said plurality of neighboring sensors adapted to generate a signal in response to a particle interacting with said crystal;
an array of processor electronic channels, wherein each sensor in said array of sensors communicates with a corresponding processor electronic channel in the array of processor electronic channels to process any signals generated by each sensor in said array of sensors, said array of processor electronic channels arranged in a predefined pattern so that a signal transfer delay time between each processor electronic channel in the array of processor electronic channels is substantially the same,
wherein the processor electronic channel in said array of processor electronic channels corresponding to said first sensor electronically communicates with each processor electronic channel corresponding to a sensor in said plurality of neighboring sensors to correlate any signals received by a neighboring sensor with any signal received by the first sensor, and
wherein the body of said crystal includes a plurality slits, each slit in said plurality of slits comprising a reflective material and having a substantially uniform length, the plurality of slits originating from and having a substantially perpendicular orientation to the first surface and terminating in the body of said crystal.

2. The detector of claim 1, wherein the substantially uniform length is less than one-half a distance from said first surface to the second surface of said crystal.

3. The detector of claim 1, wherein the particle is a photon.

4. The detector of claim 1, wherein said plurality of neighboring sensors comprises eight neighboring sensors.

5. The detector of claim 1, wherein the first sensor is a transducer for detecting light and converting the detected light into an electrical signal.

6. The detector of claim 1, wherein the first sensor is any of a photomultiplier, a photodiode, or an avalanche photodiode.

7. The detector of claim 1, wherein the particle is a photon and wherein the plurality of slits within the body of said crystal terminate at a solid portion of the body adjacent to the second surface, such that when the photon interacts with said crystal, the plurality of slits direct light from the photon toward the sensor, and the solid portion allows the light to pass in a direction oblique to the orientation of slits, thereby permitting light-sharing among the first sensor and one or more of the sensors in the plurality of neighboring sensors.

8. The detector of claim 1, wherein said crystal comprises any of bismuth geranium orthsilicate, lutetium orthosilicate, barium fluoride, thallium-activated sodium iodide, yttrium orthosilicate, or cesium iodide.

9. A system, comprising:
(a) a detector comprising a crystal and a plurality of sensors,
said crystal having an inner surface, an outer surface, and a plurality of substantially parallel slits of a substantially equal length originating from said inner surface, wherein the substantially equal length of the slits is less than a distance between the inner surface and the outer surface, and
said plurality of sensors communicating with the outer surface of said crystal, each respective sensor in said plurality of sensors adapted to generate an electrical signal in response to energy received by the respective sensor when a particle interacts with said crystal; and
(b) a plurality of processor electronic channels communicating with said detector, the plurality of processor electronic channels arranged so that a signal transfer delay time between each processor electronic channel in the array of processor electronic channels is substantially the same and so that logical or actual neighboring processor electronic channels correspond to neighboring sensors in said detector, the plurality of processor electronic channels adapted to receive and process a plurality of digital signals derived from electrical signals generated by said plurality of sensors, each processor electronic channel in the plurality of processor electronic channels comprising a processor having a capability of signal correlation between logical or actual neighboring processor electronic channels in said plurality of processor electronic channels.

10. The system of claim 9, wherein each slit in the plurality of substantially parallel slits comprises a reflective material to direct an energy from the particle toward the plurality of sensors.

11. The system of claim 9, wherein the substantially equal length of the plurality of substantially parallel slits in said crystal are less than one-half the distance between the inner surface and the outer surface.

12. The system of claim 9, wherein each respective digital signal in the plurality of digital signals comprises (i) a time stamp corresponding to a time when a corresponding electrical signal was generated by a sensor in said plurality of sensors, and (ii) data related to a property, other than a time the electrical signal was generated, of the electrical signal.

13. The detector of claim 9, wherein said crystal comprises any of bismuth geranium orthsilicate, lutetium orthosilicate, barium fluoride, thallium-activated sodium iodide, yttrium orthosilicate, or cesium iodide.

14. The detector of claim 9, wherein the particle is a photon.

15. The detector of claim 9, wherein a sensor in said plurality of sensors is a photomultiplier, a photodiode, or an avalanche photodiode.

16. The detector of claim 9, wherein said plurality of processor electronic channels communicate to sum an incident photon energy across more than one sensor in said plurality of sensors.

17. The detector of claim 9, wherein each processor electronic channel of said plurality of processor electronic channels comprises at least two processors, wherein a first processor of said at least two processors is associated with a bypass switch and a bypass register, said bypass switch having (i) a first state that causes a signal in said plurality of digital signals to bypass said first processor and be stored in said bypass register and (ii) a second state that causes a signal in said plurality of digital signals to be input into said first processor.

* * * * *